United States Patent
Robson et al.

(10) Patent No.: US 10,577,406 B2
(45) Date of Patent: *Mar. 3, 2020

(54) FKBP-L POLYPEPTIDES AND USES IN ANGIOGENESIS-MEDIATED DISORDERS

(71) Applicant: ALMAC DISCOVERY LIMITED, Craigavon (GB)

(72) Inventors: Tracy Robson, Northern Ireland (GB); Andrea Valentine, Craigavon (GB); Martin Gerard O'Rourke, Craigavon (GB); David Hirst, Northern Ireland (GB)

(73) Assignee: ALMAC DISCOVERY LIMITED (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/169,460

(22) Filed: May 31, 2016

(65) Prior Publication Data

US 2016/0340402 A1   Nov. 24, 2016

Related U.S. Application Data

(63) Continuation of application No. 12/303,343, filed as application No. PCT/GB2007/002107 on Jun. 8, 2007, now Pat. No. 9,381,228.

(30) Foreign Application Priority Data

Jun. 9, 2006 (GB) .................................. 0611405.2

(51) Int. Cl.
| | | |
|---|---|---|
| C07K 14/705 | (2006.01) |
| A61K 45/06 | (2006.01) |
| A61K 31/00 | (2006.01) |
| A61K 31/7105 | (2006.01) |
| A61K 38/17 | (2006.01) |
| C12N 9/90 | (2006.01) |
| A61K 9/127 | (2006.01) |
| A61K 31/4412 | (2006.01) |
| A61K 39/395 | (2006.01) |

(52) U.S. Cl.
CPC ............ *C07K 14/705* (2013.01); *A61K 9/127* (2013.01); *A61K 31/00* (2013.01); *A61K 31/4412* (2013.01); *A61K 31/7105* (2013.01); *A61K 38/177* (2013.01); *A61K 38/1709* (2013.01); *A61K 39/3955* (2013.01); *A61K 45/06* (2013.01); *C12N 9/90* (2013.01); *C12Y 502/01008* (2013.01)

(58) Field of Classification Search
None
See application file for complete search history.

(56) References Cited

U.S. PATENT DOCUMENTS

| | | | |
|---|---|---|---|
| 3,194,732 A | 7/1965 | Neuhauser | |
| 3,773,919 A | 11/1973 | Boswell et al. | |
| 4,179,337 A | 12/1979 | Davis et al. | |
| 4,485,045 A | 11/1984 | Regen | |
| 4,544,545 A | 10/1985 | Ryan et al. | |
| 5,073,627 A | 12/1991 | Curtis et al. | |
| 5,359,030 A | 10/1994 | Ekwuribe | |
| 5,438,040 A | 8/1995 | Ekwuribe | |
| 5,478,925 A | 12/1995 | Wallach et al. | |
| 5,519,115 A | 5/1996 | Mapelli et al. | |
| 5,677,278 A | 10/1997 | Gospodarowicz et al. | |
| 5,681,811 A | 10/1997 | Ekwuribe | |
| 5,766,883 A | 6/1998 | Balance et al. | |
| 5,876,969 A | 3/1999 | Fleer et al. | |
| 6,180,095 B1 | 1/2001 | Greenwald et al. | |
| 6,413,507 B1 | 7/2002 | Bentley et al. | |
| 6,413,607 B1 | 7/2002 | Bentley et al. | |
| 6,576,618 B1 | 6/2003 | Herndon et al. | |
| 6,856,185 B2 | 2/2005 | Sully | |
| 6,903,078 B1 | 6/2005 | Williams | |
| 2002/0086821 A1 | 7/2002 | Rosen et al. | |
| 2002/0168650 A1 | 11/2002 | Gillis et al. | |
| 2004/0047835 A1* | 3/2004 | Bianco ............... A61K 31/00 424/78.17 |
| 2004/0053388 A1 | 3/2004 | Eckert et al. | |
| 2007/0105133 A1* | 5/2007 | Clarke .............. C12N 5/0693 435/6.12 |

FOREIGN PATENT DOCUMENTS

| | | |
|---|---|---|
| DE | 3218121 | 11/1983 |
| EP | 0052522 | 5/1982 |
| EP | 0058481 | 10/1986 |
| EP | 0142541 | 7/1987 |
| EP | 0088046 | 12/1987 |
| EP | 0143949 | 10/1988 |
| EP | 0036676 | 9/1990 |

(Continued)

OTHER PUBLICATIONS

Robson et al. The therapeutic and diagnostic potential of FKBPL; a novel anticancer protein. Drug Discovery Today. 17 (11/12): 544-548, Jun. 2012.*

(Continued)

*Primary Examiner* — Alana Harris Dent

(74) *Attorney, Agent, or Firm* — Finnegan, Henderson, Farabow, Garrett & Dunner LLP

(57) ABSTRACT

Disclosed are methods and compositions that employ FKBP-L polypeptides for modulating angiogenesis and/or tumor metastasis. The FKBP-L polypeptides may be used for the treatment of disorders mediated by angiogenesis such as cancer.

46 Claims, 70 Drawing Sheets

Specification includes a Sequence Listing.

(56) References Cited

FOREIGN PATENT DOCUMENTS

| EP | 0413622 | 2/1991 | |
|---|---|---|---|
| EP | 0497366 | 8/1992 | |
| WO | WO 94/10308 | 11/1994 | |
| WO | WO 98/49305 | 11/1998 | |
| WO | WO 99/65939 | 12/1999 | |
| WO | WO 01/02569 A2 | 1/2001 | |
| WO | WO 02/44416 A2 | 6/2002 | |
| WO | WO 02/068579 A2 | 9/2002 | |
| WO | WO 03/000878 A2 | 1/2003 | |
| WO | WO-2004042346 A2 * | 5/2004 | ........... C12Q 1/6881 |

OTHER PUBLICATIONS

Williams et al. (British Medical Journal 1: 1689-1691, 1979).*
Abdollhi, A et al., "Endostatin: The logic of antiangiogenic therapy," Drug Resistance Updates, 2005, 8:59-74.
Amin, M. et al., "Migration inhibitory factor up regulates vascular cell adhesion molecule-1 and intercellular adhesion molecue-1 via Src, PI3 kinase, and NFκB," Blood, 2006, 107:2252-2261.
Ashton, A. et al., Inhibition of Endothelial Cell Migration, Intercellular Communication, and Vascular Tube Formation, by Thromboxane $A_2$, J. Biol. Chem., 1999, 274:35562-35570.
Breedveld, F., "Therapeutic monoclonal antibodies," Lancet, 2000, 335:735-740.
Brummelkamp, T. et al., "A System for Stable Expression of Short Interfering RNAs in Mammalian Cells," Science, 2002, 296:550-553.
Cao, G, et al., "Involvement of Endothelial CD44 during in Vivo Angiogenesis," Am. J. Pathol., 2006, 169:325-336.
Dauty, E. et al., "Dimerizable Cationic Detergents with a Low cmc Condense Plasmid DNA into Nanometric Particles and Transfect Cells in Culture," J. Am. Chem. Soc., 2001, 123:9227-9234.
Duxbury, M. et al., "CEACAM6 gene silencing impairs anoikis resistance and in vivo metastatic ability of pancreatic adenocarcinoma cells," Oncogene, 2004, 23:465-473.
Elbashir, S. et al., "Duplexes of 21-nucleotide RNAs mediate RNA interference in cultured mammalian cells," Nature, 2001, 411:494-498.
Eppstein, D. et al., "Biological activity of liposome-encapsulated murine interferon γ is mediated by a cell membrane receptor." Proc. Natl. Acad. Sci. USA, 1985, 82:3688-3692.
Filleur, S. et al., "SIRNA-mediated Inhibition of Vascular Endothelial Growth Factor Severely Limits Tumor Resistance to Antiangiogenic Thrombospondin-1 and Slows Tumor vascularization and Growth," Cancer Research. 2003, 63:3919-3922.
Folkman, J., "Angiogenesis in cancer, vascular, rheumatoid and other disease," Nature Med., 1995, 1:27-31.
Fountoulakiss, M. et al., "Purification and Biochemical Characterization of a Soluble Human Interferon γ Receptor Expressed in *Eschericia coli*," J. Biol. Chem., 1995, 265:13208-13275.
Garcea, G. et al., "Angiogenesis of gastrointestinal tumours and their metastases—a target for intervention?," Eur. J. Cancer., 2004, 40:1302-1313.
Garman, A. et al., "The preparation and properties of novel reversible polymer-protein conjugates," FEBS Letters, 1987, 223:361-365.
GENBank Accession No. NP_071393.2, Jan. 25, 2009.
GENBank Accession No. NM_022110.3; [gl:34304364], Jan. 25, 2009.
Gossen, M. et al., "Inducible gene expression system for higher eukaryotic cells," Curr. Opin. Biotechnol., 1994, 5:516-520.
Greenwald, R. et al., "Drug Delivery Systems Empolying 1,4- or 1,6-Elimination: Poly(ethylene glycol) Produgs of Amine-Containing Compounds," J. Med. Chem., 1999,42:3657-3667.
Greenwald, R. et al., "Drug Delivery Systems Based on Trimethyl Lock Lactonization: Poly(ethylene glycol) Prodrugs of Amino-Containing Compounds," J. Med. Chem., 2000, 43:475-487.

Hengge, U. et al., "Expression of Naked DNA in Human, Pig, and Mouse Skin," J. Clin. Invest., 1996, 97:2911-2916.
Hwang, K. et al., "Hepatic uptake and degradation of unilamellar sphingomyelin/cholesterol liposomes: A kinetic study," Proc. Natl. Acad. Sci. USA, 1980, 77:4030-4034.
Iwahori, A et al., "Synthesis of Reversed Magainin 2 Analogs Enhanced Antibacterial Activity," Biol. Pharm. Bull., 1997, 20:267-270.
Jascur, T. et al., "Regulation of p21$^{WAF1/CIP1}$ Stability by WISp39, a Hsp90 Binding TPR Protein," Molecular Cell, 2005, 17:237-249.
Jeschke, M. et al., "The structure and composition of liposomes can affect skin regeneration, morphology and session in growth factor expression acute wounds," Gene Ther., 2005, 12:1718-1724.
Jones, A., "Analysis of polypeptides and proteins," Adv. Drug Delivery Rev., 1993.10:29-90.
Khatua, S. et al., "Overexpression of the EGFR/FKBP12/HIF-2α Pathway Identified in Childhood Astrocytomas by Angiogenesis Gene Profiling," Cancer Research. 2003, 63:1865-1870.
Koehl, G. et al., "Rapamycin and tumor growth: mechanisms behind its anticancer activity," Transplantation Reviews, 2005, 19:20-31.
Kumar, S. et al., "What is New in Wound Healing?," Turk J. Med. Sci., 2004, 34:147-160.
Lee, S. et al., "Expression of small interfering RNAs targeted against HIV-1 rev transcripts in human cells," Nature Biotechnology, 2002, 19:500-505.
Lee, S., et al., "Drug Delivery Systems Employing 1,6-Elimination: Releasable Poly(ethylene glycol) Conjugates of Proteins." Bioconjugate Chem., 2001, 12:163-169.
Leng, L. et al., "Insight into the biology of Macrophage Migration Inhibitory Factor (MIF) revealed by the cloning of its cell surface receptor," Cell Res., 2006:16:162-168.
Leng, L. et al., "MIF Signal Transduction Initiated by Binding to CD74," J. Exp. Med, 2003,197:1407-1478.
Li, S. et al., "Characterization of cationic lipid-protamine-DNA (LPD) complexes for intravenous gene delivery," Gene Therapy, 1998, 5:930-937.
Lindemann, D. et al., "Versatile Retrovirus Vector Systems for Regulated Gene Expression In Vitro and In Vivo," Molecular Medicine, 1997, 3:466-476.
Luo, D. et al., "Synthetic DNA delivery systems," Nature Biotechnology, 2000, 18:33-37.
McAllister, C. et al., Analysis in *Neisseria meningitides* and other *Neisseria* species of genes homoloaous to the FKBP immunophilin family, Mol. Microbiology, 1993, 10:13-23.
Merrifield, R. et al., "Retro and retroenantio analogs of cecropin-melittin hybrids," Proc. Natl. Acad. Sci. USA. 1995, 92:3449-3453.
Meyer-Siegler, K. et al., "Inhibition of machrophage migration Inhibitory factor decreases proliferation and cytokine expression in bladder cancer cells," BMC Cancer, 2004, 4:34-45.
Miyagashi, M. et al., "U6 promoter-drive siRNAs with four uridine 3' overhangs efficiently suppress targeted gene expression in mammalian cells," Nature Biotechnology, 2002, 19:497-500.
Morgan, B. et al., "Approaches to the Discovery of Non-Peptide Ligands for Peptide Receptors and Peptidases," Ann. Reports Med. Chem., 1989, 24:243-252.
Naujokas, M. "The Chondroitin Sulfate Form of Invariant Chain Can Enhance Stimulation of T Cell Responses through Interaction with CD44." Cell, 1993, 74:257-268.
Naujokas, M. et al., "Potent Effects of Low Levels of MHC Class II-Associated Invariant Chain on CD4+ T Cell Development." Immunity. 1995, 3:359-372.
Niidome, T. et al., "Gene Therapy Progress and Prospects: Nonviral vectors," Gene Therapy, 2002, 9:1647-1852.
Nozawa, H. et al., "Small interfering RNA targeting epidermal growth factor receptor enhances chemosensitivity to cisplatin, 5-fluorouracil and docetaxel in head and neck squamous cell carcinoma," Cancer Sci., 2006, 97:1115-1124.
Olive, D. et al., "New medical treatments for endometriosis," Best Pract. Res. Clinic. Obstet. Gynaecol., 2004, 18:319-326.
Paul, C. et al., "Effective expression of small interfering RNA in human cells," Nature Biotechnology, 2002, 20:505-508.

(56) References Cited

OTHER PUBLICATIONS

Pearson, W. et al., "Improved tools for biological sequence comparison," Proc. Natl. Acad. Sci. USA, 1988. 85:2444-2448.
Powell, J., "Update on hemangiomas and vascular malformations," Curr. Opin. Pediatr., 1999, 11:457-463.
Ren, Y. et al., "Inhibition of tumor growth and metastasis in vitro and in vivo by targeting macrophase migration inhibitory factor in human neuroblastoma," Oncogene, 2006, 25:3501-3508.
Reynolds, A. et al., "Rational siRNA design for RNA Interference," Nat Biotechnol., 2004, 22:320-330.
Roberts, M. et al., "Chemistry for peptide and protein PEGylation," Adv. Drug Delivery Rev., 2002, 54:459-476.
Roberts, M. et al., "Attachment of Degradable Poly(ethylene glycol) to Proteins Has the Potential To Increase Therapeutic Efficacy," J. Pharm. Sci., 1998. 87:1440-1445.
Robson, T. et al., "A Novel Human Stress Response-Related Gene with a Potential Role in Induced Radioresistance," Radiation Research, 1999, 152:451-461.
Robson, T. et al., "Gene regulation by low-dose ionizing radiation in a normal human lung epithelial cell line," Biochem J. Transactions. 1997, 25:335-342.
Robson, T. et al., "Increased repair and cell survival in cells treated with DIR1 antisense oligoncleotides: implications for induced radioresistance," Int. J. Radiat., 2000, 76:617-623.
Shiffelers, R. et al., "Cancer siRNA therapy by tumor selective delivery with ligand-targeted sterically stabilized nanoparticle." Nucleic Acids Research, 2004, 32:e149.
Schwartz, B. et al.; "Synthetic DNA-compacting peptides derived from human sequence enhance cationic lipid-mediated gene transfer in vitro and in vivo," Gene Therapy, 1999, 6:282-292.
Shi, X. et al.. "CD44 Is the Signaling Component of the Macrophage Migration Inhibitory Factor-CD74 Recutor Complex," Imunity, 2006, 25:595-606.
Simon, R. et al., "Peptoids: A modular approach to drug discovery," Proc. Natl. Acad. Sci. USA, 1992, 89:9367-9371.
Siprashvili, Z. and Khavari, P., "Lentivectors for Regulated and Reversible Cutaneous Gene Deilvery," Molecular Therapy, 2004, 9:93-100.
Soutschek, J. et al., "Therapeutic silencing of an endogenous gene by systemic administration of modified siRNAs," Nature, 2004, 432:173-178.
Springer, M. et al., "VEGF Gene Delivery to Muscle: Potential Role for Vasculogenesis in Adults," Molecular Cell. 1998, 2:549-558.
Sun, B. et al., "Macrophage Migration Inhibitory Factor Promotes Tumor invasion and Metastasis via the Rho-Dependent Pathway," Clinical Cancer Research, 2005, 11:1050-1058.
Takeshita, F. et al., "Efficient delivery of small interfering RNA to bone-metastatic tumors by using anticollagen in vivo," Proc. Nat'l. Acad. Sci. USA, 2005, 102:12177-12182.
Tuschl, T., "Expanding small RNA interference," Nature Biotechnology, 2002, 20:446-448.
Tuting, T, et al., "DNA Immunization Targeting the Skin: Molecular Control of Adaptive Immunity," J. Invest Dermatol, 1998, 111:183-188.
Wang, C. et al., "In Vivo Gene Therapy with Interleukin-12 Inhibits-Primary Vascular Tumor Growth and Induces Apoptosis in a Mouse Model," J. Invest Dermatol, 1999, 112:775-781.
Wilbur, W. et al., "Rapid similarity searches of nucleic acid and protein data banks," Proc. Natl. Acad. Sci. USA, 1983, 80:726-730.
Wu, H. et al., "Topical transfection using plasmid DNA in a water-in-oil nanoemulsion," Int. J. Pharmaceut., 2001, 221:23-34.
Yu, W. et al., "Topical Gene Delivery to Murine Skin," J. Invest. Dermatol., 1999, 112:370-375.
Zalipsky. S. et al., "New Detachable Poly(ethylene glycol) Conjugates: Cysteine-Cleavable Lipopolymers Regenerating Natural Phospholipid, Diacyl Phosphatidylethanolamine," Bioconjugate Chem., 1999, 10:703-707.
Zimmermann, T. et al., "RNAi-mediated gene silencing in non-human primates," Nature, 2006, 441:111-114.
Zwicker, J. et al., "Cell-cycle regulation of gene expression by transcriptional repression," TIG, 1997, 13:3-6.
Remington's Pharmaceutical Sciences, 16th edition (Oslo, A. ed.), 1980.
Short Protocois in Molecular Biology, $4^{th}$ ed., Ch. 2 (Ausubel, F. ed.), 1999, John Wiley & Sons, New York, NY.
International Search Report dated Jun. 6, 2008 corresponding to Application No. PCT/GB2007/002107.
Written Opinion of the International Searching Authority dated Jun. 8, 2008 corresponding to Application No. PCT/GB2007/002107.
Abuchowski, A. et al., Soluble Polymer-Enzyme Adducts, Enzymes as Drugs, Chap. 13, 1981, pp. 367-383, John Wiley & Sons, New York, NY.
Eckstein, F., "Nucleoside Phosphorothioates," Ann. Rev. Biochem., 1985, 54:367-402
Folkman, J., "Tumor Angiogenesis: Therapeutic Implications," N. Engl. J. Med., 1971, 285:1182-1186.
Langer, R., "Controlled release of macromolecules," Chemtech, 1982, 12:98-105.
Langer, R., "Biocompatibiiiry of polymeric delivery systems for macromolecules," J. Biomedical Materials Res., 1981, 15:267-277.
Lee, F. et al., "Glucocorticoids regulate expression of dihydrofolate reductase cDNA in mouse mammary tumour virus chimaeric plasmids." Nature, 1961, 294:228-232.
Lip, G., et al., "Thrombogenesis, atherogenesis and angiogenesis in vascular disease: a new 'vascular triad'," Ann. Med., 2004, 36:119-125.
Needleman, S. et al., "A General Method Applicable to the Search for Similarities in the Amino Acid Sequence of Two Proteins," J. Mol. Biol., 1970, 48:443-453.
Nishikawa, M. et al., "Nonviral Vectors in the New Millennium: Delivery Barriers in Gene Transfer," Human Gene Therapy, 2001, 12:861-870.
Pearlman, R. et al., "Analysis of Protein Drugs," Peptide and Protein Drug Delivery, Chap. 6,1991, pp. 247-301, Marcel-Dekker, Inc., New York, NY.
Sidman, K. et al., "Controlled Release of Macromolecules and Pharmaceuticals from Synthetic Polypeptides Based on Glutamic Acid," Biopolymers, 1983. 22:547-556.
Smith, T. et al., "Comparison of Bioosequences," Adv. Appl. Math., 1981. 2:482-489.
Stewart, J, et al., "Solid Phase Peptide Synthesis," $2^{nd}$ edition, 1984, Pierce Chemical Co., Rockford, IL.
Sun, B. et al., "Induction of macrophage migration inhibitory factor by lysophosphatidic acid: Relevance to tumor growth and angiogenesis," Int. J. Mol. Med., 2003, 12:633-641.
European Patent Office Communication Pursuant to Article 94(3) EPC, Application No. 07733118.9-2107, dated Dec. 11, 2009.
European Patent Office, Communication Pursuant to Article 94(3) EPC, Application No. 07733118.9-2107, dated May 10, 2011.
Gura et al. (Science 278: 1041-1042, Nov. 7, 1997).
Fountoulakis, M. et al., "Purification and Biochemical Characterization of a Soluble Human Interferon γ Receptor Expressed in *Escherichia coil*," J. Biol. Chem., 1995, 265:13268-13275.
Olive, D. et al., "New medical treatments for endometriosis," Best Pract. Res. Clinic. Obstet. Gynaecol., 2004, 18:319-328.
Lee, F. et al., Glucocorticoids regulate expression of dihydrofolate reductase cDNA in mouse mammary tumour virus chimaeric plasmids, Nature, 1981, 294:228-232.
Lee, Vincent, ed. Peptide and Protein Drug Delivery, 247-301. Marcel Dekker, Inc., New York, N.Y., Pubs. (1991).
Leng, L. et al., "MIF Signal Transduction Initiated by Binding to CD74," J. Exp. Med, 2003:197:1467-1476.
Reynolds, A. et al., "Rational siRNA design for RNA Interference," Nat Biotechnol., 2004, 22:326-330.
Sidman, K. et al., "Release of Macromolecules and Pharmaceuticals from Synthetic Polypeptides Based on Glutamic Acid," Biopolymers, 1983, 22:547-556.
Bertl et al., "Inhibition of angiogenesis and endothelial cell functions are novel sulforaphane-mediated mechanisms in chemoprevention," Molecular Cancer Therapy, Mar. 2006, vol. 5, issue 3, 12 pages.

(56) References Cited

OTHER PUBLICATIONS

Staton et al., "Current methods for assaying angiogenesis in vitro and in vivo," International Journal of Experimental Pathology, 2004, vol. 85, 233-248, 16 pages.

Vincent et ai., "Inhibition of endothelial cell migration by cerivastatin, an HMG-CoA reductase inhibitor: contribution to its anti-angiogenic effect," FEBS Letters, Apr. 2001, 159-166, 8 pages.

\* cited by examiner

FIG. 1A

SEQ ID NO: 1  MRGSHHHHHGMASMTGGQQMGRDLYDDDDKDRWGSMETPPVNTIGEKDTSQPQQEWEKNLRENLDSVI
QIRQQPRDPPTETLELEVSPDPASQILEHTQGAEKLVAELEGDSHKSHGSTSQMPEALQASDLWYCPDG
SFVKKIVIRGHGLDKPKLGSCCRVLALGFPFGSGPPEGWTELTMGVGPWREETWGELIEKCLESMCQGE
EAELQLPGHTGPPVGLTLASFTQGRDSWELETSEKEALAREERARGTELFRAGNPEGAARCYGRALRLL
LTLPPGPPERTVLHANLAACQLLLGQPQLAAQSCDRVLEREPGHLKALYRRGVAQAALGNLEKATADL
KKVLAIDPKNRAAQEELGKVVIQGKNQDAGLAQGLRKMFG

SEQ ID NO: 2  METPPVNTIGEKDTSQPQQEWEKNLRENLDSVIQIRQQPRDPPTETLELEVSPDPASQILEHTQGAEKLV
AELEGDSHKSHGSTSQMPEALQASDLWYCPDGSFVKKIVIRGHGLDKPKLGSCCRVLALGFPFGSGPPEG
WTELTMGVGPWREETWGELIEKCLESMCQGEEAELQLPGHTGPPVGLTLASFTQGRDSWELETSEKEALA
REERARGTELFRAGNPEGAARCYGRALRLLLTLPPGPPERTVLHANLAACQLLLGQPQLAAQSCDRVLE
REPGHLKALYRRGVAQAALGNLEKATADLKKVLAIDPKNRAAQEELGKVVIQGKNQDAGLAQGLRKMFG

SEQ ID NO: 3  METPPVNTIGEKDTSQPQQEWEKNLRENLDSVIQIRQQPRDPPTETLELEVSPDPASQILEHTQGAEKLV   Δ200
AELEGDSHKSHGSTSQMPEALQASDLWYCPDGSFVKKIVIRGHGLDKPKLGSCCRVLALGFPFGSGPPEG   FKBP-L
WTELTMGVGPWREETWGELIEKCLESMCQGEEAELQLPGHTGPPVGLTLASFTQGRDSW

SEQ ID NO: 4  METPPVNTIGEKDTSQPQQEWEKNLRENLDSVIQIRQQPRDPPTETLELEVSPDPASQILEHTQGAEKLV   Δ151
AELEGDSHKSHGSTSQMPEALQASDLWYCPDGSFVKKIVIRGHGLDKPKLGSCCRVLALGFPFGSGPPEG   FKBP-L
WTELTMGVGP

SEQ ID NO: 5  METPPVNTIGEKDTSQPQQEWEKNLRENLDSVIQIRQQPRDPPTETLELEVSPDPASQILEHTQGAEKLV   Δ86
AELEGDSHKSHGSTS

SEQ ID NO: 6  METPPVNTIGEKDTSQPQQEWEKNLRENLDSVIQIRQQPRDPPTETLELEVSPDPAS   Δ58 FKBP-L

SEQ ID NO: 7  METPPVNTIGEKDTSQPQQEWEKNLRENLDSVIQIRQQPRDPPTETL   Δ48

SEQ ID NO: 8  METPPVNTIGEKDTSQPQQEWEKNLRENLDSVIQIRQQP   Δ40 FKBP-L

SEQ ID NO: 9  METPPVNTIGEKDTSQPQQEWEKNLRENLDSVI   Δ34

SEQ ID NO: 10  QIRQQPRDPPTETLELEVSPDPAS   FKBP-L 24mer

| | | |
|---|---|---|
| SEQ ID NO: 11 | QQPRDPPTETLELEVSPD | Peptide 1 |
| SEQ ID NO: 12 | QIRQQPRDPPTETLELEVSPDPAS | Peptide 2 |
| SEQ ID NO: 13 | PyroGlu-IRQQPRDPPTETLELEVSPDPAS-PEG-C(Alexa488) | Peptide 3 |
| SEQ ID NO: 14 | IRQQPRDPPTETLELEVSPDPAS | Peptide 4 |
| SEQ ID NO: 15 | QIRQQPRDPPTETLELEVSPD | Peptide 5 |
| SEQ ID NO: 16 | QIRQQPRDPPTETLELEV | Peptide 6 |
| SEQ ID NO: 17 | QIRQQPRDPPTETLE | Peptide 7 |
| SEQ ID NO: 18 | QIRQQPRDPPTE | Peptide 8 |
| SEQ ID NO: 19 | QQPRDPPTETLELEVSPDPAS | Peptide 9 |
| SEQ ID NO: 20 | RDPPTETLELEVSPDPAS | Peptide 10 |
| SEQ ID NO: 21 | PTETLELEVSPDPAS | Peptide 11 |
| SEQ ID NO: 22 | TLELEVSPDPAS | Peptide 12 |
| SEQ ID NO: 23 | RQQPRDPPTETLELEVSP | Peptide 13 |
| SEQ ID NO: 24 | RQQPRDPPTETLELEVS | Peptide 14 |
| SEQ ID NO: 25 | RQQPRDPPTETLELEV | Peptide 15 |
| SEQ ID NO: 26 | PRDPPTETLELEVSPD | Peptide 16 |
| SEQ ID NO: 27 | RDPPTETLELEVSPD | |

FIG. 1B

SEQ ID NO: 28    AC-QIRQQPRDPPTETLELEVSPDPAS-NH₂    Peptide 17

SEQ ID NO: 29    METPPVNTIGEKDTSQPQQEMEKNLRENLDSVIQIRQQPRDPPTETLELEVSPDPASQILEHTQGAEKLV    PUBMED database
                 AELEGDSHKSHGSTSQMPEALQASDLMYCPDGSFVKKIVIRGHGLDKPKLGSCCRVLALGFPFGSGPPEG
                 WTELTMGVGPMREETWGELIEKCLESMCQGEEAELQLPGHSGPPVRLTLASFTQGRDSWELETSEKEALA
                 REERARGTELFRAGNPEGAARCYGRALRLLTLPPPGPPERTVLHANLAACQLLLGQPQLAAQSCDRVLE
                 REPGHLKALYRRGVAQAALGNLEKATADLKKVLAIDPKNRAAQEELGKVVIQGKNQDAGLAQGLRKMFG

FIG. 1C

SEQ ID NO: 30    Full-length FKBPL cDNA (PUBMED Database)

ATGGAGACGCCACCAGTCAATACAATTGGAGAAAAGGACACCTCTCAGCCCGCAACAAGAGTGGGAAAAGA
ACCTTCGGGAGAACCTTGATTCAGTTATTCAGATTAGGCAGCAGCCCTCCTGAGACCCTCCTACCGAAACGCT
TGAGCTGGAAGTAAGCCCAGATCCAGCCAGCCAAATTCTAGAGCATATCAAGGAGCTGAAAAACTGGTT
GCTGAACTTGAAGGAGACTCTCATAAGTCTCATGGATCAACCAGTCAGATCGTAATCCGTGGCCATGGCCCTTCAAGCTT
CTGATCTCTGGTACTGCCCCCGATGGGAGCTTTGTCAAGAAGATCGTAATCCGTGGCCATGGCTTGGACAA
ACCCAAACTAGGCTCCTGCTGCCGGGTACTGGGCCATGGAGGGAGAAACTTGGGGGAGCTCATAGAGAAATGCT
TGGACAGAGCTAACTATGGGCGTAGGGCGTAGGGCCATGGAGGGAGGAAACTTGGGGGCACTCTGGAACCTCCTGTCAGGCT
TGGAGTCCATGTCAAGGTGTCAAGGTGAGGAAGCAGAGCTTCAGCTGCCTGGGAGACTAGCGAGAAGGAAGCCCTGGCC
CACACTGGCATCCTTCACTCAAGGGGCACAGAACTATTTCGAGCTGGGAACCCTGAAGGAGCTGCCCGATGCTATG
AGGGAAGAACGTGCAAGGGGCACAGAACTATTTCGAGCTGGGAACCCTGAAGGAGCTGCCCGATGCTATG
GACGGGCTCTTCGGCTGTGCTCCTGACTTTACCCCACCTGGCCCTCCAGAACGAACTGTCCTTCATGCCAA
TCTGGCTGCCTGTCAGTTGTGCTAGGGCAGCCTCAGTTGGCAGCCAGAGCTGTGACCGGGTGTTGGAG
CGGGAGCCTGGCCATTTAAAGGCCTTATACCGAAGGGGGTTGCCCAGGCTGCCCTTGGGAACCTGGAAA
AAGCAACTGCTGACCTCAAGAAGGTGCTGGGCGATAGATCCCAAAAACCGGGCAGCCCCAGGAGGAACTGGG
GAAGGTGGTCATTCAGGGGAAGAACCAGGATGCAGGGCTCAGGGTCTGCGCAAGATGTTTGGCTGA

FIG. 2A

SEQ ID NO: 31    Full-length FKBPL cDNA

ATGGAGACGCCACCAGTCAATACAATTGGAGAAAAGGACACCTCTCAGCCCGCAACAAGAGTGGGAAAAGA
ACCTTCGGGAGAACCTTGATTCAGTTATTCAGATTAGGCAGCAGCCCGAGACCCTCCTACCGAAACGCT
TGAGCTGGAAGTAAGCCCAGATCCAGCCAGCCAAATTCTAGAGCATACTCAAGGAGCTGAAAAACTGTT
GCTGAACTTGAAGGAGACTCTCATAAGTCTCATGATCAACCAGTCAGATGCCAGAGGCCCTTCAAGCTT
CTGATCTCTGGTACTGCCCCGATGGGAGCTTTGTCAAGAAGATCGTAATCCGTGGCCATGGCTTGGACAA
ACCCAAACTAGGCTCCTCCTGCTGCCGGGTACTGGCTTTGGGTTTCCTTTCGGATCAGGCCCGCCAGAGGGC
TGGACAGAGCTAACTATGGGCGTAGGGCGTAGGGCCATGGAGGGAGGAAACTTGGGGGAGCTCATAGAGAAATGCT
TGGAGTCCATGTGTCAAGGTGAGGAAGCAGAGCTTCAGCTGCCTGGGCACACTGGACCTCCTGTCGGGCT
CACACTGGCATCCTTCACTCAAGGCCCAGAACCTGGGAGCTGGAGACTAGCGAGAAGGAAGCCCTGGCC
AGGGAAGAACGTGCAAGGGCACACAGAACTATTTCACCCCACCTGGGAACCCTGAAGGAGCTGCCCGATGCTATG
GACGGGCTCTTCGGCTGCTCCTGACTTTACCCCACCTGGCCCTCCAGAACGAACTGTCCTTCATGCCAA
TCTGCCTGTCAGTTGTTGCTAGGGCAGCCTCAGTTGGCAGCCCAGAGCTGTGACCGGGTGTTGGAG
CGGGAGCCTGGCCATTTAAAGCCTTATACCGAAGGGGGTTGCCCAGGCTGCCCTTGGAACCTGGAAA
AAGCAACTGCTGACCTCAAGAAGGTGCTGGCGATAGATCCCAAAAACCGGGCAGCCCAGGAGGAACTGGG
GAAGGTGGTCATTCAGGGGGAAGAACCAGCAGGATGCAGCAGGGCTGGCTCAGGGCTCGCCGCAAGATGTTTGGCTGA

FIG. 2B

SEQ ID NO: 32    Δ34 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTTAG

SEQ ID NO: 33    Δ40 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCG

SEQ ID NO: 34    Δ48 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGA

SEQ ID NO: 35    Δ58 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCCAGATCCAGCCAGCTAA

SEQ ID NO: 36    Δ86 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCAGATCCAGCCAAATTCTAGAGCATACTCAAGGAGCTGAAAAACTG
GTGCTGAACTTGAAGGAGACTCTCATAAGTCTCATGGATCAACCAGTTAG

FIG. 2C

SEQ ID NO: 37    Δ151 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCCCCGAGACCCTCCTACCGAAACG
CTTGAGCTGGAAGTAAGCCCAGATCCAGCCAGTCTAGAGCATACTCAAGGAGCTGAAAAACTG
GTTGCTGAACTTGAAGGAGACTCTCATAAGTCTCATGGATCAACCAGTCAGATGCCAGAGGCCCTTCAA
GCTTCTGATCTCTGGTACTGCCCCGATGGGAGCTTTGTCAAGAAGATCGTAATCCGTGGCCATGGCTTG
GACAAACCCAAACTAGGCTCCTGCTGCCGGGTACTGGCTTTGGGGTTTCCTTTCGGATCAGGGCCGCCA
GAGGGCTGACAGAGCTAACTATGGGCGTAGGGCCATGA

SEQ ID NO: 38    Δ200 FKBPL (PUBMED Database)
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCTCCTACCGAAACG
CTTGAGCTGGAAGTAAGCCCAGATCCAGCCAGTCTAGAGCATACTCAAGGAGCTGAAAAACTG
GTTGCTGAACTTGAAGGAGACTCTCATAAGTCTCATGGATCAACCAGTCAGATGCCAGAGGCCCTTCAA
GCTTCTGATCTCTGCCCCGATGGGAGCTTTGTCAAGAAGATCGTAATCCGTGGCCATGGCTTG
GACAAACCCAAACTAGGCTCCTGCCGGGCTATGGGCCATGGTTCCTTTCGGATCAGGGCCGCCA
GAGGGCTGACAGAGCTAACTATGGGCGTAGGGCCATGGTCAAGGTGTCAAGGTGAGGAAGCAGAGCTTCAGCTGCCTGGGCACTCTGGACCTCCT
AAATGCTTGGAGTCCATGTGTCAAGGTGAGGAAGCAGAGCTTCAGCTGCCTGGCACTCTGGACCTCCT
GTCAGGCTCACACTGGCCATCCTTCACTCAAGGCCGAGACTCCTGGTAG

FIG. 2D

SEQ ID NO: 39    Δ200 FKBPL which was cloned into pcDNA3.1

ATGGAGACGCCACCAGTCAATACAATTGGAGAAAAGGACACCCTCTCAGCCGCAACAAGAGTGGGAAAAGA
ACCTTCGGGAGAACCTTGATTCAGTTATTCAGATTAGGCAGCAGCCCCGAGACCCTCCTACCGAAACGCT
TGAGCTGGAAGTAAGCCCAGATCCAGCCAGCCCAAATTCTAGAGCATACTCAAGGAGCTGAAAAACTGGTT
GCTGAACTTGAAGGAGACTCTCATAAGTCTCATGATCAACCAGTCAGATGCCAGAGGCCCTTCAAGCTT
CTGATCTCTGGTACTGCCCCGATGGGAGCTTTGTCAAGAAGATCGTAATCCGTGGCCATGGCTTGGACAA
ACCCAAACTAGGCTCCTGCTGCCGGGTACTGGGCGTAGGGCCATGGAGGAAACTTGGGAGGAGCTCATAGGGGC
TGGACAGAGCTAACTATGGGCGTAGGGCCATGGAGGAAGCAGACTTCAGCTGCCTGGGCACACTGGACCTCCTGTCGGGCT
TGGAGTCCATGTGTCAAGGTGAAGGTGAAGCAGAGCTTCAGCTGCCTGGGCACACTGGACCTCCTGTCGGGCT
CACACTGGCCATCCTTCACTCAAGGCCCGAGACTCCTGGTAG

FIG. 2E

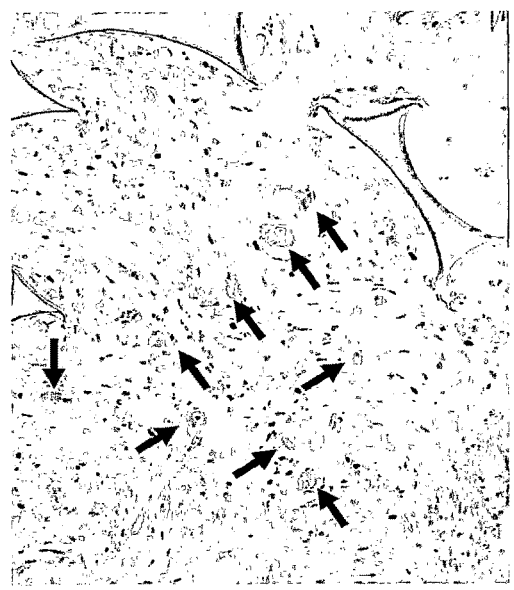
FIG. 8A  FGF alone (H + E)
FIG. 8B  FGF + FKBPL (H + E)

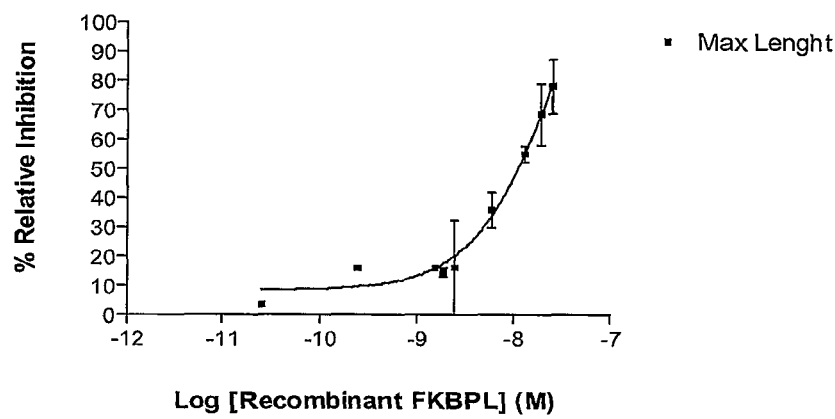
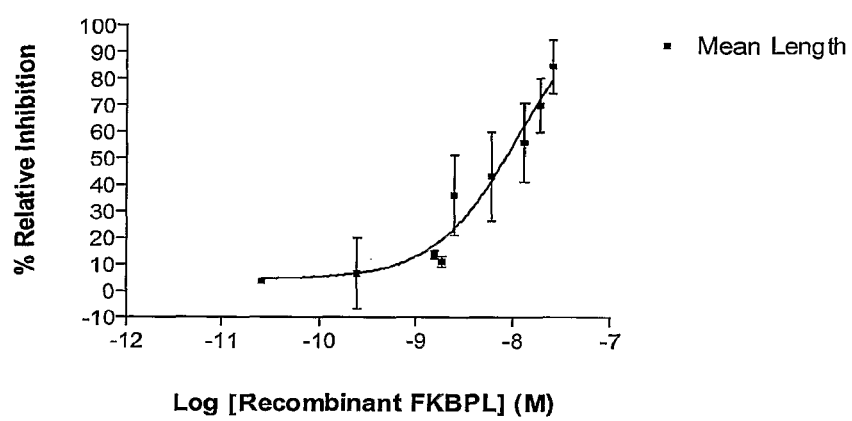
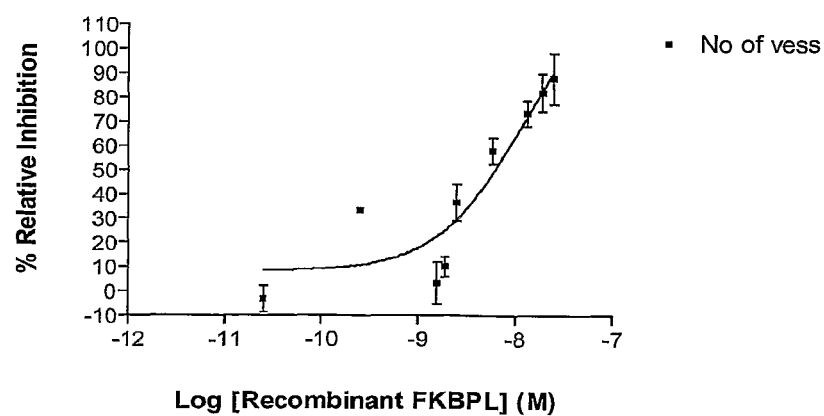
FIG. 10

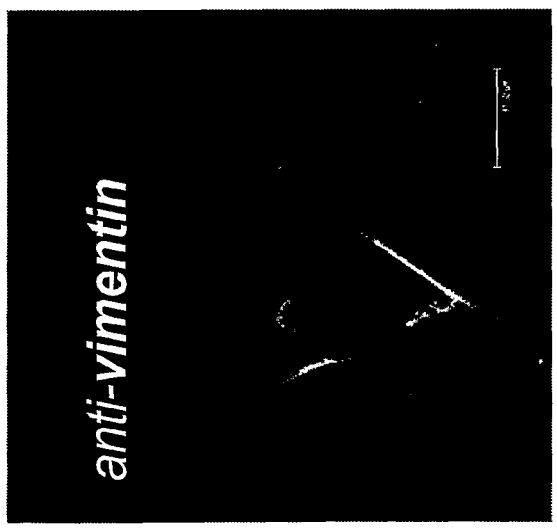 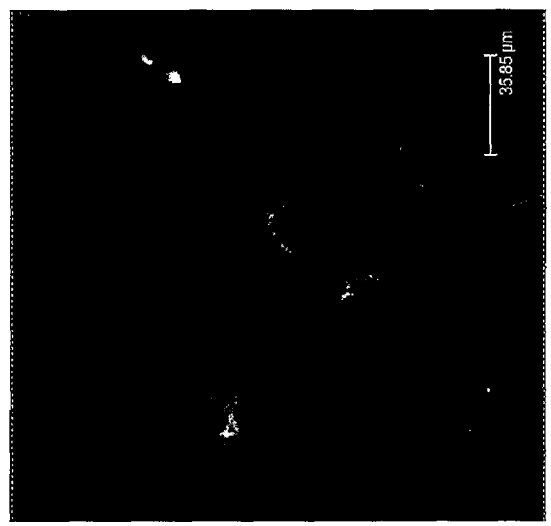
FIG. 13

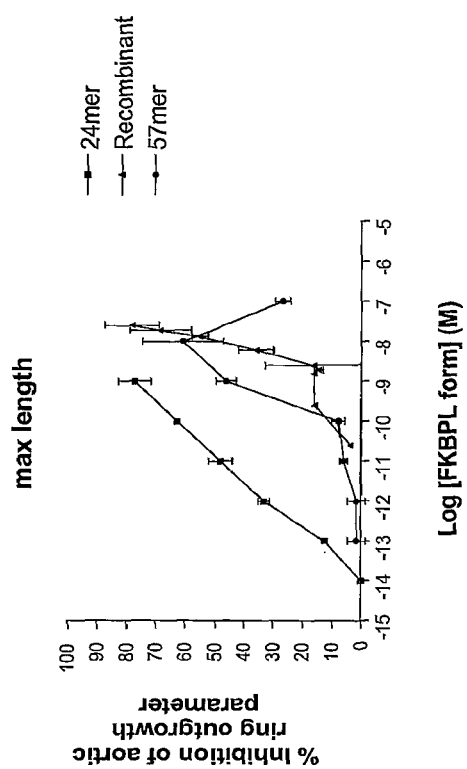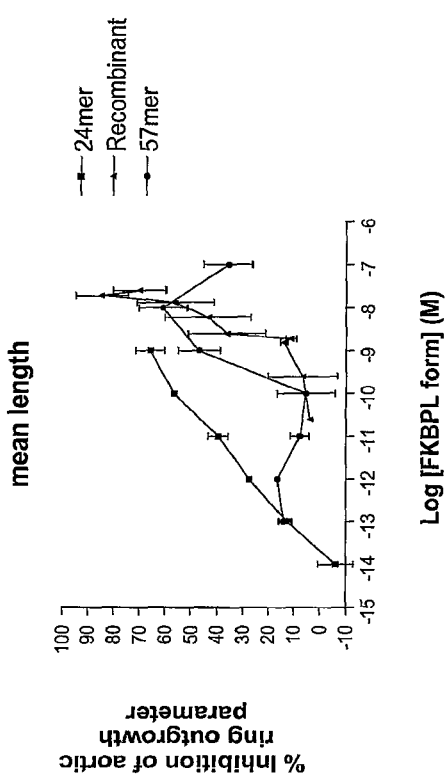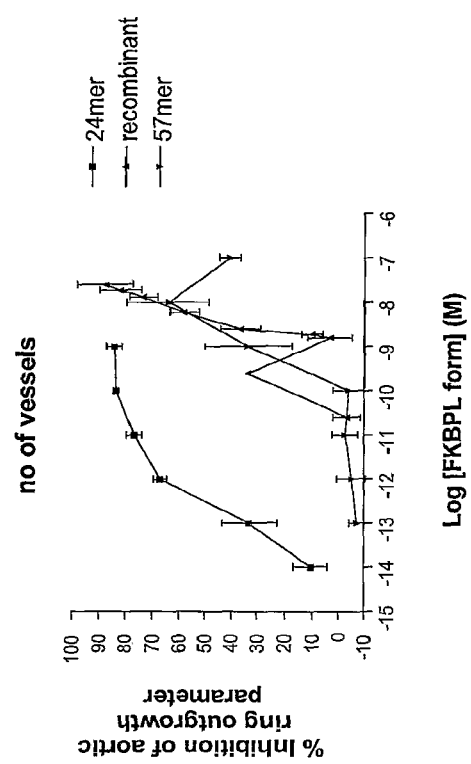
FIG. 24A

| Compound | Mean Length | Max. Length | No of Vessels |
|---|---|---|---|
| rFKBP-L | 8.79nM | 8.55nM | 1.16nM |
| 57mer | 0.32nM | 0.2nM | 0.53nM |
| 24mer | 2.2pM | 1.96pM | 0.2pM |

FIG. 24B

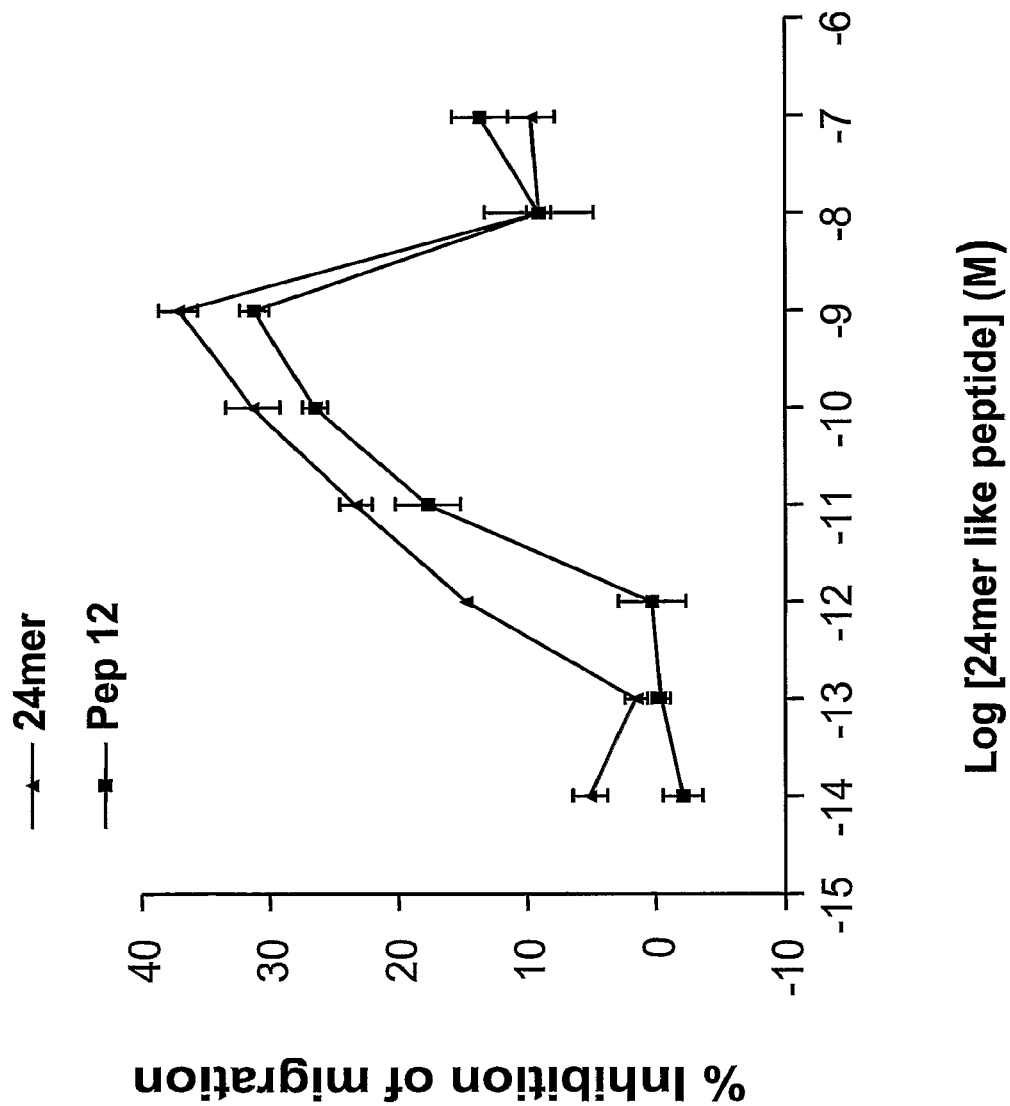

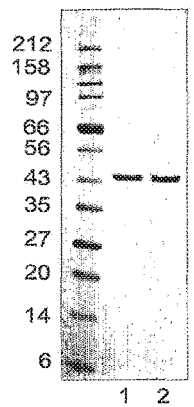
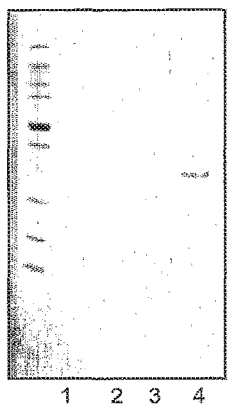
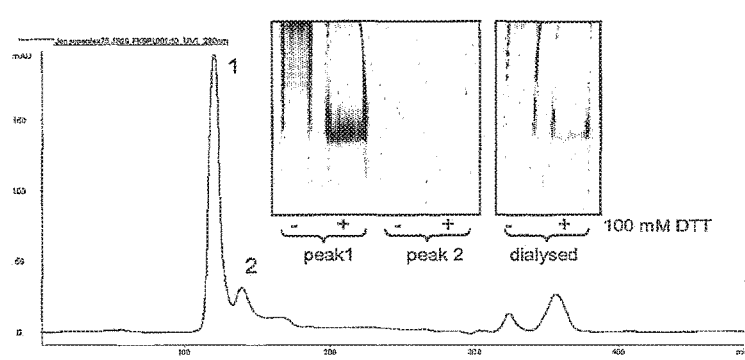
FIG. 35A   FIG. 35B   FIG. 35C
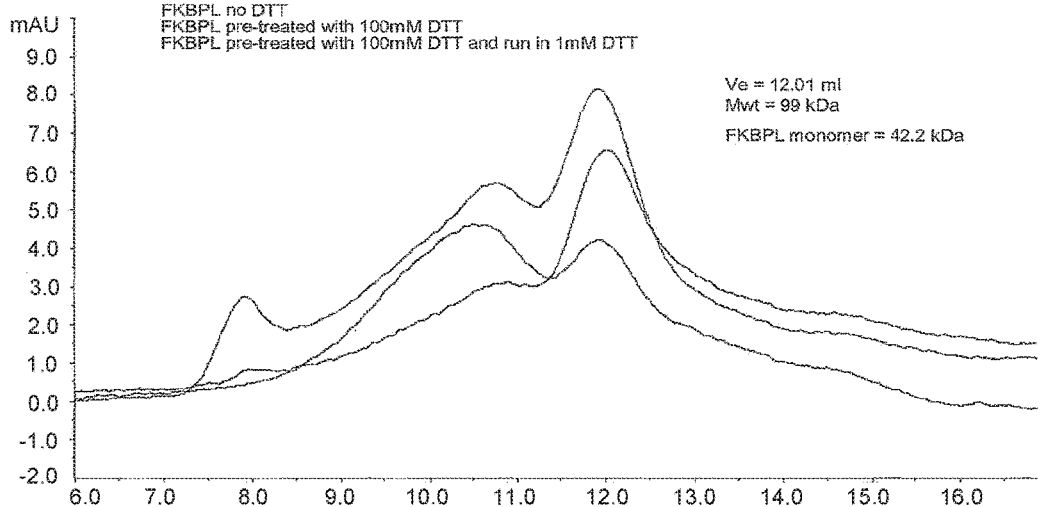
FIG. 36

FKBP-L POLYPEPTIDES AND USES IN ANGIOGENESIS-MEDIATED DISORDERS

PRIORITY CLAIM TO RELATED APPLICATIONS

This application is a continuation of U.S. patent application Ser. No. 12/303,343, filed Dec. 3, 2008 and issued as U.S. Pat. No. 9,381,228, which is a U.S. National Stage Entry of PCT/GB2007/002107, filed Jun. 8, 2007, and claims priority to UK Patent Application No. 0611405.2 to Robson et al., filed Jun. 9, 2006. The entire disclosure of UK Patent Application No. 0611405.2 to Robson et al, is incorporated by reference herein.

FIELD OF THE INVENTION

The present invention relates to FKBP-L polypeptides, FKBP-L peptides, FKBP-L peptide derivatives, and uses thereof.

BACKGROUND OF THE INVENTION

Angiogenesis is the formation of new blood vessels from pre-existing vasculature and may be controlled by intricate signaling via soluble factors. Pathologies associated with angiogenesis may include cancer (Folkman J. (1971) *N. Engl. J. Med.* 285:1182; Folkman J. (1999) *Nature Med.* 1: 27-31), arteriosclerosis (Lip, G. Y., Blann, A. D. (2004) *Ann Med.* 36(2) 119-125), psoriasis (Powell, J. (1999) *Curr. Opin. Pediatr.* 11: 457-463), endometriosis (Olive, D. L., Lindheim, S. R., Pritts, E. A. (2004) *Best Pract. Res. Clinc. Obstet. Gynaecol.* 18(2) 319-328) and some ocular disorders like diabetic retinopathy (Folkman J. (1999) *Nature Med.* 1: 27-31). Angiogenesis may also be necessary for wound repair since the new vessels provide nutrients to support the active cells, promote granulation tissue formation and facilitate the clearance of debris. Approximately 60% of the granulation tissue mass may be composed of blood vessels which also supply the necessary oxygen to stimulate repair and vessel growth. It is well documented that angiogenic factors are present in wound fluid and promote repair while antiangiogenic factors inhibit repair. In tumors, when endothelial cells are exposed to soluble factors which stimulate angiogenesis, they may undergo several physiological changes including a massive increase in proliferation, degradation and invasion through the existing vessel basement membrane, and migration away from the blood vessel to a new location. At the new location the endothelial cells may again proliferate and form capillary tubules before ultimately forming a highly disorganised tumor vasculature (Garcea G, Lloyd T D, Gescher A, Dennison A R, Steward W P, Berry D P. (2004) *Eur J Cancer.* June; 4099):1302-13). Activated endothelial cells may show a distinct pattern of gene expression, which leads to modification of the principal cellular functions involved in angiogenesis. These include the regulation of proteolytic balance leading to localised pericellular matrix degradation, synthesis of adhesion molecules involved in extracellular matrix interaction, and most importantly, cytoskeletal reorganization involved in cell migration (Garcea G, Lloyd T D, Gescher A, Dennison A R, Steward W P, Berry D P. (2004) *Eur J Cancer.* June; 4099):1302-13).

Novel anti-angiogenic compounds have been shown to inhibit a range of endothelial markers, which have been identified as being up-regulated in activated endothelial cells. These may include receptors, matrix metalloproteins, and adhesion proteins. The success rate of these inhibitors has been quite high. Recently the novel anti-angiogenic compound Avastin, a VEGF antibody, has passed FDA approval and anti-angiogenesis has now become recognised as the fourth modality used in the treatment of cancer (Abdollhi A., Hlatky L., Huber P. E. (2005) *Drug Resistance Updates,* February-April; 8:59-74). These therapies may have the following advantages over conventional chemotherapeutic treatments. First, angiogenesis is primarily an onco-foetal mechanism, thus minimal side effects should be expected when administered, even after prolonged treatment. Secondly, tumor-associated angiogenesis is a physiological host mechanism and its pharmacological inhibition should, consequently, not lead to the development of resistance. Finally the tumor mass itself is difficult to target, where the endothelial cells that line the supplying vasculature are frequently classed as vulnerable.

Pro-angiogenic compounds may also be therapeutic. For example, pro-angiogeneic compounds which may promote wound repair include angiogenic cytokines, such as FGF, VEGF, TGF-beta, angiopoietin, and mast cell tryptase.

A novel polypeptide and its gene have been recently identified and partially characterised. This new polypeptide has been named FKBP-L, DIR1 or WISP39. This gene has been demonstrated as having a role in stress responses (Robson, T., Lohrer, H., Bailie, J. R., Hirst, D. G., Joiner, M. C., Arrand, J. E. (1997) *Biochemical J. Transactions* 25, 335-341). It has also been shown that repression of the FKBP-L gene can protect against cellular X-ray and UV-induced oxidative cellular damage (Robson, T., Joiner, M. C., McCullough, W., Price, M. E., McKeown, S. R., Hirst, D. G. (1999) *Radiation Research* 152, 451-461; Robson, T., Price, M. E., Moore, M. L., Joiner, M. C., McKelvey-Martin, V. J., McKeown, S. R., Hirst, D. G., (2000) *Int. J. Radiat*). FKBP-L may also stabilize newly synthesised p21 (a cyclin dependent kinase inhibitor and a critical regulator of cell cycle) by forming a trimeric complex with p21 and Hsp90 (Jascur, T. et al (2005) Molecular Cell, Vol. 17, 237-249).

There is a need to provide new therapeutics that can modulate angiogeneis and cell migration. Such therapeutics may be important as stand-alone treatments, or to be used in conjunction with other therapeutic agents.

SUMMARY OF THE INVENTION

Embodiments of the present invention relate to the use of FKBP-L polypeptides to modulate angiogenesis and cell migration. The present invention may be embodied in a variety of ways.

For example, in certain embodiments, the FKBP-L and fragments thereof may be used to modulate angiogenesis. Also, in some embodiments, the FKBP-L polypeptides may be used to modulate cell migration and/or metastasis of tumor cells. The action of FKBP-L may be mediated by CD44. Thus, the FKBP-L polypeptide may, in certain embodiments, be used to modulate angiogenesis, cell migration and/or metastasis of cells that express CD44.

In some embodiments, the present invention comprises methods of treating a disorder mediated by or associated with at least one of cell migration, and/or angiogenesis, and/or tumor metastasis. The method may comprise administering a therapeutically effective amount of: (i) an active compound comprising an isolated FKBP-L polypeptide, a biologically active fragment of a FKBP-L polypeptide, or a biologically active derivative of a FKBP-L polypeptide or a fragment thereof, or (ii) a polynucleotide encoding such a FKBP-L polypeptide to a subject in need thereof.

In other embodiments, the present invention comprises the use of (i) an active compound comprising an isolated FKBP-L polypeptide or a biologically active fragment of a FKBP-L polypeptide, or a biologically active derivative of a FKBP-L polypeptide or fragment thereof, or (ii) a polynucleotide encoding such a FKBP-L polypeptide, fragment or derivative in the manufacture of a medicament for use in treating a disorder mediated by or associated with at least one of cell migration, angiogenesis, and/or tumor metastasis.

There are additional features of the invention which will be described hereinafter. It is to be understood that the invention is not limited in its application to the details set forth in the following claims, description and figures. The invention is capable of other embodiments and of being practiced or carried out in various ways.

BRIEF DESCRIPTION OF THE DRAWINGS

The present invention may be better understood by reference to the following non-limiting drawings.

FIGS. 1A, 1B, and 1C show alternative amino acid sequences of full-length FKPB-L, fragments of FKBP-L in accordance with alternative embodiments of the present invention.

FIGS. 2A, 2B, 2C, 2D, and 2E show polynucleotide sequences encoding for FKBP-L and some of its deletion mutants and variants in accordance with alternative embodiments of the present invention.

FIGS. 8A and 8B illustrate the effect of the full-length recombinant protein FKBP-L on angiogenesis in vivo using the mouse sponge assay, in accordance with an embodiment of the present invention where FIG. 8A shows treatment of cells with bovine fibroblast growth factor (bFGF) alone, and FIG. 8B shows treatment of cells with bFGF with full length FKBP-L polypeptide.

FIG. 10 illustrates a dose response of the effect of full length FKBP-L recombinant polypeptide on the ex vivo rat aortic ring explant model of angiogenesis in accordance with alternate embodiments of the present invention.

FIG. 13 shows changes in cytoskeletal morphology of migrating endothelial cells on exposure to full length FKBP-L recombinant polypeptide in accordance with an embodiment of the present invention, where HMEC-1 intermediate filaments were stained using anti-vimentin.

FIG. 20A and FIG. 20B illustrate the sequencing results of several of the FKBP-L deletion mutants, and FIG. 20C illustrates the inhibitory effects of transiently transfected FKBP-L deletion mutants on wound closure in accordance with alternate embodiments of the present invention.

FIGS. 24A and 24B show the effect of candidate peptides spanning the active domain of FKBP-L (i.e, FKBP-L 24mer peptide, SEQ ID NO: 10; the FKBP-L 57mer, SEQ ID NO: 6; and full length recombinant His-tagged FKBP-L, SEQ ID NO: 1) on the mean length, maximum length (max length), and number of vessels (no. of vessels) for angiogenic sprouting using the rat aortic ring assay in accordance with alternate embodiments of the present invention.

FIG. 28A shows the effect of addition of the FKBP-L 24mer at day 7, and FIG. 28B shows an experiment where aortic rings were initially exposed to FKBP-L 24mer and then the 24mer removed, in accordance with alternate embodiments of the present invention.

FIGS. 34A, 34B, 34C, 34D, 34E, 34F, 34G, 34H, 34I, 34J, 34K, and 34L show the response of various modified/truncated versions of the FKBP-L 24mer: a PEG-modified FKBP-L 24mer (FIG. 34A), a FKBP-L 24mer with an N-terminal pyroglutamic acid (FIG. 34B), and truncated forms of 24mer FKBP-L peptide (FIG. 34C, FIG. 34D, FIG. 34E, FIG. 34F, FIG. 34G, FIG. 34H, FIG. 34I, FIG. 34J, FIG. 34K, and FIG. 34L). All are compared to the 24mer peptide in the in vitro HMEC-1 wound scrape assay in accordance with alternate embodiments of the present invention.

FIGS. 35A, 35B, and 35C show purification of recombinant FKBP-L in accordance with alternate embodiments of the present invention, where FIG. 35A shows an SDS PAGE gel run under reducing conditions showing purified recombinant FKBP-L protein before and after dialysis (lanes 1 & 2 respectively); and FIG. 35B shows an SDS PAGE comparison of dialysed recombinant FKBP-L before and after treatment with DTT (lanes 3 & 4). Lane 3 is non-reduced sample, lane 4 is sample reduced with 50 mM DTT. FIG. 35C shows further purification of recombinant FKBP-L by gel filtration. Inserts show native PAGE analysis of both peaks from gel filtration purification along with dialysed protein, with (+) and without (−) 100 mM DTT.

FIG. 36 shows gel permeation chromatographic analysis of recombinant FKBP-L in accordance with alternate embodiments of the present invention.

DETAILED DESCRIPTION

Definitions

Figure 3:
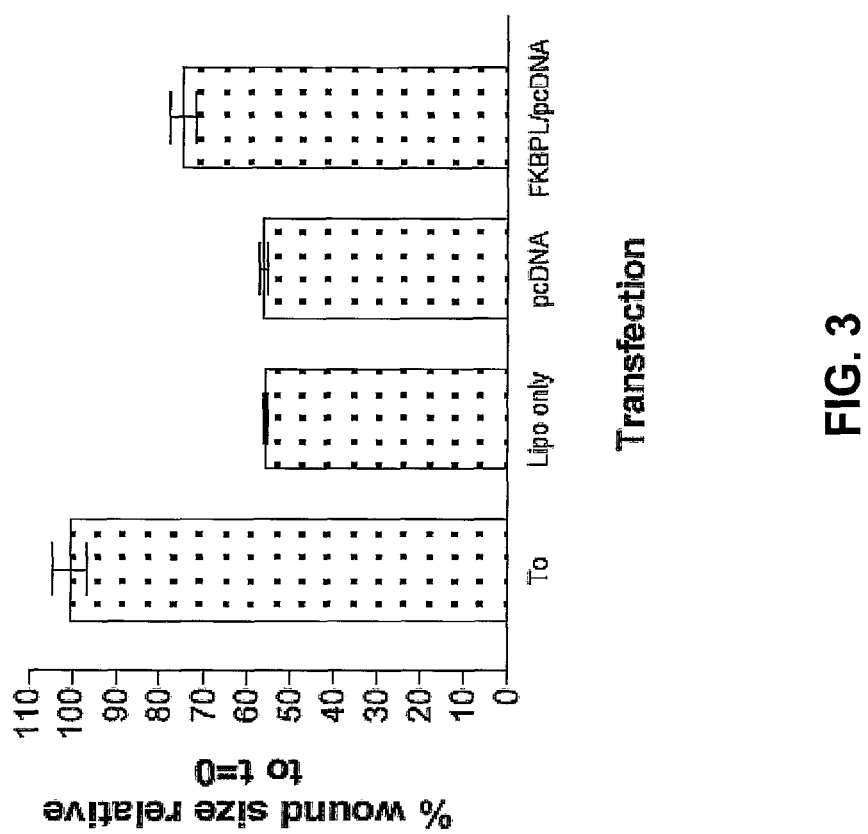
FIG. 3 shows the inhibitory effects of transiently transfected FKBP-L cDNA (SEQ ID NO: 31) on HMEC-1 wound closure in accordance with one embodiment of the present invention.

Unless defined otherwise, all technical and scientific terms used herein have the same meaning as commonly understood by one of ordinary skill in the art. Practitioners are particularly directed to Current Protocols in Molecular Biology (Ausubel) for definitions and terms of the art. Abbreviations for amino acid residues are the standard 3-letter and/or 1-letter codes used in the art to refer to one of the 20 common L-amino acids.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, the terms "portion" and "fragment" are used interchangeably to refer to parts of a polypeptide, nucleic acid, or other molecular construct.

As used herein, the term "biologically active FKBP-L polypeptide" (e.g., fragment and/or modified polypeptides) is used to refer to a polypeptide that displays the same or similar amount and type of activity as the full-length FKBP-L polypeptide. In this context "biological activity" of an FKBP-L polypeptide, fragment or derivative includes any one of anti-angiogenic activity, inhibition of tumour cell growth and/or proliferation, inhibition of tumour cell migration and/or metastasis. Biological activity of FKBP-L fragments or derivatives may be tested in comparison to full length FKBP-L using any of the in vitro or in vivo assays described in the accompanying examples, such as for example wound closure or wound scrape assay, in vitro cell migration assay, Matrigel™ assay for cell-cell adhesion, mouse sponge assay, aortic ring explant assay, MTT proliferation assay, HMEC-1 tube formation assay in vivo tumour cell growth assay. In this regard, deliberate amino acid substitutions may be made in the polypeptide on the basis of similarity in polarity, charge, solubility, hydrophobicity, or hydrophilicity of the residues, as long as the specificity of activity (i.e., function) is retained.

As used herein a "subject" may be an animal. For example, the subject may be a mammal. Also, the subject may be a human. In alternate embodiments, the subject may be either a male or a female. In certain embodiments, the subject may be a patient, where a patient is an individual who is under medical care and/or actively seeking medical care for a disorder or disease.

"Polypeptide" and "protein" are used interchangeably herein to describe protein molecules that may comprise either partial or full-length proteins. The term "peptide" is used to denote a less than full-length protein or a very short protein unless the context indicates otherwise.

As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extrachromasomal) or may be integrated into a host cell chromosome. In one embodiment, the vector may comprise an expression vector capable of producing a protein derived from at least part of a nucleic acid sequence inserted into the vector.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M NaHPO$_4$, 7% sodium dodecyl sulfate (SDS), at 65° C., and washing in 0.25 M NaHPO$_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, 4$^{th}$ Ed., Chapter 2, John Wiley & Sons, N.Y). For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [γ-$^{32}$P]ATP, or incorporation of radiolabeled nucleotides such as [α-$^{32}$P]dCTP by random primer labeling. Alternatively, probes may be labeled by incorporation of biotinylated or fluorescein labeled nucleotides, and the probe detected using Streptavidin or anti-fluorescein antibodies.

The terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. When utilizing BLAST and Gapped BLAST programs, the default parameters of the respective programs (e.g., BLASTN; available at the Internet site for the National Center for Biotechnology Information) may be used. In one embodiment, the percent identity of two sequences may be determined using GCG with a gap weight of 1, such that each amino acid gap is weighted as if it were a single amino acid mismatch between the two sequences. Or, the ALIGN program (version 2.0), which is part of the GCG (Accelrys, San Diego, Calif.) sequence alignment software package may be used.

The binding properties of a protein comprising either a receptor or a ligand can be expressed in terms of binding specificity, which may be determined as a comparative measure relative to other known substances that bind to the receptor. Standard assays for quantifying binding and determining binding affinity are known in the art and include, e.g., equilibrium dialysis, equilibrium binding, gel filtration, surface plasmon resonance, the use of a labeled binding partners, ELISAs and indirect binding assays (e.g., competitive inhibition assays). For example, as is well known in the art, the dissociation constant of a protein can be determined by contacting the protein with a binding partner and measuring the concentration of bound and free protein as a function of its concentration.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made.

As used herein, the term "similar" or "homologue" when referring to amino acid or nucleotide sequences means a polypeptide having a degree of homology or identity with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA*, 80:726-730). For example, homologous sequences may be taken to include an amino acid sequences which in alternate embodiments are at least 70% identical, 75% identical, 80% identical, 85% identical, 90% identical, 95% identical, 96% identical, 97% identical, or 98% identical to each other.

As used herein, the term at least 90% identical thereto includes sequences that range from 90 to 99.99% identity to the indicated sequences and includes all ranges in between. Thus, the term at least 90% identical thereto includes sequences that are 91, 91.5, 92, 92.5, 93, 93.5. 94, 94.5, 95, 95.5, 96, 96.5, 97, 97.5, 98, 98.5, 99, 99.5 percent identical to the indicated sequence. Similarly the term "at least 70% identical includes sequences that range from 70 to 99.99% identical, with all ranges in between. The determination of percent identity is determined using the algorithms described herein.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

As used herein, the term "linked" identifies a covalent linkage between two different groups (e.g., nucleic acid sequences, polypeptides, polypeptide domains) that may have an intervening atom or atoms between the two groups that are being linked. As used herein, "directly linked" identifies a covalent linkage between two different groups (e.g., nucleic acid sequences, polypeptides, polypeptide domains) that does not have any intervening atoms between the two groups that are being linked.

As used herein, "ligand binding domain" refers to a domain of a protein responsible for binding a ligand. The term ligand binding domain includes homologues of a ligand binding domain or portions thereof. In this regard, deliberate amino acid substitutions may be made in the ligand binding site on the basis of similarity in polarity, charge, solubility, hydrophobicity, or hydrophilicity of the residues, as long as the binding specificity of the ligand binding domain is retained.

As used herein, a "ligand binding site" comprises residues in a protein that directly interact with a ligand, or residues involved in positioning the ligand in close proximity to those residues that directly interact with the ligand. The interaction of residues in the ligand binding site may be defined by the spatial proximity of the residues to a ligand in the model or structure. The term ligand binding site includes homologues of a ligand binding site, or portions thereof. In this regard, deliberate amino acid substitutions may be made in the ligand binding site on the basis of similarity in polarity, charge, solubility, hydrophobicity, or hydrophilicity of the residues, as long as the binding specificity of the ligand binding site is retained. A ligand binding site may exist in one or more ligand binding domains of a protein or polypeptide.

As used herein, the term "interact" refers to a condition of proximity between two molecules or portions of a single molecule (e.g., different domains in a peptide). The interaction may be non-covalent, for example, as a result of hydrogen-bonding, van der Waals interactions, or electrostatic or hydrophobic interactions, or it may be covalent.

As used herein, a "ligand" refers to a molecule or compound or entity that interacts with a ligand binding site, including substrates or analogues or parts thereof. As described herein, the term "ligand" may refer to compounds that bind to the protein of interest. A ligand may be an agonist, an antagonist, or a modulator. Or, a ligand may not have a biological effect. Or, a ligand may block the binding of other ligands thereby inhibiting a biological effect. Ligands may include, but are not limited to, small molecule inhibitors. These small molecules may include peptides, peptidomimetics, organic compounds and the like. Ligands may also include polypeptides and/or proteins.

As used herein, "modulate" refers to changing or altering the biological activity of a molecule of interest. A "modulator" compound may increase or decrease activity, or change the physical or chemical characteristics, or functional or immunological properties, of the molecule of interest. A modulator compound of the present invention may include natural and/or chemically synthesized or artificial FKBP-L peptides, peptide mimetics, modified peptides (e.g., phosphopeptides, cyclic peptides, peptides containing D- and unnatural amino-acids, stapled peptides, peptides containing radiolabels), or peptides linked to antibodies, carbohydrates, monosaccharides, oligosaccharides, polysaccharides, glycolipids, heterocyclic compounds, nucleosides or nucleotides or parts thereof, and/or small organic or inorganic molecules (e.g., peptides modified with PEG or other stabilizing groups). Thus, the FKBP-L polypeptides of the invention also includes a chemically modified peptides or isomers and racemic forms.

An "agonist" comprises a compound that binds to a receptor to form a complex that elicits a pharmacological response specific to the receptor involved.

An "antagonist" comprises a compound that binds to an agonist or to a receptor to form a complex that does not give rise to a substantial pharmacological response and can inhibit the biological response induced by an agonist.

The term "peptide mimetics" refers to structures that serve as substitutes for peptides in interactions between molecules (Morgan et al., 1989, *Ann. Reports Med. Chem.*, 24:243-252). Peptide mimetics may include synthetic structures that may or may not contain amino acids and/or peptide bonds but that retain the structural and functional features of a peptide, or agonist, or antagonist. Peptide mimetics also include peptoids, oligopeptoids (Simon et al., 1972, *Proc. Natl. Acad, Sci., USA*, 89:9367); and peptide libraries containing peptides of a designed length representing all possible sequences of amino acids corresponding to a peptide, or agonist or antagonist of the invention.

As used herein, the term "EC50" is defined as the concentration of an agent that results in 50% of a measured biological effect. For example, the EC50 of a therapeutic agent having a measurable biological effect may comprise the value at which the agent displays 50% of the biological effect.

As used herein, the term "IC50" is defined as the concentration of an agent that results in 50% inhibition of a measured effect. For example, the IC50 of an antagonist of binding may comprise the value at which the antagonist reduces ligand binding to a ligand binding site by 50%.

As used herein, an "effective amount" means the amount of an agent that is effective for producing a desired effect in a subject. The term "therapeutically effective amount"

denotes that amount of a drug or pharmaceutical agent that will elicit therapeutic response of an animal or human that is being sought. The actual dose which comprises the effective amount may depend upon the route of administration, the size and health of the subject, the disorder being treated, and the like.

The term "pharmaceutically acceptable carrier" as used herein may refer to compounds and compositions that are suitable for use in human or animal subjects, as for example, for therapeutic compositions administered for the treatment of a disorder or disease of interest.

The term "pharmaceutical composition" is used herein to denote a composition that may be administered to a mammalian host, e.g., orally, parenterally, topically, by inhalation spray, intranasally, or rectally, in unit dosage formulations containing conventional non-toxic carriers, diluents, adjuvants, vehicles and the like.

The term "parenteral" as used herein, includes subcutaneous injections, intravenous, intramuscular, intracisternal injection, or infusion techniques.

A "stable" formulation is one in which the polypeptide or protein therein essentially retains its physical and chemical stability and biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation of interest may be kept at 40° C. for 1 week to 1 month, at which time stability is measured. The extent of aggregation following lyophilization and storage can be used as an indicator of peptide and/or protein stability. For example, a "stable" formulation is one wherein less than about 10% and preferably less than about 5% of the polypeptide or protein is present as an aggregate in the formulation. An increase in aggregate formation following lyophilization and storage of the lyophilized formulation can be determined. For example, a "stable" lyophilized formulation may be one wherein the increase in aggregate in the lyophilized formulation is less than about 5% or less than about 3%, when the lyophilized formulation is incubated at 40° C. for at least one week. Stability of the fusion protein formulation may be measured using a biological activity assay such as a binding assay as described herein.

FKBP-L Polypeptides as Modulators of Cell Migration, Angiogenesis, and Tumor Metastasis The present invention recognizes that FKBP-L, fragments of FKBP-L and modified FKBP-L and fragments thereof, can inhibit cell migration and may possess potent angiogenesis modulating properties. Embodiments of the present invention relate to FKBP-L derived peptides and their use. The present invention may be embodied in a variety of ways.

Thus, in certain embodiments, the FKBP-L polypeptides of the present invention may show anti-angiogenic properties. Also, in some embodiments, the FKBP-L polypeptides of the present invention may be used to modulate cell migration and/or metastasis of tumor cells. The action of the FKBP-L polypeptides of the present invention may, in certain embodiments, be mediated by CD44. Thus, in some embodiments of the present invention, FKBP-L polypeptides may be used to modulate angiogenesis, cell migration, and/or metastasis of cells that express CD44.

In certain embodiments, the invention may be used to treat disorders mediated by or associated with cell migration. For example, FKBP-L peptides can be used to inhibit or combat tumor invasion and metastasis. Or, in some embodiments, FKBP-L peptides may be used to inhibit the migration of cells involved in wound healing. In yet other embodiments, FKBP-L peptides may be used to inhibit angiogenesis to thereby treat disorders mediated by angiogenesis.

Thus, in some embodiments, the present invention comprises a method of treating a disorder mediated by or associated with at least one of cell migration, angiogenesis, or tumor metastasis, where the method comprises administering a therapeutically effective amount of: (i) an active compound comprising an isolated FKBP-L polypeptide or a biologically active fragment of a FKBP-L polypeptide, or a biologically active derivative of a FKBP-L polypeptide or a fragment thereof, or (ii) a polynucleotide encoding such a FKBP-L polypeptide, fragment, or derivative to a patient in need thereof.

For example, in some embodiments, the present invention comprises a method of modulating angiogenesis or tumor metastasis, the method comprising administering a therapeutically effective amount of an active compound comprising an isolated FKBP-L polypeptide or a biologically active fragment of a FKBP-L polypeptide, or a biologically active derivative of a FKBP-L polypeptide or a fragment thereof, or a polynucleotide encoding such a FKBP-L polypeptide, fragment or derivative to a subject in need thereof.

In other embodiments, the present invention comprises the use of: (i) an active compound comprising an isolated FKBP-L polypeptide or a biologically active fragment of a FKBP-L polypeptide, or a biologically active derivative of a FKBP-L polypeptide or a fragment thereof, or (ii) a polynucleotide encoding such a FKBP-L polypeptide, fragment or derivative in the manufacture of a composition or medicament for the treatment of a disorder mediated by or associated with at least one of cell migration and/or angiogenesis. For example, in one embodiment, the present invention comprises the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use as an inhibitor of angiogenesis.

A variety of disorders that are mediated by or associated with angiogenesis and/or cell migration may be treated with the compositions and/or medicaments of the present invention. Thus, in alternate embodiments, the medicament may be used in the treatment of at least one of angiogenesis-associated inflammation, ocular disorders mediated by angiogenesis, wound healing, or cancer.

Thus, in one embodiment, the present invention comprises the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use in the treatment of angiogenesis-associated inflammation.

In other embodiments, the disorder associated with angiogenesis is an ocular disorder, for example, macular degeneration and other ocular disorders described herein. Alternatively, the disorder associated with angiogenesis is arteriosclerosis, arthritis, psoriasis or endometriosis. Thus, in alternate embodiments, the invention provides a method of treatment of at least one of an ocular disorder, arteriosclerosis, arthritis, psoriasis or endometriosis, the method comprising administering a therapeutically effective amount of an active compound comprising an isolated FKBP-L polypeptide, a biologically active fragment of a FKBP-L polypeptide, or a biologically active derivative of a FKBP-L polypeptide or a fragment thereof, or a polynucleotide encoding such a FKBP-L polypeptide, fragment or a derivative thereof, to a subject in need thereof. Or, the present invention may comprise the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use in the treatment of ocular disorders mediated by angiogenesis. For example, in alternate embodiments, the FKBP-L peptide or polynucleotide may be used for the manufacture of a medicament for the treatment of macular degenerative disease or diabetic retinopathy. Or, the present invention may comprise the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use in the treatment of at least one of arteriosclerosis, psoriasis, arthritis, or endometriosis.

In certain embodiments, the invention provides methods of treatment of cancer. For example, in some embodiments the present invention provides a method of treating cancer comprising administering a therapeutically effective amount of an active compound comprising an isolated FKBP-L polypeptide, a biologically active fragment of a FKBP-L polypeptide, or a biologically active derivative of a FKBP-L polypeptide or a fragment thereof, or a polynucleotide encoding such a FKBP-L polypeptide, fragment or derivative thereof, for at least one of treating cancer, inhibiting tumor cell migration and/or metastasis, or inhibiting tumor cell growth and/or proliferation. In an embodiment, the inhibition of tumor cell migration and metastasis is by inhibition of angiogenesis. For example, the present invention may comprise the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use in the treatment of cancer. In certain embodiments, the compounds and compositions of the present invention may prevent tumor cell growth and/or metastasis. In an embodiment, the inhibition of tumor cell migration and metastasis is by inhibition of angiogenesis. Thus, in one embodiment, the present invention may comprise the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use as an inhibitor of tumor cell migration and/or metastasis. In yet other embodiments, the present invention may comprise the use of (i) an active compound comprising an isolated FKBP-L polypeptide or a biologically active fragment of a FKBP-L polypeptide, or a biologically active derivative of a FKBP-L polypeptide or fragment thereof or (ii) a polynucleotide encoding such a FKBP-L polypeptide, fragment or derivative in the manufacture of a medicament for use as an inhibitor of tumor cell growth and/or proliferation.

The expression FKBP-L polypeptides is used in the specification according to its broadest meaning. It designates the naturally occurring proteins as shown in SEQ ID NOS: 1, 2 and 29 together with homologues due to polymorphisms, other variants, mutants and portions of said polypeptide which retain their angiogenesis modulating activities. For example, in certain embodiments, the FKBP-L polypeptide comprises SEQ ID NO: 1 with an N-terminal sequence (see amino acid residues in bold font in SEQ ID NO: 1 as shown in FIG. 1) that includes a poly-histidine tag of six histidine residues attached to the N-terminus of the protein, or SEQ ID NO: 2 with a Threonine at position 181 and a Glycine at position 186 of the wild-type sequence. Or, a polypeptide of SEQ ID NO: 29 (GENBank Accession No. NP_071393; NM_022110; [gi:34304364]) may be used. Example constructs of other FKBP-L polypeptides (e.g., fragments and other modifications) of the present invention are shown in FIG. 1. Also, example constructs of polynucleotide constructs encoding for FKBP-L polypeptide constructs are provided in FIG. 2.

Embodiments of the present invention comprise an isolated FKBP-L polypeptide or a biologically active fragment of a FKBP-L polypeptide, or a biologically active derivative of such a FKBP-L polypeptide or fragment for use as a medicament. Thus, alternate embodiments of the present invention comprise use of a FKBP-L peptide or nucleotide that encodes a FKBP-L peptide as described herein wherein the FKBP-L polypeptide comprises the amino acid sequence shown in SEQ ID NO: 10, or the amino acid sequence shown in SEQ ID NO:1, SEQ ID NO:2, or SEQ ID NO: 29, or the amino acid sequence shown in any one of SEQ ID NOs: 3 to 7, or 11 to 28, or an amino acid sequence at least 90% identical to the amino acid sequence shown in any one of SEQ ID NOs: 1 to 29. Or, a sequence that comprises at least 18 contiguous amino acids of SEQ ID NO: 10 (e.g., SEQ ID NOs: 11, 16, 23) may be used. References herein to peptides (and to uses thereof) which are shown as modified, such as SEQ ID NOs: 12, 13 and 28, should be interpreted as encompassing peptides of identical amino acid sequence without the listed modification (and uses thereof) unless otherwise stated.

As described herein, the methods and compositions of the present invention may utilize a full-length FKBP-L polypeptide, or fragments of the polypeptide. Thus, certain embodiments of the present invention comprise a FKBP-L derivative which comprises or consists of an effective portion of the N-terminal amino acid sequence of naturally occurring FKBP-L. This sequence may comprise or consist of an active N-terminal portion of the FKBP-L polypeptide. In alternate embodiments, the polypeptide may comprise or consist of amino acids 1 to 57 of SEQ ID NO: 2 (i.e., SEQ ID NO: 6), or amino acids 34-57 of SEQ ID NO:2 (i.e., SEQ ID NO: 10). Or, the peptide may comprise or consist of a sequence that comprises at least 18 contiguous amino acids of SEQ ID NO: 10 (e.g., SEQ ID NOs: 11, 16, or 23). In alternate embodiment, the polypeptide used in the methods and compositions of the present invention may comprise or consist of one of the amino acid sequences shown in any one of SEQ ID NOs: 1-7, 10-29. In certain embodiments, the present invention comprises a biologically active fragment of FKBP-L, wherein said polypeptide includes no more than 200 consecutive amino acids of the amino acid sequence shown in SEQ ID NO:1, SEQ ID NO:2, or SEQ ID NO: 29.

As described herein, the peptides may be modified (e.g., to contain PEG and/or His tags or other modifications). Or, the present invention may comprise isolated polypeptides having a sequence at least 70%, or 75%, or 80%, or 85%, or 90%, or 95%, or 96%, or 97%, or 98%, or 99% identical to the amino acid seqeunces as set forth in any one of SEQ ID NOS: 1-29. Or, the isolated peptide or the peptide used for preparation of a medicament may comprise or consist of a sequence having at least 70%, or 75%, or 80%, or 85%, or 90%, or 95%, or 96%, or 97%, or 98%, or 99% identity to at least 18 contiguous amino acids of SEQ ID NO: 10 (e.g., SEQ ID NOs: 11, 16, 23).

The FKBP-L derivative of the invention may be of variable length as long as it retains its antiangiogenic/proangiogenic activity and can be used according to the various aspects of the invention described above. Functional equivalents of FKBP-L are also encompassed by the present invention. For example, in certain embodiments, a functional equivalent may comprise or consist of a small molecule which can bind CD44 and/or prevent binding of a ligand (e.g. MIF) to a complex containing CD44 and CD74. Or, a functional equivalent may comprise or consist of a small molecule that will act in a similar manner as FKBP-L and its peptide derivatives to inhibit at least of cell migration, angiogenesis and/or metastasis.

The dose of the FKBP-L polypeptide administered may vary depending upon the disorder being treated. In alternate embodiments, a dosage to be achieved in vivo would be equivalent to an in vitro level of greater than $10^{-12}$ M, or $10^{-11}$ M, or $10^{-10}$ M, or $10^{-9}$ M, or $10^{-8}$ M, or $10^{-7}$ M, or $10^{-6}$ M, or $10^{-5}$ M. Thus, a dosage to be achieved in vivo may be equivalent to an in vitro level of $10^{-12}$ M to $10^{-5}$ M, or $10^{-11}$ M to $10^{-6}$ M, or $10^{-10}$ M to $10^{-7}$ M, or $10^{-9}$ M to $10^{-7}$ M or ranges therein. In alternate embodiments, the dosage used may be equivalent to an in vitro level of about 1-10000 ngml$^{-1}$, or about 10-5000 ngml$^{-1}$, or about 100-1000 ngml$^{-1}$. Or, in certain embodiments, the dosage may comprise from about 0.00001 to 500 mg/kg/day, or from about 0.0001 to 300 mg/kg/day, or from about 0.003 to 100 mg/kg/day, or from about 0.03 to 30 mg/kg/day, or from about 0.1 mg/kg/day to 10 mg/kg/day, or from about 0.3 mg/kg/day to 3 mg/kg/day.

In an embodiment, the FKBP-L polypeptide is administered to a subject in need thereof. As used herein, a subject in need thereof is a subject who may be benefited by the administration of FKBP-L.

In yet other embodiments, the present invention comprises an isolated nucleic acid molecule which encodes a protein or polypeptide comprising the amino acid sequence as set forth in any one of SEQ ID NOs: 1-29, or a biologically active fragment thereof, and the use of such molecules for the preparation of medicaments and/or as therapeutic agents. In an embodiment, a biologically active fragment comprises or consists of at least 18 contiguous amino acids of SEQ ID NO: 10 (e.g., SEQ ID NOS:11, 16, 23).

For example, embodiments of the present invention comprise the use of a polynucleotide that encodes a FKBP-L peptide, a biologically active fragment of a FKBP-L peptide, or biologically active derivative thereof, wherein the polynucleotide encoding the FKBP-L polypeptide, fragment or derivative comprises the nucleotide sequence shown in any one of SEQ ID NOs: 30-39.

Also, the present invention comprises isolated nucleic acids that encode for FKBP-L peptides. The nucleic acid molecule may comprise a nucleic acid molecule having the sequence as set forth in SEQ ID NOs: 30-39, or a fragment thereof, wherein the nucleic acid molecule encodes for a polypeptide having the sequence of SEQ ID NOs: 1-28, or a fragment of these polypeptides. In an embodiment, a fragment comprises or consists of at least 18 contiguous amino acids of SEQ ID NO: 10 (e.g., SEQ ID NOS: 11, 16, 23). In certain embodiments, degenerate nucleic acid molecules, comprising a degenerate variation in the third position of the amino acid codon such that the same amino acid is encoded by the degenerate sequence, may be used to encode the FKBP-L polypeptides, fragments and/or derivatives of the present invention. Thus, in certain embodiments, the present invention may comprise isolated nucleic acid molecules having a sequence at least 70%, or 75%, or 80%, or 85%, or 90%, or 95%, or 96%, or 97%, or 98%, or 99% identical to SEQ ID NOS: 30-39 or fragments thereof.

The present invention also include primers that may be used to produce polynucleotide fragments of SEQ ID NO: 31, where such fragments encode the FKBP-L peptides shown in FIG. 1. Thus, in alternate embodiments, the present invention include oligonucleotide primers comprising the sequences as set forth in SEQ ID NOS: 45-58 or a sequence at least 70%, or at least 80%, or at least 85%, or at least 90%, or at least 95%, or at least 96%, or at least 97%, or at least 98%, or at least 99% identical thereto.

In yet other embodiments, the present invention comprises vectors containing the isolated nucleic acid molecules of the present invention. In certain embodiments, the present invention also comprise cells transfected with such vectors, such that a FKBP-L polypeptide is expressed. Such embodiments are described in more detail herein.

In yet other embodiments, the present invention comprises an isolated nucleic acid molecule which is antisense to the coding strand of the FKBP-L gene or portion thereof and the use of such molecules for the preparation of medicaments and/or as therapeutic agents. Thus, in yet another embodiment, the present invention comprises a polynucleotide that is at least 70%, or 75%, or 80%, or 85%, or 90%, or 95%, or 96%, or 97%, or 98%, or 99% identical to a nucleic acid sequence that is antisense to the coding strand of an mRNA encoding a FKBP-L polypeptide of the invention.

In certain embodiments, the anti-sense molecules can be used to advantageously promote angiogenesis and/or cell migration and in the treatment of disorders mediated by or associated with at least one of angiogenesis or cell migration. For example, in one embodiment, the present invention comprises the use of an antisense oligonucleotide or siRNA capable of specifically down-regulating expression of FKBP-L in the manufacture of a medicament for use as a modulator to promote angiogenesis. Also, in certain embodiments, the present invention comprises the use of an antisense oligonucleotide or siRNA capable of specifically down-regulating expression of FKBP-L in the manufacture of a medicament for use as a modulator to promote at least one of hematopoiesis or vasculogenesis. In one embodiment, the present invention comprises the use of an antisense oligonucleotide or siRNA capable of specifically down-regulating expression of FKBP-L in the manufacture of a medicament for use to promote wound healing. Also, the present invention may comprise the use of an antisense oligonucleotide or siRNA capable of specifically down-regulating expression of FKBP-L in the manufacture of a medicament for use in the treatment of at least one of peptic ulcer, a bone fracture, or keloids.

In other embodiments, the present invention may comprise the use of an antisense oligonucleotide or siRNA capable of specifically down-regulating expression of FKBP-L in the manufacture of a medicament for use in the treatment of pardentitis or pardontopathy mediated by angiogenesis. In other embodiments, the present invention may comprise the use of an antisense oligonucleotide or siRNA capable of specifically down-regulating expression of FKBP-L in the manufacture of a medicament for use in the treatment or regulation of the reproductive system, such as ovulation, mestruation and placentation. In yet other embodiments, the present invention may comprise the use of an antisense oligonucleotide or siRNA capable of specifically down-regulating expression of FKBP-L in the manufacture of a medicament for use in the treatment or regulation of the dysfunction in the brain and nervous system, such as may be caused by stroke. Use of an antisense oligonucleotide or siRNA capable of specifically down-regulating expression of FKBP-L may therefore be useful in the treatment of certain types of dementia and/or mental retardation.

Additional aspects of certain embodiments of the present invention are discussed in more detail below.

FKBP-L Modulates Cell Migration, Angiogenesis and Metastasis

In certain embodiments, FKBP-L and fragments thereof may be used to modulate angiogenesis. In one embodiment, FKBP-L or fragments thereof may be used to inhibit angiogenesis. For example, transfection of cells with FKBP-L may inhibit endothelial cell migration and angiogenesis (FIG. 3) indicating that FKBP-L protein is a potential anti-migratory protein. The dose-dependent nature effect of FKBP-L on cell migration is shown in FIG. 4. Thus, it can be seen that a dose of $10^{-6}$ M full length His-tagged FKBP-L is effective to prevent cell migration.

In certain embodiments, FKBP-L may be secreted from certain types of cells such as endothelial cells (FIG. 5), and tumor cells. Thus, in an embodiment, the anti-angiogenic action of FKBP-L may be via receptor activation. The secretion of FKBP-L from endothelial cells indicates that application of FKBP-L protein or over-expression of FKBP-L using a cDNA construct may both be able to exert anti-angiogenic effects observed both in vitro and in vivo.

Figure 6:
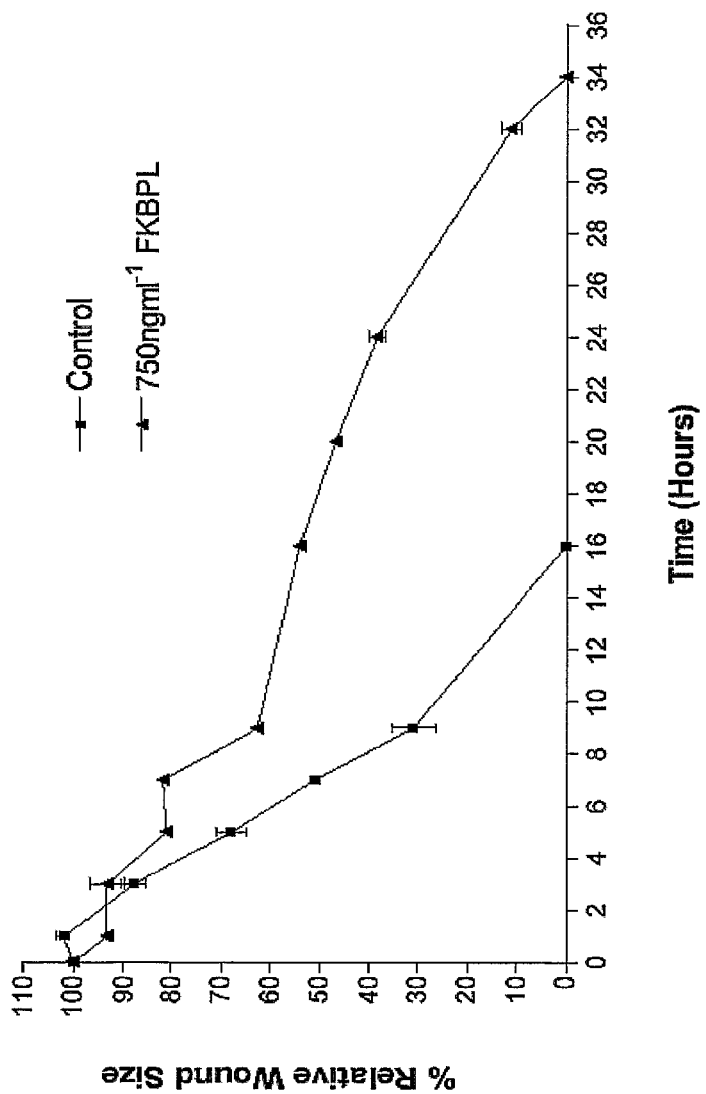
FIG. 6 illustrates the inhibitory effect of full length FKBP-L recombinant polypeptide on HMEC-1 wound closure over time in accordance with one embodiment of the present invention.

In certain embodiments, FKBP-L exhibits an effect on cell migration over a physiologically relevant time period. For example, HMEC-1 cells treated with full length His-tagged recombinant FKBP-L polypeptide (SEQ ID NO: 1) may exhibit decreased wound closure for up to 2 to 3 days (FIG. 6). Thus, application of FKBP-L protein may be for hours, days or weeks as required to inhibit cell migration and/or angiogenesis.

The effect of FKBP-L on cell migration and/or angiogenesis may, in certain embodiments, be effective for any cells that are influenced by cell migration and/or angiogenesis. Thus, as described in detail in the Examples herein, full length recombinant FKBP-L (e.g., SEQ ID NO: 1) exhibits anti-migratory action over a broad dose range in a variety of models for angiogenesis, including HMEC-1 wound closure (FIGS. 3, 4, and 6), and HMEC-1 tube formation (FIG. 7), the mouse sponge assay (FIGS. 8, 9A and 9B), and the aortic ring explant model (FIG. 10).

Figure 11A:
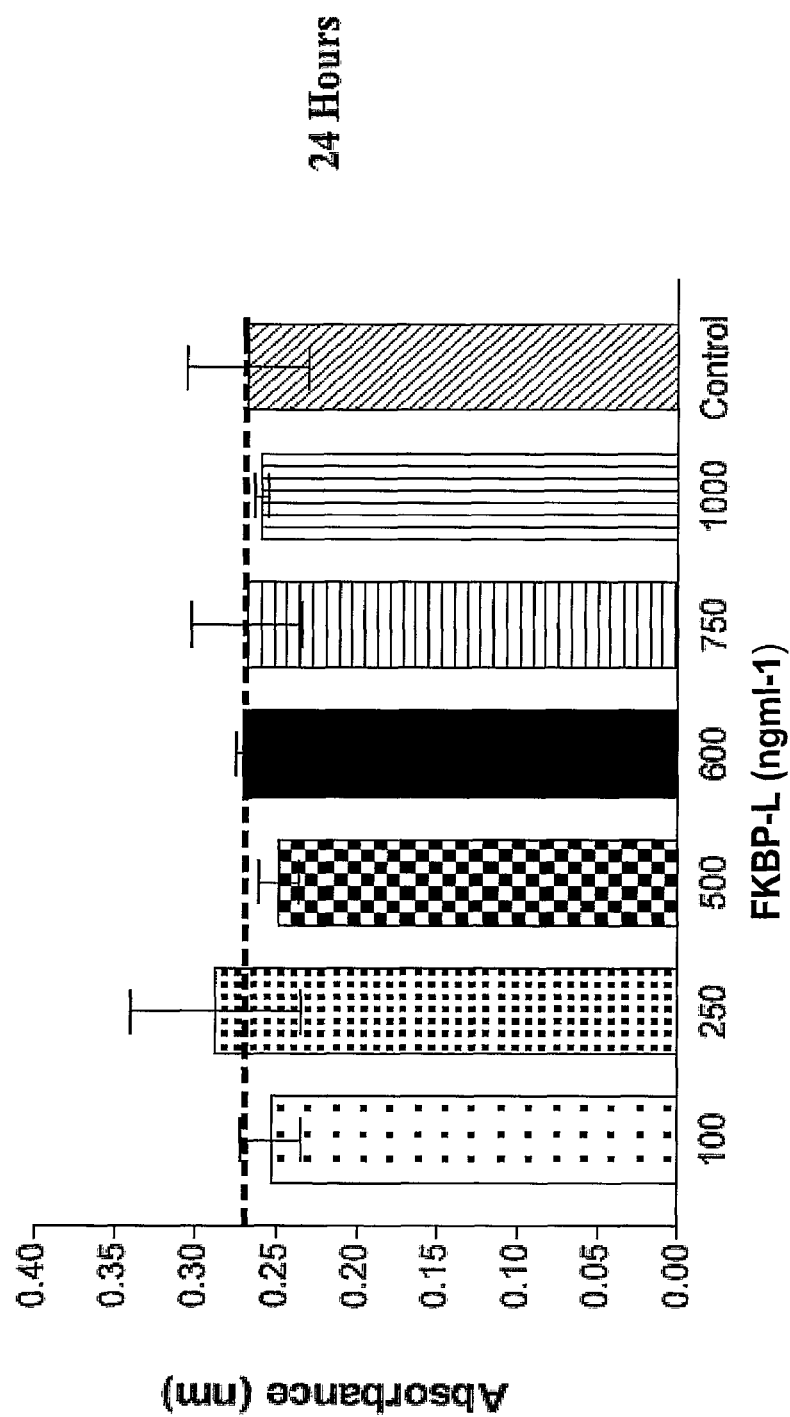
FIGS. 11A and 11B show the effect of full length recombinant FKBP-L polypeptide at a range of concentrations on the viability or proliferation of HMEC-1 in the MTT assay after 24 hours (FIG. 11A) and 48 hours (FIG. 11B) in accordance with alternate embodiments of the present invention.
Figure 11B:
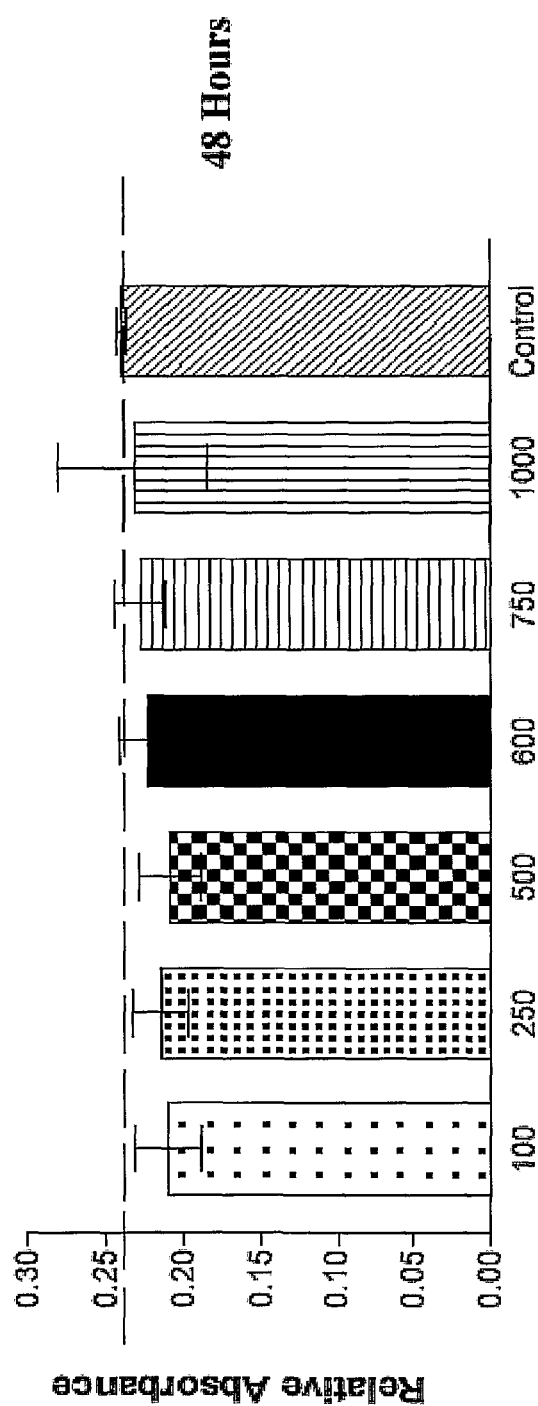

Also, in an embodiment, the effect of FKBP-L on cell mobility and/or angiogenesis is not due to toxicity of the compound. Thus, where cells are exposed to recombinant full-length FKBP-L for up to 48 hours, the may be no indication of toxicity (FIGS. 11A and 11B).

Figure 12:
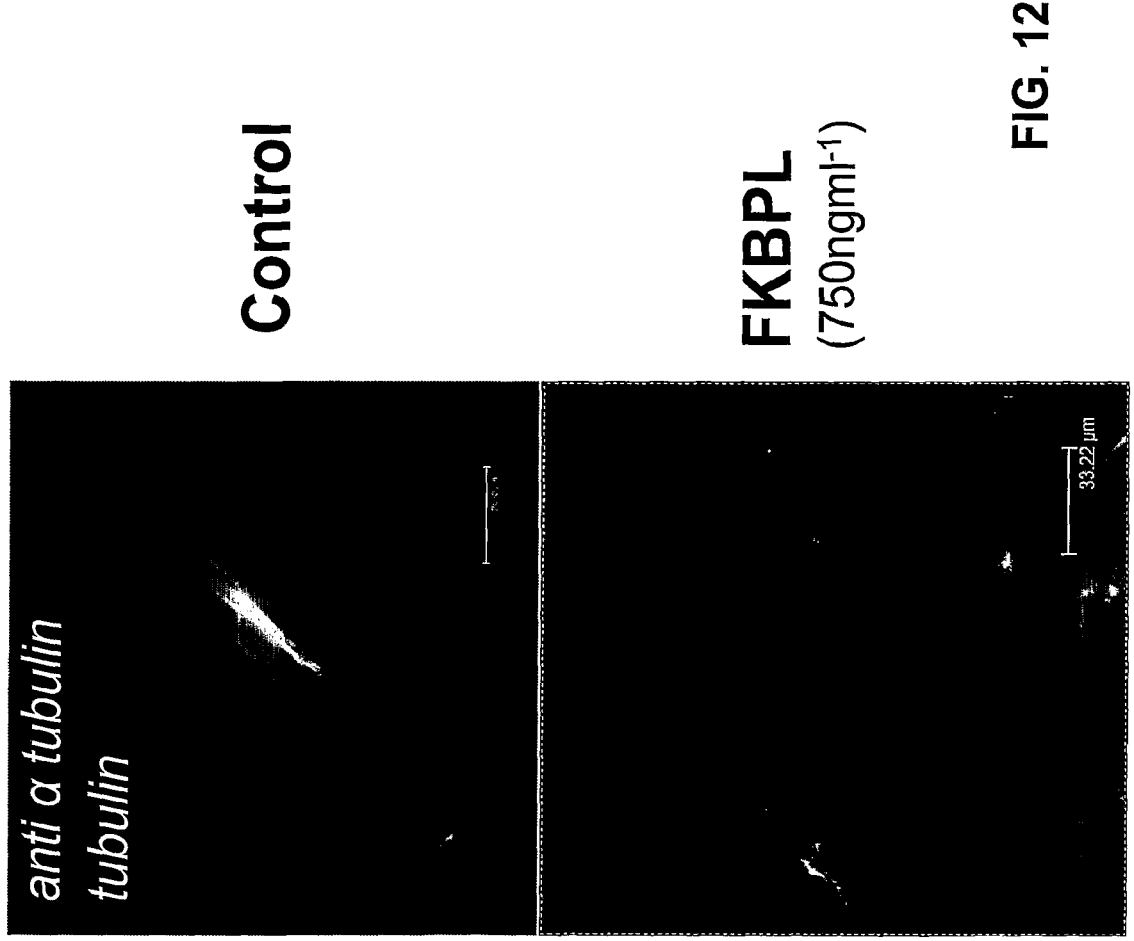
FIG. 12 shows changes in cytoskeletal morphology of migrating endothelial cells on exposure to full length FKBP-L recombinant polypeptide in accordance with an embodiment of the present invention, where HMEC-1 microtubules were stained using anti-tubulin.

There may be a variety of mechanisms by which FKBP-L acts on the cell. In an embodiment, the mechanism of FKBP-L mediated inhibition of migration may be directed at the cytoskeleton (FIGS. 12 and 13). For example, in certain embodiments, FKBP-L may lead to disruption or other changes in the cytoskeletal filaments.

Figure 14A:
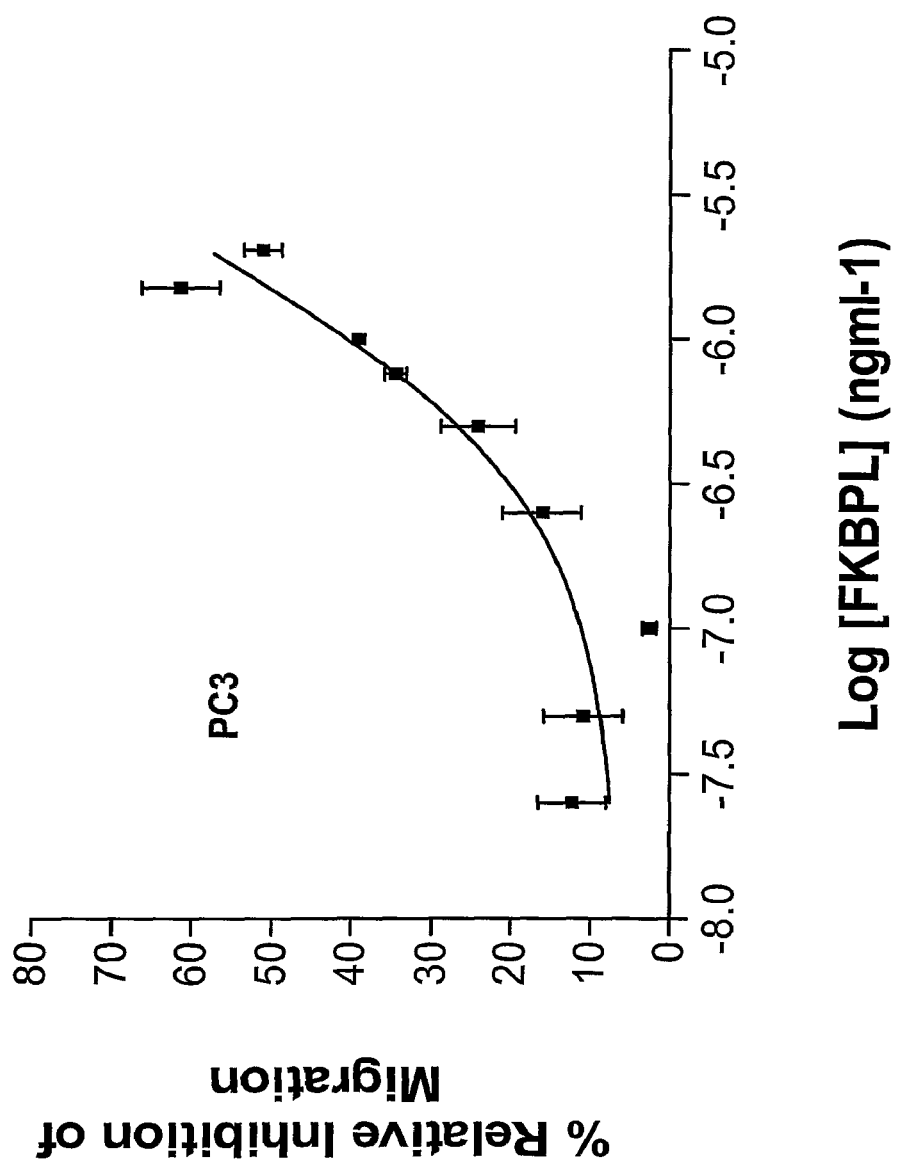
FIGS. 14A, 14B, and 14C illustrate the effect of full length recombinant polypeptide FKBP-L on PC3 (FIG. 14A), MDA (FIG. 14B) and HT29 (FIG. 14C) tumor cell migration in accordance with alternate embodiments of the present invention.
Figure 14B:
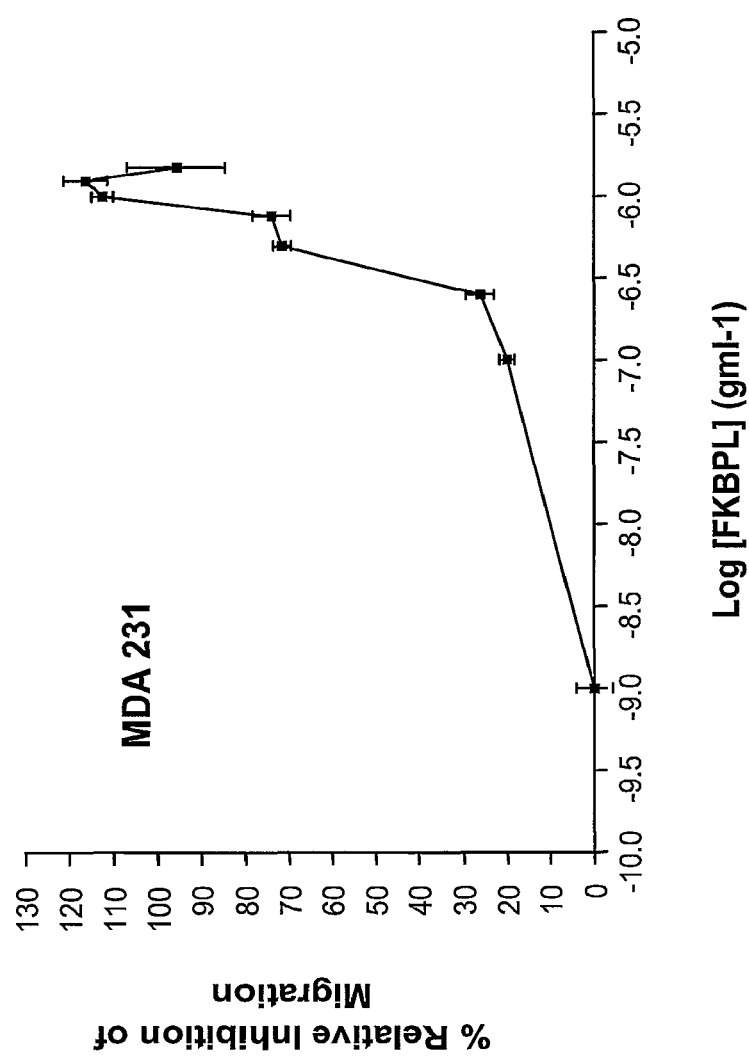
Figure 14C:
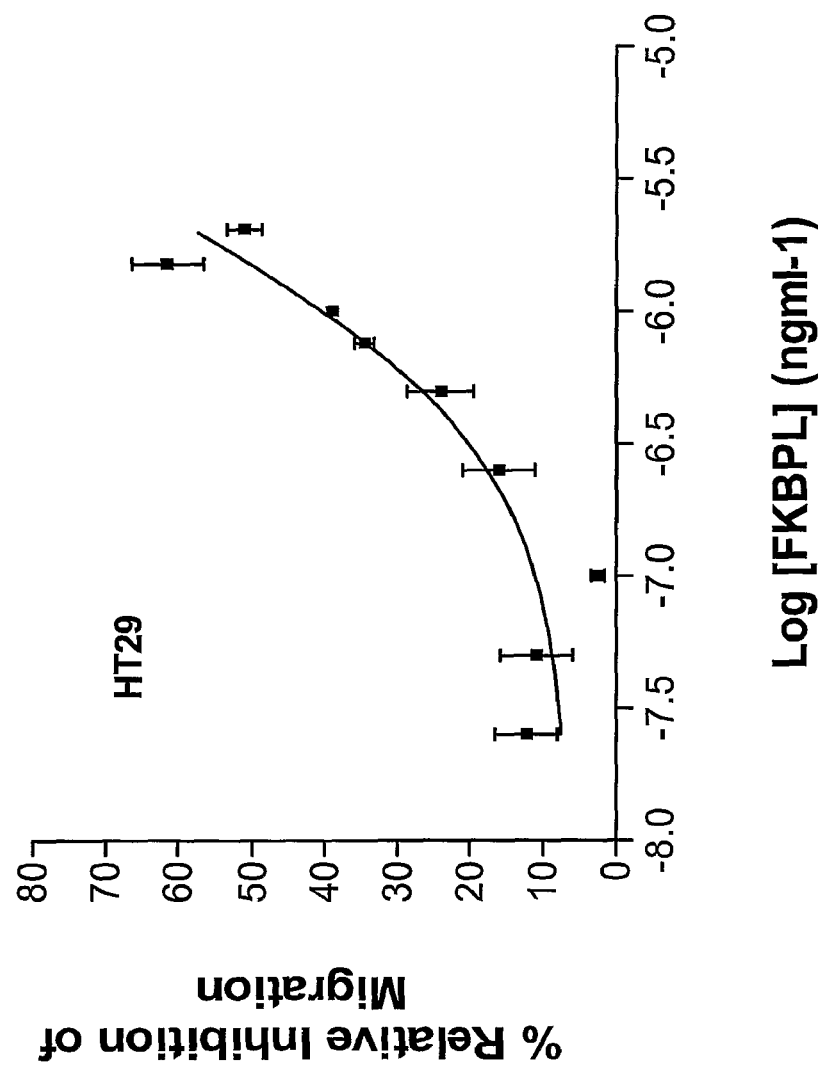

The anti-angiogenic effects of FKBP-L indicate that FKBP-L may have antitumorigenic and/or antimetastatic activity. For example, as shown in FIG. 14, panels A, B, and C, full length recombinant FKBP-L polypeptide may inhibit tumor cell migration in a dose-dependent manner, indicating that FKBP-L may be useful as a therapeutic agent to reduce tumor cell invasion and metastasis of tumor cells that depend on migration to metastasize. In certain embodiments, treatment of tumors in vivo with an expression construct that encodes a full length FKBP-L polypeptide by gene therapy (FIG. 15) leads to a reduction in tumor growth.

FKBP-L Interaction with Genes Involved in Angiogenesis

A variety of biochemical pathways may be modulated by FKBP-L. In certain embodiments, FKPB-L may lead to an increase in the expression of certain genes associated with angiogenesis and/or cell migration. For example, in certain embodiments, transfection with an anti-sense FKPB-L nucleic acid may lead to an increase in the expression of PI3K, Rho GTPase activating protein-oligophrenia 1, ROCK, Microtubule associated protein 1B, MMP-like 1 protein, and/or TNF ligand superfamily member 1 protein (see Example 12 herein). Elevated RhoA, RhoC, ROCK I, and ROCK II expression is known to be associated with tumor progression and it has been suggested that Rho and ROCK signaling contribute to the morphologic changes and metastatic behaviour of some tumor cells. Thus, in certain embodiments, overexpression of FKBP-L may inhibit angiogenesis, and FKBP-L repression using antisense oligonucleotides may promote angiogenesis by activation of genes associated with angiogenesis, such as Rho and ROCK.

FKBP-L Interaction with CD44

CD74 is expressed in antigen presenting cells. A primary function of CD74 is the intracellular sorting of MHC class II molecules. CD74 is expressed on carcinomas of renal, lung, gastric and thymic origin and by certain sarcomas. Additionally, CD74 may be expressed in response to certain tumor genes. For example, INF-γ-induced CD74 surface expression in breast carcinoma lines may be enhanced by retinoblastoma protein. Thus, the restricted expression of CD74 by normal tissues, and its rapid internalization may make CD74 an attractive therapeutic agent for both cancer and immunologic disease.

Macrophage Inhibitory Factor (MIF) may also be involved in tumorigenesis. High levels of MIF are seen in human tumors and correlate with grading and prognosis. Moreover MIF may be involved in angiogenesis, tumor growth and metastasis via a Rho-dependent pathway (Amin et al., 2006, Blood, 107:2252-2261; Ren et al., 2006, Oncogene, 25:3501-3508; Sun et al., 2005, Clin. Cancer Res., 11:1050-1058; Sun et al., 2003, Int. J. Mol. Med., 12:633-641). MIF signal transduction can be initiated by binding to CD74 (Leng et al., 2003, J. Exp. Med., 197:1467-1476). It is also thought that activation of CD74 requires interaction with CD44 (Naujokas et al., 1993, Cell, 74:257-268; and Naujokas et al., 1995, Immunity, 3:359-372). MIF has been shown to interact in a complex with both CD74 and CD44 and inhibition of this complex results in decreased proliferation in bladder cancer cells (Meyer-Siegler et al., 2004, BMC Cancer, July 12; 4:34; see also Leng et al., 2006, Cell Res., 16:162-168).

The formation of a complex between MIF, CD44 and CD74 may be important for MIF-mediated biological signaling (Shi et al., Immunity, 2006, 25(4):595-606).

In certain embodiments, FKBP-L may act by interacting with CD44. In an embodiment, FKBP-L may bind to CD44 and prevent CD44 from interacting with CD74. If FKBP-L, or a portion thereof, is able to displace CD74 from CD44, the FKBP-L polypeptide may prevent the formation of the complex of CD44-CD74-MIF that is required for MIF-induced signal transduction. Or, in other embodiments, FKBP-L may act by alternative mechanisms.

CD44 is believed to be expressed by most epithelial cells and has been implicated in angiogenesis (Cao et al., 2006, Am. J. Pathol., 169:325-336). Thus, in one embodiment, CD44 may be required for FKBP-L inhibition of endothelial cell migration and/or angiogenesis. Also, in an embodiment, CD44 can be required for FKBP-L inhibition of tumor cell migration. Thus, as shown in FIGS. 16 and 17A-17E, full length recombinant FKBP-L, in certain embodiments, can inhibit tumor cell migration in tumor cell lines that express CD44 (i.e., CD44 positive or CD44 +ve), but not in CD44 negative (CD44 −ve) tumor cell lines, suggesting that FKBP-L may inhibit tumor metastases in a subset of CD44 positive tumor cell lines. HMEC-1 cells are also positive for CD44 (not shown). In an embodiment, inactivation of CD44 (e.g., using an siRNA specific to CD44) results in preventing FKBP-L mediated inhibition of tumor cell migration (e.g., FIG. 18), demonstrating that CD44 may be involved in FKBP-L inhibition of tumor cell migration and/or metastasis.

In an embodiment, FKBP-L may interact directly with CD44. For example, exogenously overexpressed FKBP-L (e.g., SEQ ID NO: 1 generated from SEQ ID NO: 31) may interact with endogenous CD44 in wounded monolayers (FIG. 19; Example 16). In an embodiment, there is no significant interaction between endogenous FKBP-L and CD44 in non-wounded monolayers, suggesting that a critical level of FKBP-L needs to be expressed before the interaction with CD44 can be detected. Furthermore, this interaction may only occur in endothelial cells that are primed for migration (i.e. in wounded monolayers).

Thus, in embodiments, full length FKBP-L is active against CD44 positive microvascular endothelial cells (FIG. 16) and therefore can target these cells within solid tumors to prevent further microvessel outgrowth to support tumour growth. As such, FKBP-L may target the vasculature rather than a specific tumor type, and may be active against a majority, if not all, solid tumours and micrometastases. Also, as discussed in more detail below, FKBP-L peptides display similar activity. For example, amino acids 34-57 of FKBP-L (i.e., the FKBP-L "24mer"), amino acids 1-57 of FKBP-L (i.e., the FKBP-L "1-57mer") and other FKBP-L peptides from the N-terminus of FKBP-L protein may inhibit migration of tumor cells that express CD44. Thus, FKBPL polypeptide and its derivatives can inhibit endothelial cell migration and/or tumor cell migration with implications for angiogenesis and invasion in a manner that is consistant with FKBP-L interacting with CD44.

Fragments of FKBP-L

Embodiments of the present invention recognize that certain regions of the N-terminus of the FKBP-L protein may display biological activity. Thus, in certain embodiments, expression constructs that express full length wild-type (WT) FKBP-L, or, in alternate embodiments, truncated mutants, such as but not limited to Δ48, Δ58, Δ86, Δ151, Δ200 may inhibit wound closure (FIG. 20). The amino acid sequence of each of these constructs is shown in FIG. 1. For example, in certain embodiments, WT-FKBP-L and Δ58 inhibited wound closure by 36.2% and 48.8% respectively. There may be a minimum amount of sequence that is required for activity. For example, in certain embodiments, truncated FKBP-L Δ34 may fail to significantly inhibit wound closure, suggesting that the active domain is deleted in this mutant. These experiments may therefore indicate that the active domain resides between amino acids 34 and 57 of full-length (e.g., SEQ ID NO: 2) FKBP-L.

Figure 20A:
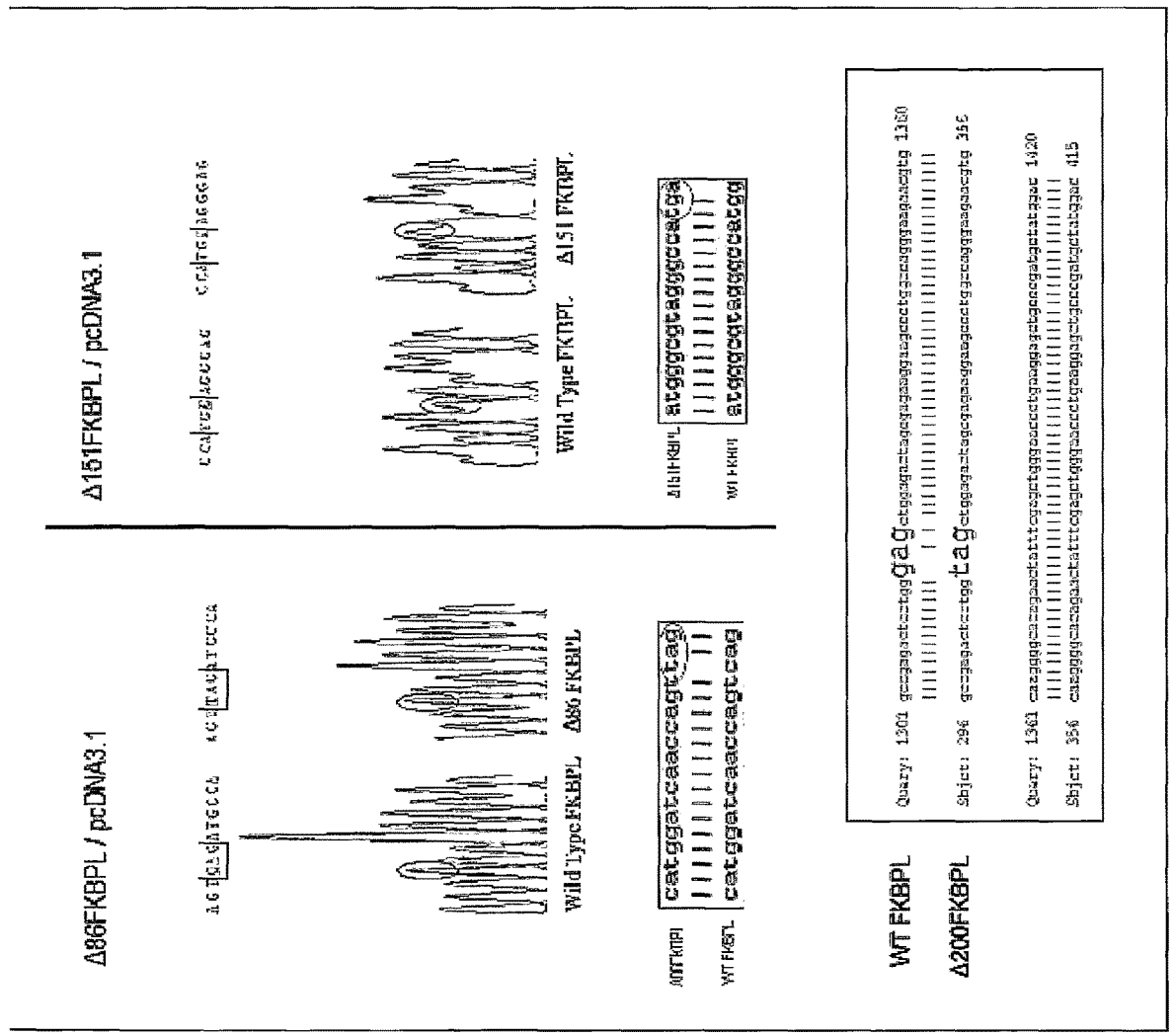
FIGS. 20A, 20B, and 20C illustrate FKBP-L deletion mutants, where
Figure 20B:
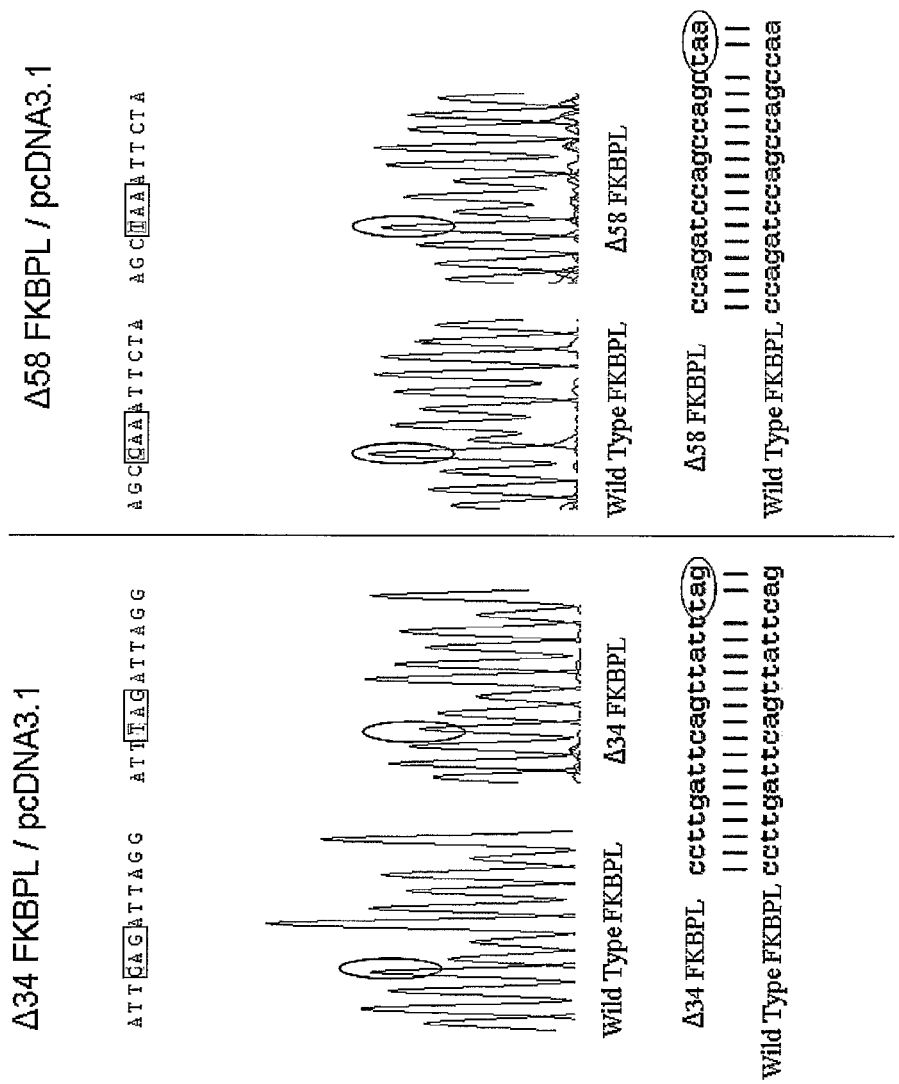
Figure 20C:
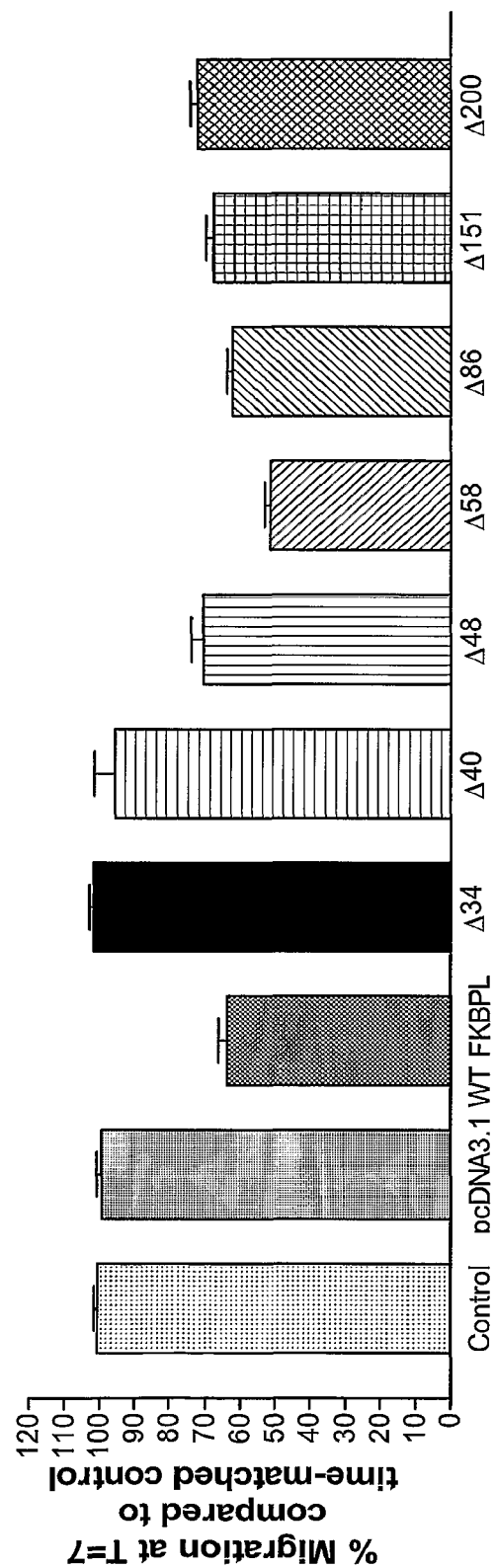

Thus, as shown in FIG. 20A-20C, in certain embodiments, the domain important for its anti-angiogenic activity may be located between amino acids 34 to 57 (i.e. in the N-terminus) of FKBP-L.

In certain embodiments, the portion of FKBP-L between amino acids 34 and 57 exhibits the same biological activity as full-length FKBP-L. In some embodiments, the FKBP-L 24mer may display increased potency as compared to the full-length FKBP-L. For example, the FKBP-L 24mer peptide (SEQ ID NO: 10) may exhibit similar or more potent biological activity as compared to full-length recombinant FKBP-L (e.g., SEQ ID NO: 1) with respect to inhibition of endothelial cell migration/wound closure (FIG. 21), the inhibition of the formation of endothelial cell-to-cell contacts in the Matrigel tube formation assay (FIG. 22), angiogenic sprouting (FIGS. 23A, 23B, 24A and 24B), the ability of cells to invade (FIG. 25), and/or the ability of cells to adhere (FIG. 26). In certain embodiments, however, the FKBP-L 24mer and the FKBP-L 1-57mer display increased potency as compared to full length FKBP-L (see e.g., FIGS. 21, 22 and 24).

In certain embodiments, the biological activity of FKBP-L can require CD44. For example, the FKBP-L 24mer peptide (SEQ ID NO: 10) may act in a similar manner to full-length recombinant FKBP-L (rFKBP-L), and inhibit MDA-231 and PC3 tumor cell migration. These tumor cells are both CD44 positive (CD44 +ve) (i.e., express CD44 protein) (FIGS. 27A and 27B) indicating that the FKBP-L 24mer may be able to inhibit tumor metastases in a subset of CD44 +ve tumor cell lines. In an embodiment, FKBP-L and its derivatives can inhibit tumor cell migration and invasion and endothelial cell migration in a manner that is consistant with FKBP-L interacting with CD44.

Figure 28A:
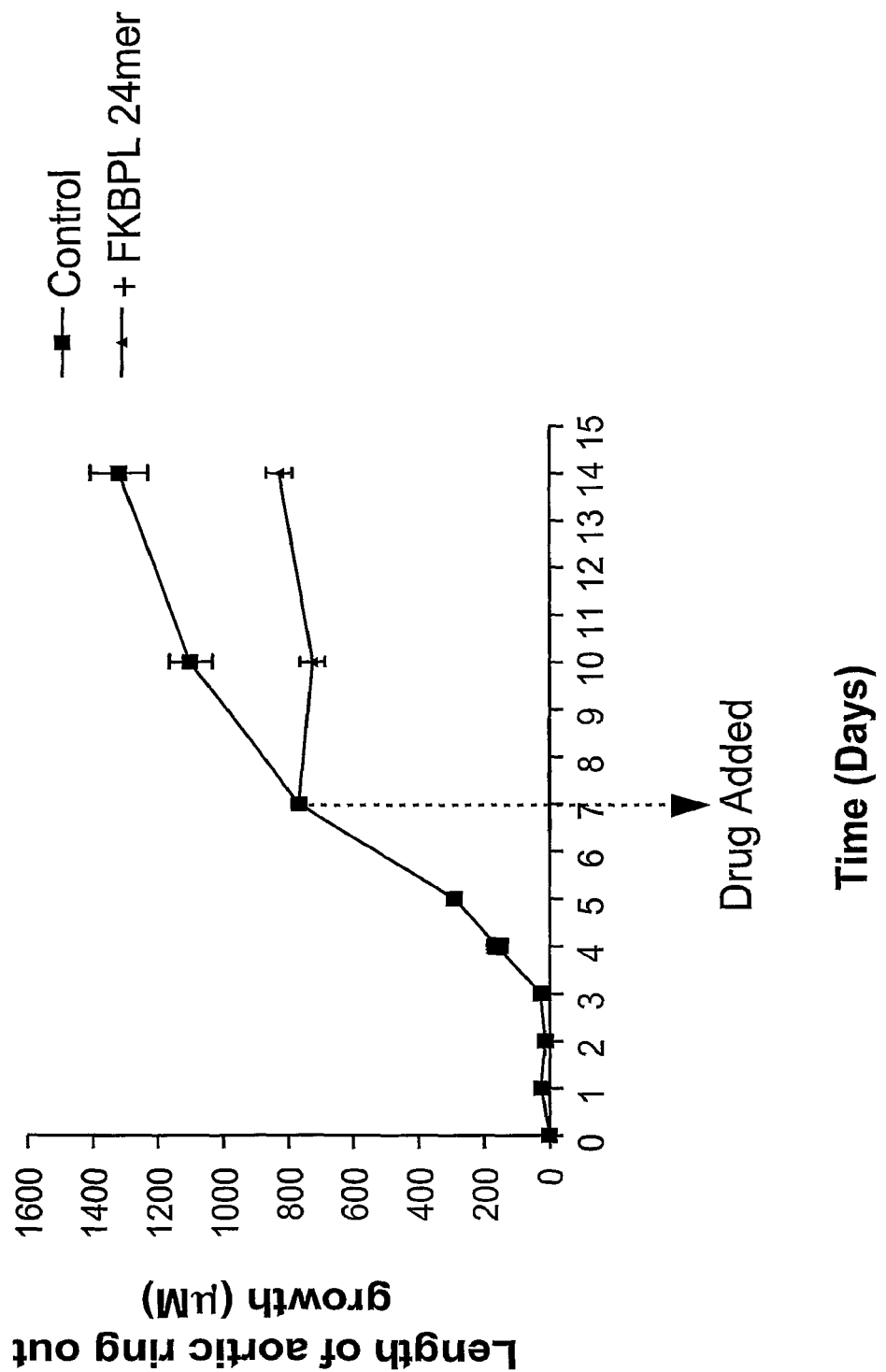
FIGS. 28A and 28B show that the FKBP-L 24mer is an angiostatic inhibitor, where
Figure 28B:
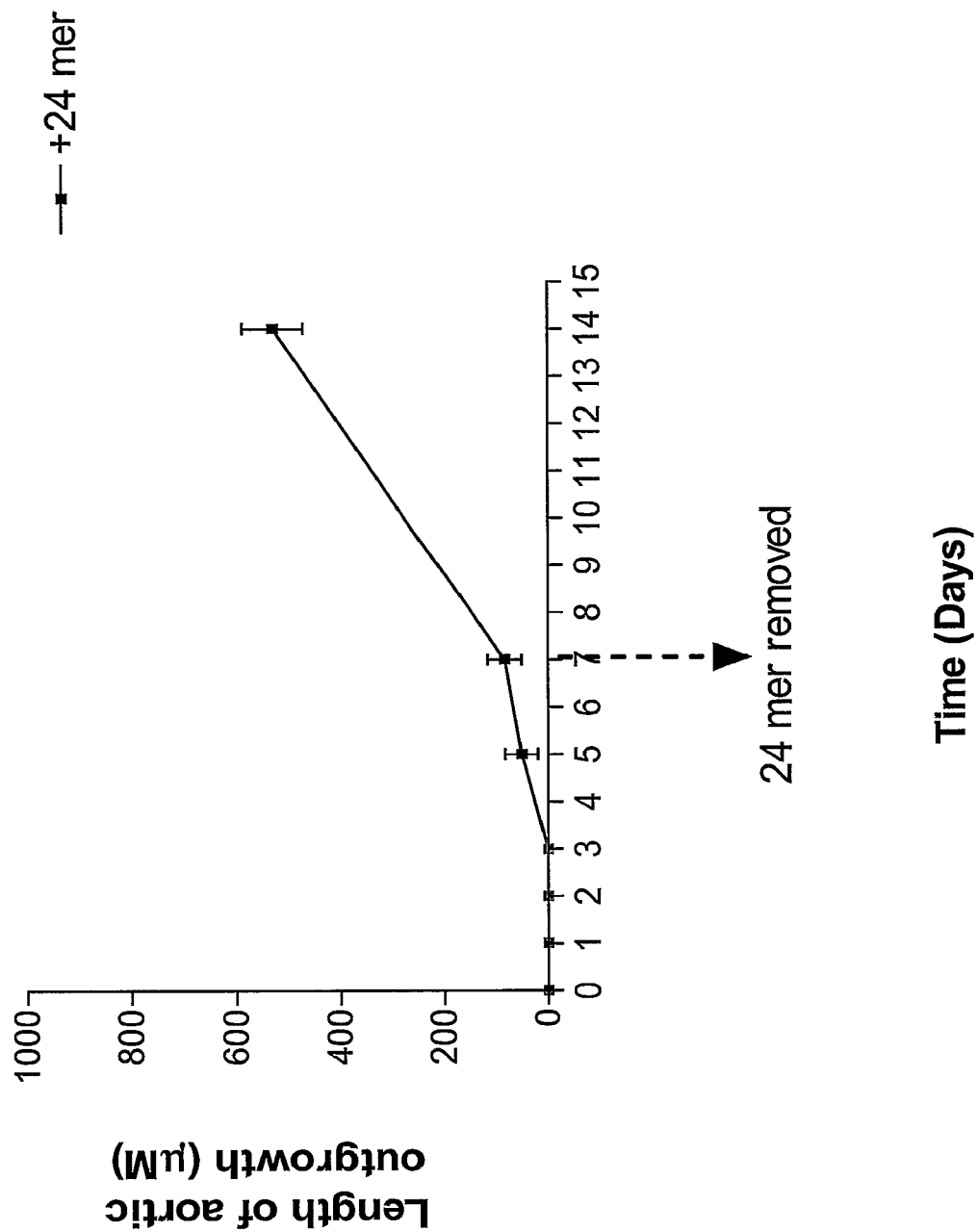

Also in certain embodiments, the FKBP-L 24mer peptide (SEQ ID NO: 10) is an angiostatic inhibitor (FIGS. 28A and 28B). Thus, the FKPB-L 24mer may inhibit vessel development when the vessels are either mature or freshly embedded. However, in an embodiment, the FKBP-L polypeptide may act by a static mechanism in that it stops vessel development when added, but has little to no residual effect when removed.

Also, in certain embodiments, the FKBP-L 24mer inhibits angiogenesis in vivo using the mouse sponge assay (FIG. 29) and also inhibits mouse endothelial cell migration in vitro (FIG. 30) over a broad dose range, demonstrating that this human peptide is also active in mouse. This is supported by the data provided in FIGS. 29 and 31.

Figure 31A:
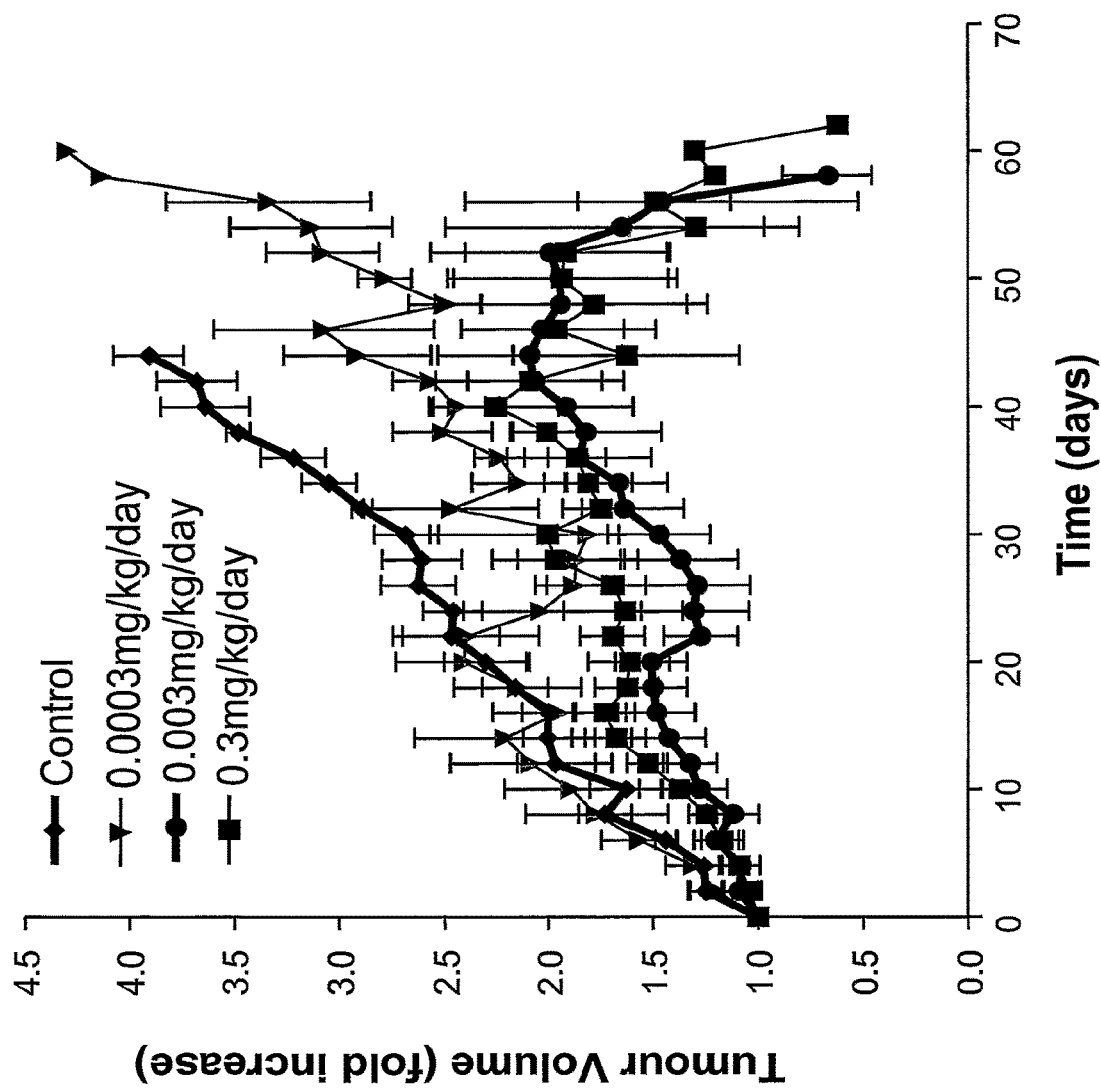
FIGS. 31A, 31B, 31C, 31D, and 31E show that the FKBP-L 24mer peptide (SEQ ID NO: 10) inhibits DU145 tumor growth in vivo after daily IP injection (FIG. 31A); increases survival (FIG. 31B, FIG. 31C, and FIG. 31D); and is not toxic (FIG. 31E), in accordance with alternate embodiments of the present invention.
Figure 31B:
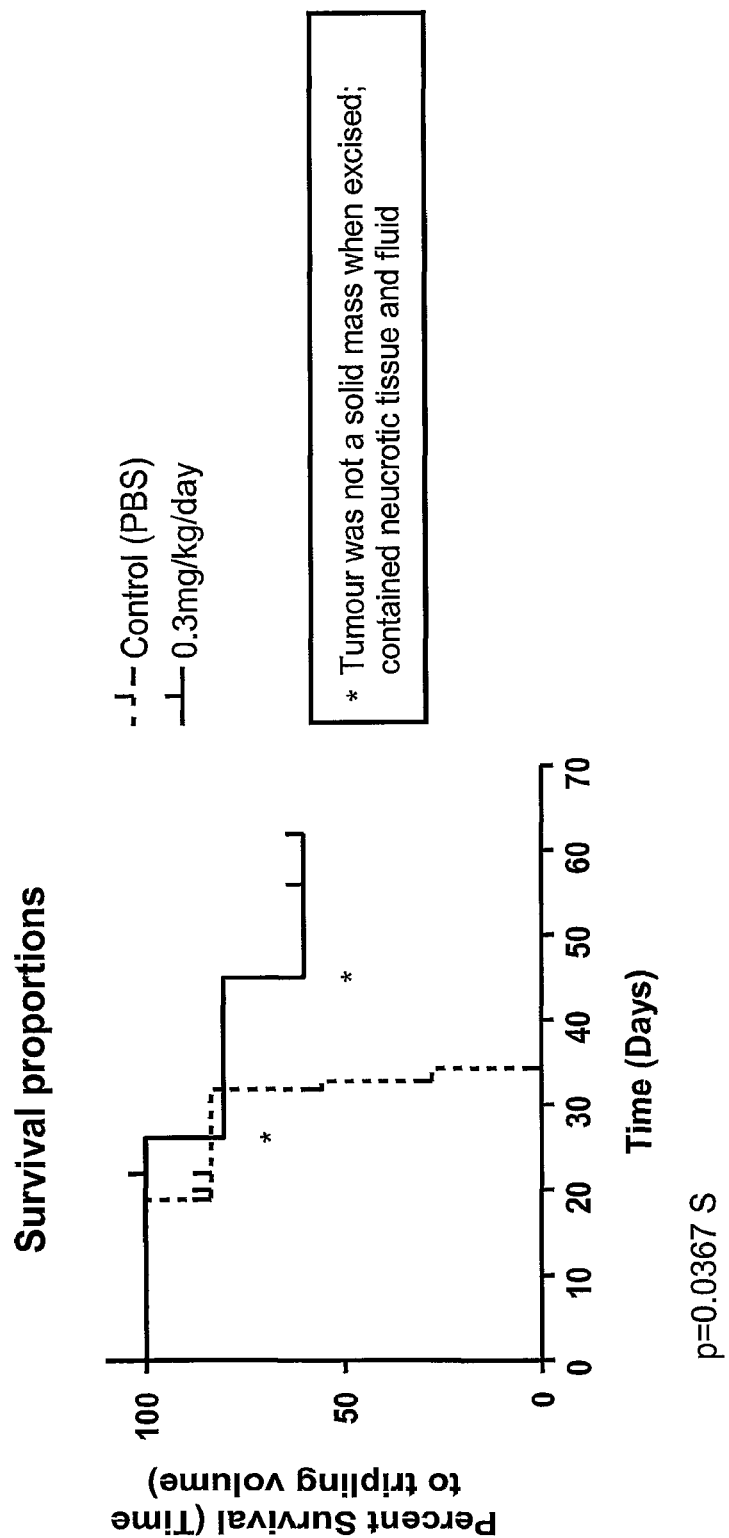
Figure 31C:
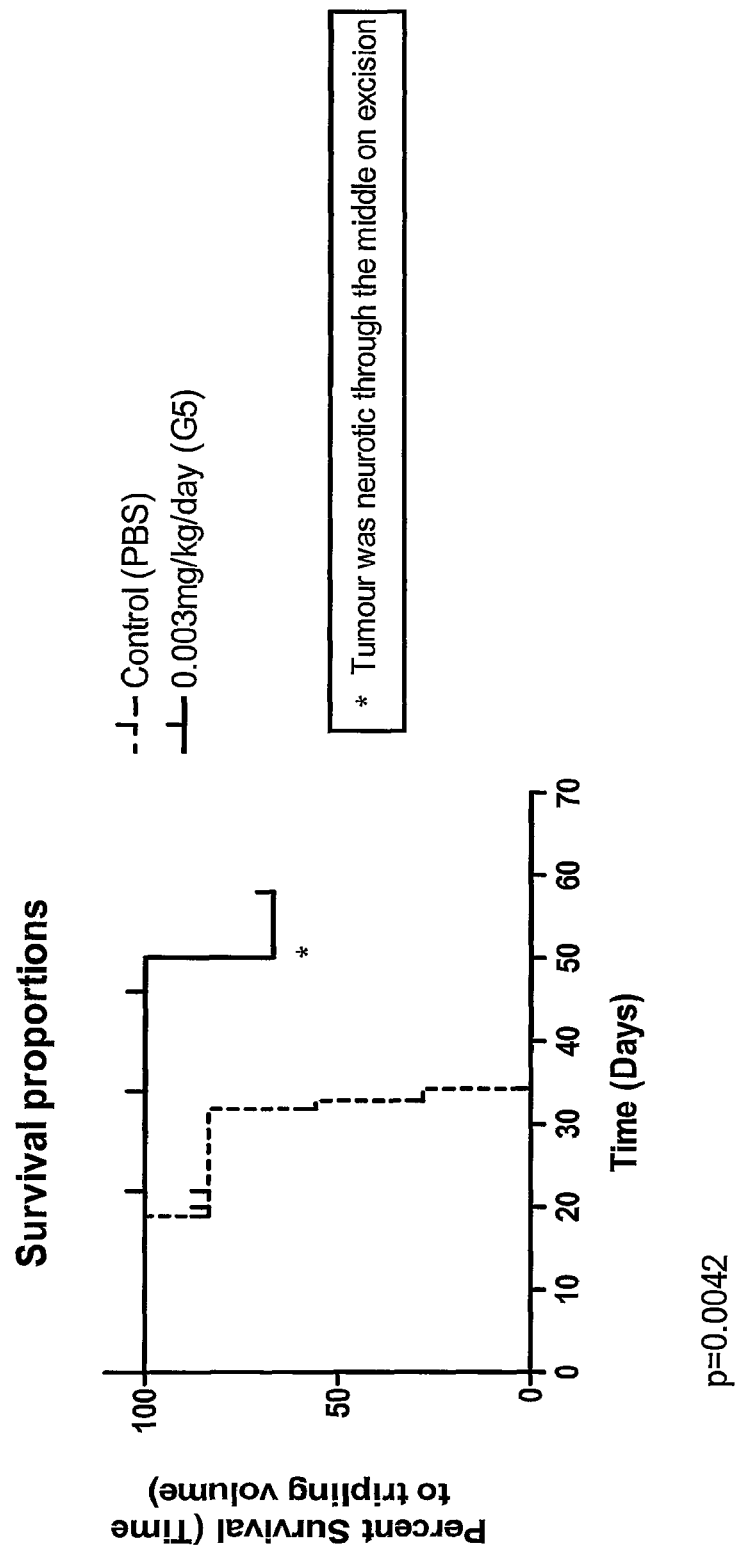
Figure 31D:
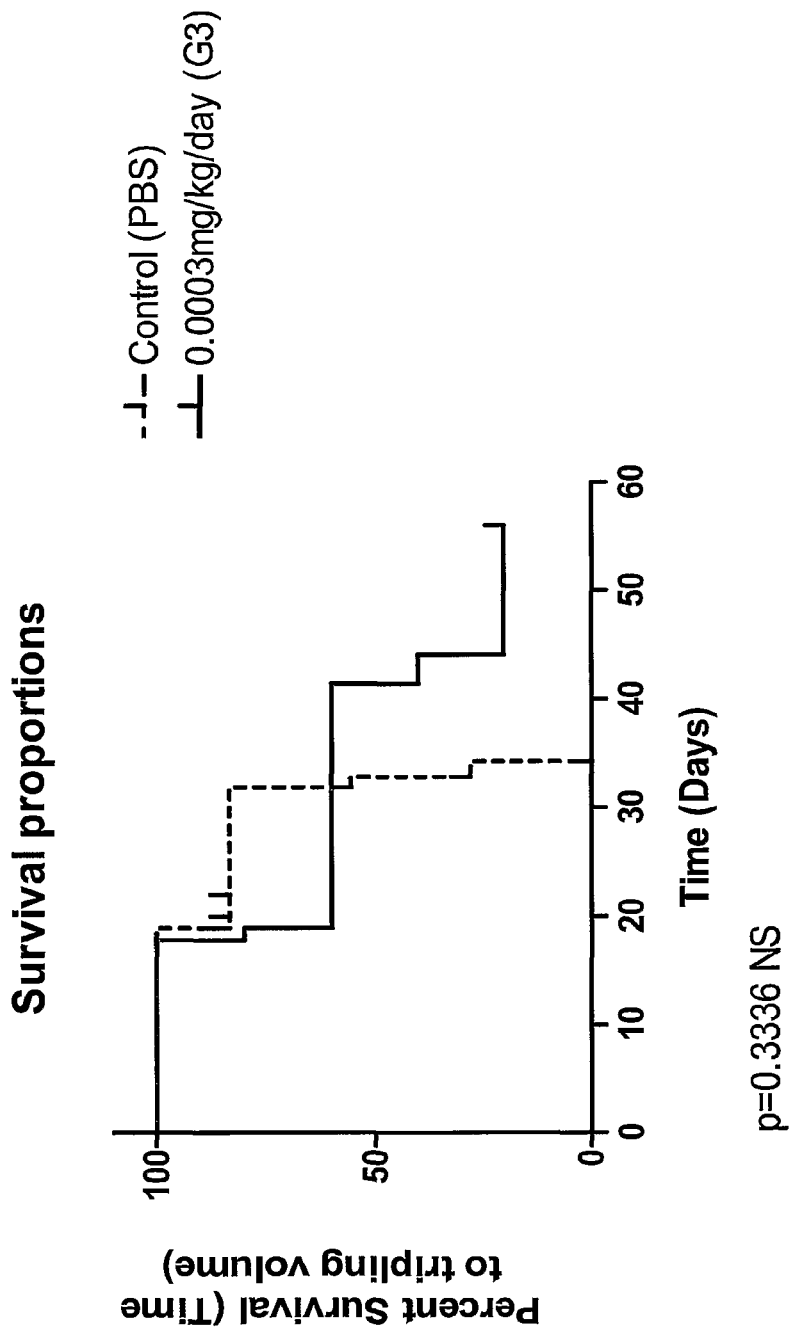

Similar to the full length FKBP-L protein, the FKBP-L 24mer peptide (SEQ ID NO: 10) may, in certain embodiments, inhibit tumor cell growth in vivo (FIG. 31A). Also, mice treated with the FKBP-L 24mer showed significantly increased survival (FIG. 31B-D). Thus, as shown in FIG. 31A, treatment by i.p.

injection with the 24mer FKBP-L peptide at doses of either 0.3 mg/kg/day or $3 \times 10^{-3}$ mg/kg/day significantly slowed the growth of DU145 tumors in SCID mice compared to vehicle only treated tumors. In an embodiment, tumors treated with these doses of 24mer FKBP-L peptide show evidence of a necrotic center as is typical of the effects seen with anti-angiogenics.

Figure 31E:
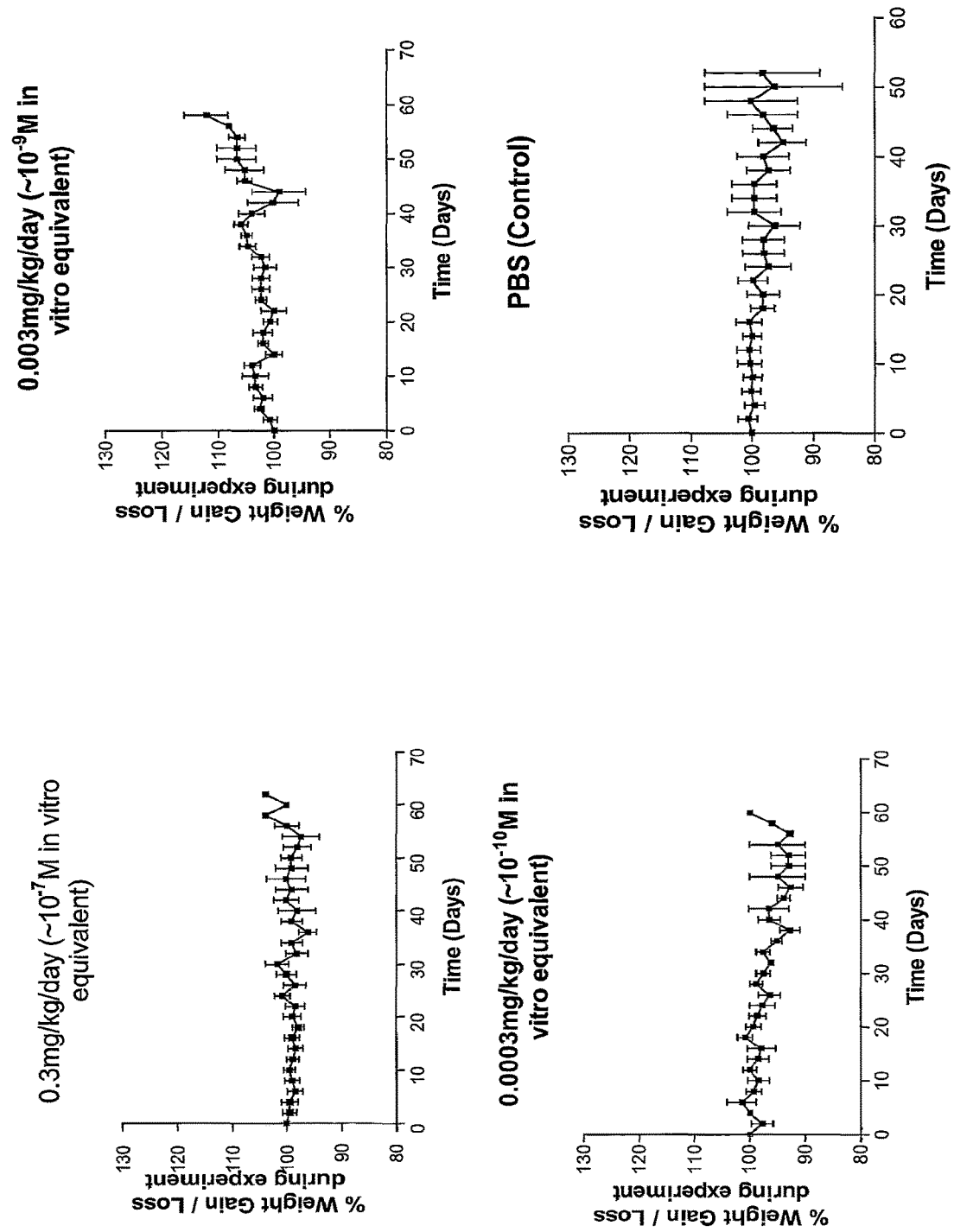
Figure 32:
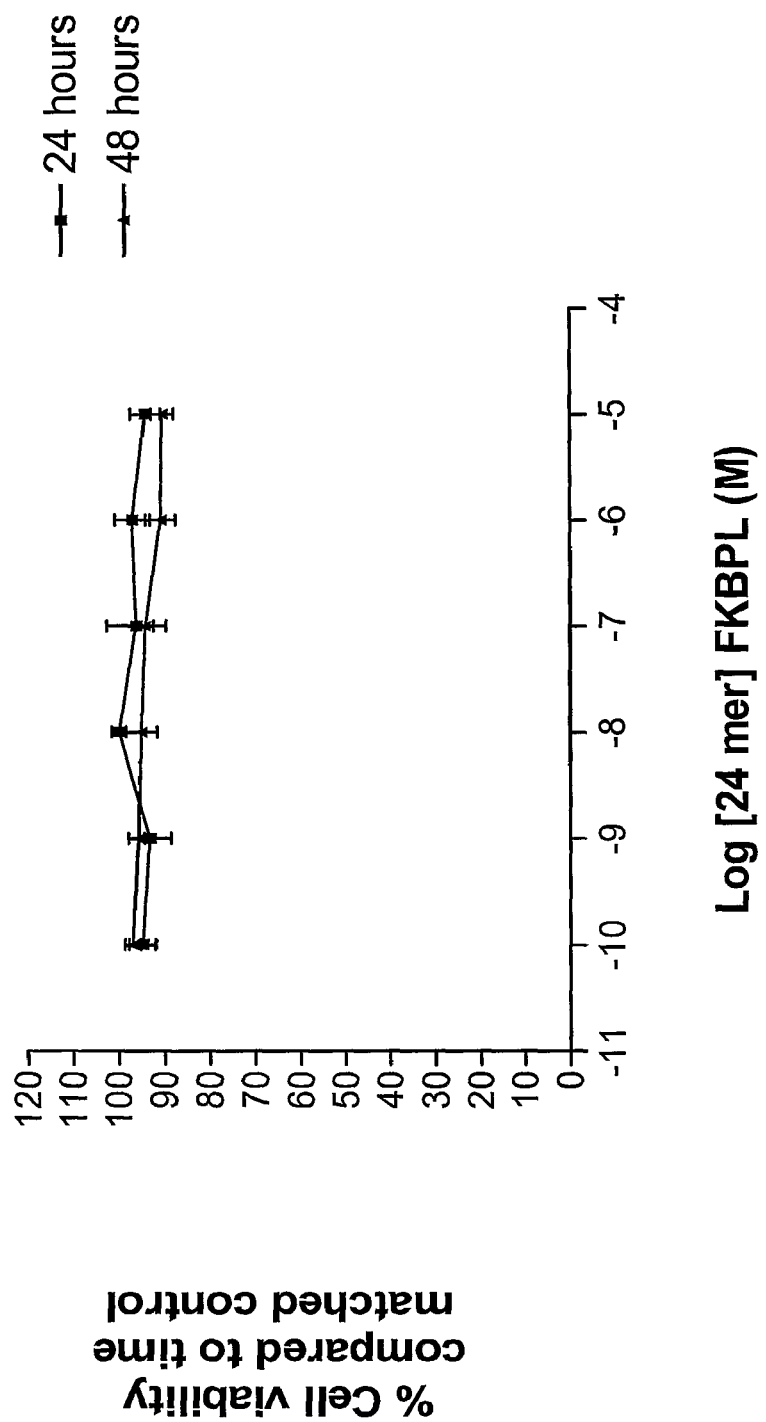
FIG. 32 shows the effect of the FKBP-L 24mer peptide (SEQ ID NO: 10) on the viability or proliferation of HMEC-1 cells using the MTT assay in accordance with alternate embodiments of the present invention.

In an embodiment, the activity of the FKBP-L 24mer peptide, like the full-length FKBP-L, is not due to toxicity of the peptide (FIGS. 31E, 32 and 33).

In certain embodiments, portions or fragments of the FKBP-L 24mer peptide (SEQ ID NO: 10) may be used as therapeutic agents. Example 29 (FIG. 34) provides examples of peptide fragments of the FKBP-L 24mer that may have similar activity and potency as the FKBP-L 24, FKBP-L 1-57, and full length FKBP-L.

FKBP-L Derivatives

As described above, a FKBP-L derivative for use in the invention means a polypeptide modified by varying the amino acid sequence of FKBP-L, e.g. SEQ ID NO:1, SEQ ID NO: 2, or SEQ ID NO:29, or a fragment thereof, or a polypeptide at least 70%, 75%, 80%, 85%, 90%, 95%, 96%, 97%, 98%, or 99% identical thereto, or such peptides that have be modified by the addition of a functional group (e.g., PEG). Generation of such peptides may be performed by manipulation of the nucleic acid encoding the polypeptide or by altering the protein itself.

In SEQ ID NO: 2, the FKBP-L insert(originally cloned into PUC18 by Cambridge Bioscience and now cloned into pcDNA3.1); had two inserted point mutations compared to the sequence that is deposited on the PUBMED database (SEQ ID NO: 29). There is a point mutation at 540 bp (from start codon): TCT to ACT which therefore converts a serine (S) to a Threonine (T) (amino acid: 181). There is also a point mutation at 555 bp (from start codon): AGG to GGG which therefore converts an Arginine (R) to a Glycine (G) (amino acid: 186). Both FKBP-L polypeptides (SEQ ID NO: 2 and SEQ ID NO: 29) display biological activity.

FKBP-L derivatives include analogues of the natural FKBP-L amino acid sequence and may involve insertion, addition, deletion and/or substitution of one or more amino acids, while providing a polypeptide capable of effecting similar angiogenic effects to the portions corresponding to the truncated mutants, Δ48 (SEQ ID NO:7), Δ58 (SEQ ID NO:6), Δ86 (SEQ ID NO: 5), Δ151 (SEQ ID NO:4), or Δ200 (SEQ ID NO:3) (FIG. 1). Also included in the FKBP-L derivatives of the present invention are polypeptides derived from Δ58 (SEQ ID NO:6), including the FKBP-L 24mer (SEQ ID NO 10) and peptides 1-17 (SEQ ID NOs: 12-28) shown in FIG. 1.

Thus, in certain embodiments, the N-terminal domain (amino acids 34-57) of FKBP-L is important for the anti-angiogenic properties. FIG. 20C and Example 17 shows a study in which various FKBP-L fragments where compared for effectiveness in inhibiting migration of cells as compared to time-matched negative controls. In an embodiment, the Δ58 fragment displays maximum inhibitory activity of the tested fragments.

The portion of the FKBP-L polypeptide providing inhibition of angiogenesis may be found in the polypeptide comprising the portion of FKBP-L in common to active peptides Δ48 (SEQ ID NO:7) and Δ58 (SEQ ID NO:6). This polypeptide may comprise SEQ ID NO: 10 (FIG. 1).

Thus, FKBP-L derivatives used in the methods and compositions of the present invention also include fragments, portions or mutants of the naturally occurring FKBP-L. In certain embodiments, the fragments are selected from the N-terminal domain of FKBP-L. In certain embodiment, the fragments are selected from amino acids 1 to 85 of full-length FKBP-L (e.g., SEQ ID NOs: 2 or 29). Preferably such analogues involve the insertion, addition, deletion and/or substitution of 5 or fewer amino acids, more preferably of 4 or fewer, even more preferably of 3 or fewer, most preferably of 1 or 2 amino acids only.

FKBP-L derivatives according to the invention also include multimeric peptides including such FKBP-L polypeptide, analogue or fragment sequences e.g. SEQ ID NOs: 1-7, SEQ ID NO: 10-28, and prodrugs including such sequences. For example, in certain embodiments FKBP-L or fragments of FKBP-L may form multimers by the formation of disulfide bonds between monomers.

Derivatives of the FKBP-L polypeptide of the invention may include the polypeptide linked to a coupling partner, e.g., an effector molecule, a label, a drug, a toxin and/or a carrier or transport molecule. Techniques for coupling the polypeptides of the invention to both peptidyl and non-peptidyl coupling partners are well known in the art.

A "fragment" of a FKBP-L polypeptide means a stretch of amino acid residues of at least 6 amino acids.

FKBP-L derivatives of the invention include fusion peptides. For example, derivatives may comprise polypeptide peptides of the invention linked, for example, to antibodies that target the peptides to diseased tissue, for example, tumor tissue or the retina.

The FKBP-L polypeptide or their analogues may be fused with the constant domain of immunoglobulins (IgA, IgE, IgG, IgM), or portions thereof (CH1, CH2, CH3, or any combination thereof), resulting in chimeric polypeptides. These fusion polypeptides or proteins can facilitate purification and may show an increased half-life in vivo. Such fusion proteins may be more efficient in binding and neutralizing other molecules than monomeric polypeptides or fragments thereof alone. See, e.g., Fountoulakis et al., J. Biochem., 270:3958-3964 (1995).

Fusion proteins of the invention also include FKBP-L polypeptides fused with albumin, for example recombinant human serum albumin or fragments or variants thereof (see, e.g., U.S. Pat. No. 5,876,969, EP Patent 0413622 and U.S. Pat. No. 5,766,883).

The use of polynucleotides encoding such fusion proteins described herein is also encompassed by the invention. The use of a polynucleotide fused to a cytotoxic agent is also encompassed by the invention. In this instance the FKBP-L polypeptide may bind to a receptor and the cytotoxic drug could be internalised.

For example, in alternate embodiments, derivatives may include: site-specific PEGylation (or the like) of peptide to increase half life; or incorporation unnatural amino acids and back bone modifications to stabilize against proteolysism; or cyclic derivatives (to provide proteolytic resistance); or to block the N- and C-termini to prevent or reduce exopeptidase and/or proteinase activity; or to join together multiple copies of peptides either in a contiguous chain via linkers chain or in a dendrimer type of approach to increase 'avidity' with cell surface CD44. For example, trimeric covalently linked derivatives of 24mer may be used as derivatives of FKBP-L. Or, the FKBP-L 24mer may be attached to a domain which homotrimerises to form non-covalent trimers. Or, biotin derivatives of peptides which will form tetrameric complexes with streptavidin may be used as derivatives of FKBP-L. Or, FKBP-L or fragments of FKBP-L may form multimers by the formation of disulfide bonds between monomers. In addition, FKBP-L may form oligomers through non-covalent associations, possibly through the predicted tetratricopeptide repeat domains within the protein sequence.

Reverse Peptide Analogues

Analogues for use in the present invention further include reverse-or retro-analogues of natural FKBP-L proteins, portion thereof or their synthetic derivatives. See, for example, EP 0497 366, U.S. Pat. No. 5,519,115, and Merrifield et al., 1995, PNAS, 92:3449-53, the disclosures of which are herein incorporated by reference. As described in EP 0497 366, reverse peptides are produced by reversing the amino acid sequence of a naturally occurring or synthetic peptide. Such reverse-peptides may retain the same general three-dimensional structure (e. g., alpha-helix) as the parent peptide except for the conformation around internal protease-sensitive sites and the characteristics of the N- and C-termini. Reverse peptides are purported not only to retain the biological activity of the non-reversed "normal" peptide but may possess enhanced properties, including increased biological activity. (See Iwahori et al., 1997, Biol. Pharm. Bull. 20: 267-70). Derivatives for use in the present invention may therefore comprise reverse peptides of natural and synthetic FKBP-L proteins.

Peptides (including reverse peptides and fragments of either) for use in the invention may be generated wholly or partly by chemical synthesis or by expression from nucleic acid. The peptides for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984).

Multimeric Peptides

As described above, the peptides may be in the form of multimers. Thus multimers of 2, 3 or more individual FKBP-L polypeptide monomeric units, or two or more fragments of FKBP-L, are within the scope of the invention.

In one embodiment, such multimers may be used to prepare a monomeric peptide by preparing a multimeric peptide that includes the monomeric unit, and a cleavable site (i.e., an enzymatically cleavable site), and then cleaving the multimer to yield a desired monomer.

In one embodiment, the use of multimers can increase the binding affinity for a receptor.

The multimers can be homomers or heteromers. As used herein, the term homomer, refers to a multimer containing only polypeptides corresponding to a specific amino acid sequence (e.g., SEQ ID NO: 1, SEQ ID NO: 2, SEQ ID NO: 10, or SEQ ID NO: 29), or variants, splice variants, fusion proteins, or other FKBP-L analogues or derivatives described herein. These homomers may contain FKBP-L peptides having identical or different amino acid sequences. For example, the multimers can include only FKBP-L peptides having an identical amino acid sequence, or can include different amino acid sequences. The multimer can be a homodimer (e.g., containing only FKBP-L peptides, these in turn may have identical or different amino acid sequences), homotrimer or homotetramer.

As used herein, the term heteromer refers to a multimer containing one or more heterologous polypeptides (i.e., non-FKBP-L peptide or polypeptides) in addition to the FKBP-L (poly)peptides described herein.

The multimers may be the result of hydrophobic, hydrophilic, ionic and/or covalent associations and/or may be indirectly linked, by for example, liposome formation. Thus, in one embodiment, multimers are formed when the FKBP-L peptides described herein contact one another in solution. In another embodiment, heteromultimers are formed when FKBP-L and non-FKBP-L (poly)peptides contact antibodies to the (poly)peptides described herein (including antibodies to the heterologous (poly)peptide sequence in a fusion protein described herein) in solution. In other embodiments, multimers described herein may be formed by covalent associations with and/or between the FKBP-L peptides (and optionally non-FKBP-L peptides) described herein.

Such covalent associations can involve one or more amino acid residues contained in the FKBP-L sequence (e.g., that recited in SEQ ID NOs: 1-28. In one embodiment, the covalent associations are the consequence of chemical or recombinant manipulation. Alternatively, such covalent associations can involve one or more amino acid residues contained in the heterologous polypeptide sequence in a FKBP-L fusion protein. In one example, covalent associations are between the heterologous sequence contained in a fusion protein described herein (see, e.g., U.S. Pat. No. 5,478,925). In another specific example, covalent associations of fusion proteins described herein are using heterologous polypeptides sequence from another protein that is capable of forming covalently associated multimers, for example, oesteoprotegerin (see, e.g., International Publication NO: WO 98/49305). In another embodiment, two or more polypeptides described herein are joined through peptide linkers. Examples include those peptide linkers described in U.S. Pat. No. 5,073,627. Proteins comprising multiple FKBP-L peptides separated by peptide linkers can be produced using conventional recombinant DNA technology.

Multimers may also be prepared by fusing the FKBP-L (poly)peptides to a leucine zipper or isoleucine zipper polypeptide sequence. Among the known leucine zippers are naturally occurring peptides and derivatives thereof that dimerize or trimerize. Examples of leucine zipper domains suitable for producing soluble multimeric proteins described herein are those described in PCT application WO 94/10308. Recombinant fusion proteins comprising a polypeptide described herein fused to a polypeptide sequence that dimerizes or trimerizes in solution can be expressed in suitable host cells, and the resulting soluble multimeric fusion protein can be recovered from the culture supernatant using techniques known in the art.

The multimers may also be generated using chemical techniques known in the art. For example, polypeptides to be contained in the multimers described herein may be chemically cross-linked using linker molecules and linker molecule length optimisation techniques known in the art (see, e.g., U.S. Pat. No. 5,478,925). Additionally, the multimers can be generated using techniques known in the art to form one or more inter-molecule cross-links between the cysteine residues located within the sequence of the polypeptides desired to be contained in the multimer (see, e.g., U.S. Pat. No. 5,478,925). Further, polypeptides described herein may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925). Additionally, techniques known in the art can be used to prepare liposomes containing two or more C-12-C peptides desired to be contained in the multimer (see, e.g., U.S. Pat. No. 5,478,925).

Alternatively, those multimers including only naturally-occurring amino acids can be formed using genetic engineering techniques known in the art. Alternatively, those that include post-translational or other modifications can be prepared by a combination of recombinant techniques and chemical modifications. In one embodiment, the FKBP-L peptides are produced recombinantly using fusion protein technology described herein or otherwise known in the art (see, e.g., U.S. Pat. No. 5,478,925, which is herein incorporated by reference in its entirety). For example, polynucleotides coding for a homodimer described herein can be generated by ligating a polynucleotide sequence encoding a FKBP-L peptide described herein to sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925). The recombinant techniques described herein or otherwise known in the art can be applied to generate recombinant FKBP-L (poly)peptides that contain a transmembrane domain (or hydrophobic or signal peptide) and that can be incorporated by membrane reconstitution techniques into liposomes (see, e.g., U.S. Pat. No. 5,478,925).

Pro-Drugs

The polypeptides described herein are intended, at least in some embodiments, to be administered to a human or other mammal to treat or prevent a disorder associated with angiogenesis. Peptides are typically administered parenterally, e.g., by intravenous, subcutaneous, or intramuscular injection, or via the intranasal cavity, and may be readily metabolized by plasma proteases. In some cases the FKBP-L peptide may be delivered in microcapsules of poly(DL-lactide-co-glycolide)—controlled release over 30 days.

Various prodrugs have been developed that enable parenteral and oral administration of therapeutic peptides. Peptides or polypeptides can be conjugated to various moieties, such as polymeric moieties, to modify the physiochemical properties of the peptide drugs, for example, to increase resistance to acidic and enzymatic degradation and to enhance penetration of such drugs across mucosal membranes. For example, Abuchowski and Davis have described various methods for derivatizating enzymes to provide water-soluble, non-immunogenic, in vivo stabilized products ("Soluble polymers—Enzyme adducts," Enzymes as Drugs, Eds. Holcenberg and Roberts, J. Wiley and Sons, New York, N.Y. (1981)).

Thus, in certain embodiments, the FKBP-L peptides may be conjugated to polymers, such as dextrans, polyvinyl pyrrolidones, glycopeptides, polyethylene glycol and polyamino acids. The resulting conjugated polypeptides retain their biological activities and solubility in water for parenteral applications. In an embodiment, the FKBP-L peptides may be coupled to polyethylene glycol or polypropylene glycol having a molecular weight of 500 to 20,000 Daltons to provide a physiologically active non-immunogenic water soluble polypeptide composition (see e.g., U.S. Pat. No. 4,179,337 and Garman, A. J., and Kalindjian, S. B., FEBS Lett., 1987, 223, 361-365). The polyethylene glycol or polypropylene glycol may protect the polypeptide from loss of activity and the composition can be injected into the mammalian circulatory system with substantially no immunogenic response. In other embodiments, the FKBP-L is coupled to an oligomer that includes lipophilic and hydrophilic moieties (see e.g., U.S. Pat. Nos. 5,681,811, 5,438,040 and 5,359,030).

Prodrugs can be prepared for example, by first preparing a maleic anhydride reagent from polydispersed MPEG5000 and then conjugating this reagent to the polypeptides disclosed herein. The reaction of amino acids with maleic anhydrides is well known. The hydrolysis of the maleylamide bond to reform the amine-containing drug is aided by the presence of the neighbouring free carboxyl group and the geometry of attack set up by the double bond. The peptides can be released (by hydrolysis of the prodrugs) under physiological conditions.

The polypeptides can also be coupled to polymers, such as polydispersed PEG, via a degradable linkage, for example, the degradable linkage shown (with respect to pegylated interferon α-2b) in Roberts, M. J., et al., Adv. Drug Delivery Rev., 2002, 54, 459-476.

The polypeptides can also be linked to polymers such as PEG using 1,6 or 1,4 benzyl elimination (BE) strategies (see, for example, Lee, S., et al., Bioconjugate Chem., (2001), 12, 163-169; Greenwald, R. B., et al., U.S. Pat. No. 6,180,095, 2001; Greenwald, R. B., et al., J. Med. Chem., 1999, 42, 3657-3667.); the use of trimethyl lock lactonization (TML) (Greenwald, R. B., et al., J. Med. Chem., 2000, 43, 475-487); the coupling of PEG carboxylic acid to a hydroxy-terminated carboxylic acid linker (Roberts, M. J., J. Pharm. Sci., 1998, 87(11), 1440-1445), and PEG prodrugs involving families of MPEG phenyl ethers and MPEG benzamides linked to an amine-containing drug via an aryl carbamate (Roberts, M. J., et al., Adv. Drug Delivery Rev., 2002, 54, 459-476), including a prodrug structure involving a meta relationship between the carbamate and the PEG amide or ether (U.S. Pat. No. 6,413,507 to Bently, et al.); and prodrugs involving a reduction mechanism as opposed to a hydrolysis mechanism (Zalipsky, S., et al., Bioconjugate Chem., 1999, 10(5), 703-707).

The FKBP-L polypeptides of the present invention have free amino, amido, hydroxy and/or carboxylic groups, and these functional groups can be used to convert the peptides into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of various polymers, for example, polyalkylene glycols such as polyethylene glycol.

Prodrugs also include compounds wherein PEG, carbonates, carbamates, amides and alkyl esters which are covalently bonded to the above peptides through the C-terminal carboxylic acids. For example, Peptide 1 as used herein is FKBP-L peptide having C-terminal PEG groups. Thus, embodiments of the present invention comprise site-specific PEG addition.

In certain embodiments, enzyme inhibitors may be used to slow the rate of degradation of proteins and peptides in the gastrointestinal tract. Or, the pH in the digestive tract may be manipulated to inactivate local digestive enzymes. Or, permeation enhancers may be used to improve the absorption of peptides by increasing their paracellular and transcellular transports. Or, nanoparticles may be used as particulate carriers to facilitate intact absorption by the intestinal epithelium, especially, Peyer's patches, and to increase resistance to enzyme degradation. In other embodiments, liquid emulsions may be used to protect the drug from chemical and enzymatic breakdown in the intestinal lumen, or micelle formulations may be used for poorly water-solubilised drugs.

Thus, in alternate embodiments, the polypeptides can be provided in a suitable capsule or tablet with an enteric coating, so that the peptide is not released in the stomach. Alternatively, or additionally, the polypeptide can be provided as a prodrug, such as the prodrugs described above. In one embodiment, the polypeptides are present in these drug delivery devices as prodrugs.

Prodrugs comprising the polypeptides of the invention or pro-drugs from which peptides of the invention (including analogues and fragments) are released or are releasable are considered to be analogues of the invention.

Use of isotopically-labelled peptides or peptide prodrugs are also encompassed by the invention. Such peptides or peptide prodrugs are identical to the peptides or peptide prodrugs of the invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine and chlorine, such as $^2H$, $^3H$, $^{13}C$, $^{14}C$, $^{15}N$, $^{18}O$, $^{17}O$, $^{125}I$, and $^{35}S$, respectively. Polypeptides of the present invention, prodrugs thereof, and/or the prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled peptides and prodrugs thereof can generally be prepared by carrying out readily known procedures, including substituting a readily available isotopically-labelled reagent for a non-isotopically-labelled reagent, e.g., a labelled amino acid.

Nucleic Acids

Peptides for use in the present invention may be produced by use of nucleic acid in an expression system. For example, in one aspect, nucleic acids which may be used in the invention include any isolated polynucleotide encoding the polypeptides of the invention. In a preferred embodiment, the polynucleotide comprises any one of the nucleic acid sequences as shown in SEQ ID NOs: 30-39 (FIG. 2). Sequences that encode for additional fragments of FKBP-L, e.g., SEQ ID NOs: 10-28, may be derived from the full-length nucleic acid sequence, and include degenerate nucleic acid sequences, as is known in the art. Examples 1, 2, and 17 provide descriptions of vectors that may be used to express FKBP-L polypeptides of the present invention.

Nucleic acid molecules that encode the FKBP-L polypeptides for use in the present invention may comprise DNA or RNA. The nucleic acid constructs may be produced recombinantly, synthetically, or by any means available to those in the art, including cloning using standard techniques.

The nucleic acid molecule may be inserted into any appropriate vector. A vector comprising a nucleic acid of the invention forms a further aspect of the present invention. In one embodiment the vector is an expression vector and the nucleic acid is operably linked to a control sequence which is capable of providing expression of the nucleic acid in a host cell. A variety of vectors may be used. For example, suitable vectors may include viruses (e. g. vaccinia virus, adenovirus, etc.), baculovirus); yeast vectors, phage, chromosomes, artificial chromosomes, plasmids, cosmid DNA and liposomes, polyplexes, or cells (e.g. mesenchymal stem cells, macrophages).

The vectors may be used to introduce the nucleic acids of the invention into a host cell. A wide variety of host cells may be used for expression of the nucleic acid of the invention. Suitable host cells for use in the invention may be prokaryotic or eukaryotic. They include bacteria, e.g. *E. coli*, yeast, insect cells and mammalian cells. Mammalian cell lines which may be used include but are not limited to, Chinese hamster ovary (CHO) cells, baby hamster kidney cells, NSO mouse melanoma cells, monkey and human cell lines and derivatives thereof and many others.

A host cell strain that modulates the expression of, modifies, and/or specifically processes the gene product may be used. Such processing may involve glycosylation, ubiquination, disulfide bond formation and general post-translational modification.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 2nd ed., Ausubel et al. eds. , John Wiley & Sons, 1992 and, Molecular Cloning: a Laboratory Manual: $3^{rd}$ edition Sambrook et al., Cold Spring Harbor Laboratory Press, 2000.

Pharmaceutical Compositions

The invention further provides pharmaceutical compositions comprising a FKBP-L polypeptide (or nucleic acid encoding a FKBP-L polypeptide). Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be, for example, oral, intravenous, or topical.

The formulation may be a liquid, for example, a physiologic salt solution containing non-phosphate buffer at pH 6.8-7.6, or a lyophilised powder.

Dose

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

In alternate embodiments, a dose range of the FKBPL 24mer would be from 30 mg/kg/day to 0.00003 mg/kg/day, or 3 mg/kg/day to 0.0003 mg/kg/day, to 0.3 mg/kg/day to 0.03 mg/kg/day. These doses are equivalent to $10^{-5}M$ to $10^{-12}M$, or $10^{-6}M$ to $10^{-11}M$, or $10^{-7}M$-$10^{-10}M$ in vitro, respectively.

Administration

A. FKBP-L Peptides

Polypeptides of and for use in the present invention may be administered alone but will preferably be administered as a pharmaceutical composition, which will generally comprise a suitable pharmaceutical excipient, diluent or carrier selected dependent on the intended route of administration.

The polypeptides may be administered to a patient in need of treatment via any suitable route. The precise dose will depend upon a number of factors, including the precise nature of the peptide.

Some suitable routes of administration include (but are not limited to) oral, rectal, nasal, topical (including buccal and sublingual), subcutaneous, vaginal or parenteral (including subcutaneous, intramuscular, intravenous, intradermal, intrathecal and epidural) administration.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos 4,485,045 and 4,544,545. Ordinarily, the liposomes are of the small (about 200-800 Angstroms) unilamellar type in which the lipid content is greater than about 30 mol. percent cholesterol, the selected proportion being adjusted for the optimal rate of the polypeptide leakage.

Examples of the techniques and protocols mentioned above and other techniques and protocols which may be used in accordance with the invention can be found in Remington's Pharmaceutical Sciences, 16th edition, Oslo, A. (ed), 1980.

Also, targeting therapies may be used to deliver the active agent e.g. polypeptide more specifically, e.g. to neoplastic tissue or retinal tissue, by the use of targeting systems such as antibody or cell specific ligands.

In other embodiments, purified recombinant or synthetic peptides can be treated with agents to attach moieties to the protein that can facilitate crosslinking. These moieties can be photoactivatable crosslinkers such as benzophenone or chemical crosslinkers such as maleimide or activated esters. Thus for example, it is possible to react cysteine residues in FKBPL with maleimide derivatives of benzophenone, or maleimide derivatives of phenyl azide for photoactivatable crosslinking or with heterobifunctional cross-linking agents containing maleimide and an activated ester for example. As is known in the art, there are a variety of hetero and homo bifunctional crosslinkers that could be attached to FKBPL and then used to crosslink to other biomolecules through amide, thioether, hydrazone, oxime etc forming reactions. In an embodiment, it is possible to introduce these cross-linking agents into synthetic peptides in a site-specific manner using total chemical synthesis procedures. Alternatively, photoactivatable groups may be introduced specifically at the C-terminus, or crosslinking agents may be introduced into recombinant FKBPL in a specific fashion using protein ligation approaches.

The FKBP-L peptide may also be administered with additional therapeutic agents as described in more detail herein.

B. Nucleic Acids Encoding FKBP-L or Anti-Sense/siRNA FKBP-L

In an embodiment, the coding sequence of a FKBP-L polypeptide or an nucleic acid is inserted into an expression vector. A regulatory sequence comprising a promoter that is operable in the host cell of interest may then be linked to cDNA sequence using molecular techniques. Other regulatory sequences can also be used, such as one or more of an enhancer sequence, an intron with functional splice donor and acceptance sites, a signal sequence for directing secretion of the recombinant polypeptide, a polyadenylation sequence, other transcription terminator sequences, and a sequence homologous to the host cell genome. Other sequences, such as an origin of replication, can be added to the vector as well to optimize expression of the desired product. Also, a selectable marker may be included in the vector for selection of the presence thereof in the transformed host cells.

The regulatory sequences may be derived from various sources. For example, one or more of them can be normally associated with the coding sequence, or may be derived from, or homologous with, regulator systems present in the host cell of interest. The various components of the expression vector can be linked together directly or via linkers that constitute sites of recognition by restriction enzymes as is known in the art.

Any promoter that would allow expression of the nucleic acid that encodes for FKBP-L polypeptide can be used in the present invention. For example, mammalian promoter sequences that can be used are those from mammalian viruses that are highly expressed and that have a broad host range.

The promoter may be a promoter that is expressed constitutively in most mammalian cells. Examples of suitable elements which make possible constitutive expression in eukaryotes are promoters which are recognized by the RNA polymerase III or viral promoters, CMV enhancer, CMV promoter, SV40 promoter or LTR promoters, e.g. from MMTV (mouse mammary tumor virus (e.g., Lee et al., 1981, *Nature,* 214, 228-232) and other viral promoter and activator sequences, derived from, for example, HBV, HCV, HSV, HPV, EBV, HTLV or HIV. Other examples of elements which make possible regulated expression in eukaryotes are the tetracycline operator in combination with a corresponding repressor (Gossen M., et al., 1994, *Curr. Opin. Biotechnol.,* 5, 516-20). In an embodiment, the expression of the FKBP-L sequence may takes place under the control of tissue-specific promoters.

Alternatively, the promoter may be a promoter that is turned on at a particular time in the cell cycle or developmental phase. For example, the constructs may comprise regulatable elements which make possible tissue-specific expression in eukaryotes, such as promoters or activator sequences from promoters or enhancers of those genes which code for proteins which are only expressed in certain cell types. Examples of regulatable elements which make possible cell cycle-specific expression in eukaryotes are promoters of the following genes: cdc25A, cdc25B, cdc25C, cyclin A, cyclin E, cdc2, E2F-1 to E2F-5, B-myb or DHFR (see e.g., U.S. Pat. Nos. 6,856,185; 6,903,078; and Zwicker J. and Muller R., 1997, *Trends Genet.,* 13, 3-6). The use of cell cycle regulated promoters may be used where expression of the polypeptides or nucleic acids used according to the invention is to be restricted to proliferating cells. Other examples include promoters controlled by hypoxia, radiation, heat, or the like.

In another embodiment, an enhancer element can be combined with a promoter sequence. Such enhancers may not only amplify, but also can regulate expression of the gene of interest. Suitable enhancer elements for use in mammalian expression systems are, for example, those derived from viruses that have a broad host range, such as the SV40 early gene enhancer, the enhancer/promoters derived from the LTR of the Rous Sarcoma Virus, and from human cytomegalovirus. Additionally, other suitable enhancers include those that can be incorporated into promoter sequences that will become active only in the presence of an inducer, such as a hormone, a metal ion, or an enzyme substrate, as is known in the art.

In another embodiment of the present invention, a transcription termination sequence may be placed 3' to the translation stop codon of the coding sequence for the gene of interest. Thus, the terminator sequence, together with the promoter, would flank the coding sequence.

The expression vector may also contain an origin of replication such that the vector can be maintained as a replicon, capable of autonomous replication and stable maintenance in a host. Such an origin of replication includes those that enable an expression vector to be reproduced at a high copy number in the presence of the appropriate proteins within the cell, for example, the 2μ and autonomously replicating sequences that are effective in yeast, and the origin of replication of the SV40 vital T-antigen, that is effective in COS-7 cells. Mammalian replication systems may include those derived from animal viruses that require trans-acting factors to replicate. For example, the replication system of papovaviruses, such as SV40, the polyomavirus that replicate to extremely high copy number in the presence of the appropriate vital T antigen may be used, or those derived from bovine papillomavirus and Epstein-Barr virus may be used.

In some cases, the expression vector can have more than one replication system, thus, allowing it to be maintained, for example, in mammalian cells for expression and in a procaryotic host for cloning and amplification (see e.g., U.S. Pat. No. 5,677,278).

In one embodiment, the expression vector can be made to integrate into the host cell genome as an integrating vector. The integrating vector herein may contain at least one polynucleotide sequence that is homologous to the host cell genome that allows the vector to integrate. For example, in one embodiment, bacteriophage or transposon insertion sequences may be used.

In certain embodiments of the present invention, one or more selectable markers can be included in the expression vector to allow for the selection of the host cells that have been transformed. Selectable markers that can be expressed in a host cell include genes that can render the host cell resistant to drugs such as tunicamycin, G418, ampicillin, chloramphenicol, erythromycin, kanamycin (neomycin), and tetracycline. Selectable markers also include biosynthetic genes, such as those in the histidine, tryptophan, and leucine biosynthetic pathways, such as ade2, his4, leu2, trp1, or that provide the host cells with the ability to grow in the presence of toxic compounds, such as a metal, may be used.

A variety of methods may be used to transfer a polynucleotide encoding for FKBP-L polypeptide and/or a nucleic acid encoding FKBP-L anti-sense DNA or FKBP-L siRNA into host cells. Thus, the formulations of the present invention may comprise specific components that facilitate transfer of nucleic acids into cells.

For example, to allow for the introduction of nucleic acids in a eukaryotic and/or prokaryotic cell by transfection, transformation or infection, the nucleic acid can be present as a plasmid, as part of a viral or non-viral vector. Suitable viral vectors may include baculoviruses, vaccinia viruses, lentiviruses (see e.g., Siprashvili and Khavari, *Mol. Ther.*, 2004, 9, 93-100), adenoviruses, adeno-associated viruses and herpesviruses. Examples of vectors having gene therapy activity are virus vectors, for example adenovirus vectors or retroviral vectors (Lindemann et al., 1997, *Mol. Med.*, 3, 466-76; Springer et al., 1998, *Mol. Cell.*, 2, 549-58). Also, eukaryotic expression vectors are suitable in isolated form for gene therapy use as naked DNA can penetrate certain cells (Hengge et al., 1996, *J. Clin. Invest.*, 97, 2911-6; Yu et al., 1999, *J. Invest. Dermatol.*, 112, 370-5). Another form of gene therapy vectors can be obtained by applying the above described nucleic acid to gold particles and shooting these into tissue, preferably into the skin, or cells with the aid of the so-called gene gun (Wang et al., 1999, *J. Invest. Dermatol.*, 112, 775-81, Tuting et al., 1998, *J. Invest. Dermatol.*, 111, 183-8).

In alternate embodiments, liposomes may be used to facilitate transfer of a polynucleotide encoding FKBP-L into cells. Liposomes are artificially-made small vesicles with a lipid bilayer membrane comprised of phospholipids (Jeschke, M. G. et al., *Gene Ther.*, 12, 1718-24 (2005); U.S. Pat. No. 6,576,618). Nucleic acids, proteins, and other biological materials can be enclosed in liposomes for delivery to mammalian cells through fusion with the cell's plasma membrane. Liposomes may be an attractive delivery system because they are non-viral, stable and can interact with the cell membrane.

Liposomes can be comprised of cationic, anionic, or neutral lipids, and mixtures thereof (Luo, D. & Saltzman, W. M., *Nat. Biotech.*, 18, 33-37 (1999)). For DNA transfer, the lipids can also be modified chemically to incorporate chemical groups to facilitate DNA condensation or release. Cationic lipids, such as quaternary ammonium detergents, cationic derivatives of cholesterol and diacylglycerol, and lipid derivatives of polyamines, may be favored for cell transfection because they decrease the net negative charge of the DNA and facilitate its interaction with cell membranes (Nishikawa, M. & Huang, L., *Hum. Gene Ther.*, 12, 861-70 (2001)). Neutral lipids, such as dioleoylphosphityletha-nolamine (DOPE), glycerol dilaurate, polyoxyethylene-10-stearyl ether (POE-10), and cholesterol, may be added as 'helper lipids' in cationic-lipid DNA complexes to facilitate the release of the DNA from the endosome after endocytic uptake of the complex. Auxiliaries that increase DNA transfer, such as polymers or proteins that are bound to the DNA or synthetic peptide-DNA molecules that make it possible to transport DNA into the nucleus of the cell more efficiently can also be used (see e.g., Niidome, T. & Huang, L., *Gene Ther.*, 9, 1647-52 (2002)). Thus, cationic polymers, such as polylysine or protamine, can be used in lipid-DNA complexes as they cause tight condensation of DNA, which prevents complex aggregation and nuclease degradation. For example, mixing 1,2-dioleoyl-3-(trimethylammonium)propane) (DOTAP) liposomes with protamine sulfate prior to mixing with plasmid DNA produced small 135 nm particles that were stable and resulted in a high level of gene expression in a variety of tissues (e.g., lung., liver, heart) (Li, S. et al., *Gene Ther.*, 5, 930-37 (1998)). Inclusion of cholesterol as a helper lipid may increase the transfection efficiency of liposome-peptide-DNA complexes. Also, luciferase or β-galactosidase gene DNA may be precompacted with short peptides derived from human histone or protamine before addition of a cationic lipid (Lipofectamine RPR 115335 or RPR 120535) or polymer (polyethylenimine) to achieve enhanced transfection efficiency, even in the presence of serum (see e.g., Schwartz, B. et al., *Gene Ther.*, 6, 282-92 (1999)).

As is known in the art, liposomes may be made by heating lipids to form a lipid phase (Wu, H. et al., *Int. J. Pharmaceut.*, 221, 23-24 (2001)). An aqueous phase containing water, salts or buffer may then be mixed with the lipid phase by passing the mixture back and forth between syringes under cooling conditions, followed by sonication until a final liposome size of 100 to 140 nm is reached. The DNA or protein to be included in the liposome is then added (as a solution) by inversion mixing. The choice of lipids used, their ratio, the concentration of DNA used in creating the liposomes and the amount of liposomes added will generally require empirical determination for optimization. Auxiliaries to facilitate DNA transfer, such as peptides, can be mixed with the DNA prior to adding to the liposome mixture but the DNA-auxiliary must maintain sufficiently high aqueous solubility to be properly encapsulated within the external lipid phase of the liposome.

Alternatively, small unilamellar vesicles can be prepared by ultrasonic treatment of a liposome suspension comprised of cationic lipids, such as Cytofectin GS 2888, mixed with 1,2-dioleyloxypropyl-3-trimethylammonium bromide (DOTMA) or dioleoylphosphati-dylethanolamine bromide (DPOE). After inversion mixing, the DNA or protein may be bound ionically to the surface of the liposomes, in a ratio that maintains a positive net charge on the complex while having DNA complexed to 100% of the liposomes. Also, dimerizable cationic thiol detergents may be used to prepare liposomes for delivery of DNA (see e.g., Dauty, E. et al., *J. Am. Chem. Soc.*, 123, 9227-34 (2001)). Upon oxidation, the thiol groups in the lipid can convert to disulfides and cause the DNA-lipid complex to form a stable nanometric particle that can bind electrostatically to cell surface anionic heparin sulfate proteoglycans for cellular uptake. Once inside the cell, the reductive environment provided by intracellular glutathione reduces the disulfides back to thiols and releases the DNA.

Therapeutic Antibodies

In another embodiment the invention relates to therapeutic use of an antibody having immunological specificity for FKBP-L (or fragments or functional equivalents thereof, as discussed below) to specifically down-regulate the activity of FKBP-L in vivo. Such antibodies are useful in the treatment of disease conditions which benefit from specific down-regulation of FKBP-L activity, in particular diseases/conditions which benefit from stimulation/up-regulation of angiogenesis. In specific embodiments the invention encompasses use of an antibody having immunological specificity for FKBP-L (or a fragment or functional equivalent thereof) to promote angiogenesis. An embodiment relates to use of an antibody having immunological specificity for FKBP-L (or a fragment or functional equivalent thereof) to promote wound healing.

The term "antibody" as used herein encompasses purified or isolated naturally occurring antibodies of any isotype having the required immunological specificity, as well as synthetically produced antibodies or structural analogs thereof. Preparations of antibody can be polyclonal or monoclonal. Reference to such an "antibody" as described above includes not only complete antibody molecules, but also fragments thereof which retain substantial antigen (i.e. FKBP-L) binding capability. It is not necessary for any effector functions to be retained in such fragments, although they may be included. Suitable antibody fragments which may be used include, inter alia, F(ab')$_2$ fragments, scAbs, Fv, scFv fragments and nanoantibodies etc. Antibody fragments which contain the idiotype of the molecule can be generated by known techniques, for example, such fragments include but are not limited to the F(ab')2 fragment which can be produced by pepsin digestion of the antibody molecule; the Fab' fragments which can be generated by reducing the disulfide bridges of the F(ab')2 fragments and the Fab fragments which can be generated by treating the antibody molecule with papain and a reducing agent. Other antibody fragments with the required antigen binding activity can be prepared by recombinant expression techniques generally known in the art.

Chimeric humanized and fully humanized monoclonal antibodies can be made by recombinant engineering. By addition of the human constant chain to F(ab')2 fragments it is possible to create a humanized monoclonal antibody which is useful in immunotherapy applications where patients making antibodies against the mouse Ig would otherwise be at a disadvantage. Breedveld F. C. Therapeutic Monoclonal Antibodies. Lancet 2000 Feb. 26; 335, P 735-40. Recombinant therapeutic monoclonal antibodies may be advantageously prepared by recombinant expression in mammalian host cells (e.g. CHO cells).

Monoclonal antibodies with immunological specificity for FKBP-L can be prepared by immunisation of a suitable host animal (e.g. mouse or rabbit) with a suitable challenging antigen (e.g. full length FKBP-L or an epitope thereof).

Therapeutic Uses

The polypeptides and nucleic acids of and for use in the invention may be used in the control and/or treatment of a wide variety of clinical conditions in mammals, including humans. The polypeptides and methods of the invention may be used in the treatment of a condition or disorder for which anti-angiogenic or pro-angiogenic agents may be therapeutically useful.

As used herein, "treatment" or "therapy" includes any regime that can benefit a human or non-human animal. The treatment may be in respect of an existing condition or may be prophylactic (preventative treatment). Treatment may include curative, alleviation or prophylactic effects.

Cell migration, angiogenesis and related indications (e.g., tumor growth and/or metastasis) can be inhibited by administering an effective amount of a FKBP-L polypeptide or a nucleic acid encoding said peptide to a patient in need of such treatment. The methods can be used to treat tumors, various autoimmune disorders, hereditary disorders, ocular disorders and other angiogenesis-mediated or angiogenesis-associated disorders.

Alternatively, angiogenesis may be promoted by administering an antisense FKBP-L nucleic acid (e.g., siRNA) or antibodies to FKBP-L to a patient in need of such treatment. The methods could be used to treat wound healing, including that of most tissues such as skin and bone and the treatment of chronic ulcers (diabetic or otherwise).

The therapeutic and diagnostic methods described herein typically involve administering an effective amount of the peptides, nucleic acids or compositions including the polypeptide or nucleic acid of the invention to a patient. The exact dose to be administered will vary according to the use of the compositions and on the age, sex and condition of the patient, and can readily be determined by the treating physician. The compositions may be administered as a single dose or in a continuous manner over a period of time. Doses may be repeated as appropriate.

The compositions and methods can be used to treat angiogenesis-mediated disorders including haemangioma, solid tumors, leukemia, lymphoma metastasis, telangiectasia, psoriasis, endometriosis, arteriosclerosis, scleroderma, pyogenic granuloma, myocardial angiogenesis, Crohn's disease, plaque neovascularisation, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularisation, macular degeneration, peptic ulcer, Helicobacter related diseases, fractures, keloids, and vasculogenesis. Specific disorders that can be treated, and compounds and compositions useful in these methods, are described in more detail below.

Carcinomas/Tumors

Tumors that may be treated include those tumors whose growth is promoted by angiogenesis. In one embodiment such tumors may express CD44. Carcinomas that may be treated using the compounds, compositions and methods of the invention may include colorectal carcinoma, gastric carcinoma, signet ring type, oesophageal carcinoma, intestinal type, mucinous type, pancreatic carcinoma, lung carcinoma, breast carcinoma, renal carcinoma, bladder carcinoma, prostate carcinoma, testicular carcinoma, ovarian carcinoma, endometrial carcinoma, thyroid carcinoma, liver carcinoma, larynx carcinoma, mesothelioma, neuroendocrine carcinomas, neuroectodermal tumors, melanoma, gliomas, neuroblastomas, sarcomas, leiomyosarcoma, MFII, fibrosarcoma, liposarcoma, MPNT, and chondrosarcoma.

For treatment of cancer, FKBP-L may be administered with other chemotherapeutic and/or chemopreventative agents known in the art. Such agents may include, but are not limited to antiangiogenics, endostatin, angiostatin and VEGF inhibitors, thalidomide, and others, or cytotoxic drugs such as adriamycin, daunomycin, cis-platinum, etoposide, taxol, taxotere and alkaloids, such as vincristine, farnesyl transferase inhibitors, and antimetabolites such as methotrexate. In alternate embodiments, FKBP-L peptides or polynucleotides encoding FKBP-L polypeptides may be used with cancer therapeutics such as the following: (a) cancer growth inhibitors including, but not limited to bortezomib, erlotinib, gefitinib, imatinib and sorafenib; (b) gene therapy approaches, e.g., using nucleic acid constructs that encode tumor suppressor gene or siRNAs to oncogenes; (c) cancer vaccines; (d) interferon; (e) Aldesleukin; (f) monoclonal antibodies including, but not limited to 90Y-Ibritumomab tiuxetan, ADEPT, Alemtuzumab, Bevacizumab, Cetuximab, Gemtuzumab, Iodine 131 tositumomab, Panitumumab, Rituximab, Trastuzumab; (g) chemotherapy drugs including, but not limited to Amsacrine, Bleomycin, Busulfan, Capecitabine, Carboplatin, Carmustine, Chlorambucil, Cisplatin,Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Gliadel implants, Hydroxycarbamide, Idarubicin, Ifosfamide, Irinotecan, Leucovorin, Liposomal doxorubicin, Liposomal daunorubicin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Teniposide, Thiotepa, Tioguanine, Topotecan, Treosulfan, Vinblastine, Vincristine, Vindesine, and Vinorelbine; (h) radiotherapy; (i) hormonal therapies including, but not limited to Anastrozole, Bicalutamide, Buserelin, Cyproterone, Diethylstilbestrol, Exemestane, Flutamide, Fulvestrant, Goserelin (Breast), Goserelin (Prostate), Letrozole, Leuprorelin, Medroxyprogesterone, Megestrol acetate, Tamoxifen, Toremifene, and Triptorelin; (j) supportive therapies including, but not limited to bisphosphonates, blood transfusions, Erythropoietin, haematopoietic, growth factors, plasma exchange, platelet transfusions and steroids; and (k) other treatments including, but not limited to hyperbaric oxygen therapy, hyperthermia treatment, and photodynamic therapy. Such therapies may be used with FKBP-L treatment either alone or as complementary therapies.

Ocular Disorders Mediated by Angiogenesis

Various ocular disorders are mediated by angiogenesis, and may be treated using the active compounds, compositions and methods described herein. One example of a disease mediated by angiogenesis is ocular neovascular disease, which is characterized by invasion of new blood vessels into the structures of the eye and is the most common cause of blindness. In age-related macular degeneration, the associated visual problems are caused by an ingrowth of chorioidal capillaries through defects in Bruch's membrane with proliferation of fibrovascular tissue beneath the retinal pigment epithelium. In the most severe form of age-related macular degeneration (known as "wet" ARMD) abnormal angiogenesis occurs under the retina resulting in irreversible loss of vision. The loss of vision is due to scarring of the retina secondary to the bleeding from the new blood vessels. Current treatments for "wet" ARMD utilize laser based therapy to destroy offending blood vessels. However, this treatment is not ideal since the laser can permanently scar the overlying retina and the offending blood vessels often re-grow. An alternative treatment strategy for macular degeneration is the use of anti-angiogenesis agents to inhibit the new blood vessel formation or angiogenesis which causes the most severe visual loss from macular degeneration.

Angiogenic damage is also associated with diabetic retinopathy, retinopathy of prematurity, corneal graft rejection, neovascular glaucoma and retrolental fibroplasia. Other diseases associated with corneal neovascularisation include, but are not limited to, epidemic keratoconjunctivitis, Vitamin A deficiency, atopic keratitis, superior limbic keratitis, pterygium keratitis sicca, periphigoid radial keratotomy, and corneal graph rejection. Diseases associated with retinal/choroidal neovascularization include, but are not limited to, diabetic retinopathy, macular degeneration, presumed myopia, optic pits, chronic retinal detachment, hyperviscosity syndromes, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Thus, in certain embodiments of the invention, the active compounds, compositions and methods of the invention may be used in the treatment of angiogenesis-mediated ocular disorders, for example, macular degeneration.

Inflammation

The FKBP-L polypeptides may also be used to treat angiogenesis-mediated disorders, such as angiogenesis-associated inflammation, including various forms of arthritis, such as rheumatoid arthritis and osteoarthritis. In these methods, treatment with combinations of the compounds described herein with other agents useful for treating the disorders, such as cyclooxygenase-2 (COX-2) inhibitors, which are well known to those of skill in the art.

The blood vessels in the synovial lining of the joints can undergo angiogenesis. The endothelial cells form new vascular networks and release factors and reactive oxygen species that lead to pannus growth and cartilage destruction. These factors are believed to actively contribute to rheumatoid arthritis and also to osteoarthritis. Chondrocyte activation by angiogenic-related factors contributes to joint destruction, and also promotes new bone formation. The methods described herein can be used as a therapeutic intervention to prevent bone destruction and new bone formation.

Pathological angiogenesis is also believed to be involved with chronic inflammation. Examples of disorders that can be treated using the compounds, compositions and methods described herein include ulcerative colitis, Crohn's disease, bartonellosis, and atherosclerosis.

Combination Therapies

In treating a specific disease using a polypeptide, nucleic acid or method of the invention, in the treatment of a specific disease, the peptides or nucleic acids may be combined with various existing therapeutic agents used for that disease.

The combination of FKBP-L polypeptides as described herein with an anti-histamine ($H_1$ antagonist) can be particularly favoured for use in the prophylaxis and treatment of asthma and rhinitis. Examples of anti-histamines are chlorpheniramine, brompheniramine, clemastine, ketotifen, azatadine, loratadine, terfenadine, cetirizine, astemizole, tazifylline, levocabastine, diphenhydramine, temelastine, etolotifen, acrivastine, azelastine, ebastine, mequitazine, KA-398, FK-613, mizolastine, MDL-103896, levocetirizine, mometasone furoate, DF-1111301, KC-11404, carebastine, ramatroban, desloratadine, noberastine, selenotifen, alinastine, E-4716, efletirizine, tritoqualine, norastemizole, ZCR-2060, WY-49051, KAA-276, VUF-K-9015, tagorizine, KC-11425, epinastine, MDL-28163 terfenadine, HSR-609, acrivastine and BMY-25368.

Additionally or alternatively, the polypeptides of the invention may advantageously be employed in combination with one or more other therapeutic agents, including an antibiotic, anti-fungal, anti-viral, anti-histamine, non-steroidal anti-inflammatory drug or disease modifying anti-rheumatic drug.

In other embodiments, for treating rheumatoid arthritis, the FKBP-L polypeptides may be combined with agents such as TNF-alpha inhibitors, for example, anti-TNF monoclonal antibodies (such as Remicade, CDP-870 and $D_2 E_7$) and TNF receptor immunoglobulin molecules (such as Enbrel®), COX-2 inhibitors (such as meloxicam, celecoxib, rofecoxib, valdecoxib and etoricoxib) low dose methotrexate, leflunomide, hydroxychloroquine, d-penicillamine, auranofin or parenteral or oral gold.

In yet other embodiments, the FKBP-L polypeptides may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The FKBP-L polypeptides may also be used in combination with anticancer agents such as antiangiogenics, endostatin, angiostatin and VEGF inhibitors and others, or cytotoxic drugs such as adriamycin, daunomycin, cis-platinum, etoposide, taxol, taxotere and alkaloids, such as vincristine, farnesyl transferase inhibitors, and antimetabolites such as methotrexate. Other anti-cancer agents and therapeutic methods such as a cancer growth inhibitor, gene therapy, a cancer vaccine, interferon, Aldesleukin, a monoclonal antibody, a chemotherapy drug, radiotherapy, hormonal therapy or other supportive therapies that may be used with FKBP-L are described herein.

Additionally or alternatively, the FKBP-L polypeptides may also be used in combination with antiviral agents such as Viracept, AZT, aciclovir and famciclovir, and antisepsis compounds such as Zovant, tifacogin, NOX-100 and 13R270773.

The FKBP-L polypeptides may also be used in combination with anti-osteoporosis agents such as roloxifene, droloxifene, lasofoxifene or fosomax and immunosuppressant agents such as FK-506 and rapamycin.

The FKBP-L polypeptides may also be combined with one or more of the following: (a) leukotriene biosynthesis inhibitors: 5-lipoxygenase (5-LO) inhibitors and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2alkylsulfonamides, 2,6-di-tert-butylphenol hydrazones; the class of methoxytetrahydropyrans which includes Zeneca ZD-2138; the compound SB-210661 and the class to which it belongs; the class of pyridinyl-substituted 2-cyanonaphthalene compounds to which L-739,010 belongs; the class of 2-cyanoquinoline compounds to which L-746,530 belongs; the classes of indole and quinoline compounds to which MK-591, MK-886, and BAY X 1005 belong; (b) receptor antagonists for leukotrienes $LTB_4$, $LTC_4$, $LTD_4$, and $LTE_4$ selected from the group consisting of the phenothiazin-3-one class of compounds to which L-651,392 belongs; the class of amidino compounds to which CGS-25019c belongs; the class of benzoxaolamines to which ontazolast belongs; the class of benzenacarboximidamides to which BIIL 2841260 belongs; and the classes of compounds to which zafirlukast, ablukast, montelukast, praniukast, verlukast (MK-679), RG-12525, Ro-2459913, iralukast (CGP 45715A), and BAY X 7195 belong; (c) PDE4 inhibitors including inhibitors of the isoform PDE4D; (d) 5-Lipoxygenase (5-LO) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of $LTB_4$, $LTC_4$, $LTD_4$, and $LTE_4$ ; (g) antihistaminic $H_1$ receptor antagonists including cetirizine, loratadine, desloratadine, fexofenadine, astemizole, azelastine, and chlorpheniramine; (h) gastroprotective $H_2$ receptor antagonists; (i) alpha$_1$- and alpha$_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (j) alpha$_1$- and alpha$_2$-adrenoceptor agonists in combination with inhibitors of 5-lipoxygenase (5-LO); (k) anticholinergic agents including ipratropium bromide; tiotropium bromide; oxitropium bromide; pirenzepine; and telenzepine; (I) [3- to beta$_4$-adrenoceptor agonists including metaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate;

(o) muscarinic receptor (M1, M2, and M3) antagonists; (p) COX-1 inhibitors (NTHEs); COX-2 selective inhibitors including rofecoxib; and nitric oxide NTHEs; (q) insulin-like growth factor type I (IGF-1) mimetics; (r) cicleso-nide; (s) inhaled glucocorticoids with reduced systemic side effects, including prednisone, prednisolone, flunisolide, tri-amcinolone acetonide, beclomethasone dipropionate, budes-onide, fluticasone propionate, and mometasone furoate; (t) tryptase inhibitors; (u) platelet activating factor (PAF) antagonists; (v) monoclonal antibodies active against endog-enous inflammatory entities; (w) IPL 576; (x) anti-tumor necrosis factor (TNF-alpha) agents including Etanercept, Infliximab, and D2E7; (y) DMARDs including Lefluno-mide; (z) TCR peptides; (aa) interleukin converting enzyme (ICE) inhibitors; (bb) IMPDH inhibitors; (cc) adhesion molecule inhibitors including VLA-4 antagonists; (dd) cathepsins; (ee) MAP kinase inhibitors; (ff) glucose-6 phos-phate dehydrogenase inhibitors; (hh) gold in the form of an aurothio group together with various hydrophilic groups; (ii) immunosuppressive agents, e.g., cyclosporine, azathioprine, and methotrexate; (jj) anti-gout agents, e.g., colchicine; (kk) xanthine oxidase inhibitors, e.g., allopurinol; (ll) uricosuric agents, e.g., probenecid, sulfinpyrazone, and benzbroma-rone; (mm) antineoplastic agents, especially antimitotic drugs including the vinca alkaloids such as vinblastine and vincristine; (nn) growth hormone secretagogues; (oo) inhibi-tors of matrix metalloproteases (MMPs), i.e., the stromely-sins, the collagenases, and the gelatinases, as well as aggre-canase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11); (pp) transforming growth factor (TGFP); (qq) platelet-de-rived growth factor (PDGF); (rr) fibroblast growth factor, e.g., basic fibroblast growth factor (bFGF); (ss) granulocyte macrophage colony stimulating factor (GM-CSF); (tt) cap-saicin cream; (uu) Tachykinin NK, and NK$_3$ receptor antago-nists selected from the group consisting of NKP-608C; SB-233412 (talnetant); and D-4418; and (vv) elastase inhibi-tors selected from the group consisting of UT-77 and ZD-0892.

Wound Healing

Angiogenesis is an important step in wound healing. Use of antisense and/or siRNA and/or inhibitory antibodies to the FKBP-L polypeptide of the invention as described herein-before may be used either on its own or in combination with other therapies to promote wound healing.

Thus, embodiments of the invention also encompasses combinations of at least one of the FKBP-L compound described herein with at least one other agent useful for treating wounds. Such agents can be selected amongst bioactive compounds involved in wound healing such as growth factors, cytokines inhibitors, proteases and adhesion molecules which are well known to those of skill in the art and described for example in Kumar et al. Turk J Med Sci, 34 (2004) 147-160. For example suitable growth factors can be chosen in group consisting of TGFβ and its isoforms, PDGF, KGF, VEGF and EGF which are factors known for their importance in wound healing. FKBP-L polypeptides and derivatives can also be associated with matrix metallo-proteases or adhesion molecules like the immunoglobulin-like superfamily, the cadherins, the integrins, the receptor protein tyrosine phosphatases, the selectins and the hyaluro-nate receptors.

Alternatively or in combination with any of the wound healing compositions described above, other agents known to promote wound healing such as disinfectants, antibiotics and the like may also be used with the compounds of the invention.

In certain embodiments, anti-sense oligonucleotides, as described in more detail herein, may be used in the methods and compositions for wound healing.

Also, anti-sense FKBP-L oligonucleotides, FKBP-L siR-NAs or antibodies to FKBP-L may be applied alone or in combination with the above active ingredients may be applied topically as a powder or as a solution or dispersion and use for the manufacture of a wide variety of dressings. Such dressings may be classical dressings such as cotton or cellulosic fibres and deposited as a coating or coatings on base materials such as cellulose or cellulose acetate or nylon or regenerated cellulose, or plastic base materials, either woven or non-woven in sheet form, perforated or imperfo-rate. The antibodies to FKBP-L polypeptide may be bonded to a suitable base material, e.g., cotton gauze, plastic sheet, etc, using an appropriate adhesive formulation, e.g., pectin, gelatin, starch, innocuous vegetable gums, etc according to known procedures like that disclosed in U.S. Pat. No. 3,194,732. Alternatively the FKBP-L antibodies of the invention can be associated to more elaborate types of wounds dressings like moisture-retaining and semi-occlu-sive dressings which promote a moist environment benefi-cial to wound healing.

Anti-Sense and siRNA Oligonucleotide Therapeutics

A. Antisense RNA

As described above, the present invention may comprise an antisense nucleic acid molecule or an antisense oligo-nucleotide as therapeutic agents. In an embodiment, the antisense oligonucleotide may comprise an inhibitor RNA (e.g., RNAi or siRNA).

Antisense oligonucleotides are short fragments of DNA or RNA that have complementary sequences to a portion of, or to all of, an mRNA. Being complementary to a particular target mRNA, antisense oligonucleotides bind specifically to that mRNA. It is known to chemically modify such antisense molecules to facilitate tight binding. When binding occurs, the ability of the mRNA to be read by the cell's translational machinery is inhibited, and synthesis of the protein that it encodes is blocked. Unlike a gene knockout, this inhibition may require the continuous presence of the antisense mol-ecule; thus, it is reversible and portion can design specific inhibitors of a gene of interest based only on knowledge of the gene sequence. In one embodiment, the invention pro-vides an isolated nucleic acid molecule which is antisense to the coding strand of a nucleic acid of the invention. In yet another embodiment, it is provided a nucleic acid molecule having a nucleotide sequence that is antisense to the coding strand of an mRNA encoding a polypeptide of the invention.

The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the inven-tion. The non-coding regions ("5' and 3' untranslated regions") are the 5' and 3' sequences which flank the coding region and are not translated into amino acids.

An antisense oligonucleotide can be, for example, about 5, 10, 15, 18, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-predicted N-2-carboxyp uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). The antisense nucleic acid molecules of the invention can typically be administered to a patient. Alternatively it could be generated in situ such that they hybridize with or bind to cellular mRNA and/or genomic DNA encoding a selected polypeptide of the invention to thereby inhibit expression, e.g., by inhibiting transcription and/or translation.

The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. To achieve sufficient intracellular concentrations of the antisense molecules, vector constructs in which the antisense nucleic acid molecule is placed under the control of a strong pol II or pol III promoter are preferred.

Oligonucleotides containing natural sugars (D-ribose and D-2-deoxyribose) and phosphodiester (PO) linkages are rapidly degraded by serum and intracellular nucleases, which limits their utility as effective therapeutic agents. Chemical strategies to improve nuclease stability include modification of the sugar moiety, the base moiety, and/or modification or replacement of the internucleotide phosphodiester linkage. To date, the most widely studied analogues are the phosphorothioate (PS) oligodeoxynucleotides, in which one of the non-bridging oxygen atoms in the phos-phodiester backbone is replaced with a sulfur (Eckstein, F. Ann. Rev. Biochem. 1985, 54,367). An exemplary antisense targeting FKBP-L suitable for use in the methods of the invention is described by Robson et al. (See Robson et al., (1999) *Radiation Research* 152, 451-461; Robson, T., et al., (2000) *Int. J. Radiat*).

B. siRNAs

In certain embodiments, siRNAs to FKBP-L may be used as therapeutic agents. Small interfering RNAs (siRNAs) are powerful tools for directed post-transcriptional gene expression knockdown in mammalian cells (Elbashir et al., Duplexes of 21-nucleotide RNAs mediate RNA interference in cultured mammalian cells. Nature. 2001, 411: 494-8).

siRNAs typically comprise a double-stranded target-specific region which corresponds to the target gene to be down-regulated (i.e. FKBP-L). This double-stranded target-specific region typically has a length in the range of from 19 to 25 base pairs. In specific, non-limiting embodiments, siRNAs having a double-stranded target-specific region of 19, 20, 21, 22, 23, 24 or 25 base pairs corresponding to the target gene to be down-regulated (FKBP-L) may be used.

The target-specific region typically has a sequence 100% complementary to a portion of the target gene (FKBP-L). However, it will be appreciated that 100% sequence identity is not essential for functional RNA inhibition. RNA sequences with insertions, deletions, and single point mutations relative to the target sequence have also been found to be effective for RNA inhibition. The term "corresponding to", when used to refer to sequence correspondence between the target-specific part of the siRNA and the target region of the target gene (FKBP-L), is therefore to be interpreted accordingly as not absolutely requiring 100% sequence identity. However, the % sequence identity between the double-stranded RNA and the target region will generally be at least 90%, or at least 95% or at least 99%.

Therefore, in embodiments of the invention, siRNAs capable of specifically down-regulating expression of FKBP-L may include a double-stranded portion which comprises or consists of 19, 20, 21, 22, 23, 24 or 25 consecutive base pairs of the nucleotide sequence shown in SEQ ID NO:1, SEQ ID NO: 2, or SEQ ID NO:29, or a double-stranded portion of 19, 20, 21, 22, 23, 24 or 25 consecutive bases which is at least 90%, or at least 95%, or at least 99% identical to a portion of the nucleotide sequence shown in SEQ ID NO:1, SEQ ID NO:2, or SEQ ID NO:29, or which include one or two single nucleotide mismatches in comparison to a portion of the nucleotide sequence shown in SEQ ID NO:1 or SEQ ID NO:2.

The siRNA can be designed to target any suitable region of the FKBP-L mRNA transcript. Algorithms are available for siRNA design, based essentially on the characteristics of the primary sequence of the siRNA (eg Reynolds A, et al. Nat Biotechnol. 2004 March; 22(3):326-30. Epub 2004 Feb. 1.). An exemplary siRNA targeting FKBP-L suitable for use in the methods of the invention is described by Jascur et al. 2006, Molecular Cell, 17:237-239.

The term "down-regulation of gene expression" refers to a measurable or observable reduction in gene expression or a complete abolition of detectable gene expression, at the level of protein product and/or mRNA product from the target gene (e.g. FKBP-L). Down-regulation of gene expression is "specific" when down-regulation of the target gene (e.g. FKBP-L) occurs without manifest effects on other genes.

siRNAs may include single-stranded overhangs at one or both ends, flanking the double-stranded target-specific region corresponding to FKBP-L. In a particular embodiment, the siRNA may contain 3' overhanging nucleotides, such as two 3' overhanging thymidines (dTdT) or uridines (UU). 3' TT or UU overhangs may be included in the siRNA if the sequence of the target gene immediately upstream of the sequence included in double-stranded part of the dsRNA is AA. This allows the TT or UU overhang in the siRNA to hybridise to the target gene. Although a 3' TT or UU overhang may also be included at the other end of the siRNA it is not essential for the target sequence downstream of the sequence included in double-stranded part of the siRNA to have AA.

The double-stranded target-specific portion of the siRNA is typically formed from two annealed RNA strands comprised entirely of ribonucleotides in phosphodiester linkage. However, siRNAs which are RNA/DNA chimeras are also contemplated. These chimeras include, for example, the siRNAs comprising a double-stranded RNA with 3' overhangs of DNA bases (e.g. dTdT), as discussed above, and also double-stranded "RNAs" which are polynucleotides in which one or more of the RNA bases or ribonucleotides, or even all of the ribonucleotides on an entire strand, are replaced with DNA bases or deoxynucleotides. In other embodiments the backbone of the "RNA" strands in the siRNA may be modified, by inclusion of non-natural nucleobases and/or non-natural backbone linkages (see for example Soutschek et al. Nature. 2004 Nov. 11; 432(7014): 173-8; Zimmermann T S, et al. Nature 441, 111-4). By way of example, 2-O-methyl modifications may be included to stabilised the siRNAs (as described by Soutschek et al. ibid.).

The siRNA may be prepared in a manner known per se in the art. For example, siRNAs may be synthesised in vitro using chemical or enzymatic polynucleotide synthesis techniques well known in the art. In one approach the two separate strands of the siRNA may be synthesised separately and then annealed to form double-strands.

Unmodified "exogenous" siRNAs are known to be effective in gene silencing in vivo without the need for additional reagents (Filleur S, et al. Cancer Res 63, 3919-22; Duxbury M S, et al. Oncogene 23, 465-73). In other embodiments, siRNAs can be used in conjunction with carriers or delivery vehicles such as atelocollagen (Nozawa H, et al. Cancer Sci. 2006 October; 97(10):1115-24; Takeshita F, et al. Proc Natl Acad Sci USA. 2005 Aug. 23; 102(34):12177-82. Epub 2005 Aug. 9) or nanoparticles (Schiffelers R M, et al. Nucleic Acids Res. 2004 Nov. 1; 32(19):e149) or lipid-based carriers including, for example, oil-in water emulsions, micelles, and liposomes which promote uptake. Delivery vehicles (e.g. liposomes and nanoparticles) may be targeted to a particular tissue by coupling the vehicle to a specific ligand, such as a monoclonal antibody, sugar, glycolipid or protein.

In a further embodiment, rather than being formed of two separate RNA strands annealed together, the "siRNA" may have a foldback stem-loop or hairpin structure, wherein the annealed sequences forming the target-specific part of the siRNA are covalently linked. In one embodiment the annealed sequences may be present on a single RNA strand. RNAs having this structure are typical if the dsRNA is synthesised by expression in vivo or by in vitro transcription. The precise nature and sequence of the "loop" linking the two RNA strands is generally not material to the invention, except that it should not impair the ability of the double-stranded part of the molecule to mediate RNAi. The "loop" structure need not necessarily be formed from nucleic acid.

In one embodiment, siRNAs (or precursor structures which can be processed to produce siRNAs, for example by the action of the endogenous enzyme "dicer") may be synthesised by intracellular expression in a host cell or organism from a suitable expression vector.

A number of non-viral (e.g. plasmid) or viral expression vector systems for in vivo expression of siRNAs are known in the art. Generally, siRNAs are expressed as stem-loops, which may be rapidly processed within the cell to produce the "free" siRNA (see review by Tuschl, Nature Biotechnology, Vol. 20(5), 446-448, 2002). Vector systems for expression of siRNAs are often based on RNA Pol III promoters, since these are particularly suited to accurate expression of very short RNA sequences. Suitable vector systems are described in, for example, Brummelkamp, T. R. et al., Science, Vol. 296, 550-553, 2002; Lee, N. S. et al., Nature Biotechnology, Vol. 20, 500-505, 2002; Miyagashi, M & Taira, K. Nature Biotechnology, Vol. 20, 497-500, 2002; Paul, C. P. et al., Nature Biotechnology, Vol. 20, 505-508, 2002, the contents of which are incorporated herein by reference.

siRNAs may be formulated into pharmaceutical compositions comprising a therapeutically effective amount of the nucleic acid in combination with any standard physiologically and/or pharmaceutically acceptable carriers known in the art.

Targeting

Targeting therapies may be used to deliver the active agent e.g. polypeptide more specifically to particular tissues or cells, by using targeting systems such as antibody or cell specific ligands. These targeting systems can be covalently linked to the peptide sequence, or to a drug delivery vehicle (such as a liposome, microsphere, microparticle, microcapsule and the like). The polypeptides can also be targeted to growing tumor beds (which are associated with attached capillary beds) by incorporating the peptides into microparticles or other drug delivery vehicles that are suitably sized so that they pass through the veins but lodge in capillary beds. When lodged in the beds, the polypeptides can be locally released (rather than systemically released) at a location where they are most useful. As described above, the present invention further extends to methods of gene therapy using nucleotides of the invention.

In another embodiment, the FKBP-L peptides may be used to target cytotoxic agents to tumor cells. Thus, in an embodiment, the FKBP-L peptide may be conjugated to a cytotoxic agent using methods known in the art. The FKBP-L peptide may then, by interaction with CD44, deliver the cytotoxic agent to cells that express CD44. Where the cytotoxic agent is an agent that is able to preferentially inhibit tumor cell growth, the agent may be active againts CD44 +ve tumor cells.

Anti- or Pro-Angiogenesis Activity

Certain embodiments of the present invention may comprise assessment of angiogenic activity of the compositions of the invention. Angiogenic activity may be assessed by any means known in the art or as described herein. For example, angiogenesis activity may be assayed using any standard assays, such as the Matrigel assay and the assays used in the Examples.

EXAMPLES

The invention may be better understood by reference to the following non-limiting Examples. The designation "N" provides the number of individual experiments performed for the particular example.

Example 1

Transient Transfection of FKBP-L Inhibits Wound Closure (N=3)

Experiments were done to determine the effect of FKBP-L (SEQ ID NO: 1; FIG. 1) on wound closure. The in vitro migration assay used in these studies is a modified version of the method described by Ashton et al (1999) The J. of Biol. Chem., 1999, 274: 50, 35562-35570, . Human Microvascular Endothelial Cells (HMEC1) were plated into individual chambers on a glass slide and grown to 90% confluence.

The monolayer was transfected with a FKBP-L/pcDNA mammalian expression construct having an insert with the nucleotide sequence of SEQ ID NO: 31, in the presence of lipofectin (Invitrogen, UK). To make the expression construct, the nucleic acid fragment of SEQ ID NO: 31 was excised from a recombinant pUC18 construct using BamH1 and ligated into the BamH1 restriction site of pcDNA3.1 (Invitrogen).

Expression of the FKBP-L insert generates the full-length recombinant polypeptide in SEQ ID NO: 2. After 6 hours the transfection reagents were removed and the monolayer wounded with a pipette tip and re-supplemented with MCDB-131 and incubated for 7 hours.

The monolayer was fixed in 4% PBS buffered paraformaldehyde solution for 10 minutes. The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to the wound size at time zero.

Figure 4:
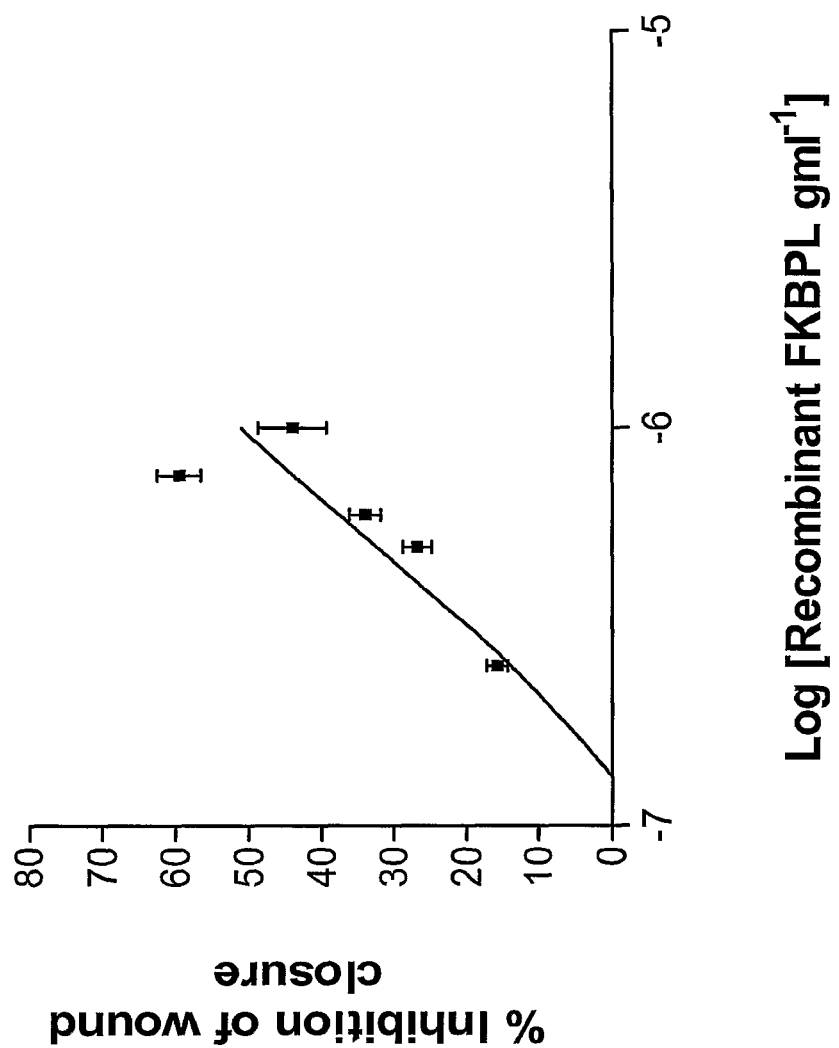
FIG. 4 illustrates a dose-response graph of the effect of a full length His-tagged FKBP-L recombinant polypeptide (SEQ ID NO: 1) on HMEC-1 migration in an in vitro wound closure assay in accordance with one embodiment of the present invention.

The results of these experiments are shown in FIG. 3. It was found that the transiently transfected FKBP-L produces a peptide equivalent to SEQ ID NO: 2 and significantly inhibited the ability of the HMEC-1 to migrate compared to lipofectin only and empty vector control. FKBP-L inhibits HMEC-1 migration by 50% compared to controls (Lipo— lipofectin reagients; pcDNA—vector only) at 7 hr following wounding. This data suggests that the FKBP-L protein is a potential anti-migratory protein.

Example 2

Full Length Recombinant FKBP-L Protein Inhibits Endothelial Cell Migration in the Wound Closure Assay (N=3)

The in vitro migration assay used in these studies is a modified version of the method described by Ashton et al (1999). HMEC-1 were plated into individual chambers on a glass slide and grown to 90% confluence overnight. The medium was removed and the monolayer wounded. The monolayer was re-supplemented with fresh medium and the required volume of recombinant full length his-tagged FKBP-L protein (SEQ ID NO: 1) was added to give the required final concentration.

In order to generate the recombinant full length FKBPL protein, the FKBPL cDNA (polynucleotide SEQ ID:31; polypeptide variant variant Thr182, Gly186; SEQ ID NO:1) was subcloned from pcDNA3.1/FKBPL into the BamHI and PstI sites of the pRSET-A vector (Invitrogen) and was expressed in BL21 (DE3) to give the corresponding N-terminal poly-histidine tagged (his-tag) protein (SEQ ID NO: 1). Expression was induced at OD 0.6 with 0.2 mM IPTG, growing cells overnight at 15° C. Cells were pelleted by centrifugation and stored at −20° C. The protein was purified using standard IMAC purification followed by desalting to remove any contaminating E. coli proteins (See example 32 for full description). The expressed recombinant protein has a calculated molecular weight of 38 kDa; the His-tagged FKBP-L which has a calculated molecular weight of 42220 Da was found to have a molecular weight of 42 kDa as ascertained by SDS polyacrylamide gel electrophoresis (SDS-PAGE).

The monolayers were incubated for 7 hours after exposure to recombinant FKBP-L protein and then fixed in 4% PBS buffered paraformaldehyde. The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to time matched sham treated controls and the % inhibition of wound closure compared to time matched controls calculated.

The results of these experiments are shown in FIG. 4. It can be seen that treatment with FKBP-L recombinant protein resulted in a significant inhibition of migration, with an optimum concentration of 750 ngml$^{-1}$ inducing a 60% inhibition of HMEC-1 migration into the denuded area of the monolayer compared to time matched controls. The findings from this experiment support the results observed with transiently transfected FKBP-L (FIG. 3).

The results also suggest that FKBP-L can inhibit endothelial cell migration when expressed intercellularly (as in the previous FIG. 3 using an expression construct) or extracellularly (i.e., by addition of recombinant protein to the tissue culture medium). This implied that either FKBP-L is inhibiting endothelial cell migration by two different mechanisms or that FKBP-L is secreted from the cell. As shown herein, FKBP-L is indeed secreted.

Example 3

FKBP-L Protein is Secreted from HMEC-1 Cells (N=1)

Human Microvascular Endothelial Cells (HMEC1) were plated onto 35 mm plastic culture plates and grown to 100% confluence. The monolayer was transfected with an haemagglutanin (HA)-tagged FKBP-L/pcDNA mammalian expression construct in the presence of lipofectin (Invitrogen, UK). This would result in expression of SEQ ID NO: 2 with a HA tag.

In order to generate the HA-tagged FKBPL plasmid, the FKBPL cDNA (polynucleotide SEQ ID NO:31; polypeptide variant variant Thr182, Gly186; SEQ ID NO:2) was excised from pUC18 by digestion with BamH1, blunt ended and directionally cloned into a blunt ended SalI site of pCMV-HA mammalian expression vector (Clontech, U.K.). This results in expression of SEQ ID NO: 2, with an N-terminal HA-tag to produce a 44 kDa protein.

After 6 hours the transfection reagents were removed and the monolayer wounded (controls were unwounded) with a pipette tip and re-supplemented with MCDB-131 and incubated for a further 7 hours. The medium was collected for analysis and the cells were then washed twice with PBS and harvested into 100 μl of 2× Laemmli buffer (Sigma) and heated to 100° C. for 10 minutes. Both cell lysates and culture medium were slot blotted onto nitrocellulose membrane and probed with monoclonal anti HA antibody (Clontech) (1:1000 dilution)in order to detect the HA-tagged FKBP-L protein, and then probed with rabbit Ig HRP-linked secondary antibody (1:7500 dilution) (Amersham Biosciences). Antibody binding was detected using SuperSignal® West Pico Chemiluminescent Substrate detection reagent (Pierce).

Figure 5:
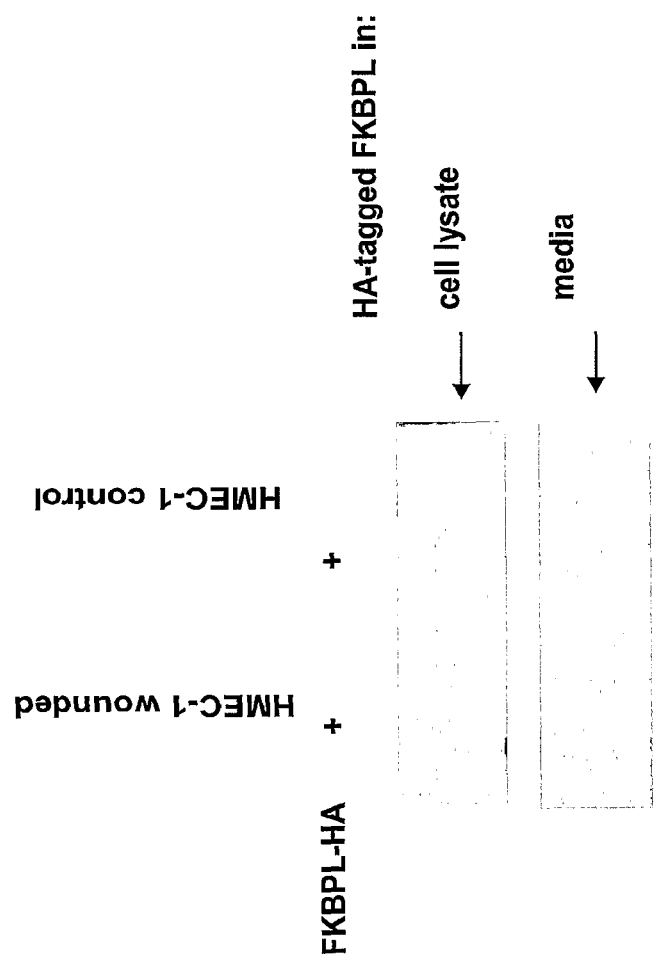
FIG. 5 illustrates that an Haemagglutanin (HA)-tagged full length FKBP-L polypeptide is actively secreted from HMEC-1 cells in accordance with one embodiment of the present invention.

The results are shown in FIG. 5. FIG. 5 is a slot/Western blot showing that transfection of an HA-tagged FKBP-L cDNA construct into either normal HMEC-1 monolayers or wounded monlayers results in secretion, into the medium, of the HA-tagged FKBP-L protein 24 h after transfection. Western blots were probed with an HA antibody.

These data indicate that under normal growth conditions FKBP-L protein is actively secreted, supporting the hypothesis that FKBP-L may be mediating its anti-angiogenic effects via receptor activation. The data also provides an explanation as to why either recombinant protein or overexpression using a cDNA construct are both able to exert anti-angiogenic effects observed both in vitro and in vivo.

Example 4

The Effect of the Full Length Recombinant Protein FKBP-L on the Wound Closure Assay Measured as a Function of Time (N=3)

The following studies were performed to determine the effect of a full length His-tagged recombinant FKBP-L protein on the wound closure assay measured as a function of time. Again, the in vitro migration assay used in these studies is a modified version of the method described by Ashton et al (1999). HMEC-1 were plated into individual chambers on a glass slide and grown to 90% confluence overnight. The medium was removed and the monolayer wounded. The monolayer was re-supplemented with fresh medium and the required volume of full length his-tagged recombinant FKBP-L (i.e., SEQ ID NO: 1) added to give the required final concentration 750 ngml$^{-1}$.

Slides were removed at fixed time points until complete closure of the wound, then fixed in 4% PBS buffered paraformaldehyde. The extent of "wound" closure was blindly assessed microscopically by an independent investigator and quantified using a calibrated eyepiece graticule (1 mm/100 µm graduation) at 20× magnification (Olympus BX 50). The extent of closure in the FKBP-L treated slides was compared to time matched sham treated controls and the % inhibition of wound closure compared to time matched controls calculated.

The results of these experiments are shown in FIG. 6. It can be seen that wound closure was overall significantly inhibited in the FKBP-L treated (750 ngml$^{-1}$) HMEC-1 cells compared to controls. 50% wound closure was observed in the control at 7 hours, whereas 50% wound closure in the FKBP-L treated monolayer was not observed until 16 hours after initial wounding, resulting in a significant delay of 9 hours. Total wound closure was observed at 16 hours in control experiments, in contrast to FKBP-L treated monolayers which remained open until 34 hours. These results indicate that the effect of a single administration of FKBP-L may be an extremely effective method of delaying wound closure in this in vitro model.

Example 5

The Effect of the Full-Length Recombinant Protein FKBP-L on the Formation of Endothelial Cell-to-Cell Contacts on the Synthetic Basement Membrane Matrigel (N=3)

In this experiment, the effect of the full length His-tagged recombinant FKBP-L protein (SEQ ID NO: 1) on the formation of endothelial cell-to-cell contacts was assessed. Samples were run in triplicate.

The in vitro tubule formation assay used in these studies is a modified version of the method described by Ashton et al (1999). In brief, assays were conducted using BD Bio-Coat™ Matrigel™ Matrix Thin Layer 24-well Multiwell Plates (BD Discovery Labware, Oxford, UK). The Matrigel™ was rehydrated with 500 µl MCDB-131 serum free medium and incubated at 37° C. for 30 minutes. Excess medium was removed and HMEC-1 were seeded at a density of 1×10$^5$ and the plates incubated at 37° C. under 5% $CO_2$/95% air for 1 hour.

Increasing concentrations of the recombinant FKBP-L protein (SEQ ID NO: 1) were added to each individual well in triplicate (250-1000 ngml$^{-1}$) and the plate was incubated for a further 18 hours. The degree of tubule formation between adjacent HMEC-1 cells was assessed in each well in five fields of view, by counting the number of cell to cell contacts between different HMEC-1 cells in the designated area. An independent investigator assessed each well and the FKBP-L treated wells were compared to sham treated controls.

Figure 7:
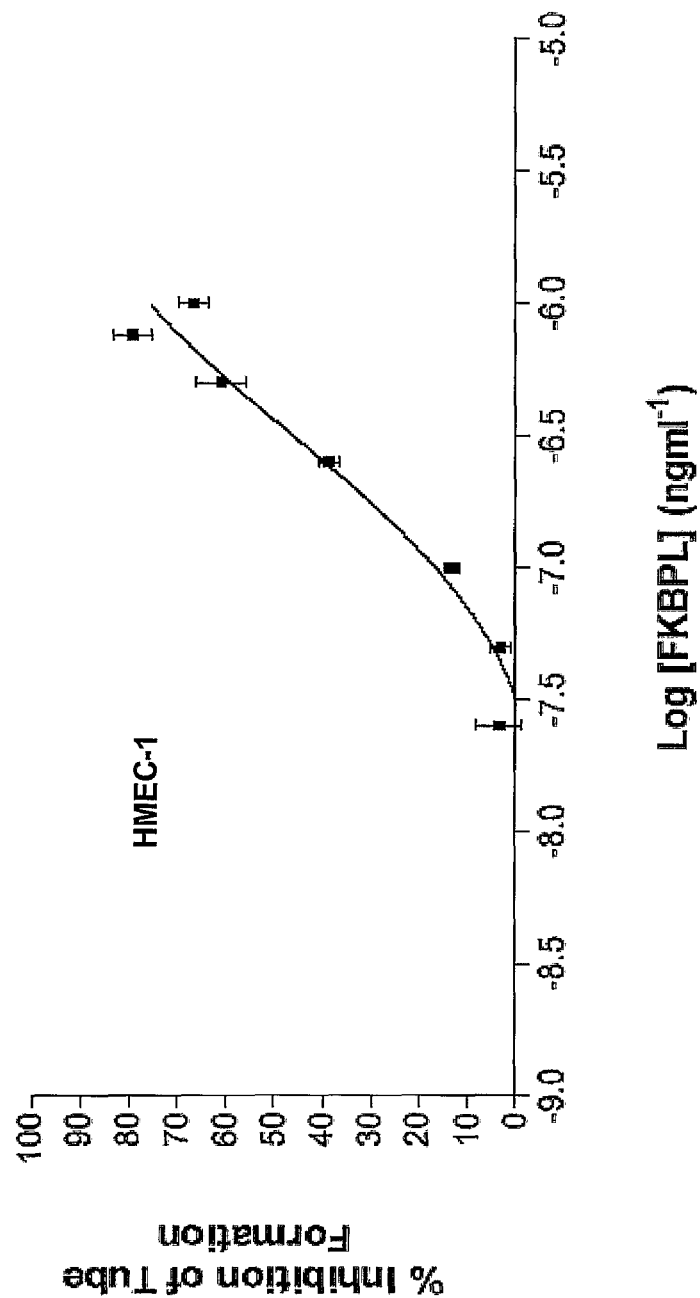
FIG. 7 illustrates a dose response graph of the effect of full length FKBP-L recombinant polypeptide on HMEC-1 tube formation on Matrigel matrix basement membrane in accordance with one embodiment of the present invention.

The results are shown in FIG. 7. It was found that recombinant FKBP-L protein inhibited the ability of the HMEC-1's to form cell to cell contacts or tubules on Matrigel in a dose dependent manner. The optimum concentration for this effect was 750 ngml$^{-1}$, with an efficacy of 80% and an EC50 potency of 314 ngml$^{-1}$. These results indicate that at these doses, FKBP-L is anti-angiogenic, preventing tube formation by HMEC-1 cells.

Example 6

The Effect of the Full Length Recombinant FKBP-L Polypeptide on Angiogenesis in Vivo using the Mouse Sponge Assay (N=1; Two Mice Per Group)

This experiment measured the effects of FKBP-L on angiogenesis using two other in vitro models, the mouse sponge assay, and the aortic ring model.

In these experiments, polyether sponges were subcutaneously implanted in C57 black mice and injected on alternate days with 10 ng bovine fibroblast growth factor (bFGF) or 10 ng bFGF+5 µg full length His-tagged recombinant FKBP-L polypeptide (SEQ ID NO: 1). After 14 days of treatment, sponges were harvested, sectioned and stained with heamatoxylin and eosin.

Figure 9:
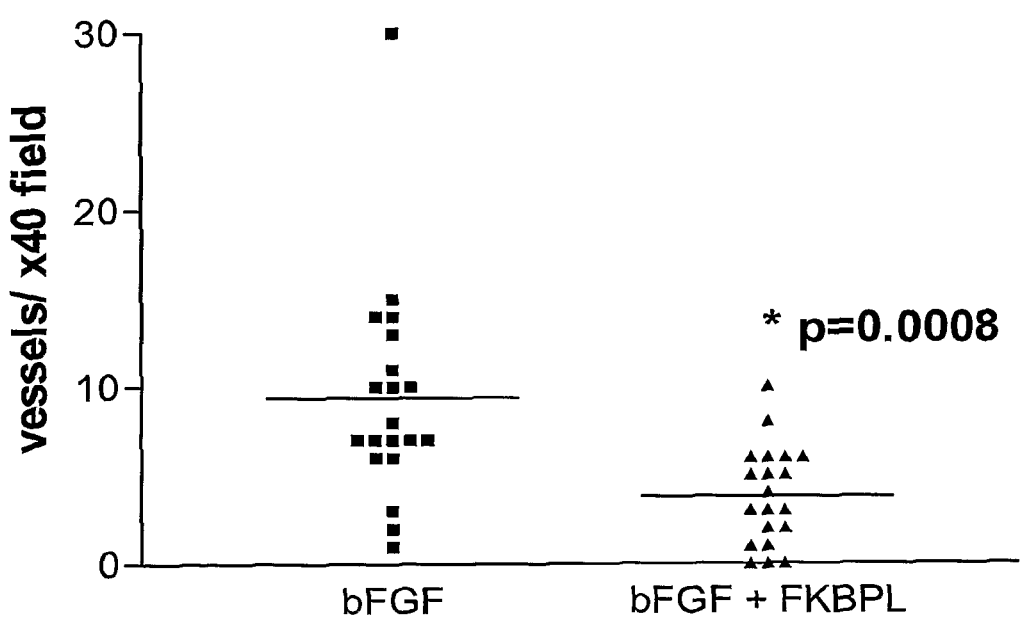
FIG. 9 shows a reduction in numbers of vessels seen upon treatment with bFGF and full length recombinant FKBP-L polypeptide (SEQ ID NO: 1) as compared to bFGF alone in accordance with alternate embodiments of the present invention.

The results are shown in FIGS. 8 and 9. In FIG. 8A, erythrocytes, which appear as dark gray cells and are indicated by arrows, can be seen within the microvessels of bFGF treated sponges. Also, it can be seen that there are large amounts of cellular ingrowth (appearing as light gray). Both the erythrocytes and cellular ingrowth are much less obvious in sponges also treated with FKBP-L (FIG. 8B). Vessel counts in sponges from 2 mice per group, counted in a blind fashion at 40× magnification are shown in FIG. 9. FKBP-L treated sponges had significantly fewer vessels than those treated with bFGF alone (p=0.0008).

The results indicate that the full-length recombinant FKBP-L polypeptide can inhibit angiogenesis in vivo, and that this polypeptide may have potential therapeutic value in a clinical setting.

Example 7

The Effect of Full-Length Recombinant FKBP-L Polypeptide on the Ex-Vivo Aortic Ring Explant Model of Angiogenesis, Investigating the Effect on Mean Length, Maximum Length and Number of Vessels Formed (N=3)

Male Wistar rats were euthanised and the thoracic aorta was aseptically removed and sectioned into 1 cm thick rings. The rings were washed ten times in sterile medium to remove any bacteria and embedded into Matrigel on 24 well plates. The wells were supplemented with 2 ml of medium and increasing concentrations of full-length His-tagged recombinant FKBP-L protein (SEQ ID 1). The plate was incubated for 8 days and post incubation the Matrigel and rings were fixed in 4% PBS buffered paraformaldehyde and stored in PBS. The extent of vessel development was blindly assessed microscopically by an independent investigator and quantified using a calibrated eyepiece graticule (1 mm/100 µm graduation) at 20× magnification (Olympus BX 50). The extent of vessel length, maximum vessel length and number of vessels in each field of view was measured and compared to time matched sham controls and the percent (%) inhibition calculated.

The results of these experiments are shown in FIG. 10. FKBP-L was seen to be a potent dose dependent inhibitor of angiogenesis in this ex-vivo model. The mean vessel length and maximum vessel length formed were significantly inhibited at 1000 ngml$^{-1}$ exhibiting 63% and 70% inhibition respectively compared to time matched controls. The number of vessels formed from the aortic explant was optimally inhibited by 65% following treatment with FKBL-L protein at 500 ngml$^{-1}$.

Example 8

The Effect of the Full Length Recombinant FKBP-L Polypeptide on the Viability or Proliferation of HMEC-1 using the MTT Assay (N=3)

These experiments assessed whether the antiangiogenic effects of full length FKBP-L protein were due to toxicity of the polypeptide. An MTT assay was used to measure cell viability/proliferation. Briefly, HMEC-1 cells were seeded (2.5×10$^3$) in 96 well plates and allowed to attach for 5 hours. The cells were treated with increasing concentrations of recombinant His-tagged FKBP-L protein (SEQ ID NO: 1) and incubated for 24 (FIG. 11A) and 48 hours (FIG. 11B). Post incubation the cells were exposed to a 5 mgml$^{-1}$ solution of 3-(-4,5-dimethylthiazol-2-yl) 2,5 diphenyl tetrazolium (MTT) for 4 hours. The cells were aspirated and 200 µl of DMSO added to reduce the salt and induce a colour change. The wells were analyzed colorimetrically at 550 nm and the results compared to untreated control cells. The experiment was repeated three times.

The results are shown in FIGS. 11A and 11B. It was found that FKBP-L had no significant effect on the proliferation of HMEC-1 cells compared to time matched controls at any of the time points measured, suggesting that the antiangiogenic effects observed in the previous assays were not caused by inhibition of cell growth or by FKBP-L-mediated toxicity.

Example 9

Changes in Cytoskeletal Morphology of Migrating Endothelial Cells on Exposure to 750 mgml$^{-1}$ Full Length Recombinant FKBP-L Polypeptide (N=2)

Immunohistochemical analysis was carried out to assess cytoskeletal morphology upon treatment with FKBP-L by staining for tubulin and vimentin. HMEC-1 were seeded in four well chamber slides and incubtated overnight until confluent monolayers had formed. Media was removed from each well and the monolayer wounded as previously described. The cells were re-supplemented with medium containing 750 ngml$^{-1}$ recombinant His-tagged FKBP-L protein (i.e., SEQ ID NO: 1). The cells were incubated for 5 hours and the chambers were removed from the slides and the cells washed four times in PBS followed by fixation in 4% PBS buffered paraformaldehyde treated with 0.1% Triton X for 20 minutes. The cells were washed three times in PBS, and blocked for 20 minutes in 2% BSA containing 0.1% Triton X. Blocked cells were washed in PBS and incubated with one of the following monoclonal primary antibodies: (A) anti α tubulin (1:500); and (B) anti-vimentin (1:200), for 90 minutes. The cells were washed in PBS followed by a 1 hour incubation with FITC conjugated anti-mouse secondary (1:30) at room temperature. The cells were mounted with Vectashield containing propidium iodide and sealed to prevent dehydration. The slides were covered in tinfoil and stored at 4° C. for analysis using fluorescence confocal microscopy.

The results are shown as FIG. 12 (anti-tubulin staining of cells) and FIG. 13 (anti-vimentin staining of cells). In the control migrating HMEC-1, the microtubules (stained using anti α tubulin) (FIG. 12: control) have a regular linear structure running in the direction of the wound thus helping the process of directional migration. Dense regions of staining can be observed at the front of the nucleus, and this microtubule organizational center (MTOC) is a good indicator that directional migration is occurring at the time of fixation. In contrast, in the FKBP-L treated cells (FIG. 12: FKBP-L) the microtubules appear to have little alignment into the wound. It can be seen that the microtubules appear slightly tortuous or wispy and aligned from left to right, the MTOC appears to sit at the side of the cell, indicating no active directional migration.

FIG. 13 shows the intermediate filaments of the HMEC-1's stained using anti-vimentin. The control (untreated) cells again appear to be organized, elongated and pointing in the direction of the wound again suggesting the cells are actively migrating (FIG. 13: control). In contrast, the intermediate filaments in the FKBP-L treated non-migrating HMEC-1's appear highly disorganized, even clumped and showing no indication that they are actively migrating into the wound (FIG. 13: FKBP-L).

The results of this confocal investigation suggest that the mechanism of FKBP-L mediated inhibition of migration may be directed at the cytoskeleton.

Example 10

The Effect of Full Length Recombinant FKBP-L on PC3, HT29 and MDA Tumor Cell Migration (N=3)

In these experiments, the effect of recombinant FKBP-L on tumor cell migration was assessed. The in vitro migration assay used in these studies is a modified version of the method described by Ashton et al (1999) see supra. PC3, MDA231, and HT29 tumor cells were plated into individual chambers on a glass slide and grown to 90% confluence overnight. The medium was removed and the monolayers wounded. The monolayer was re-supplemented with fresh medium and the required volume of His-tagged recombinant FKBP-L protein (SEQ ID NO: 1) was added to give the final concentrations shown. The monolayers were incubated for 24 hours and then fixed in 4% PBS buffered paraformaldehyde.

The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to time matched sham-treated controls and the percent inhibition of wound closure compared to time matched controls calculated.

The results are shown in FIG. 14, panels A, B, and C. It was found that recombinant FKBP-L polypeptide inhibits tumor cell migration in a dose-dependent manner. These finding indicate that FKBP-L may be useful as a therapeutic to reduce tumor cell invasion and metastasis.

Example 11

The Effect of Direct Injection of a FKBP-L cDNA Construct on DU145 Human Prostate Tumor Cell Growth in Vivo. (N=1, 4-7 Mice Per Treatment Group)

Experiments were conducted to determine the effect of direct intra-tumoral injection of a FKBP-L cDNA construct on DU145 human prostate tumor cell growth in vivo.

Cell Culture

Du145 (prostate carcinoma) cells were obtained from Cancer Research UK and cultured in RPMI 1640 medium (Invitrogen) supplemented with 10% foetal calf serum. All cell lines were grown as monolayers, incubated at 37° C. under 5% $CO_2$.

DNA Plasmid Construction

The FKBP-L/pcDNA3.1 plasmid was constructed by excision of the FKBPL cDNA using BamH1 (polynucleotide SEQ ID NO:31) from pUC18 and then directional ligation of FKBP-L into the BamHI restriction site of pcDNA3.1 (Invitrogen) as described in Example 1. The endostatin plasmid (for use as a postive anti-angiogenic control) hEndo XV/pcDNA3.1, was constructed by digesting the pBLAST hENDO XV plasmid (InVivoGen) with Hpa1 (Promega) and EcoV (Invitrogen) to release the hEndo XV insert. The hEndo XV insert was ligated directionally into the ECoRV restriction site of pcDNA3.1 (Invitrogen).

Prostate Cancer Xenograft Model

Nineteen (19) male immunocompromised (severe combined immunodeficient) mice were used (Harlan). The mice were aclimatized and caged in groups of 5 or less in a barrier care facility. Du145 (prostate carcinoma) cells were cultured as previously described. Subconfluent cells were harvested and the cell concentration was adjusted to $5 \times 10^7$ cells/ml in PBS. The dorsum of each mouse was shaved. After administrating aesthetic, each mouse received intra-dermal injections of $5 \times 10^6$ Du145 tumor cells (100 μl) bilaterally into the rear dorsum with a 26-gauge needle. The tumors were allowed to grow until they reached a volume of 100-125 $mm^3$. The mice were randomly divided into four treatment regimens: (a) untreated (4 mice); (b) empty vector (pcDNA3.1) (4 mice); (c) hEndo XV/pcDNA3.1 (4 mice); and (d) FKBP-L/pcDNA3.1 (7 mice). The mice received intratumoral injections of Lipofectamine 2000 (Invitrogen): plasmid complexes, twice weekly, every 3 or 4 days. Briefly the Lipofectamine 2000: plasmid complexes were made as for each injection per animal as follows: 25 μl of plasmid (1 μg/μl) was added to 25 μl of optimem (Invitrogen) and 10 μl of Lipofectamine 2000 (Invitrogen) was added to 40 μl of optimem. The two solutions were incubated at room temperature for 5 minutes. The 2 solutions were combined and allowed to incubate at room temperature for a further 20 minutes before tumor intra-tumor injection. The tumors were measured before each treatment. Tumor volume was calculated as: $4/3 \, \pi r^3$ (where $r=\frac{1}{2}$ GMP and GMP=$\sqrt[3]{Length \times Breadth \times Height}$).

Figure 15:
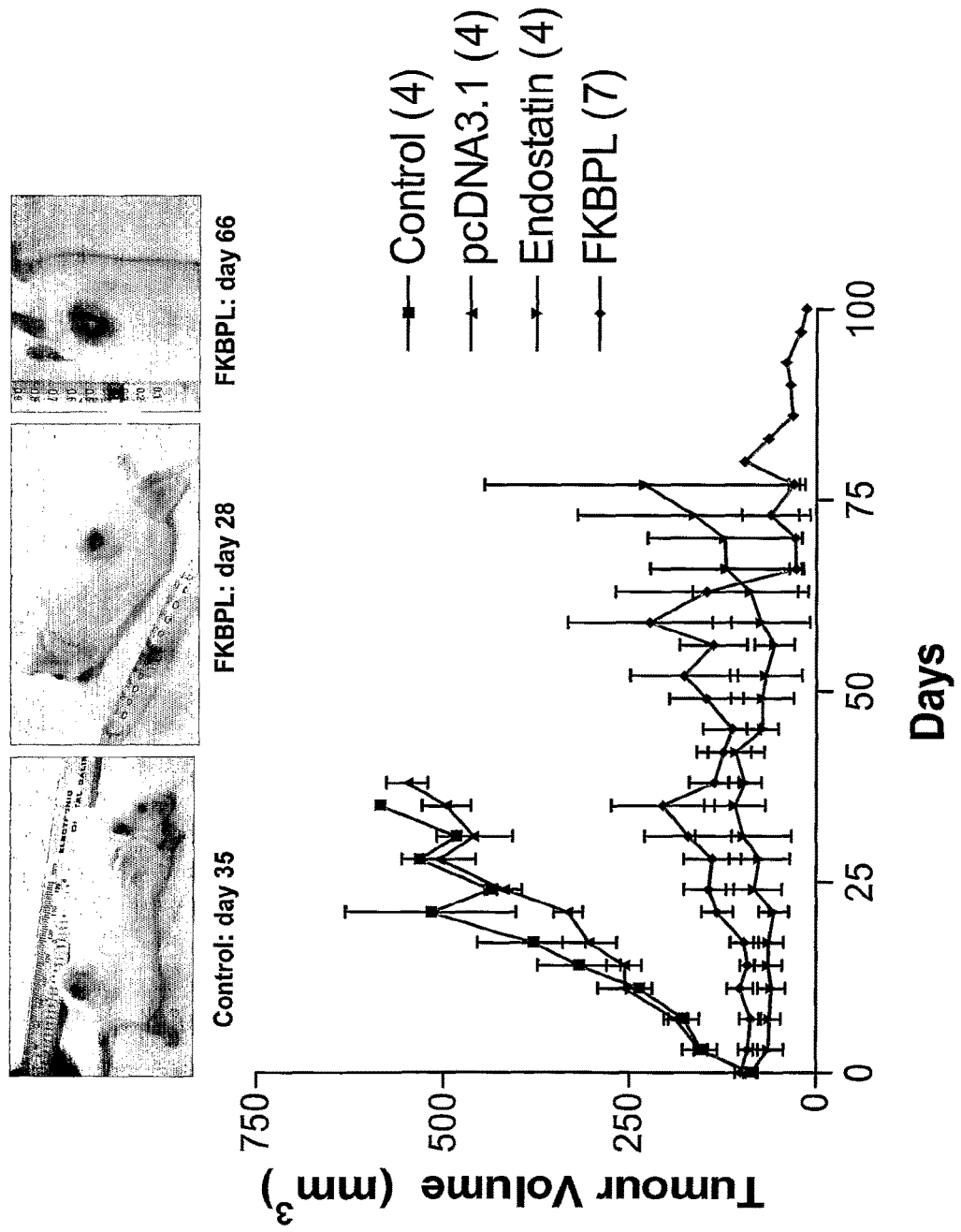
FIG. 15 illustrates the effect of direct intratumoral injection of a FKBP-L cDNA construct on DU145 human prostate tumor xenograft cell growth in vivo in accordance with an embodiment of the present invention.

The results are shown in FIG. 15. Both FKBP-L and endostatin treated tumors showed evidence of a necrotic center, i.e. they looked donut shaped. This is typical of the effects seen with anti-angiogenics. Controls reached their volume quadrupling time by ~35 days, however growth of FKBP-L treated tumors was for inhibited over 3 months (100 days) after initial treatment, with tumors only 10% of their initial volume.

Thus, it was found that intratumoral injection of a FKBP-L expression construct inhibits DU145 human tumor xenograft growth and is comparable, if not superior, to the effects seen with endostatin currently approved in at least some countries (e.g., China) for treatment of lung cancer. Again this shows the potential therapeutic value of FKBP-L gene therapy in a clinical setting.

Example 12

Genes Regulated in L132 Cells by FKBP-L Antisense Oligonucleotides Associated with Angiogenesis/Migration cDNA Microarray Analysis Total RNA was isolated from L132 cells, 8 h after exposure to FKBP-L antisense (FKBP-L antisense: 5' ATG GCC AGG CTC CCG CTC 3') (SEQ ID NO: 40) or lipofectin only as a control. Poly A+mRNA was extracted from total RNA samples using the Qiagen Oligotex kit (Qiagen, UK), according to the manufacturer's instructions. These mRNA samples (800 ng per sample) were sent to Incyte Genomics, USA where a UniGEM 2.0 microarray analysis was conducted.

Incyte's Lifearray chips enable the interrogation of up to 10,000 genes simultaneously, resulting in the comparison of gene expression levels in two different samples. Briefly, a standard reverse transcription reaction was carried out to convert both mRNA samples to cyanine-dye-labelled cDNA. mRNA from L132 cells treated with FKBP-L antisense oligonucleotides after 8 h was used to generate a Cyanine 3 (green) labelled probe and mRNA from L132 cells treated with lipofectin only after 8 hours was used to produce a Cyanine 5 (red) labelled probe. The two fluorescent probe samples were simultaneously applied to a single microarray chip containing numerous cDNA probes immobilised on a solid support in specific locations, where they competitively reacted with the arrayed cDNA molecules. Following incubation, the microarray was rinsed in a series of baths to ensure the removal of any unhybridised sample. The microarray was then captured as an image that was acquired using a scanner for fluorescent signal detection. This scanner generated data on the intensity of each spot by excitation of the fluorochromes on the array. Each element of the chip was scanned for the Cy3 (green) and then the Cy5 (red) fluorescent label to create electronic images for both dye channels. The final array images were analysed using the Incyte GEMTools software package.

Genes that are up-regulated are associated with an increase in angiogenesis (Table 1). Elevated RhoA, RhoC, ROCK I, and ROCK II expression is known to be associated with tumor progression to more advanced stages and it has been suggested that Rho and ROCK signaling contribute to the morphologic changes and metastatic behaviour of some tumor cells. This is consistent with the hypothesis that overexpression of FKBP-L inhibits angiogenesis and FKBP-L repression using antisense oligonucleotides could promote angiogenesis by activation of Rho and ROCK. The data imply that knock-down of FKBPL with antisense or a targetd siRNA could promote angiogeneis and could be used to promote healing of chronic wounds.

TABLE 1

Genes differentially expressed following exposure to FKBP-L anti-sense oligonucleotides

| Genes | Fold Increase (↑) or Decrease (↓) |
| --- | --- |
| PI3K | ↑ 3.1 |
| Rho GTPase activating protein-oligophrenin 1 | ↑ 2.0 |
| ROCK | ↑ 1.7 |
| Microtubule associated protein 1B | ↑ 1.6 |
| MMP-like 1 | ↑ 1.6 |
| TNF ligand superfamily member 1 | ↑ 1.5 |
| CYR61 | ↓ 2.4 |
| Tubulin γ | ↓ 1.6 |
| Annexin 2 | ↓ 1.6 |
| Tubulin β | ↓ 1.5 |
| Tubulin α | ↓ 1.5 |

Example 13

Inhibition of Cell Migration is Dependent on CD44 in HMEC-1 and Tumor Cell Lines DU145, PC3, HT29, MCF-7, MDA-231

RT-PCR to Detect CD74 mRNA Expression

Du145, HMEC-1, HT29, PC3, MCF-7 and MDA-231 cells were seeded into T25 tissue culture flasks and allowed to grow until they reached 70% confluency. RNA was isolated from the cells using the RNAqueous kit (Ambion, Cat #AM1912), according to manufacturer's instructions. The RNA was treated with Turbo DNA-free™ (Ambion, Cat #1906) according to manufacturers' instructions in order to remove contaminating DNA. cDNA was prepared from the RNA samples using the ImProm II™ Reverse Transcription Kit (Promega, Cat A3800). Briefly, 0.5 µg of RNA, 0.5 µg of oligo dT primer was made up to 5 µl with nuclease-free water, incubated at 70° C. for 5 min before incubating on ice for 5 min. The following reagents were then added: nuclease-free water (5.3 µl), 5× ImProm II™ Reaction Buffer (4 µl), 25 mM MgCl$_2$ (3.2 µl) 10 mM dNTP mixture (1 µl) ImProm II™ Reverse Transcriptase (1 µl) and Recombinant RNasin ribonuclease inhibitor (0.5 µl). The reverse transcription reactions were incubated at 25° C. for 5 min, 42° C. for 1 h and finally 70° C. for 15 min.

For each PCR reaction: cDNA (2 µl), 10× PCR buffer (5 µl), 10 mM dNTP mix (2 µl), 50 mM MgCl$_2$ (2 µl), Taq DNA polymerase (5 U/µl) (0.25 µl) (Invitrogen Cat #18038-018), molecular grade water (34.75 µl), and 2 µl of the appropriate forward and reverse primers (10 µM) (see Table 2) were combined. The samples were amplified using the following temperature program: 1 cycle of 94° C. for 1 min, 40 (CD74) or 25 (GAPDH) cycles of 94° C. for 45 s, 55° C. for 30 s and 72° C. for 90 s; followed by 1 cycle of 72° C. for 10 min.

TABLE 2

CD74 and GAPDH primer sequences

| | Primer Sequence | SEQ ID NO: |
| --- | --- | --- |
| CD74 | 5'-CTTCCCAAGCCTCCCAAG-3' | 41 |
| | 5'-AGAAGACGGGTCCTCCAGTT-3' | 42 |
| GAPDH | 5'-GAGTCAACGGATTTGGTCGT-3' | 43 |
| | 5'-TTGATTTTGGAGGGATCTCG-3' | 44 |

Western Blot to Detect MIF and CD44

All cell lines including the mouse endothelial cell line 2H-11 (for MIF testing only) were assessed for their CD44 and MIF status using western blot analysis. Cells were harvested in laemmli buffer (Sigma) and heated to 90° C. for 10 min. Samples were subjected to SDS-PAGE electrophoresis using the Xcell SureLock Mini-cell system (Invitrogen), transferred to nitrocellulose membranes, blocked for 1 h at room temperature in 1% milk solution and probed with either monoclonal anti-CD44H antibody (R&D Systems, Cat #BBA10) at dilution 1:500, or anti-MIF antibody (R&D Systems, Cat #AF-289-PB) at dilution 1:500 and anti-β-Actin antibody (Sigma, Cat #A 4700) at 1:5000 dilution. Blots were then probed with mouse Ig HRP-linked secondary antibody (GE Healthcare, UK, Cat NA931V) at 1:3500 dilution when probing for CD44 or β-actin or goat Ig HRP-linked secondary antibody (Santa Cruz Biotechnology, Cat #sc-2020) when probing for MIF. Antibody binding was detected using the SuperSignal West Pico Chemiluminescent Substrate (Pierce, Cat #34080).

Figure 16:
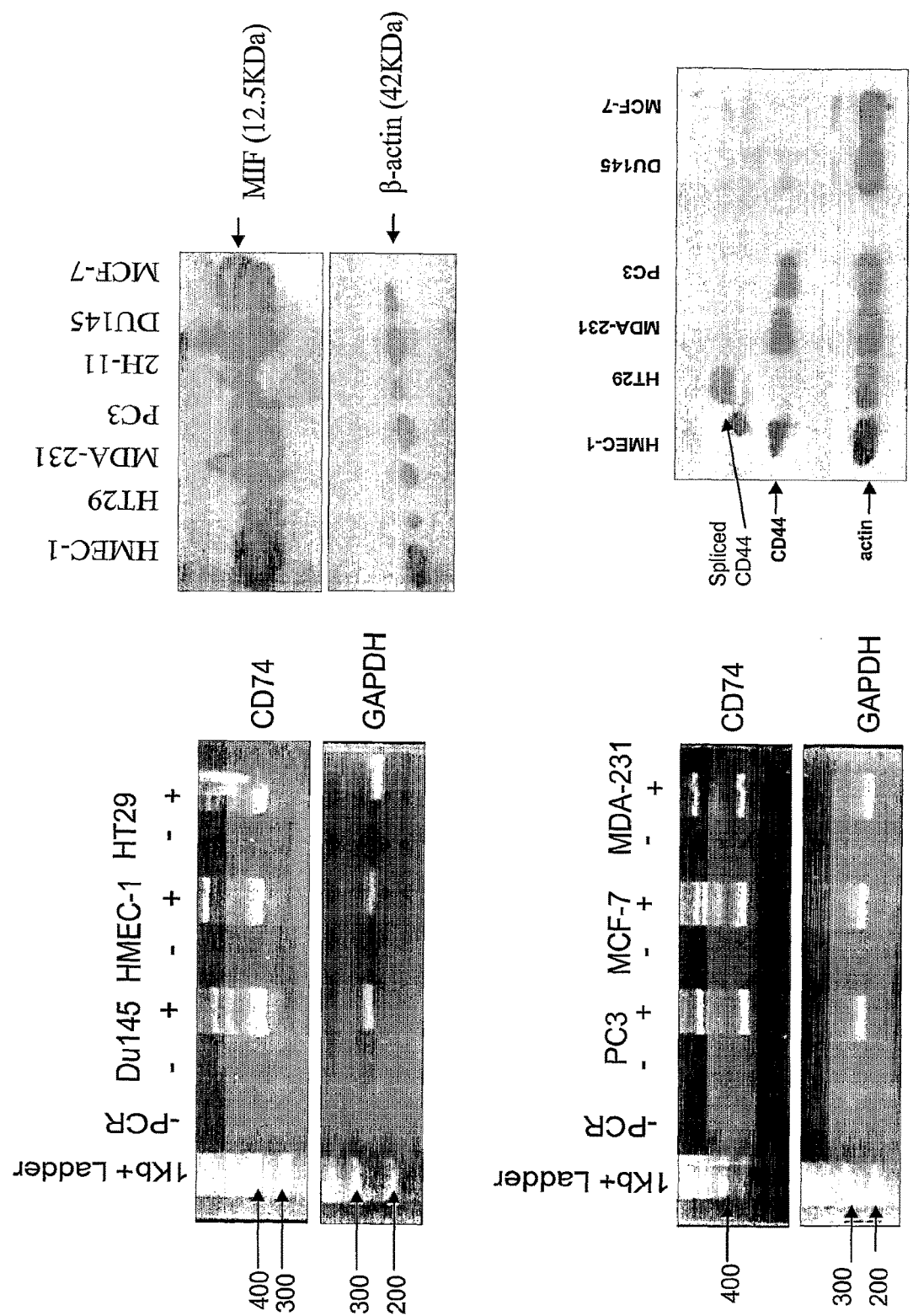
FIG. 16 shows that inhibition of cell migration is correlated to expression of CD44 in HMEC-1 and the five tumor cell lines DU145, PC3, HT29, MCF-7, MDA-231 in accordance with an embodiment of the present invention.
Figure 17A:
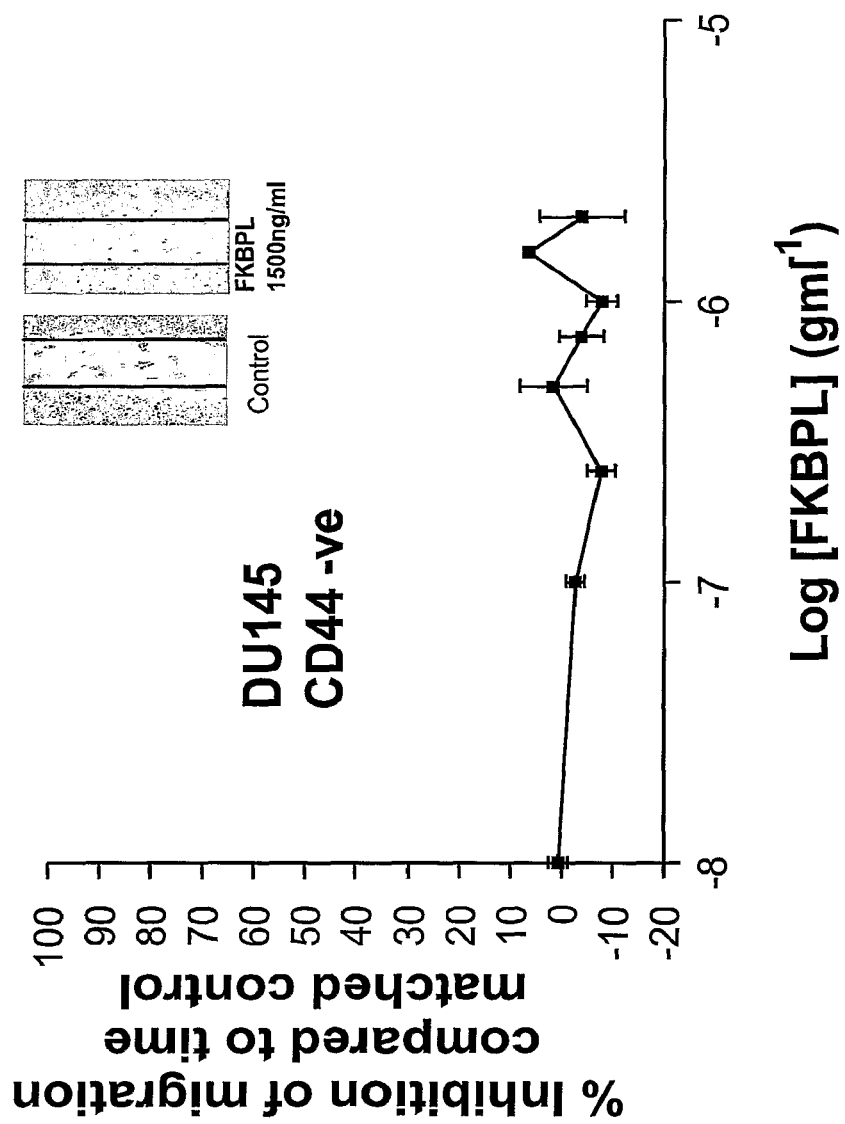
FIGS. 17A, 17B, 17C, 17D, and 17E show the effect of full length recombinant FKBP-L on DU145 (CD44 −ve) (FIG. 17A), HT29 (CD44 +ve) (FIG. 17B), PC3 (CD44 +ve) (FIG. 17C), MDA (CD44 +ve) (FIG. 17D), and MCF-7 (CD44 −ve), (FIG. 17E) tumor cell migration in accordance with an embodiment of the present invention.
Figure 17B:
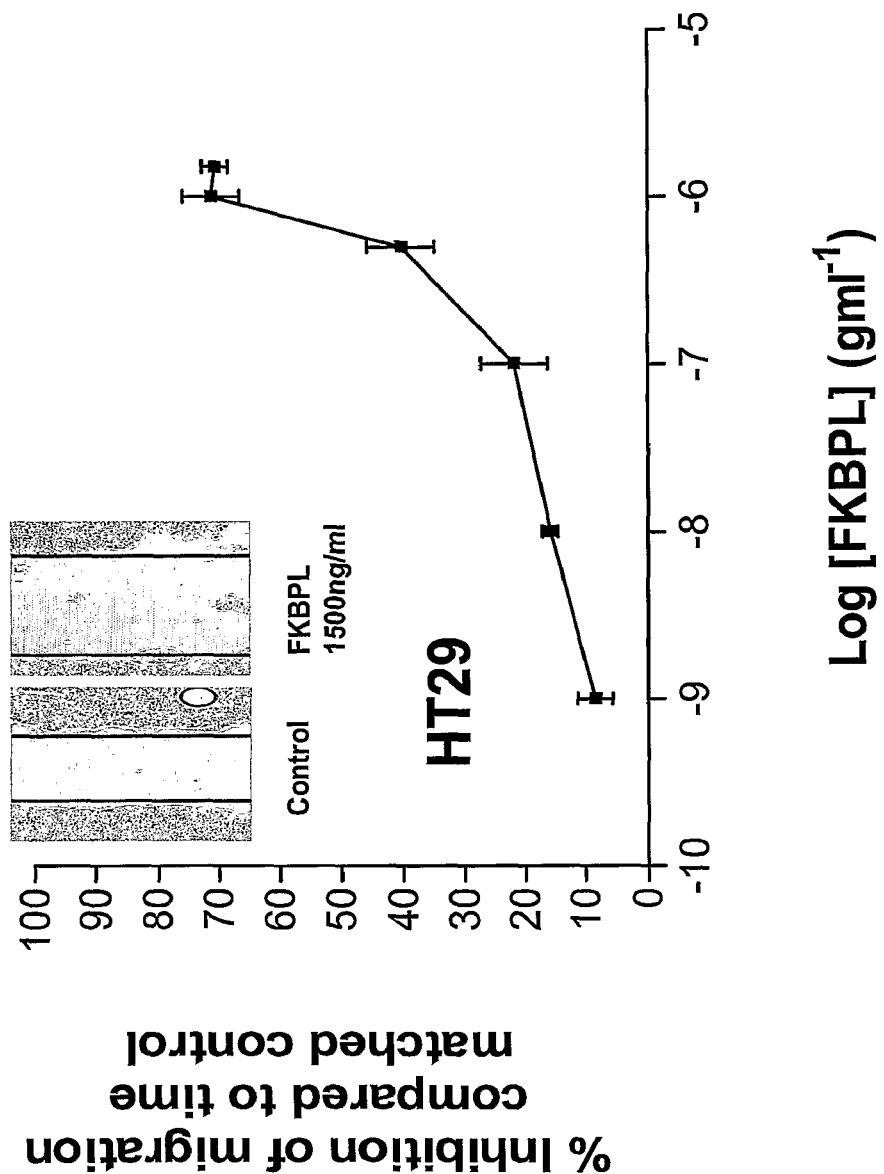
Figure 17C:
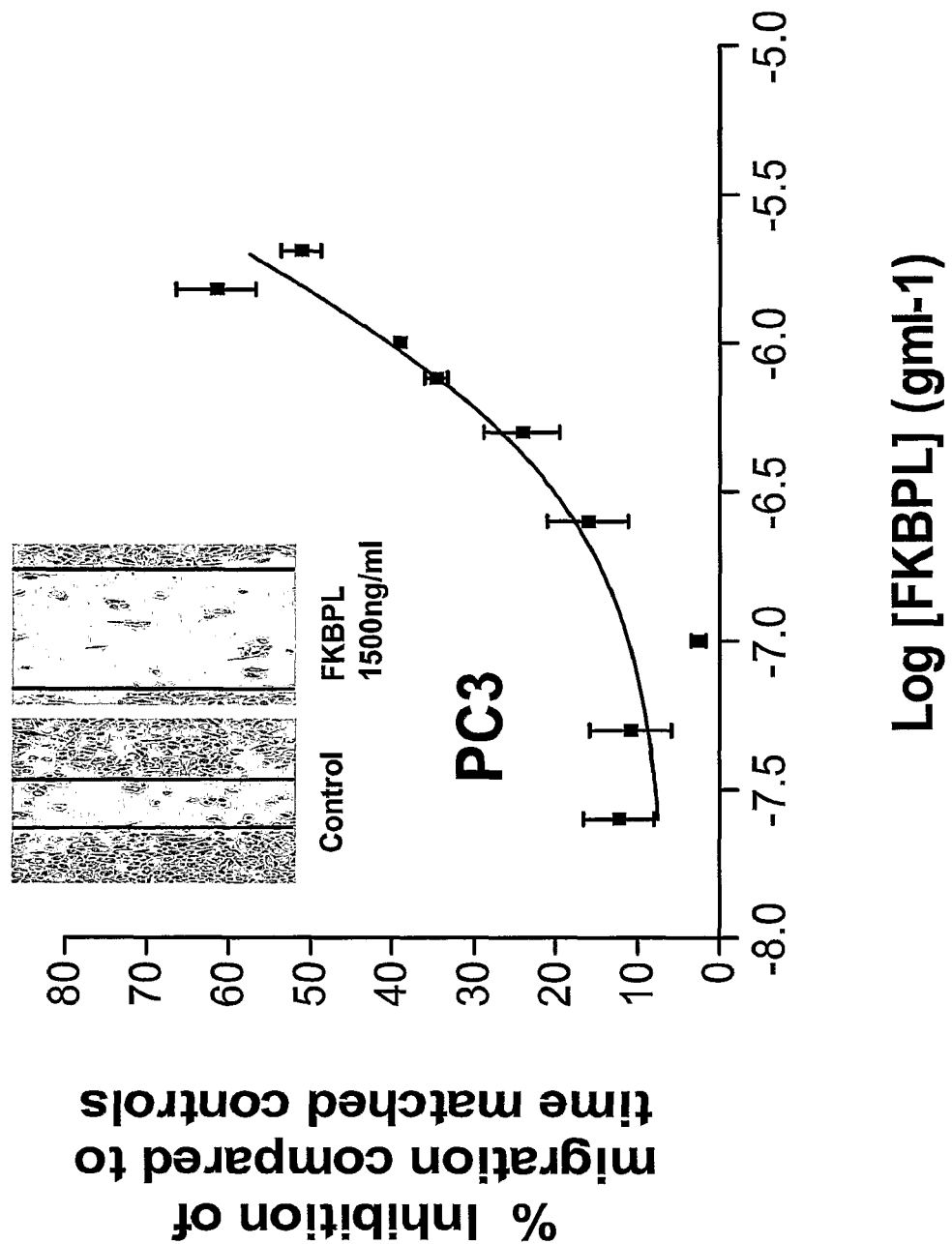
Figure 17D:
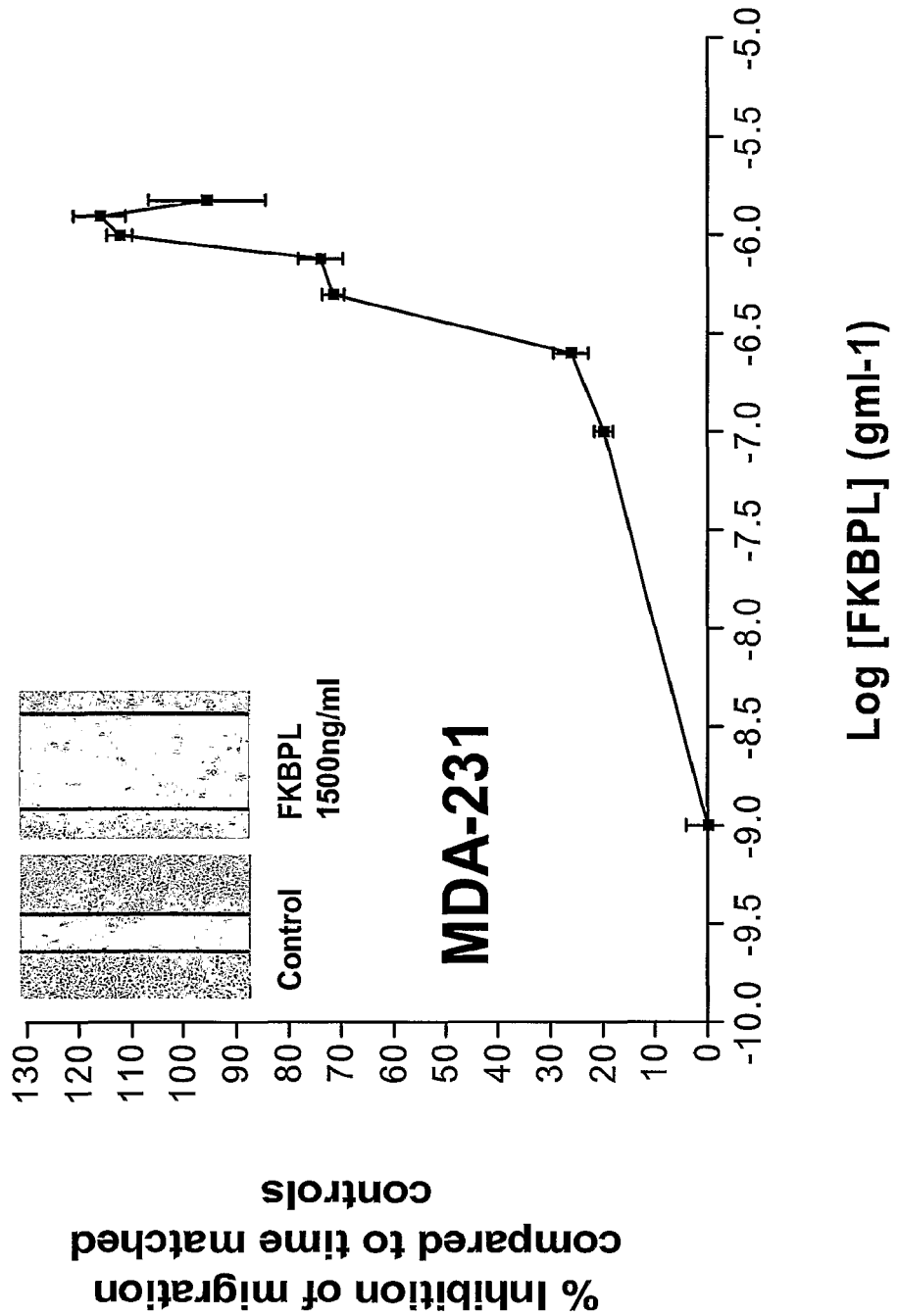
Figure 17E:
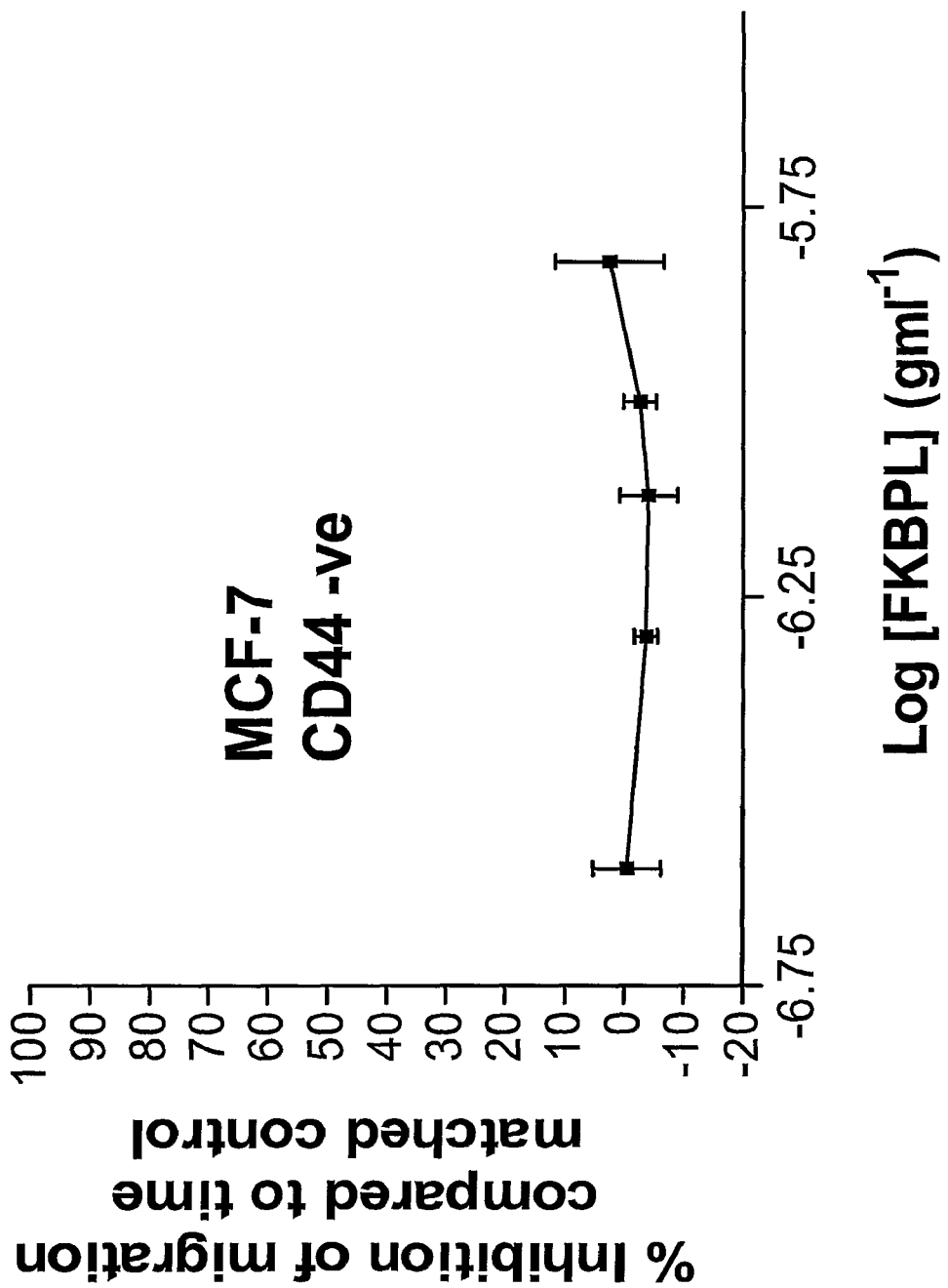

The results are shown in FIG. 16. It was found that CD74 and MIF were expressed in all cell lines previously evaluated for FKBP-L-mediated inhibition of wound closure. However, CD44 was present in PC3, MDA-231, HT29 and HMEC-1 but absent in Du145 and MCf-7. The absence of CD44 correlated with the inability of FKBP-L to inhibit wound closure in DU145 and MCF-7 (shown in Example 14 below). The data support the hypothesis that FKBP-L binds to CD44 and interferes with the CD74/MIF binding resulting in inhibition of the angiogenic signaling responses from these receptors.

Example 14

The Effect of Full Length Recombinant FKBP-L Polypeptide on PC3 (CD44 +ve), MDA (CD44 +ve), HT29 (CD44 +ve), MCF-7 (CD44 −ve) and DU145 (CD44 −ve) Tumor Cell Migration (N=3)

The in vitro migration assay used in these studies is a modified version of the method described by Ashton et al. (1999) see supra. PC3 (prostate tumor cell line; CD44 positive; CD44 +ve), MDA231 (breast tumor cell line; CD44 +ve), HT29 (Colorectal tumor cell line; CD44 +ve), MCF-7 (breast tumor cell line; CD44 negative; CD44 −ve) and DU145 (prostate tumor cell line; CD44 −ve) were plated into individual chambers on a glass slide and grown to 90% confluence overnight. The medium was removed and the monolayers wounded. The monolayer was re-supplemented with fresh medium and the required volume of recombinant His-tagged FKBP-L protein (SEQ ID NO: 1) was added to give the required final concentration. The monolayers were incubated for 24 h and then fixed in 4% PBS buffered paraformaldehyde.

The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to time matched sham treated controls and the % inhibition of wound closure compared to time matched controls calculated.

Cell lines were also assessed for their CD44 status using western blot analysis (FIG. 16). Cells were harvested in laemmli buffer (Sigma) and heated to 90° C. for 10 min. Samples were subjected to SDS-PAGE electrophoresis using the Xcell SureLock Mini-cell system (Invitrogen), transferred to nitrocellulose membranes, blocked for 1 h at room temperature in 1% milk solution and probed with either monoclonal anti-CD44H antibody (R&D Systems, Cat #BBA10) at dilution 1:500 and anti-β-Actin antibody (Sigma, Cat #A 4700) at 1:5000 dilution then probed with mouse Ig HRP-linked secondary antibody (GE Healthcare, UK, Cat NA931V) at 1:3500 dilution when probing for CD44 or β-actin or goat Ig HRP-linked secondary antibody (Santa Cruz Biotechnology, Cat #sc-2020) when probing for MIF. Antibody binding was detected using the SuperSignal West Pico Chemiluminescent Substrate (Pierce, Cat #34080).

Results of the wound closure assay are shown in FIG. 17A-17E. It can be seen that recombinant FKBP-L can inhibit tumor cell migration in CD44 +ve tumor cell lines, but not in CD44 −ve tumor cell lines. The data suggest that FKBP-L could inhibit tumor metastases in a subset of CD44 +ve tumor cell lines.

Example 15

Knock-Down of CD44 in PC3 Cells via an siRNA Targeted Approach Inhibits the FKBP-L-Mediated Inhibition of PC3 Migration (N=2)

PC3 cells were transfected for 72 h with either sicontrol non-targeting siRNA (SCR siRNA) (Dharmacon, Cat #D-001210-01-05) or CD44 targeted siRNA (CD44siRNA) (Dharmacon, Cat #009999). Briefly, $1.2 \times 10^6$ PC3 cells were seeded into two P90 dishes and incubated at 37° C. for 24 h. To transfect, 150 μl of the either sicontrol non-targeting siRNA or CD44 targeting siRNA (2 μM) was added to 450 μl of serum free medium (Tube 1). 18 μl of Dharmafect 2 transfection reagent (Dharmacon, Cat #T-2002-03) was added to 582 μl of serum free medium in duplicate (Tube 2). All tubes were incubated at room temperature for 5 min. The contents of the tubes 1 and 2 were mixed and incubated for a further 20 min at room temperature. During this incubation period, the two P90 dishes of PC3 cells were washed and 4.8 ml of complete medium was added to each dish. The appropriate siRNA transfection mix was then added dropwise and the dishes were incubated for 72 h at 37° C. The transfected cells were then seeded into chamber slides ($1.25 \times 10^5$ cells/chamber) and incubated for a further 24 h at 37° C. The monolayers were wounded and full length recombinant His-tagged FKBP-L (SEQ ID NO: 1) (1500 ng/ml) or complete medium was added to the monolayers. The monolayer was fixed after a further 24 h and the extent of wound closure was blindly assessed using a calibrated graticule. Percent inhibition of wound closure in FKBP-L-treated monolayers compared to untreated monolayers was calculated. FKBP-L inhibited the migration of the SCR siRNA treated cells by 21.7%, but had no effect on CD44 siRNA treated cells.

Western blot analysis was carried out to confirm knockdown of CD44 in PC3 cells. 144 h post-transfection with either sicontrol non-targeting siRNA (50 nM) or CD44 targeted siRNA (50 nM) cells were harvested in laemmli buffer (Sigma) and heated to 90° C. for 10 min. Samples were subjected to SDS-PAGE electrophoresis using the Xcell SureLock Mini-cell system (Invitrogen), transferred to nitrocellulose membranes, blocked for 1 h at room temperature in 1% milk solution and probed with monoclonal anti-CD44H antibody (R&D Systems, Cat #BBA10) at dilution 1:500, and anti-β-Actin antibody (Sigma, Cat #A 4700) at 1:5000 dilution. The blot was then probed with mouse Ig HRP-linked secondary antibody (GE Healthcare, UK, Cat NA931V) at 1:3500 dilution. Antibody binding was detected using the SuperSignal West Pico Chemiluminescent Substrate (Pierce, Cat #34080).

Figure 18:
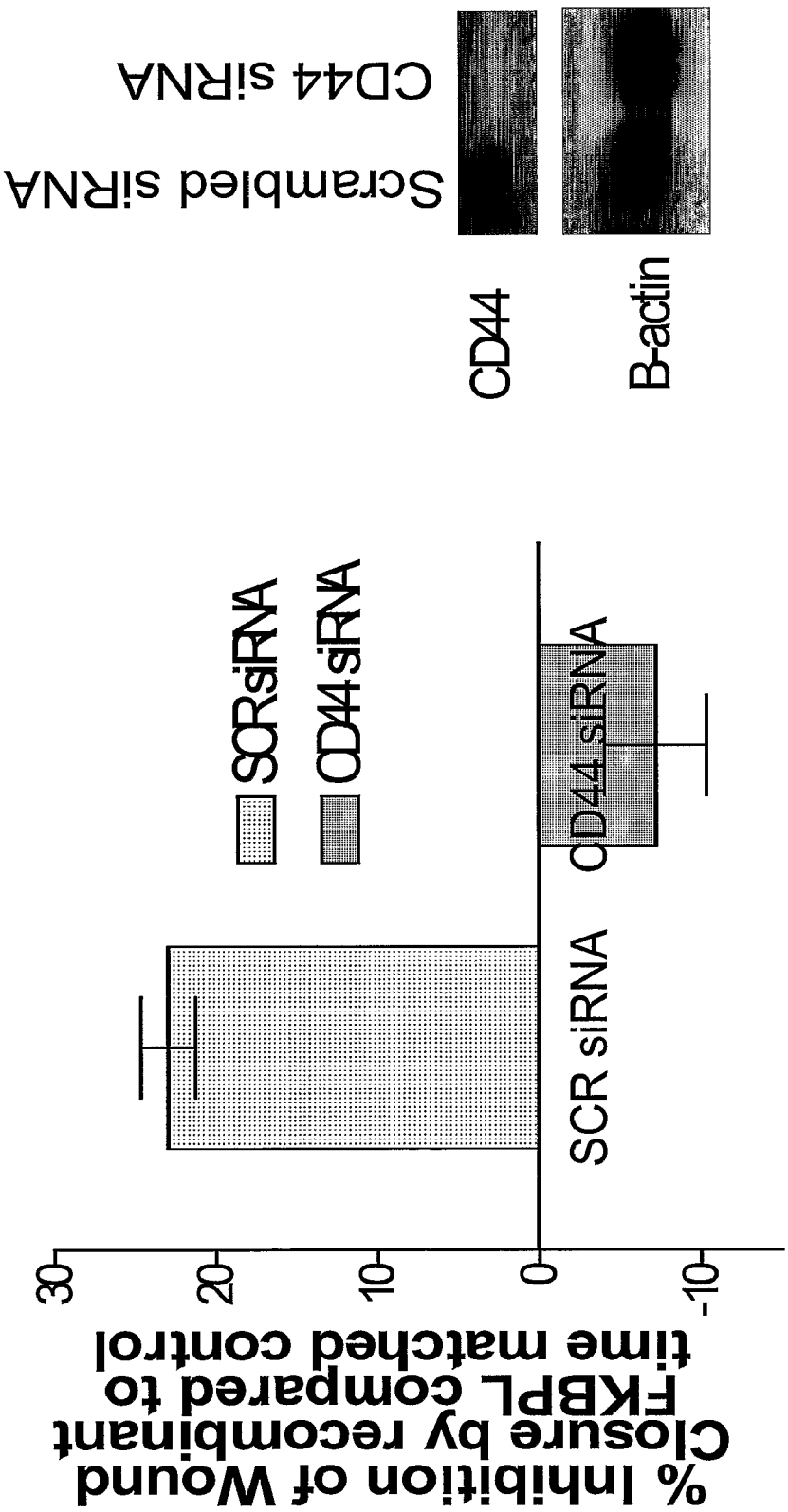
FIG. 18 shows that knock-down of CD44 in PC3 cells via an siRNA targeted approach inhibits the FKBP-L-mediated inhibition of PC3 migration in accordance with an embodiment of the present invention.

Results are shown in FIG. 18. It was found that FKBP-L can inhibit migration in the CD44 +ve cell line, PC3, in the presence of the control siRNA. By knocking down CD44 with CD44 siNA (see CD44 siRNA lane), it was found that the FKBP-L-mediated inhibition of migration is dependent on the presence of CD44. These data also correlate with the need for endogenous CD44 in cell lines such as HMEC-1, PC3, MDA-231 and HT29 in order to promote FKBP-L-mediated inhibition of migration. Such FKBP-L mediated inhibition of migration is not detected in cell lines lacking CD44 i.e MCF-7 and DU145.

Example 16

FKBP-L Interacts with Endogenous CD44 in Wounded HMEC-1 Monolayers

Four P90 tissue culture dishes were seeded with HMEC-1 cells, so that they were 90% confluent 24 h later. The four P90 dishes of HMEC-1 cells were transfected with the FKBP-L/pcDNA3.1 DNA construct. Briefly the Lipofectin: FKBP-L/pcDNA3.1 plasmid complexes were made up for each p90 dish as follows: 4 μg of plasmid was added to optimem (Invitrogen) to a final volume of 400 μl and 40 μl of Lipofectin (Invitrogen) was added to 360 μl of optimem. The two solutions were incubated at room temperature for 45 min. The 2 solutions were combined and allowed to incubate at room temperature for a further 15 min. During this incubation period, the P90 dishes were washed twice with PBS and 3.2 ml of Optimem was added to each dish. The Lipofectin/plasmid complexes were gently added to the dishes and incubated at 37° C. for 6 h. The transfection medium was then removed from the cells and replaced with complete medium. The cells were incubated for a further 18 h at 37° C. The HMEC-1 monolayers were wounded (3 wounds per P90 dish) and incubated at 37° C. for 7 h. The cells were then washed twice in ice-cold PBS and harvested in Cell Lysis buffer (PBS, 1% Igepal, 0.5% sodium deoxycholate, 0.1% SDS, 10 mM sodium molybdate, 1 EDTA-free tablet); 300 μl per P90 dish. The cell lysate was incubated at 4° C. with rotation for 30 min. The cell lysate was centrifuged at 13000 rpm for 20 min at 4° C., in order to remove cell debris. The supernatant was then pre-cleared by incubating with pre-washed agarose G beads for 1 h at 4° C. with rotation. The pre-cleared cell lysate was split into 3, ⅓ was added to agarose G-CD44 antibody conjugate, ⅓ was added to agarose G-FKBP-L antibody conjugate and ⅓ was added to prewashed beads (negative control). The antibody-agarose G/cell lysate mixtures were incubated overnight at 4° C. with rotation. The beads were then washed 3 times with ice-cold cell lysis buffer and 3 times with ice-cold PBS. The beads were then reconstituted in 60 μl of laemmli buffer.

Western blot analysis of immunoprecipitated samples was carried out to confirm interactions between FKBP-L and CD44. Samples were heated to 90° C. for 10 min. Samples were subjected to SDS-PAGE electrophoresis using the Xcell SureLock Mini-cell system (Invitrogen), transferred to nitrocellulose membranes blocked for 1 h at room temperature in 1% milk solution and probed with monoclonal anti-CD44H antibody (R&D Systems, Cat #BBA10) at dilution 1:500 and anti-FKBP-L antibody (Proteintech) at dilution 1:1000 and then probed with either mouse (CD44) or rabbit (FKBP-L) Ig HRP-linked secondary antibody (GE Healthcare, UK, Cat NA931V) at 1:3500. Antibody binding was detected using the SuperSignal West Pico Chemiluminescent Substrate (Pierce, Cat #34080).

were introduced at amino acid position 34, 40, 48, 58, 86, 151 or 200 by site directed mutagenesis (Quikchange kit, Stratagene).

For each site directed mutagenesis reaction: pcDNA3.1/FKBP-L/DIR1 (10 ng), 10× reaction buffer (5 μl), 10 mM dNTPs (2 μl), Pfu Turbo DNA polymerase (2.5 U/μl) (1 μl) molecular grade water (37 μl), QuikSolution (3 μl) and 1 μl of the appropriate forward and reverse primers (125 ng/μl) were combined. The samples were amplified using the following temperature program: 1 cycle of 95° C. for 1 minute, 18 cycles of 95° C. for 50 seconds, 60° C. for 50 seconds and 68° C. for 16 minutes; followed by 1 cycle of 68° C. for 7 minutes.

TABLE 3

Primers used to prepare FKBP-L truncated FKBP-L mutant constructs

| FKBP-L Truncated Mutant | Primer Sequence | SEQ ID NO: |
|---|---|---|
| Δ34FKBP-L/pcDNA3.1 | 5'-GAACCTTGATTCAGTTATTTAGATTAGGCAGCAGCCCCG-3' | 45 |
| | 5'-CGGGGCTGCTGCCTAATCTAAATAACTGAATCAAGGTTC-3' | 46 |
| Δ40FKBP-L/pcDNA3.1 | 5'-CAGATTAGGCAGCAGCCCTGAGACCCTCCTACCGAAAC-3' | 47 |
| | 5'-GTTTCGGTAGGAGGGTCTCAGGGCTGCTGCCTAATCTG-3' | 48 |
| Δ48FKBP-L/pcDNA3.1 | 5'-CCTACCGAAACGCTTTAGCTGGAAGTAAGCC-3' | 49 |
| | 5'-GGCTTACTTCCAGCTAAAGCGTTTCGGTAGG-3' | 50 |
| Δ58FKBP-L/pcDNA3.1 | 5'-CCCAGATCCAGCCAGCTAAATTCTAGAGCATAC-3' | 51 |
| | 5'-GTATGCTCTAGAATTTAGCTGGCTGGATCTGGG-3' | 52 |
| Δ86FKBP-L/pcDNA3.1 | 5'-CATGGATCAACCAGTTAGATGCCAGAGGCCC-3' | 53 |
| | 5'-GGGCCTCTGGCATCTAACTGGTTGATCCATG-3' | 54 |
| Δ151FKBP-L/pcDNA3.1 | 5'-GGCGTAGGGCCATGAAGGGAGGAAACTTG-3' | 55 |
| | 5'CAAGTTTCCTCCCTTCATGGCCCTACGCC-3' | 56 |
| Δ200FKBP-L/pcDNA3.1 | 5'-CCGAGACTCCTGGTAGCTGGAGACTAGC-3' | 57 |
| | 5'-GCTAGTCTCCAGCTACCAGGAGTCTCGG-3' | 58 |

Figure 19:
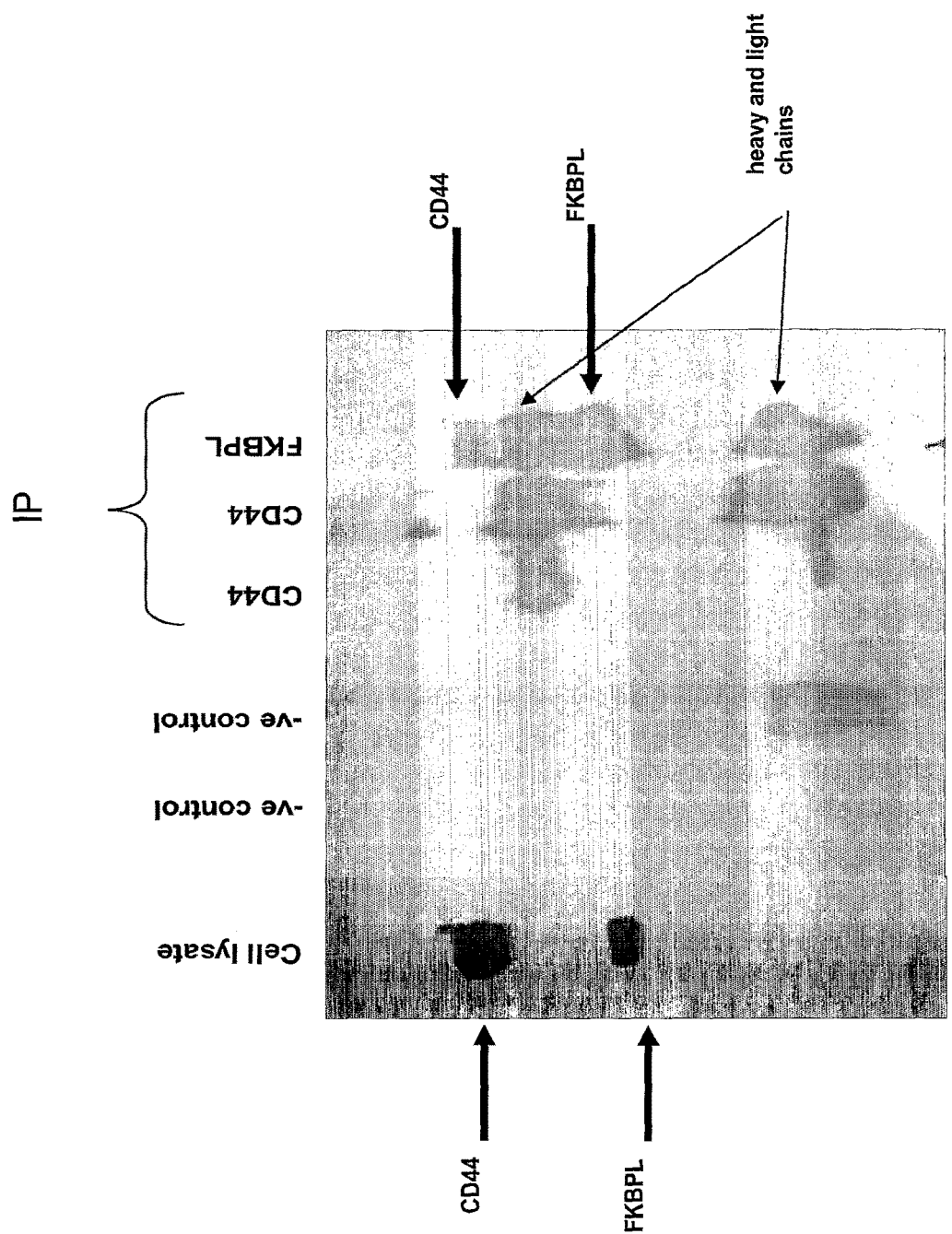
FIG. 19 shows that FKBP-L can interact with endogenous CD44 in wounded HMEC-1 monolayers in accordance with an embodiment of the present invention.

The results are shown in FIG. 19. Thus, it was found using immunoprecipitation that exogenously overexpressed FKBP-L interacts with endogenous CD44 in wounded monolayers. An interaction between endogenous FKBP-L and CD44 could only be detected in wounded, but not in non-wounded monolayers (data not shown). This suggests that a critical level of FKBP-L needs to be expressed before the interaction with CD44 can be detected. Furthermore, this interaction only occurs in endothelial cells that are primed for migration i.e. in wounded monolayers.

Example 17

The N-Terminal Domain of FKBP-L is Important for the Anti-Angiogenic Properties of FKBP-L (N-3)

Preparation of the Truncated FKBP-L Mutant Constructs

To construct the 5 FKBP-L truncated mutant plasmid constructs (Δ34FKBP-L/pcDNA3.1, Δ40FKBP-L/pcDNA3.1, Δ48FKBP-L/pcDNA3.1, Δ58FKBP-L/pcDNA3.1, Δ86FKBP-L/pcDNA3.1, Δ151FKBP-L/pcDNA3.1 and Δ200FKBP-L/pcDNA3.1); stop codons The restriction endonuclease Dpn I (10 U/μl) (1 μl) was added directly to each amplification reaction and incubated at 37° C. for 1 hour to digest the parental (non-mutated) DNA. The digested amplification reactions were transformed into XL-10-Gold Ultracompetent cells and plated onto LB agar plates containing ampicillin (100 μg/ml). One colony was picked and grown in 200 ml of LB broth containing ampicillin (100 μg/ml). Each truncated FKBP-L mutant DNA construct was purified using the Qiagen Plasmid Maxi Kit. Sequence changes in the mutated constructs were confirmed by automated DNA sequencing (Fusion Antibodies Ltd) (see e.g., FIGS. 20A and 20B).

The seven FKBP-L truncated mutant constructs were transfected to express the polypeptides (SEQ ID NOS: 3-9) shown in FIG. 1.

In Vitro Migration Assay

The in vitro migration assay used in these studies is a modified version of the method described by Ashton et al (1999). HMEC-1 were plated into individual chambers on a glass slide and grown to 90% confluence. The monolayer was transfected with either 1 μg wild-type FKBP-L/pcDNA (to express the polypeptide SEQ ID 1), Δ34FKBP-L/pcDNA3.1, Δ40FKBP-L/pcDNA3.1, Δ48FKBP-L/ pcDNA3.1, Δ58FKBP-L/pcDNA3.1, Δ86FKBP-L/pcDNA3.1, Δ151FKBP-L/pcDNA3.1 or Δ200FKBP-L/pcDNA3.1 construct (to express the polypeptides shown in FIG. 1) in the presence of lipofectin. After 6 hours the transfection reagents were removed and the monolayer wounded with a pipette tip and re-supplemented with MCDB-131 and incubated for 7 hours.

The monolayer was fixed in 4% PBS buffered paraformaldehyde solution for 10 minutes. The extent of "wound" closure was blindly assessed microscopically by an independent investigator and quantified using a calibrated eyepiece graticule (1 mm/100 μm graduation) at 20× magnification (Olympus BX 50).

The results are shown in FIG. 20C. It was found that full length wild-type FKBP-L and the truncated mutants, Δ48, Δ58, Δ86, Δ151, Δ200 inhibited wound closure. WT-FKBP-L and Δ58 inhibited wound closure by 36.2.6% and 48.8% respectively. Δ34 and Δ40 failed to significantly inhibit wound closure, suggesting that the active domain was deleted in these mutants and that the active anti-angiogenic domain resides between amino acids 34 and 57 of full-length FKBP-L.

Example 18

Evaluation of Candidate Peptides Spanning the Active Domain of FKBP-L using the Wound Scrape Assay: Comparison with Recombinant FKBP-L (N=3)

The in vitro migration assay used in these studies is a modified version of the method described by Ashton et al. (1999) see supra. HMEC-1 were plated into individual chambers on a glass slide and grown to 90% confluence overnight. The medium was removed and the monolayer wounded. The monolayer was re-supplemented with fresh medium and the required volume of the following peptides was added to achieve a dose range from $10^{-14}$-$10^{-6}$ M.

```
FKBP-L 24 mer (aa-34-57)   NH2-QIRQQPRDPPTETLELEVSPDPAS-COOH
SEQ ID NO: 10

FKBP-L 1-57                NH2 METPPVNTIGEKDTSQPQQEWEKNLRENLDSVIQI
SEQ ID NO: 6                   RQQPRDPPTETLELEVSPDPAS-COOH
```

The monolayers were incubated for 7 h and then fixed in 4% PBS buffered paraformaldehyde. The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to time matched sham treated controls and the % inhibition of wound closure compared to time matched controls calculated.

Figure 21:
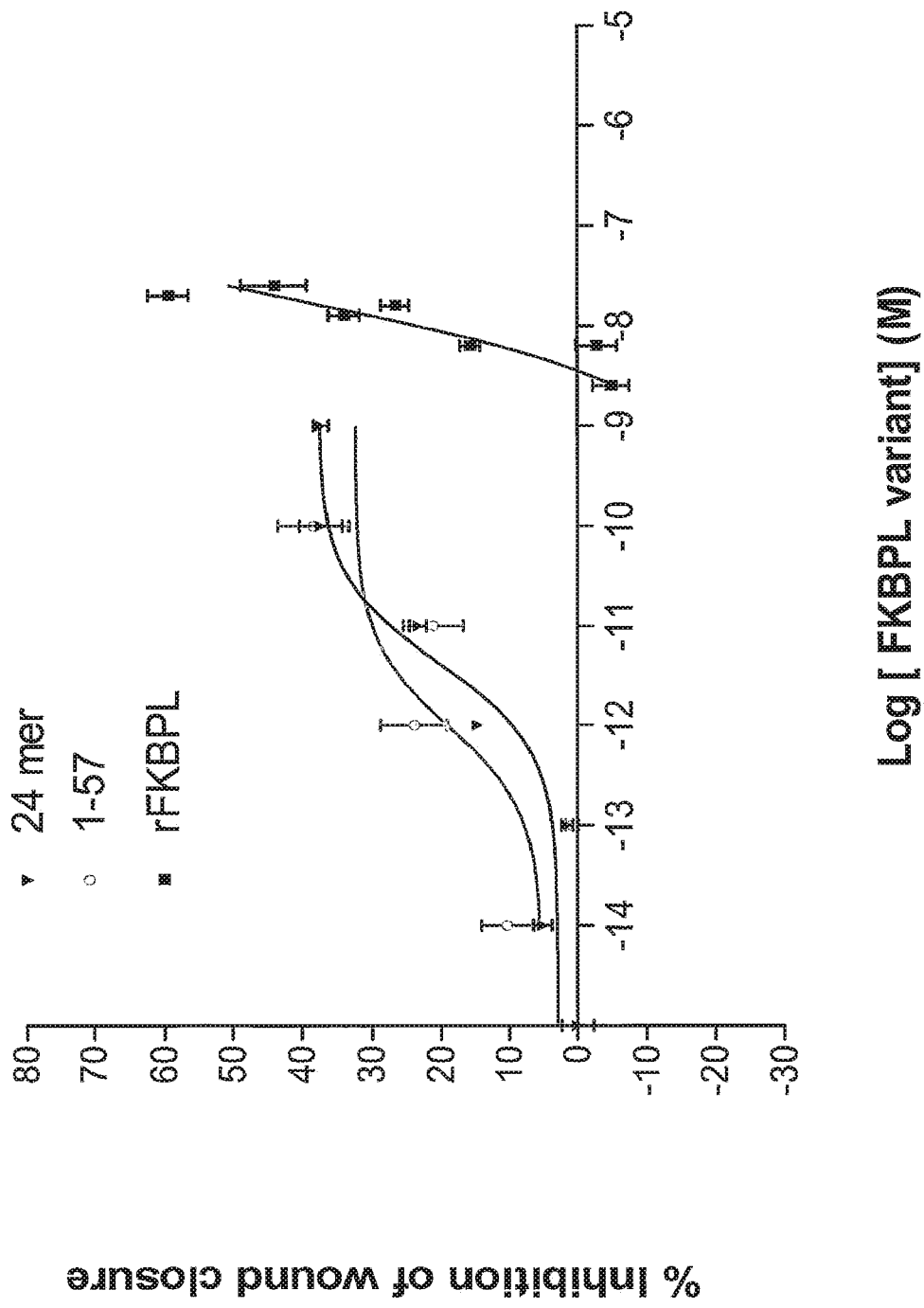
FIG. 21 shows an evaluation of full-length recombinant FKBP-L (SEQ ID NO: 1), candidate peptides FKBP-L 1-57 (1-57) (SEQ ID NO: 6) and the FKBP-L 24mer (24mer) (SEQ ID NO: 10) spanning the active domain of FKBP-L, using the wound scrape assay in accordance with alternate embodiments of the present invention.

The results of these experiments are shown in FIG. 21. In the lower dose range ($10^{-14}$-$10^{-9}$ M) the FKBP-L 24mer and 1-57mer were potent inhibitors of wound closure. Maximal inhibition was observed between $10^{-10}$ and $10^{-9}$ M, and the EC50 was very similar for each peptide. Both of these peptides showed increased potency compared with the full length recombinant protein on a mole/mole basis. In conclusion, the 24mer and 1-57mer are potent inhibitors of endothelial cell migration.

Example 19

Evaluation of Candidate Peptides Spanning the Active Domain of FKBP-L on the Formation of Endothelial Cell-to-Cell Contacts using the Synthetic Basement Membrane Matrigel in the Tube Formation Assay: Comparison with Recombinant FKBP-L (N=3)

Methods:

The in vitro tubule formation assay used in these studies is a modified version of the method described by Ashton et al. (1999). In brief, assays were conducted using BD BioCoat™ Matrigel™ Matrix Thin Layer 24-well Multiwell Plates (BD Discovery Labware, Oxford, UK). The Matrigel™ was rehydrated with 500 μl MCDB-131 serum free medium and incubated at 37° C. for 30 min. Excess medium was removed and HMEC-1 were seeded at a density of $1\times10^5$ and the plates incubated at 37° C. under 5% $CO_2$/95% air for 1 h. Increasing concentrations of FKBP-L 24mer (SEQ ID NO: 10) and 1-57mer (SEQ ID NO: 6) from $10^{-14}$-$10^{-6}$ M were used.

The plate was incubated for a further 18 h. The degree of tubule formation between adjacent HMEC-1 cells was assessed in each well in five fields of view, by counting the number of cell to cell contacts between different HMEC-1 cells in the designated area. An independent investigator assessed each well and the FKBP-L treated wells were compared to sham treated controls.

Figure 22:
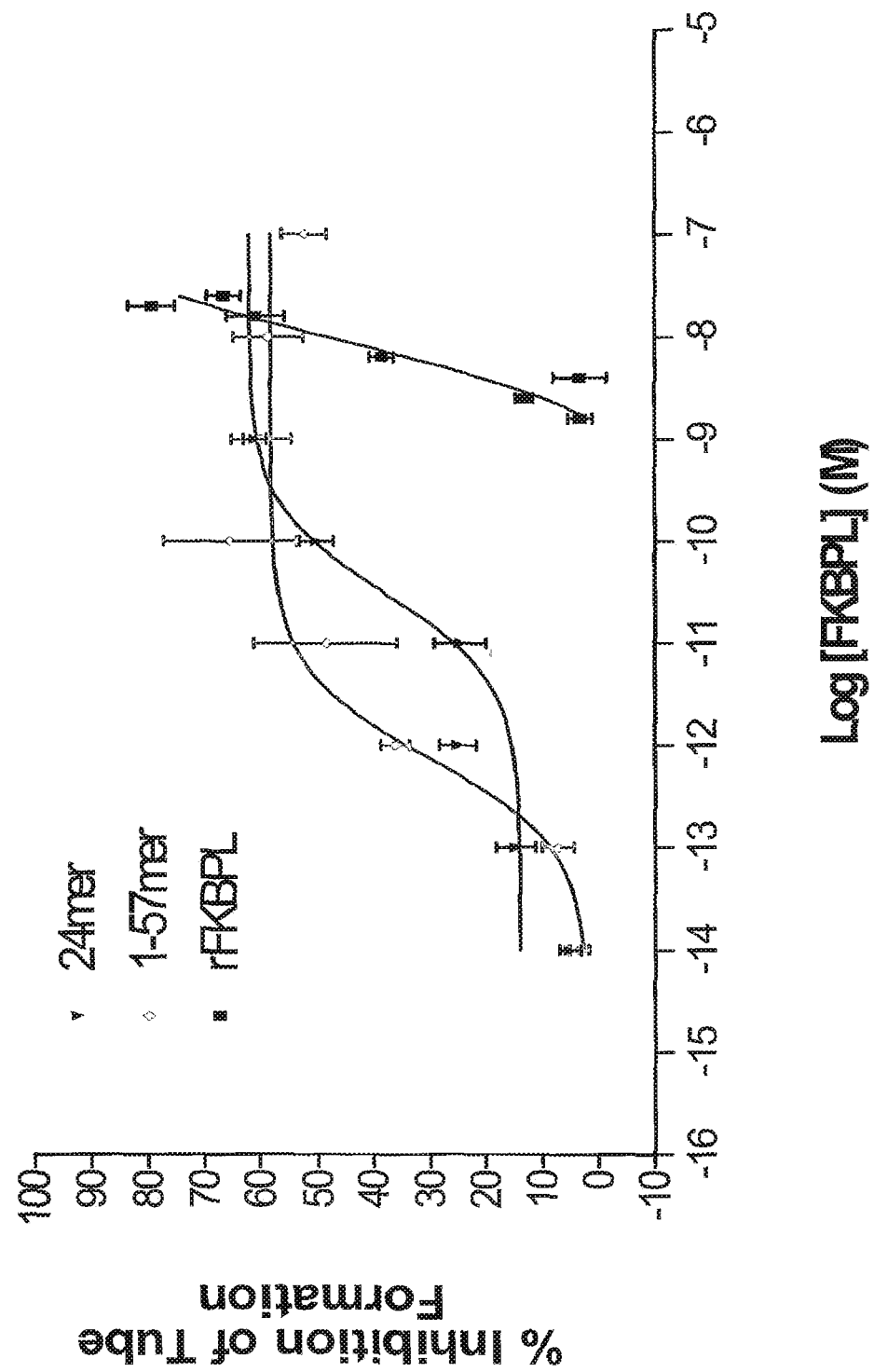
FIG. 22 shows an evaluation of full-length recombinant FKBP-L (SEQ ID NO: 1), candidate peptides FKBP-L 1-57 (1-57) (SEQ ID NO: 6), and the FKBP-L 24mer (24mer) (SEQ ID NO: 10) spanning the active domain of FKBP-L, on the formation of endothelial cell-to-cell contacts using the synthetic basement membrane Matrigel in the tube formation assay in accordance with alternate embodiments of the present invention.

The results are shown in FIG. 22. Both the FKBP-L 24mer and 1-57mer inhibited the ability of the HMEC-1's to form cell to cell contacts or tubules on Matrigel in a dose dependent manner. The 1-57mer was more effective in this assay with an EC50=0.7 pM compared to 30 pM for the 24mer. In conclusion the data suggest that the FKBP-L 24mer and the FKBP-L 1-57mer are potent inhibitors of endothelial tube formation.

Example 20

The Effect of Candidate Peptides Spanning the Active Domain of FKBP-L on Angiogenic Sprouting using the Rat Aortic Ring Assay. The Effect on Mean Length, Maximum Length and Number of Vessels Formed (n=3); Comparison to Full Length Recombinant Protein Male Wistar rats were euthanised and the thoracic aorta was aseptically removed and sectioned into 1 cm thick rings. The rings were washed ten times in sterile medium to remove any bacteria and embedded into Matrigel on 24 well plates. The wells were supplemented with 2 ml of medium and increasing concentrations of FKBP-L 24mer (SEQ ID NO: 10) and FKBP-L 1-57mer (SEQ ID NO: 6) and recombinant FKBP-L (SEQ ID NO:1).

The plate was blindly assessed by an independent investigator and quantified using a calibrated eyepiece graticule (1 mm/100 μm graduation) at 20× magnification (Olympus BX 50). The extent of vessel length, maximum vessel length and number of vessels in each field of view was measured and compared to time matched sham controls and the % inhibition calculated.

Figure 23A:
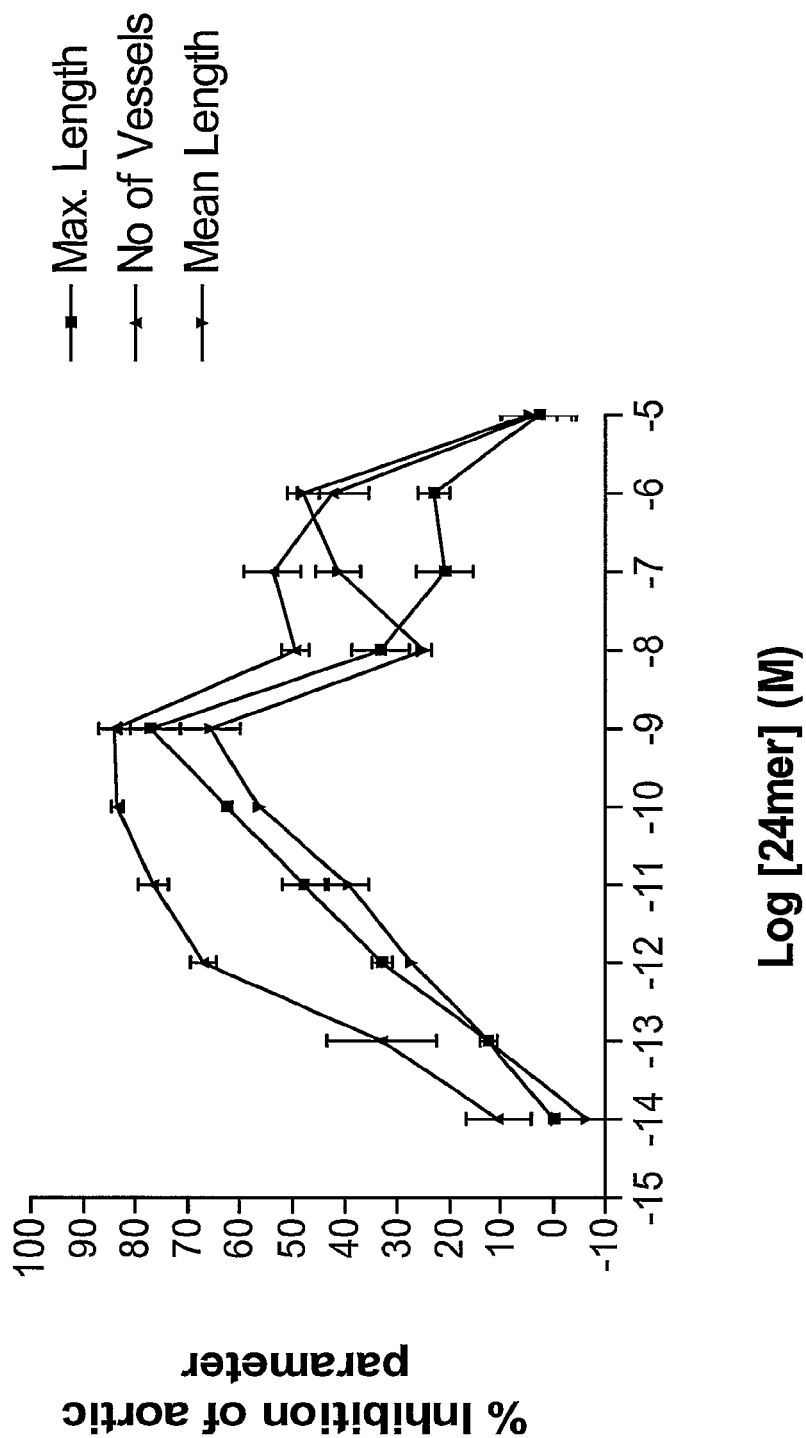
FIGS. 23A and 23B show the effect of the FKBP-L 24mer peptide (SEQ ID NO: 10) (FIG. 23A) and the FKBP-L 57mer (SEQ ID NO: 6) (FIG. 23B) peptides spanning the active domain of FKBP-L on angiogenic sprouting using the rat aortic ring assay in accordance with alternate embodiments of the present invention.
Figure 23B:
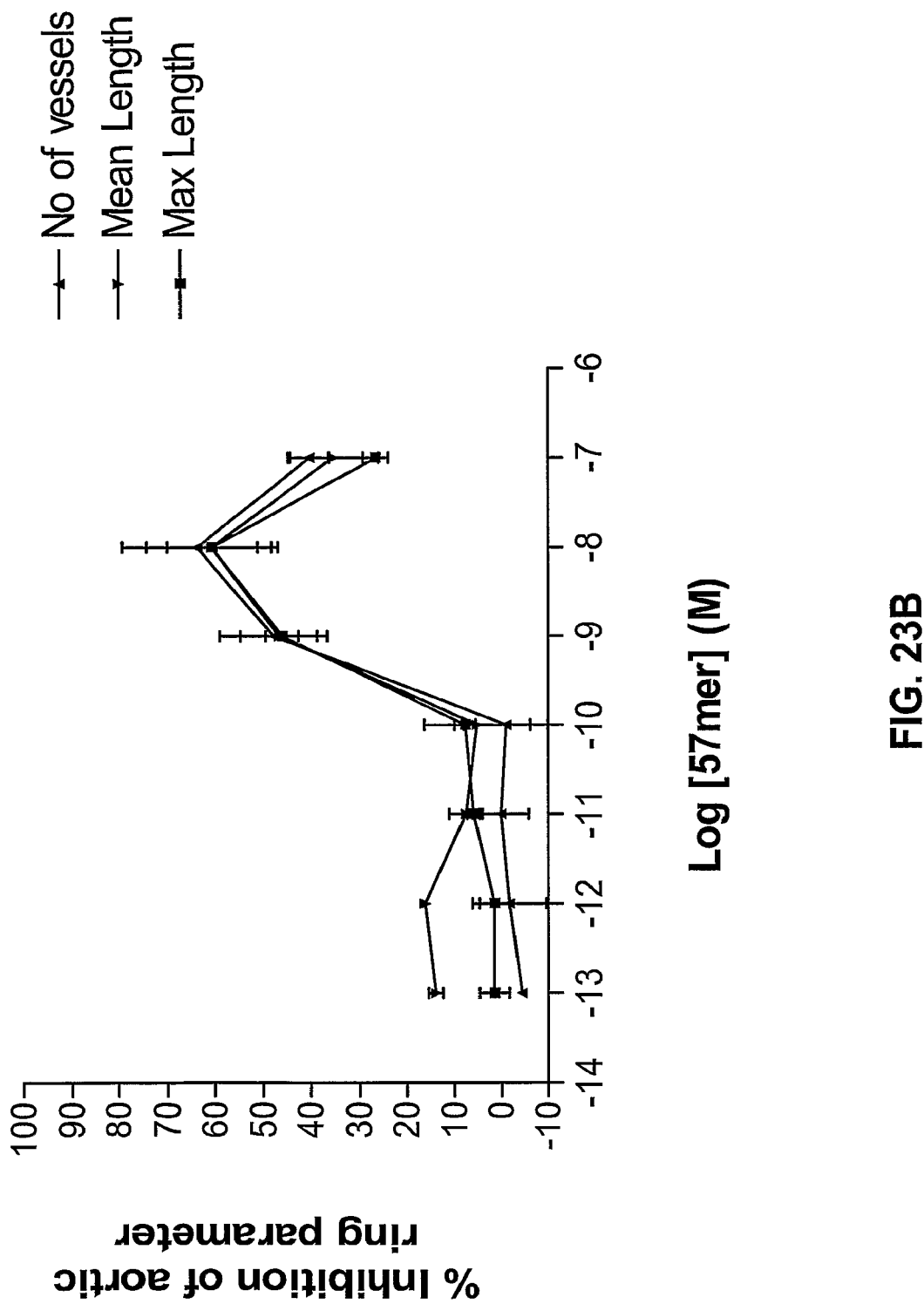

The results of these experiments are shown in FIGS. 23-24. It was found that both the FKBP-L 24mer and the FKBP-L 1-57mer were active in this assay when assessed by all three parameters i.e. extent of vessel length, maximum vessel length and number of vessels (FIGS. 23A and 23B, respectively). However, in this assay the 24mer was most potent especially in terms of number of vessels, with an IC50: 0.2 pM compared to 0.53 nM for the 1-57mer and 1.56 nM for the full length recombinant FKBP-L (FIGS. 24A and 24B). The 24mer also shows some biphasic activity. These data suggest that the 24mer may be most potent at inhibiting initial vessel sprouting and hence the decrease in the number of vessels. In summary, the FKBP-L 24mer, 1-57mer, and the recombinant FKBP-L are potent inhibits of angiogenesis.

Example 21

The Effect of the FKBP-L 24mer on Cell Invasion in a Modified Boyden Chamber System (N=3)

This assay measures the ability of cells to migrate and invade. Microvascular endothelial cells need to migrate and invade the extracellular matrix (ECM) after angiogenic stimuli. Furthermore, tumor cells need to migrate and invade the ECM in order to spread/metastasize to other sites. Both HMEC-1 (microvascular endothelial cells; CD44+ve) and two tumor cell lines, MDA-231 (breast; CD44+ve) and PC3 (Prostate; CD44+ve) were evaluated for their invasive potential in the presence of the FKBP-L 24mer.

Twelve well plate polycarbonate inserts were divided into two groups with half remaining uncoated and half coated with 100 µg/cm$^2$ of Matrigel. The coated inserts were allowed to dry overnight at room temperature in a sterile tissue culture hood. The required cell line; HMEC-1, PC3 or MDA231 was trypsinised, re-suspended in fresh medium and the cell number calculated. 5×10$^5$ cells, in a total volume of 500 µl, were added to the insert (top chamber) and 1.5 ml of complete medium added to the bottom chamber of the plate as a stimulus for invasion. FKBP-L 24mer was added to both the upper and lower chamber of the plate at the required concentration in the experimental wells. The plate was incubated for 24 h (PC3 or MDA231) or 48 h (HMEC-1).

The inserts were carefully removed from their 12 well plate and inserts without Matrigel coating were placed directly into Carnoys fixative. Inserts, which were coated with Matrigel, had the top surface of the insert wiped three times with a cotton bud to remove non-invading cells. The inserts were then placed in Carnoys and left for 10 min.

The inserts were removed from the Carnoys solution and allowed to air dry for 20 min. The dried inserts were stained in Hoescht (50 ng.ml$^{-1}$) for 30 min before washing in distilled water.

The polycarbonate inserts were cut from the holders and placed on to mounting medium on a microscope slide. A cover-slip was applied and sealed with nail varnish. The slides were stored at 4° C. until analysed.

Ten images from each insert were captured and the number of fluorescent cells per image was analysed by Lucia Imaging software. The ratio of cells visible on non-coated inserts compared to cells visible on Matrigel coated inserts was expressed as % invasion. The percent (%) invasion in the control was then compared to 24mer treated cells.

Figure 25:
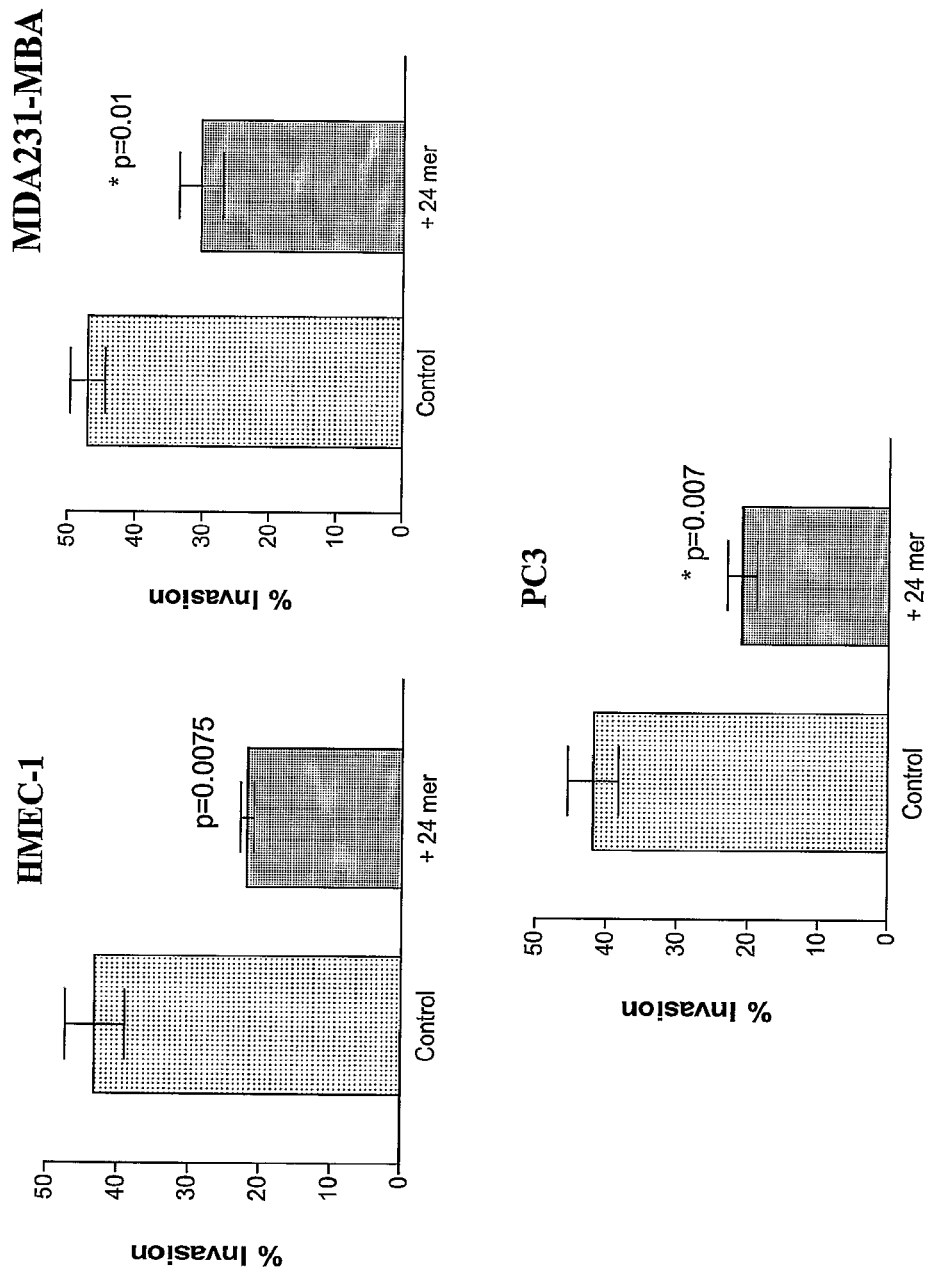
FIG. 25 shows the effect of the FKBP-L 24mer (SEQ ID NO: 10) on endothelial (HMEC-1) and tumor cell invasion (MDA231 and PC3) in a modified Boyden chamber system in accordance with alternate embodiments of the present invention.
Figure 26:
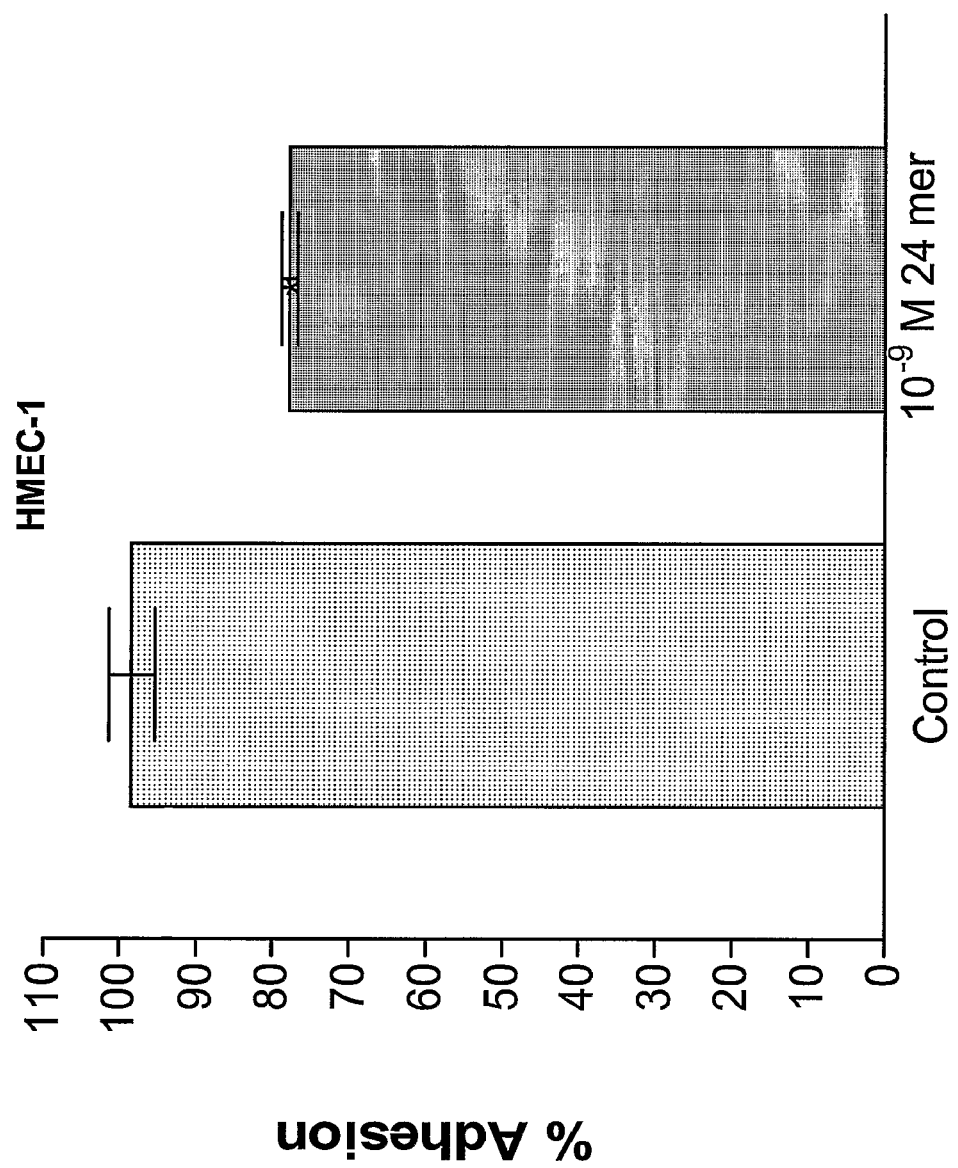
FIG. 26 shows the effect of the FKBP-L 24mer (SEQ ID NO: 10) on endothelial (HMEC-1) cell adhesion in accordance with alternate embodiments of the present invention.

The results are shown in FIG. 25. It can be seen that the FKBP-L 24mer (SEQ ID NO: 10) is a potent inhibitor of HMEC-1, PC3 and MDA-231 cell invasion. As well as providing further data to support the inhibition of HMEC-1 migration, the data indicate that the FKBP-L 24mer can also inhibit invasion through Matrigel; an important step in the angiogenic process. The data also indicate that metastasis of CD44+ve tumors could be inhibited in a clinical setting.

Example 22

The Effect of the FKBP-L 24mer on Cell Adhesion (N=3)

This assay measures the ability of cells to adhere. This is an important feature of angiogenesis and metastasis. Important mediators of leukocyte recruitment and adherence to the endothelium include E-selectin, VCAM-1, and ICAM-1 which are upregulated during inflammation, initiating leukocyte adhesion to the endothelium, and ultimately contributing to disease progression or tissue damage.

A 96-well plate was pre-coated with a thin layer of Matrigel which was allowed to set overnight. The plate wells were blocked with 0.5% BSA for 1 h at 37° C. in a 95% air/5% CO$_2$ incubator. Human microvascular endothelial cells (HMEC-1) were trypsinised and re-suspended in fresh medium and seeded at a density of 20000 cells per well. The plates were placed at 4° C. for 10 min to allow the cells to sediment to the bottom of the wells. The required amount of medium supplemented with the FKBP-L 24mer was added to each well and the plate incubated for 1 h at 37° C. The excess medium and unattached cells were removed and the wells washed three times with sterile PBS. The wells were supplemented with fresh medium and MTT added (5 mgml$^{-1}$). The plate was incubated for a further 4 h at 37° C. DMSO was added to each well to solubilise the MTT to formazen and the plate read at 540nm, with the relative absorbance of control wells compared to FBKP-L 24mer-supplemented wells.

The results are shown in FIG. 26. It can be seen that the FKBP-L 24mer is a potent inhibitor of HMEC-1 adhesion. As well as providing further data to support the inhibition of HMEC-1 migration and invasion, this assay also indicates that the FKBP-L 24mer can inhibit adhesion, an important step in the angiogenic process and other disease states.

Example 23

The Effect of the FKBP-L 24mer on MDA-231 and PC3 Tumor Cell Migration (N=3)

The in vitro migration assay used in these studies is a modified version of the method described by Ashton et al. (1999) see supra. MDA231 (breast tumor cell line; CD44 +ve) and PC3 (prostate tumor cell line; CD44 +ve) cells were plated into individual chambers on a glass slide and grown to 90% confluence overnight. The medium was removed and the monolayers wounded. The monolayer was re-supplemented with fresh medium and the required volume of FKBP-L 24mer (SEQ ID NO: 10) was added to give the required final concentration ($10^{-14}$-$10^{-7}$ M). The monolayers were incubated for 24 h and then fixed in 4% PBS buffered paraformaldehyde.

The extent of "wound" closure was blindly assessed microscopically by an independent investigator and quantified using a calibrated eyepiece graticule (1 mm/100 µm graduation) at 20× magnification (Olympus BX 50). The extent of closure in the FKBP-L treated slides was compared to time matched sham treated controls and the % inhibition of wound closure compared to time matched controls calculated.

Figure 27A:
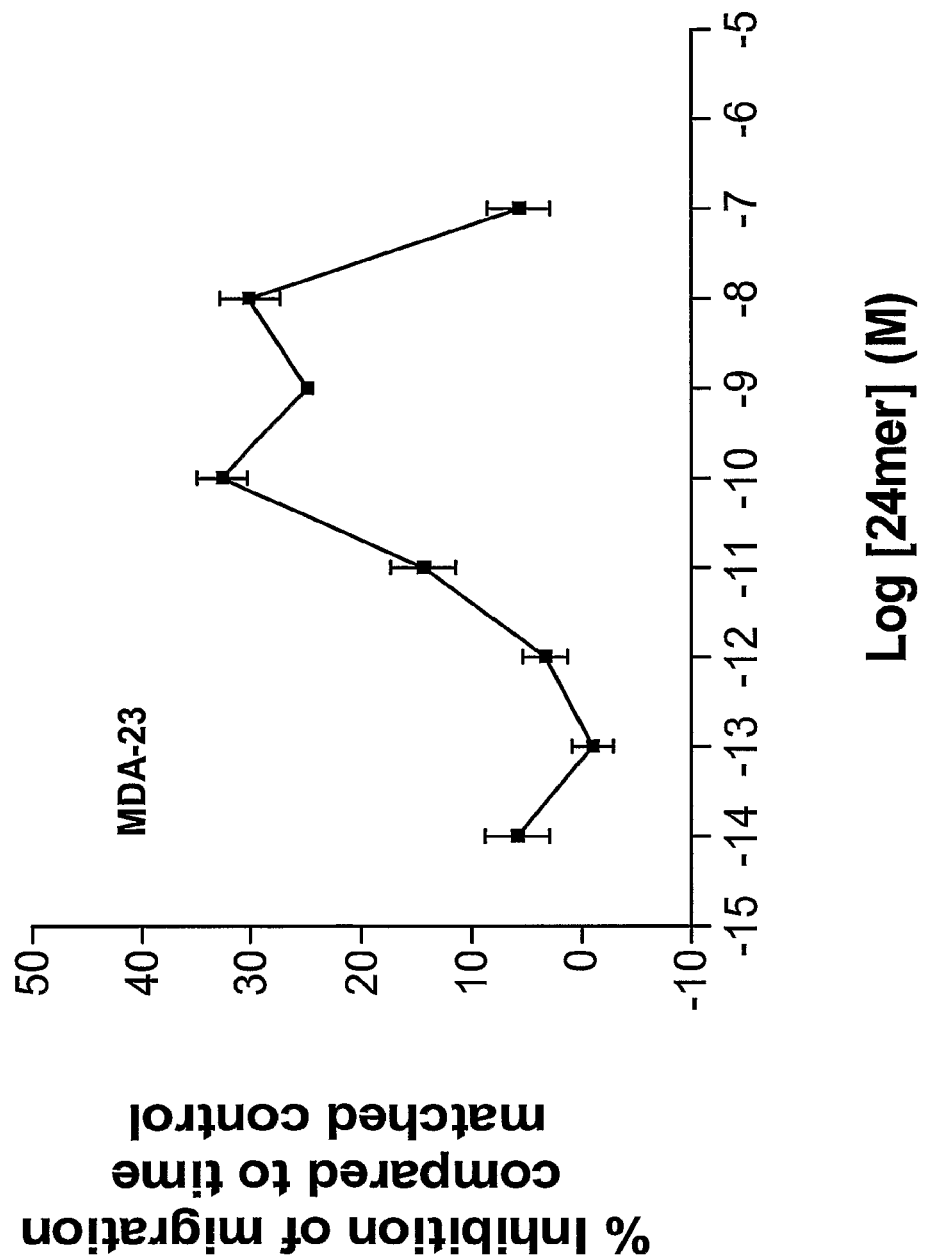
FIGS. 27A and 27B show the effect of the FKBP-L 24mer (SEQ ID NO: 10) on MDA-231 (FIG. 27A) and PC3 (FIG. 27B) tumor cell migration, in accordance with alternate embodiments of the present invention.
Figure 27B:
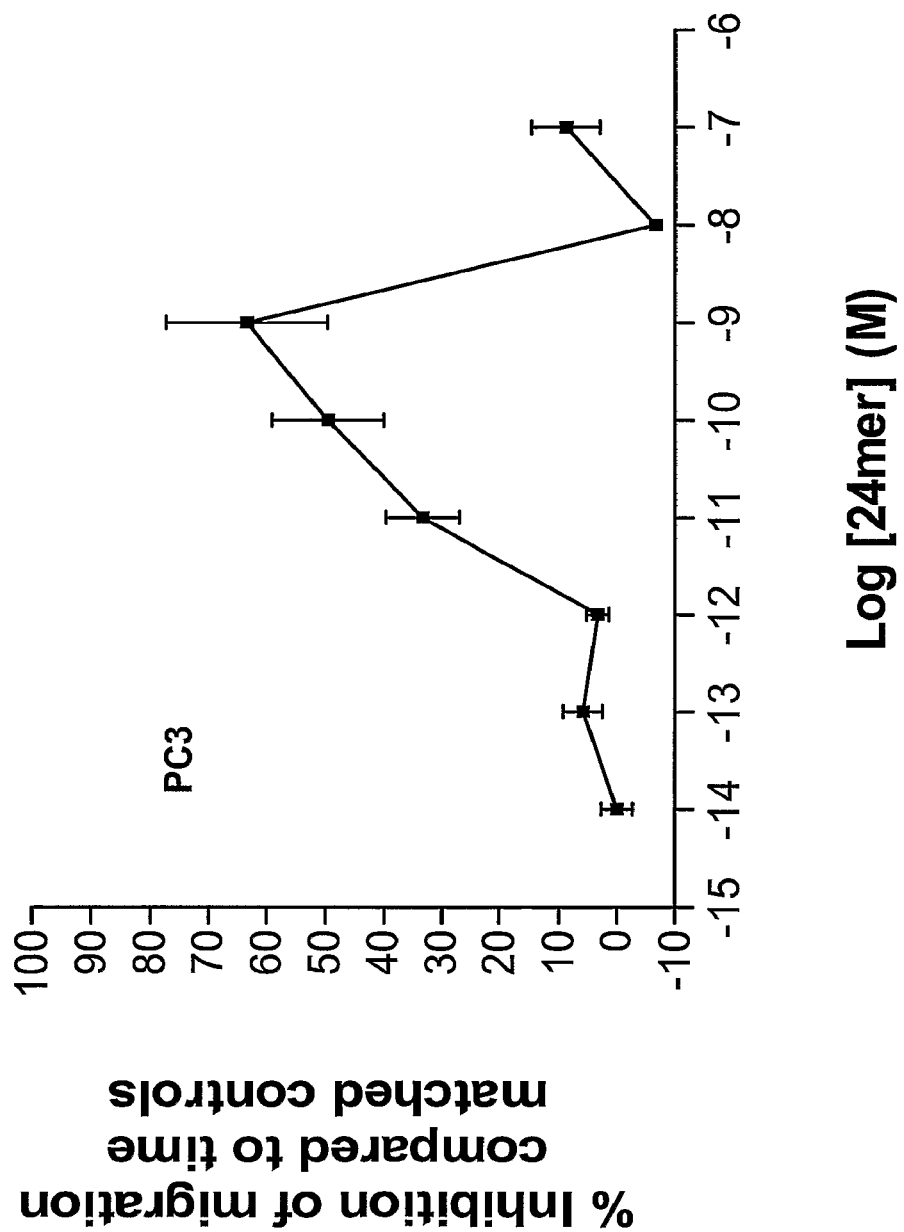

The results are shown in FIGS. 27A (MDA-23 cells) and 27B (PC3 cells). It was found that the FKBP-L 24mer can inhibit MDA-231 and PC3 tumor cell migration. These are CD44+ve tumor cell lines, again indicating that FKBP-L may act via CD44, similar to what was observed with the full length recombinant protein (FIG. 17). The data suggest that the FKBP-L 24mer could inhibit tumor metastases in a subset of CD44 +ve tumor cell lines.

Example 24

The FKBP-L 24mer is an Angiostatic Inhibitor (N=3)

In order to determine whether the FKBP-L 24mer exerted a permanent or static effect on endothelial cell sprouting the rat aortic ring assay was used. Male Wistar rats were euthanised and the thoracic aorta was aseptically removed and sectioned into 1 cm thick rings. The rings were washed ten times in sterile medium to remove any bacteria and embedded into Matrigel on 24 well plates. The wells were supplemented with 2 ml of medium. The plates were incubated for up to 15 days. Each day the Matrigel rings were photographed and returned to their incubator. Two further experiments were carried out: (A) addition of FKBP-L 24mer to the medium after the vessels had grown for seven days; and (B) addition of FKBP-L 24mer to the medium at the initial embedding stage, with subsequent removal after seven days and replacement with fresh medium for a further seven days. The extent of vessel development was quantified using a calibrated eyepiece graticule (1 mm/100 μm graduation) at 20× magnification (Olympus BX 50), and measured electronically using Lucia imaging software. Vessel length was measured and compared to time matched sham controls and the percent (%) inhibition calculated.

The results are shown in FIGS. 28A and 28B. In control conditions, vessel development was observed between days 3 and 14 reaching a maximum of 1400 μm at day 14. In a parallel experiment vessels were allowed to develop for seven days (approx. 800 μm) and the medium removed and re-supplemented with medium that contained $10^{-9}$ M FKBP-L 24mer. The addition of 24mer caused complete inhibition of vessel development when compared to time matched controls (FIG. 28A).

In a reversed experiment (FIG. 28B), the aortic rings were initially exposed to medium supplemented with the FKBP-L 24mer and incubated for seven days. The FKBP-L 24mer almost completely inhibited vessel development. The FKBP-L 24mer supplemented medium was removed from the rings and fresh medium added, resulting in the continued growth of vessels.

These experiments suggest that the FKBP-L 24mer inhibits vessel development in an angiostatic manner and when the vessels are either mature or freshly embedded.

Example 25

The FKBPL 24mer (SEQ IN NO:10) Inhibits Angiogenesis in Vivo using the Sponge Assay; Comparison to Full Length Recombinant FKBPL (N=1, 3 Mice Per Group)

This experiment evalulated the ability of the FKBP-L 24mer to inhibit angiogenesis using the mouse sponge assay. Polyether sponges were subcutaneously implanted in C57 black mice on day 0 and injected on alternate days with (a) 10 ng bFGF control (3 mice) (b) 10 ng bovine fibroblast growth factor (bFGF)+5 μg full-length his-tagged recombinant FKBPL (equivalent to $3.2×10^{-6}$ M in vitro) (3 mice) (c) 10 ng bFGF+0.35 μg FKBPL 24mer (molar equivalent of 5 μg full-length recombinant FKBPL) (3 mice) or (d) 0.11 ng FKBPL 24mer (equivalent to $10^{-9}$ M in vitro) (3 mice).

All mice were sacrificed on day 21. Sponges were removed, fixed and paraffin embedded. Five micron sections were stained with haematoxylin and eosin. Vessels were blindly counted by 3 independent assessors using ×40 magnification in 10 fields per section. The average count per sponge/mouse was then plotted for each assessor.

Figure 29:
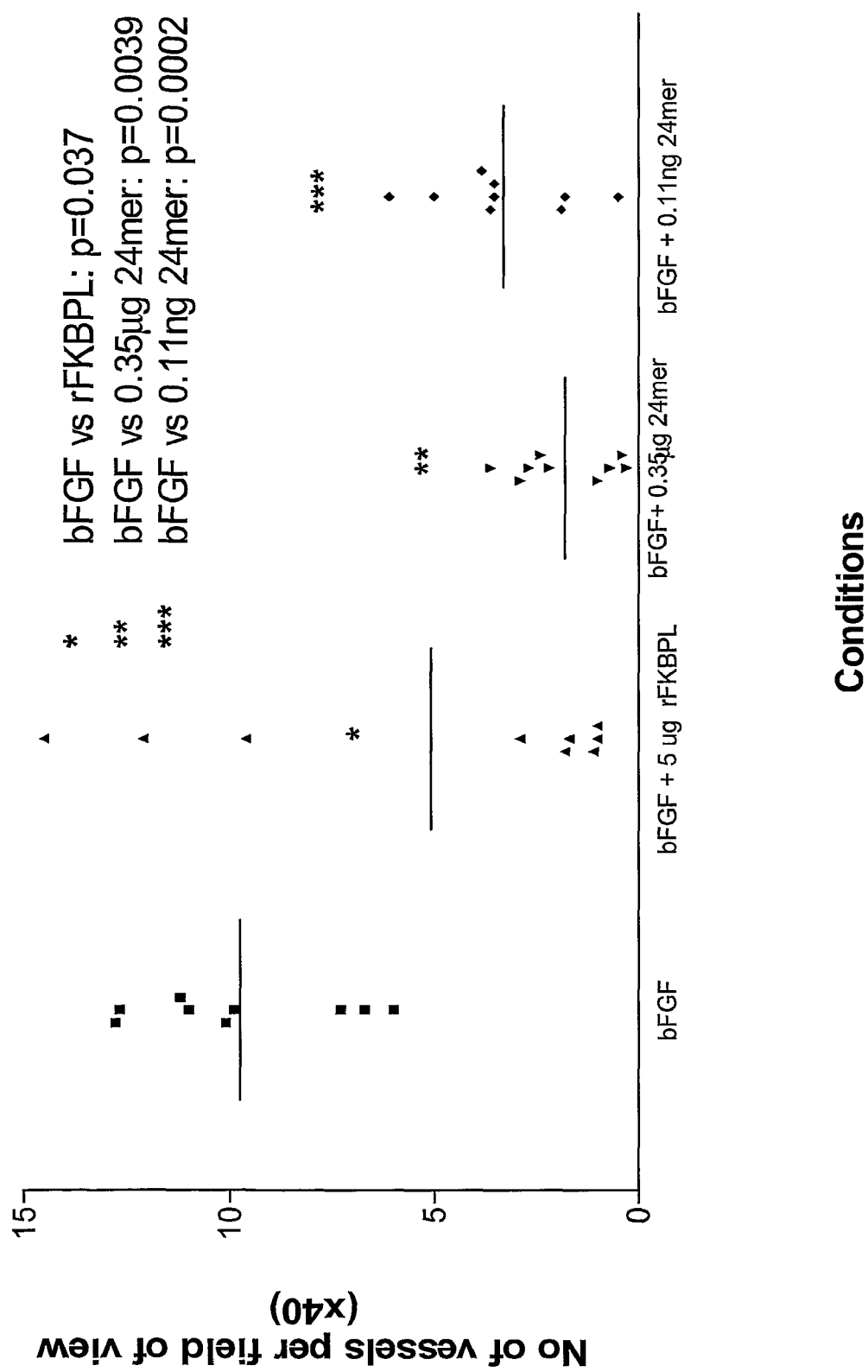
FIG. 29 illustrates that the FKBP-L 24mer inhibits angiogenesis in vivo using the mouse sponge assay; shown are numbers of vessels seen upon treatment with bFGF alone as compared to bFGF and full length recombinant FKBP-L polypeptide (rFKBP-L) (SEQ ID NO: 1), or bFGF in combination with the FKBP-L 24mer (24mer) (SEQ ID NO: 10) polypeptide, in accordance with alternate embodiments of the present invention.

The results are shown in FIG. 29. It can be seen that injection of bFGF alone resulted in a significant number of vessel growth into the sponge (mean no of vessels/×40 field=10). A 50% reduction in vessel number was observed in those sponges treated with both bFGF and 5 μg recombinant full length FKBPL. An 80% reduction in vessel number was observed in those sponges treated with both bFGF and 0.35 μg FKBPL 24mer. Even the lowest dose of FKBPL 24mer reduced vessel number by 70% compared to the bFGF alone treated sponges. These results show that the FKBPL 24mer can inhibit angiogenesis in vivo, suggesting potential therapeutic value in a clinical setting. The data also indicate that the FKBPL 24mer may be more potent than the full length FKBPL protein in inhibiting angiogenesis.

Example 26

Evaluation of the FKBPL 24mer Peptide (SEQ ID NO: 10) in a Mouse Endothelial Cell Line using the Wound Scrape Assay This experiment evaluated the ability of the FKBP-L 24mer to inhibit endothelial cell migration over a dose ranges spanning from $10^{-14}$ M to $10^{-7}$ M. The in vitro migration assay used in these studies is a modified version of the method described by Ashton et al (1999) see supra. In this assay mouse endothelial cells, 2H-11, were obtained from the American Tissue Culture Collection and were grown in D-MEM containing 10% FCS. They were plated into individual chambers on a glass slide and grown to 90% confluence overnight. The medium was removed and the monolayer wounded. The monolayer was re-supplemented with fresh medium and the required volume of the FKBPL 24mer peptide was added to achieve a dose range from $10^{-14}$-$10^{-7}$ M. The monolayers were incubated for 7 hours and then fixed in 4% PBS buffered paraformaldehyde.

The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L 24mer treated slides was compared to time matched sham treated controls and the % inhibition of wound closure compared to time matched controls calculated.

Figure 30:
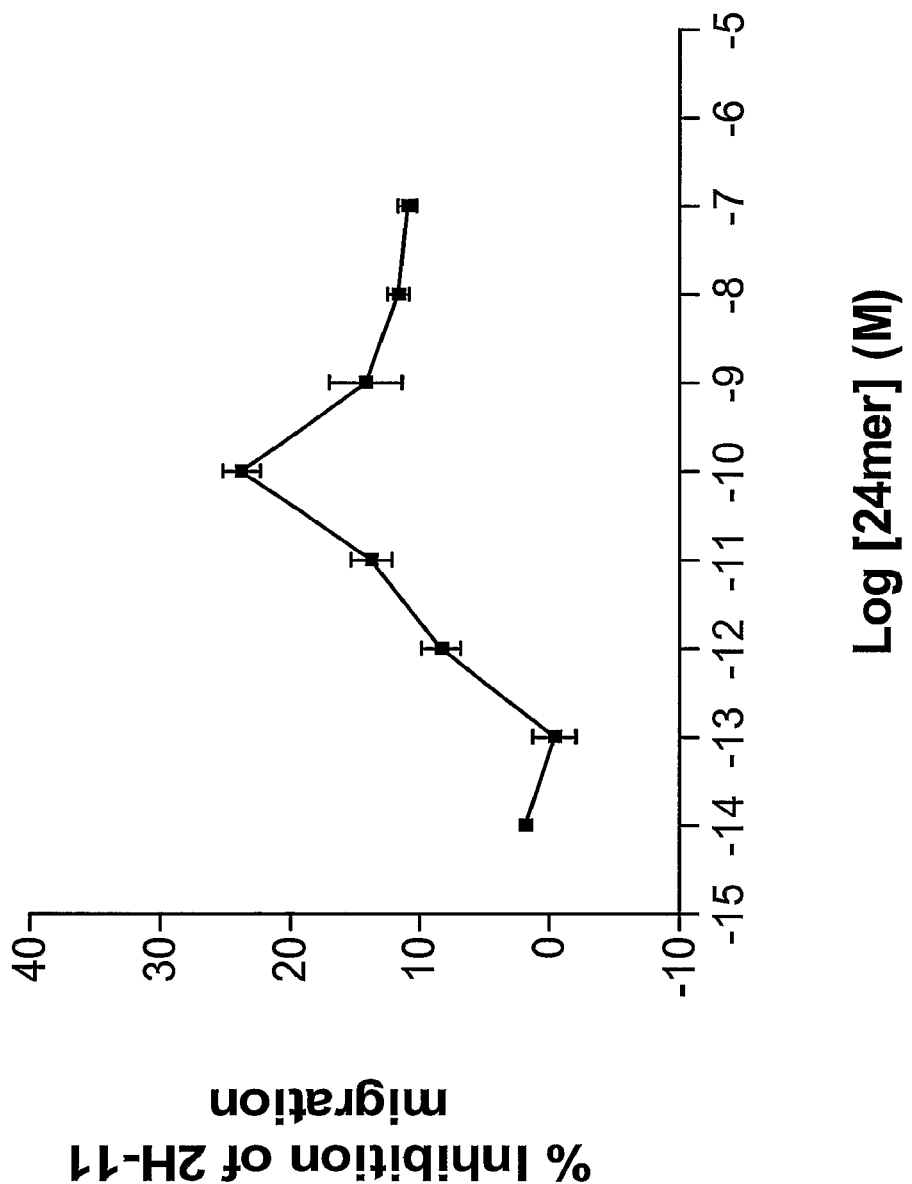
FIG. 30 illustrates inhibition of mouse endothelial cell (2H-11) migration by the FKBPL 24mer peptide (SEQ ID NO: 10) in accordance with an embodiment of the present invention.

The results of these experiments are shown in FIG. 30. It can be seen that the FKBPL 24mer inhibited wound closure in mouse endothelial cells. Maximal inhibition was observed between $10^{-9}$ and $10^{-11}$ M. The data demonstrate that the FKBPL 24mer inhibits migration of mouse endothelial cells and as such, may be an inhibitor of cell migration, angiogenesis and metastasis. The data support the in vivo experiments carried out in mice described herein (e.g. FIGS. 8,9,15,29 and 31)

Example 27

The FKBP-L 24mer Peptide (SEQ ID NO: 10 = QIRQQPRDPPTETLELEVSPDPAS) is a Potent Inhibitor of DU145 Tumor Growth in Vivo After Daily IP Injection (N=1, 6 Mice Per Treatment Group)

Cell Culture

Du145 (prostate carcinoma) cells were obtained from Cancer Research UK and cultured in RPMI 1640 medium (Invitrogen) supplemented with 10% foetal calf serum. All cell lines were grown as monolayers, incubated at 37° C. under 5% $CO_2$.

Prostate Cancer Xenograft Model 24 male immunocompromised (severe combined immunodeficient) mice were used (Harlan). The mice were acclimatised and caged in groups of 5 or less in an isolator. Du145 (prostate carcinoma) cells were cultured as previously described. Sub-confluent cells were harvested and the cell concentration was adjusted to $5 \times 10^7$ cells/ml in PBS. The dorsum of each mouse was shaved. After administrating aesthetic, each mouse received intra-dermal injections of $5 \times 10^6$ Du145 tumour cells (100 µl) bilaterally into the rear dorsum with a 26-gauge needle. The tumours were allowed to grow until they reached a volume of 150-175 $mm^3$. The mice were randomly divided into four treatment groups: (a) Control: PBS only (8 mice); (b) 24mer FKBPL peptide: 0.3 mg/kg/day (6 mice); (c) 24mer FKBPL peptide: $3 \times 10^{-3}$ mg/kg/day (6 mice); and (d) 24mer FKBPL peptide: $3 \times 10^{-4}$ mg/kg/day (5 mice).

The mice received daily IP injections (100 µl) of the above treatments. The weight and the tumour volume of each mouse were recorded every 2 days. Tumour volume was calculated as: Length×Breadth×Height×0.5236. Twenty-one days after initial treatment the following animals were sacrificed: 0.3 mg/kg/day 24mer FKBPL (2 mice), $3 \times 10^{-3}$ mg/kg/day (2 mice), $3 \times 10^{-4}$ mg/kg/day (1 mouse) and PBS (2 mice). The tumours were excised and stored in saline formalin solution for future histopathological analysis.

The results are shown in FIG. 31. It can be seen that treatment by i.p. injection with the 24mer FKBPL peptide at doses of either 0.3 mg/kg/day or $3 \times 10^{-3}$ mg/kg/day significantly slowed the growth of DU145 tumours in SCID mice compared to vehicle only treated tumours (FIG. 31A). A number of tumours treated with the most effective doses of 24mer FKBPL peptide showed evidence of a necrotic centre, i.e. they looked donut in shape. This is typical of the effects seen with anti-angiogenics.

A complete data set is shown in (FIG. 31A). Note that two PBS control-treated animals were excluded from the data shown in FIG. 31A. The first control animal was excluded because its tumor was eaten by another animal; the other control animal was excluded because its tumor was implanted too close to the tail in error, which is known to restrict growth.

Kaplan-Meier survival curves were drawn using the time for tumours to reach 3× their treatment volume as the criterion for sacrifice (FIGS. 31B-D). It can be clearly seen that the tumours of FKBPL 24mer treated animals at both 0.3 mg/kg/day (FIG. 31B) and 0.003 mg/kg/day (FIG. 31D) reached 3× their treatment volume significantly later than controls. All but two tumours (of 6) from the 0.3 mg/kg/day treatment group and one (of 6) from the 0.003 mg/kg/day treatment group failed to reach their volume tripling within the duration of the experiment. However, those tumors which did reach 3× treatment volume were clearly necrotic following gross examination. These tumors therefore were also responding but their larger size was caused by massive necrosis rather than viable tumour cells. Tumors in animals treated with the lowest dose of 0.0003 mg/kg/day were not significantly different from controls.

None of the animals lost weight after daily treatment with the 24mer suggesting that it is well-tolerated and not grossly toxic (FIG. 31E).

Example 28

The Effect of Candidate Peptides Spanning Active Domain of FKBP-L on the Viability or Proliferation of HMEC-1 using the MTT Assay (N=3)

An MTT assay was used to measure cell viability and/or proliferation. Briefly, HMEC-1 cells were seeded ($2.5 \times 10^3$) in 96 well plates and allowed to attach for 5 h. The cells were treated with FKBP-L 24mer (SEQ ID NO: 10) ($10^{-5}$-$10^{-10}$M), 1-57mer (SEQ ID NO: 6) ($10^{-9}$M and $10^{-10}$M) or medium (control).

Post incubation the cells were exposed to a 5 mgml$^{-1}$ solution of 3-(-4,5-dimethylthiazol-2-yl) 2,5 diphenyl tetrazolium (MTT) for 4 h. The cells were aspirated and 200 µl of DMSO added to reduce the salt and induce a colour change. The wells were analysed colourimetrically at 550 nm and the results compared to untreated control cells.

Figure 33A:
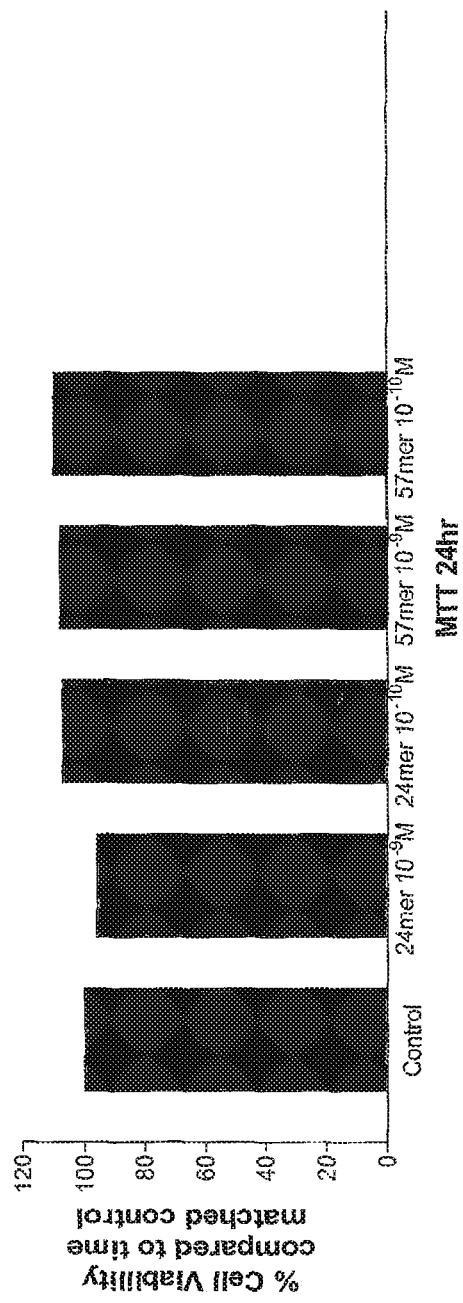
FIGS. 33A and 33B show the effect of candidate peptides spanning active domain of FKBP-L on the viability or proliferation of HMEC-1 cells upon administration for 24 hours (FIG. 33A) or 48 hours (FIG. 33B) using the MTT assay in accordance with alternate embodiments of the present invention.
Figure 33B:
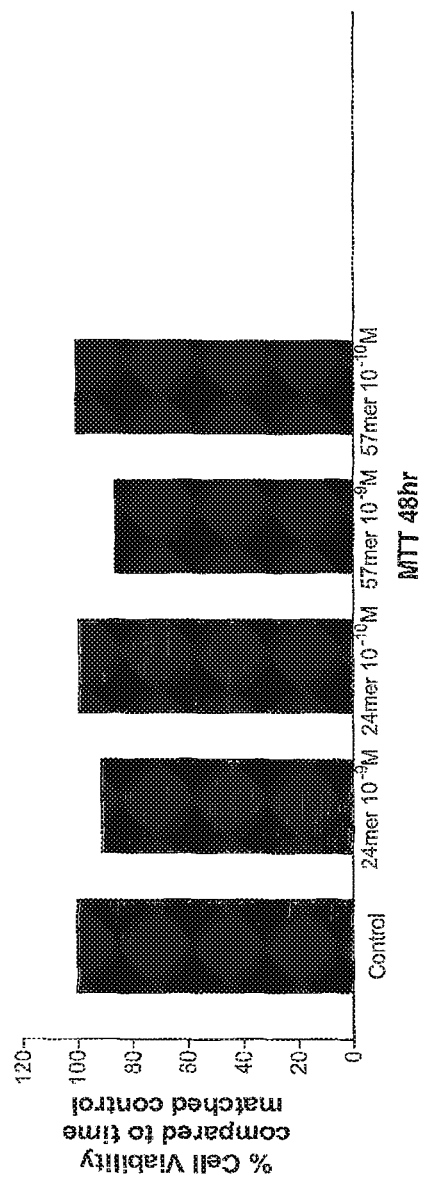
Figure 34A:
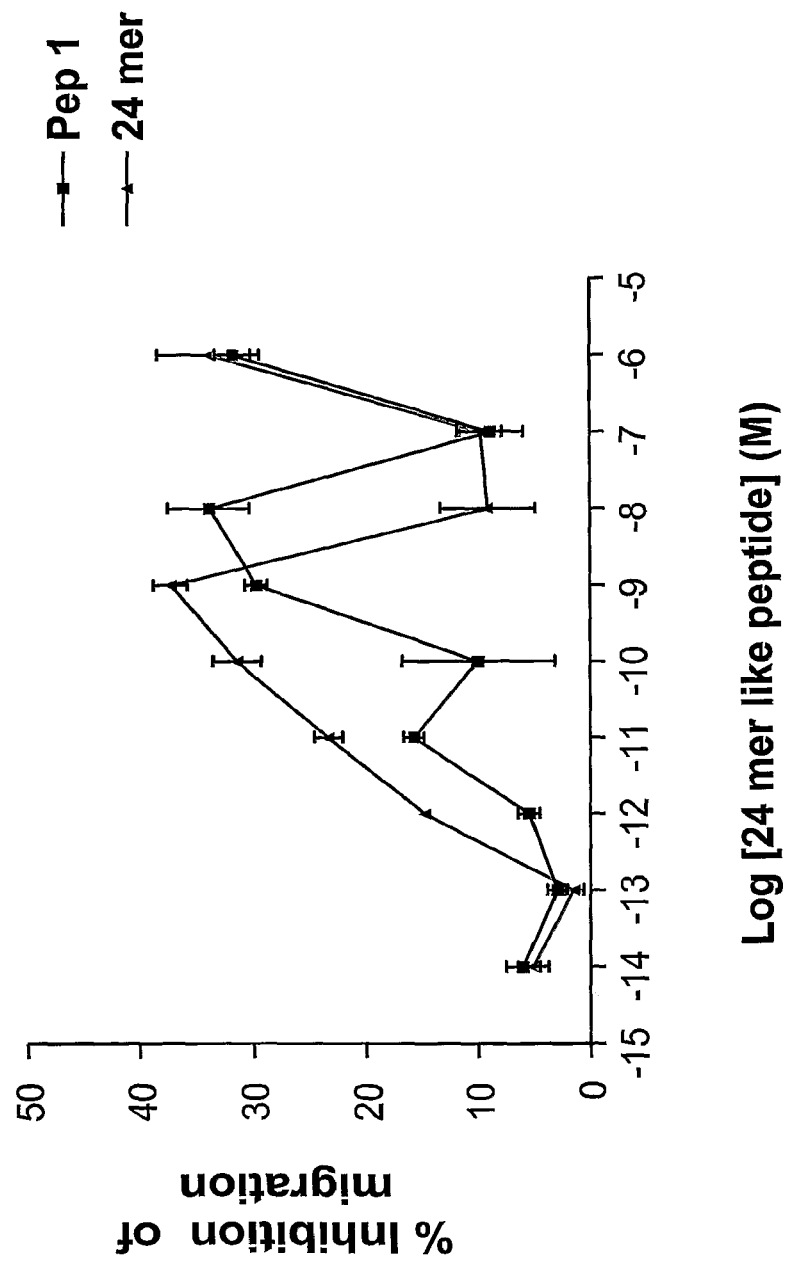
Figure 34B:
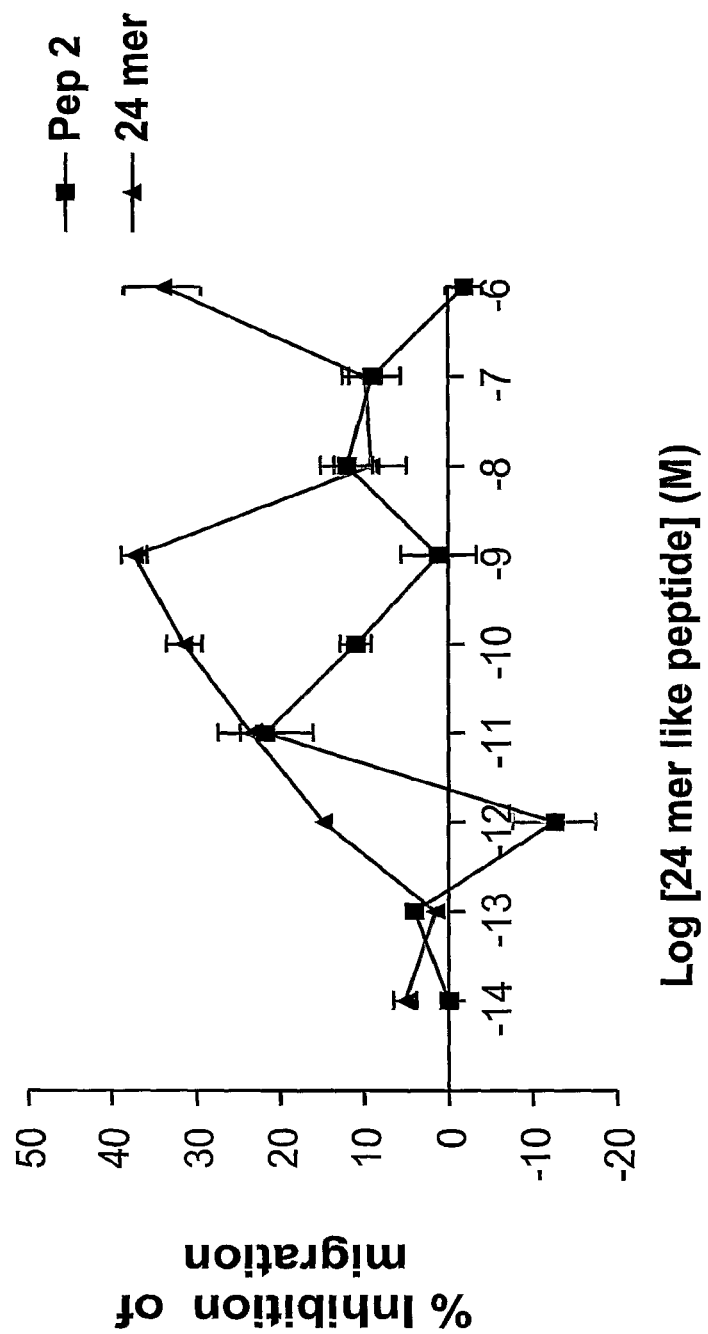
Figure 34C:
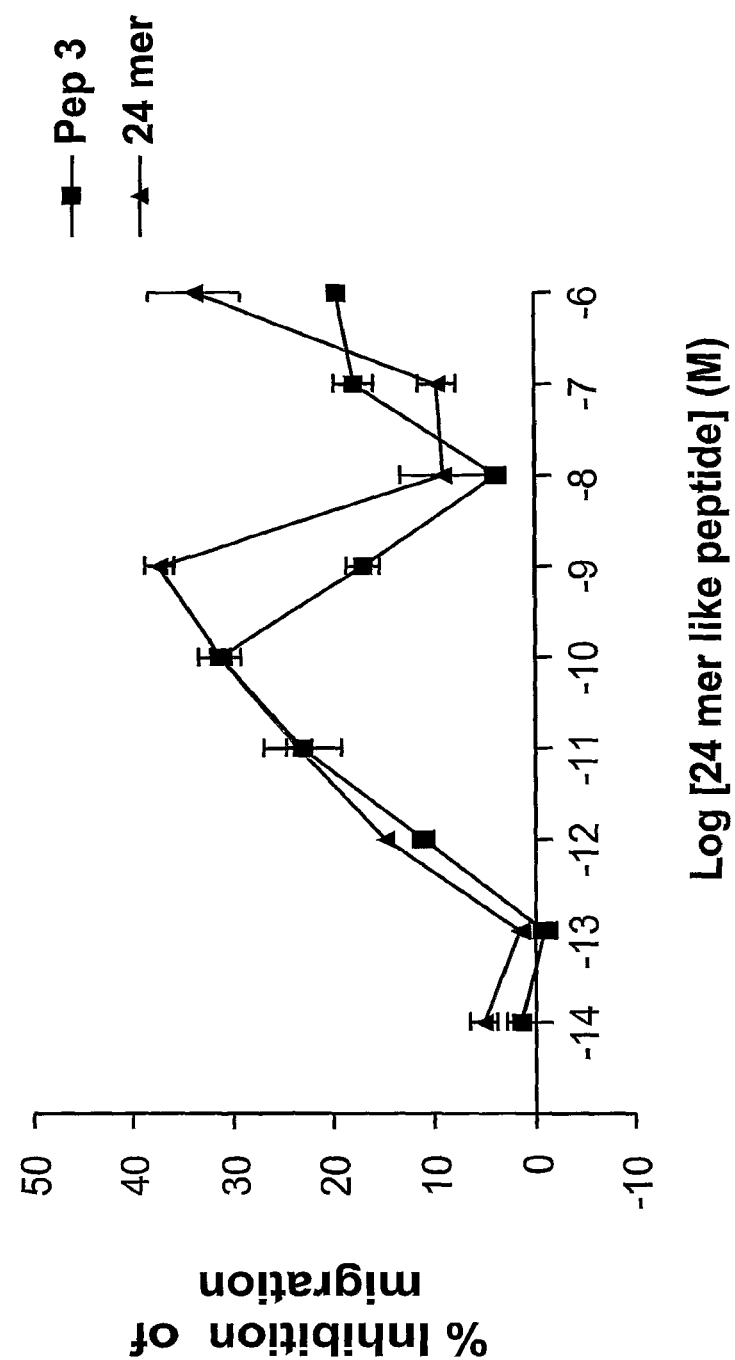
Figure 34D:
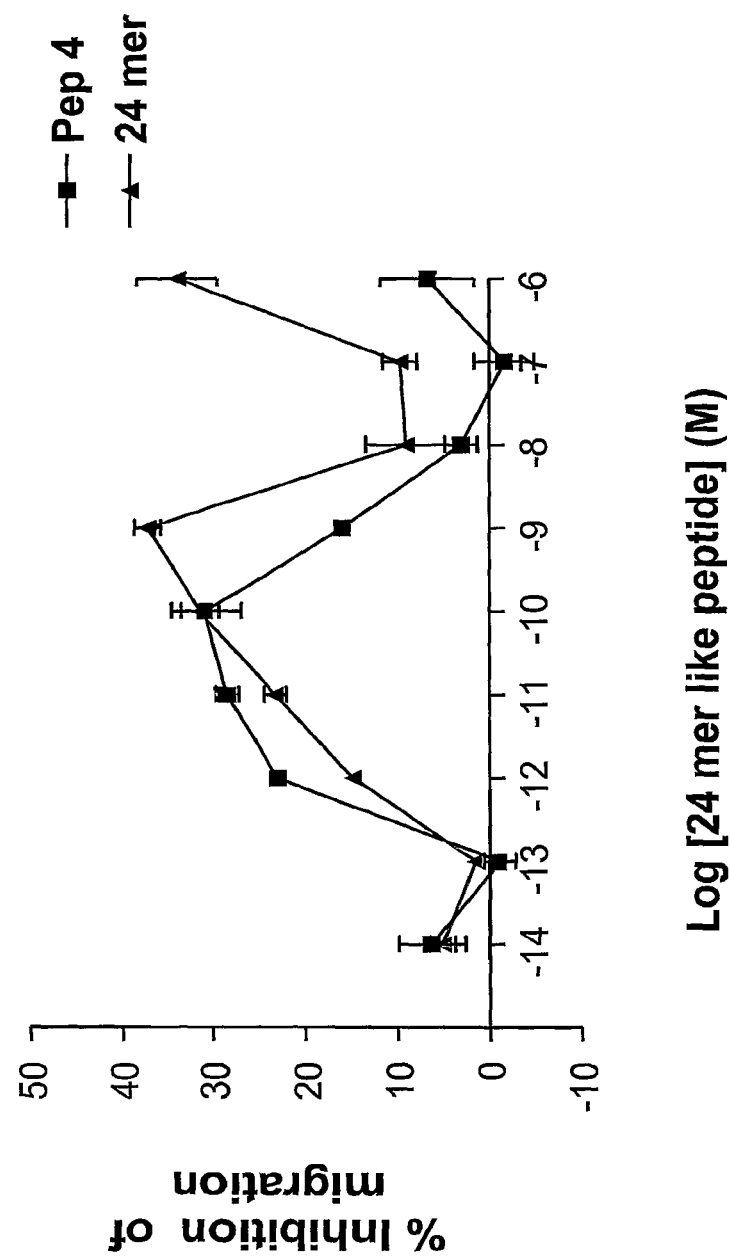
Figure 34E:
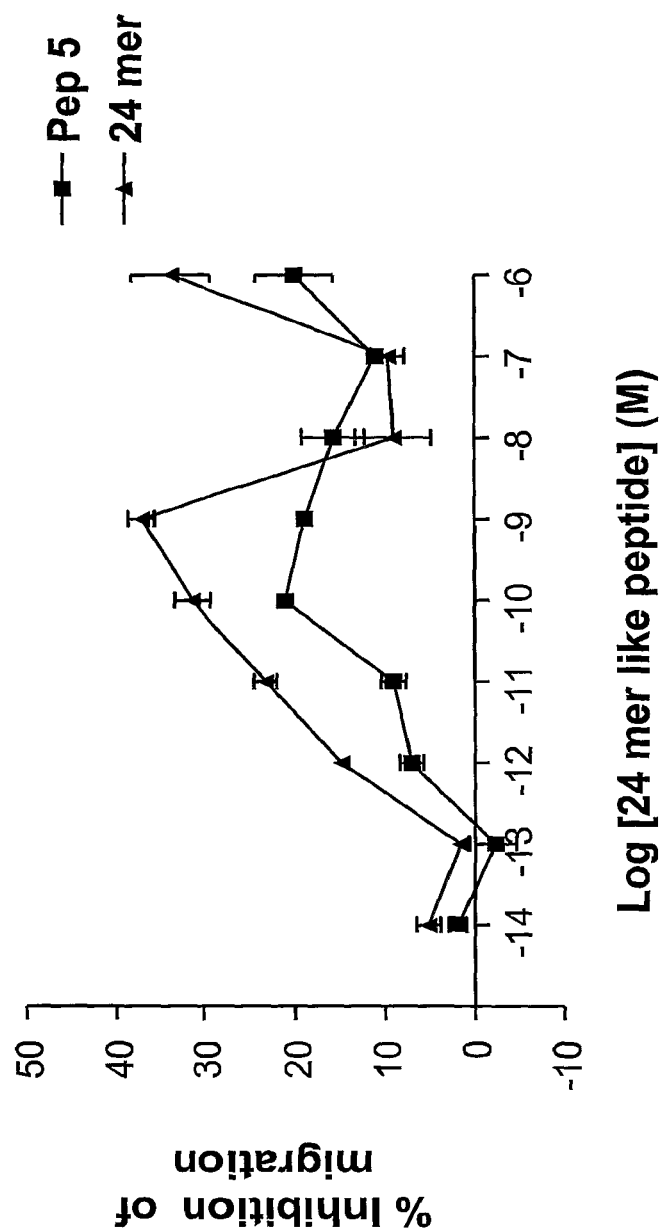
Figure 34F:
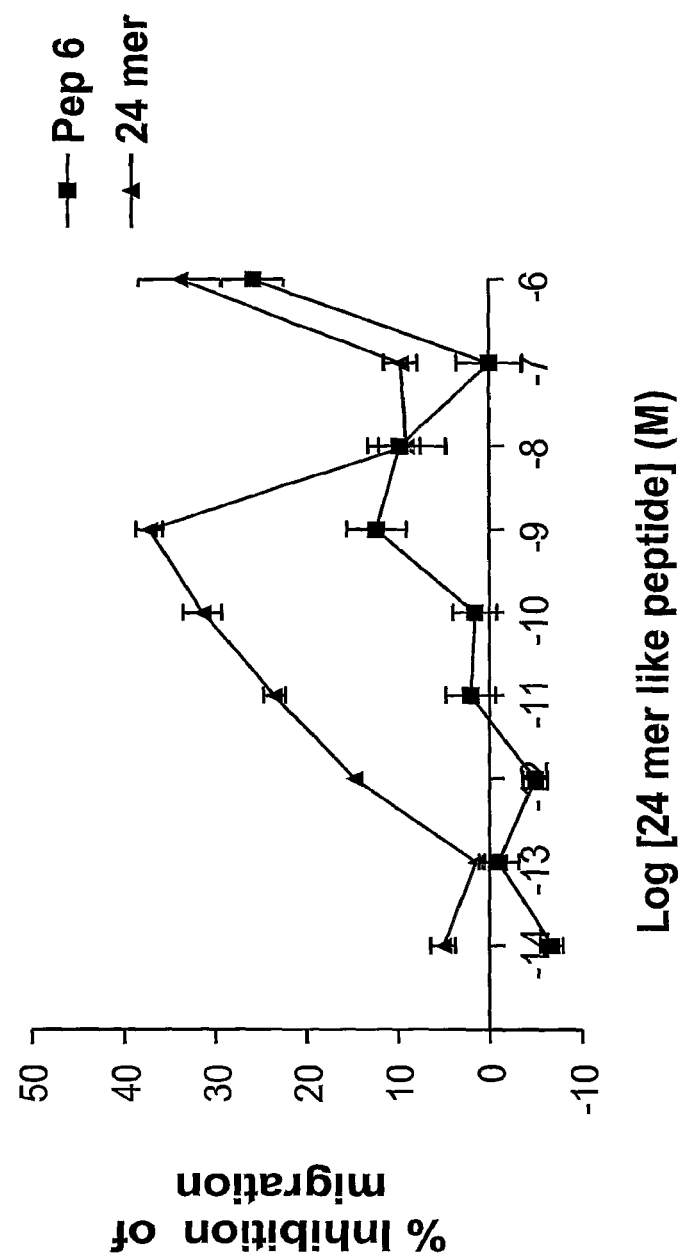
Figure 34G:
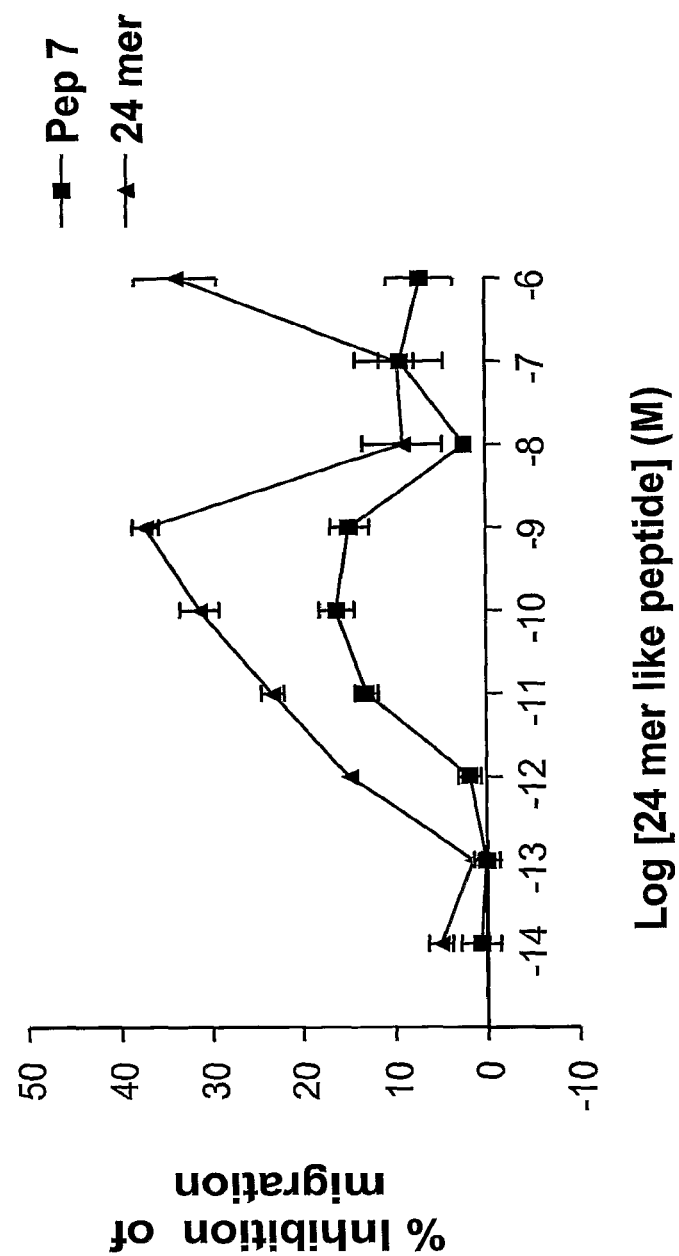
Figure 34H:
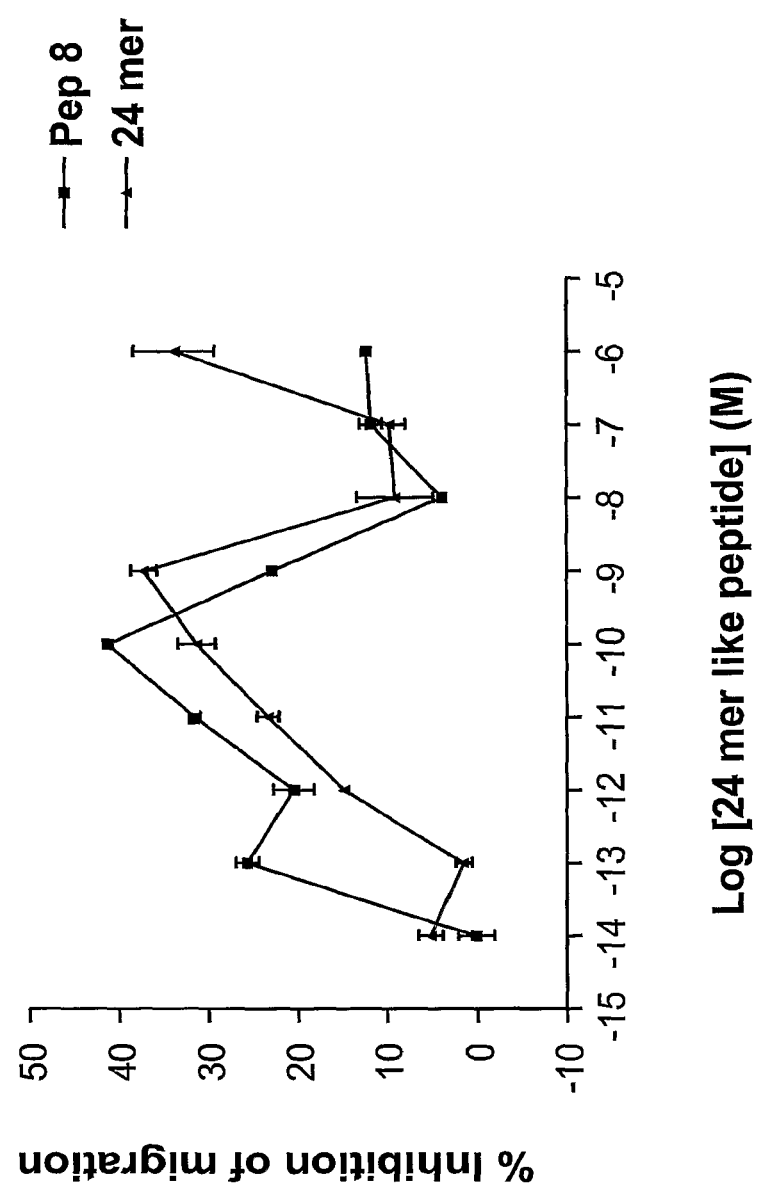
Figure 34I:
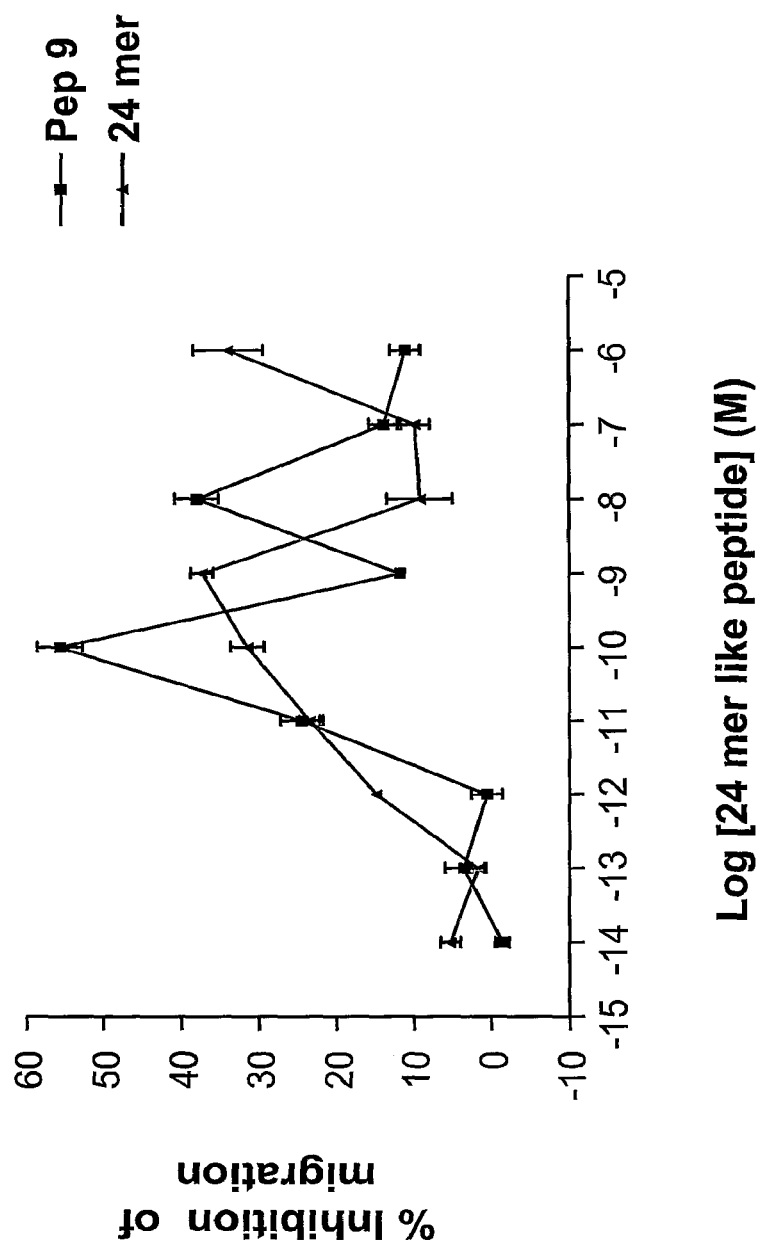
Figure 34J:
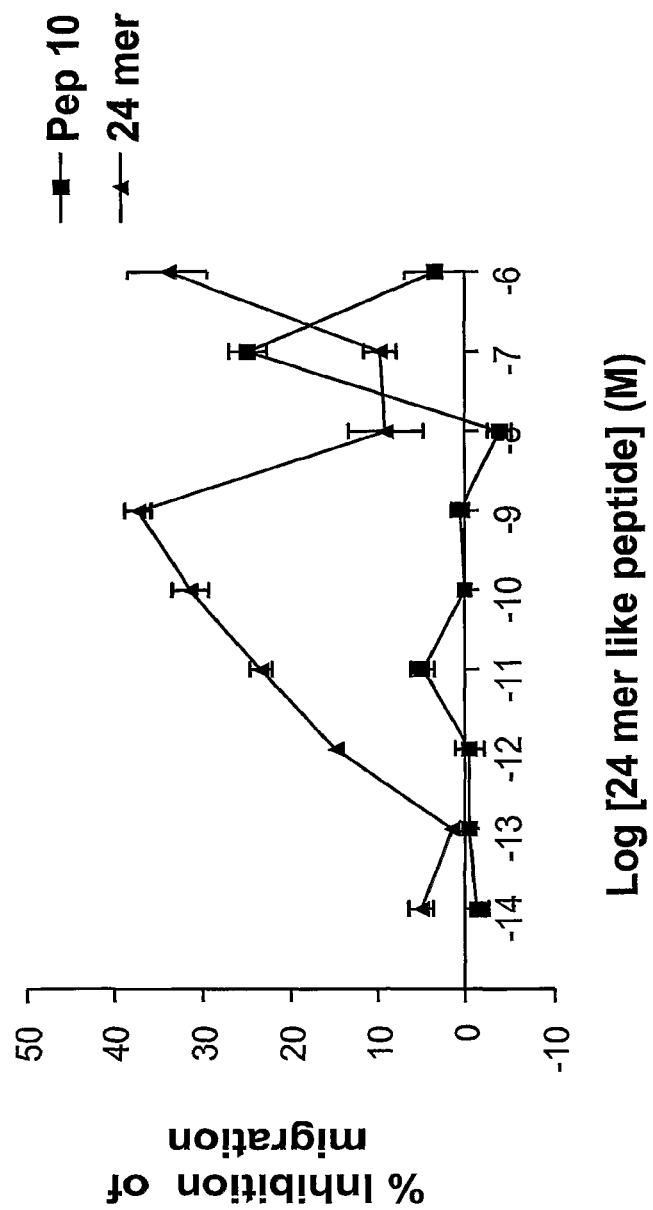
Figure 34K:
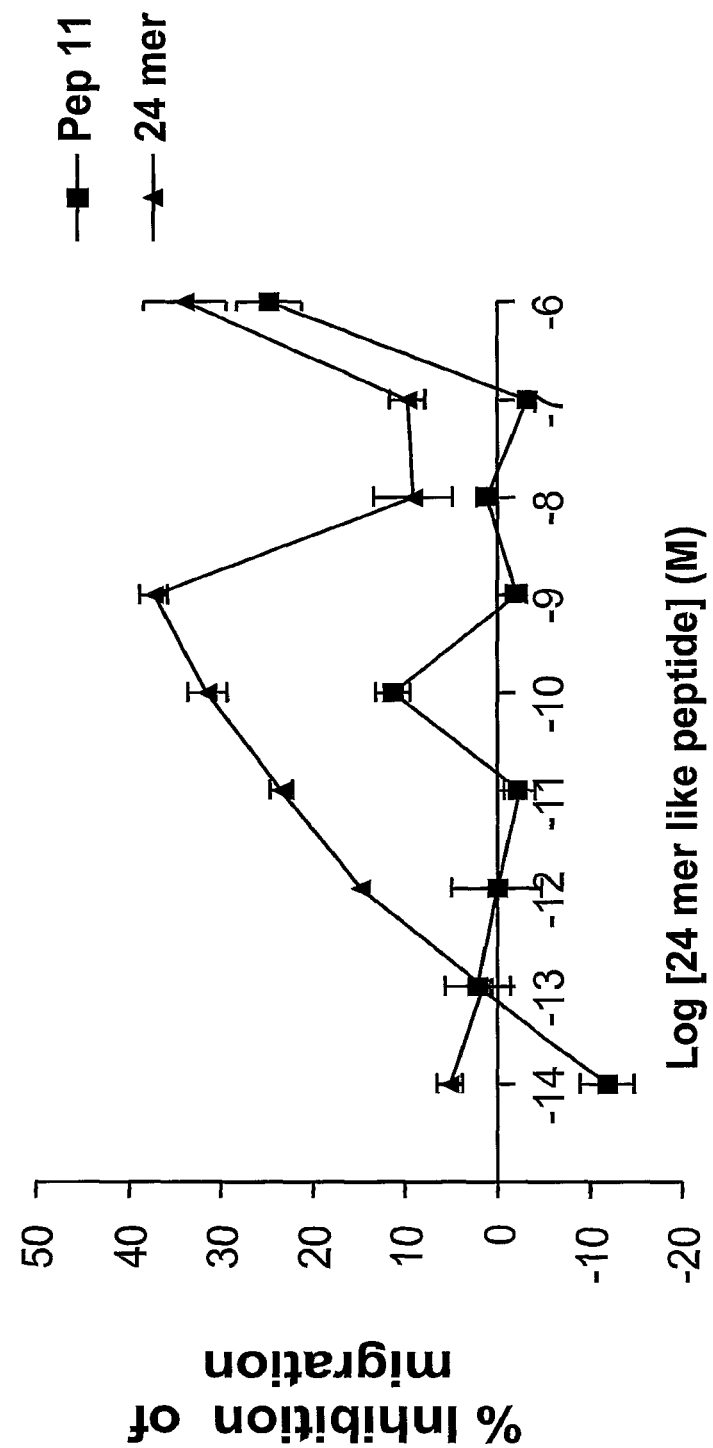

The results ares shown in FIGS. 32 and 33. FIG. 32 shows a dose range for treatment of cells with the FKBP-L 24mer and FIGS. 33A and 33B show the effect of the FKBP-L 24mer and FKBP-L 1-57 (57mer) after 24 hours and 48 hours, respectively. It can be seen that neither of the peptides had any significant effect on the proliferation of HMEC-1 cells compared to time-matched controls at any of the time points measured, suggesting that the antiangiogenic effects observed in the previous assays were not caused by inhibition of cell growth or by peptide-mediated toxicity.

Example 29

Analysis of Truncated 24mer Based Peptides in Order to Assess the Importance of Each Peptide in Terms of Inhibition of Cell Migration using the Wound Scrape Assay The in vitro migration assay used in these studies is a modified version of the method described by Ashton et al. (1999) see supra. HMEC-1 were plated into individual chambers on a glass slide and grown to 90% confluence overnight. The medium was removed and the monolayers wounded. The monolayer was re-supplemented with fresh medium and the required volume of each peptide (i.e., peptides 1-17, SEQ ID NOS: 12-28; Table 4 below) was added to give the required final concentration ($10^{-14}$-$10^{-6}$ M).

To make Peptide 1, the fluorophore Alexa488 (Invitrogen) was attached to the side-chain sulfhyrdyl functionality of a cysteine reside which was placed at the C-terminus of the 24mer sequence. A -PEG-spacer was used to link this C-terminal cysteine residue to the C-terminus of the 24mer sequence. This was done during the synthesis of the peptide by incorporating the commercially available building block Fmoc-8-amino-3,6-dioxaoctanoic acid, a polyethylene glycol spacer (NeoMPS) to give a -PEG spacer between the 24mer sequence and the C-terminal Alexa labeled cysteine. The PEG spacer/fluorophore has the structure: —NH—$(CH_2)_2$O—$(CH_2)_2$O—$(CH_2)$—CO-Cys-(Alexa488). The other peptides were also made by incorporating commercially available building blocks to generate the peptides 2-17 below.

TABLE 4

FKBP-L Peptides

| Peptide | Sequence | SEQ ID NO: |
|---|---|---|
| 1 | QIRQQPRDPPTETLELEVSPDPAS-PEG-C(Alexa488) | 12 |
| 2 | PyroGlu-IRQQPRDPPTETLELEVSPDPAS-OH | 13 |
| 3 | IRQQPRDPPTETLELEVSPDPAS-OH | 14 |
| 4 | QIRQQPRDPPTETLELEVSPD-OH | 15 |
| 5 | QIRQQPRDPPTETLELEV-OH | 16 |
| 6 | QIRQQPRDPPTETLE-OH | 17 |
| 7 | QIRQQPRDPPTE-OH | 18 |
| 8 | QQPRDPPTETLELEVSPDPAS-OH | 19 |
| 9 | RDPPTETLELEVSPDPAS-OH | 20 |
| 10 | PTETLELEVSPDPAS-OH | 21 |
| 11 | TLELEVSPDPAS-OH | 22 |
| 12 | RQQPRDPPTETLELEVSPD-OH | 23 |
| 13 | RQQPRDPPTETLELEVSP-OH | 24 |
| 14 | RQQPRDPPTETLELEVS-OH | 25 |
| 15 | PRDPPTETLELEVSPD-OH | 26 |
| 16 | RDPPTETLELEVSPD-OH | 27 |
| 17 | Ac-QIRQQPRDPPTETLELEVSPDPAS-NH$_2$ | 28 |

The monolayers were incubated for 24 h and then fixed in 4% PBS buffered paraformaldehyde. The extent of "wound" closure was blindly assessed microscopically by an independent investigator and quantified using a calibrated eyepiece graticule (1 mm/100 μm graduation) at 20× magnification (Olympus BX 50). The extent of closure in the FKBP-L treated slides was compared to time matched sham treated controls and the % inhibition of wound closure compared to time matched controls calculated.

The reults for Peptides 1-12 are shown in FIG. 34A-L, respectively and Table 5.

TABLE 5

| Peptide | low dose activity | high dose activity |
|---|---|---|
| 24 mer | +++ | +++ |
| Pep1<br>QIRQQPRDPPTETLELEVSPDPAS(488) | +++ | +++ |
| Pep 2<br>pQIRQQPRDPPTETLELEVSPDPAS | - | - |
| Pep 3<br>IRQQPRDPPTETLELEVSPDPAS | +++ | + |
| Pep 4<br>QIRQQPRDPPTETLELEVSPD | +++ | - |
| Pep 5<br>QIRQQPRDPPTETLELEV | ++ | + |
| Pep 6<br>QIRQQPRDPPTETLE | - | ++ |
| Pep 7<br>QIRQQPRDPPTE | + | - |
| Pep 8<br>QQPRDPPTETLELEVSPDPAS | ++++ | - |
| Pep 9<br>RDPPTETLELEVSPDPAS | ++++ | ++ |
| Pep 10<br>PTETLELEVSPDPAS | - | ++ |
| Pep 11<br>TLELEVSPDPAS | - | ++ |

TABLE 5-continued

| Peptide | low dose activity | high dose activity |
| --- | --- | --- |
| Pep 12 RQQPRDPPTETLELEVSPD-OH | +++ | +++ |

It was found that Peptide 12 showed activity that was about the same as the FKBP-L 24mer. These data suggest that some FKBP-L derived peptides exhibit a biphasic dose response. The data also suggest that the subregion -QQPRD-PPTETLELEVSPD- (SEQ ID NO: 11) may be a potent anti-angiogenic domain. The data further indicate that a fragment of SEQ ID NO: 10 including 18 or more contiguous amino acids (see e.g., Peptide 5, SEQ ID NO: 16; Peptide 12, SEQ ID NO: 23, and SEQ ID NO: 11) may be active as an anti-angiogenic agent. Additional peptides including this domain are shown in FIG. 1.

Example 30

Analysis of Purified Recombinant FKBP-L

Recombinant FKBP-L Protein Expression

FKBP-L (variant Thr181, Gly186), cloned into the BamHI and PstI sites of the pRSET-A vector, was expressed in BL21 (DE3) to give the corresponding N-terminal polyhistidine tagged protein (SEQ ID NO: 1). Expression was induced at OD 0.6 with 0.2 mM IPTG, growing cells overnight at 15° C. Cells were pelleted by centrifugation and stored at −20° C.

Recombinant FKBP-L Purification

Purification of protein was done under denaturing conditions, with an on-the-column refolding step. Cells were lysed in lysis buffer (100 mM $NaH_2PO_4$ pH 8.0, 10 mM Tris, 8 M urea, 150 mM NaCl, 5 mM β-mercoptoethanol) by sonicating on ice for 3× 2 mins with cooling. Cell debris and insoluble material was removed by centrifugation at 31,100 rcf for 20 mins at 4° C. The supernatant was syringe filtered through 0.45 µm filters.

A 5 ml HisTrap HP column was equilibrated in binding buffer (8 M urea, 0.5 M NaCl, 20 mM sodium phosphate buffer pH 8.0, 5 mM β-mercoptoethanol) and the cell lysate loaded onto the column. The column was washed with 10 column volumes of wash buffer (8 M urea, 0.5 M NaCl, 20 mM sodium phosphate buffer pH 8.0, 20 mM imidazole, 5 mM β-mercoptoethanol), then re-equilibrated in the binding buffer.

Bound protein was refolded slowly in a 30 ml 0-100% linear gradient of refold buffer (5 mM imidazole, 0.5 M NaCl, 20 mM sodium phosphate buffer pH 7.4, 1 mM β-mercoptoethanol), followed by 5 mins at 100% refold buffer.

Bound proteins were eluted in a 30 ml 0-100% linear gradient of elution buffer (500 mM imidazole, 0.5 M NaCl, 20 mM sodium phosphate buffer pH 7.4, 1 mM β-mercoptoethanol). Fractions were analysed by SDS PAGE and pooled accordingly. To reduce the concentrations of imidazole, NaCl and β-mercoptoethanol, protein was either dialysed against 20 mM sodium phosphate buffer pH 7.4 with 150 mM NaCl (FIG. 35A) or run through a HiLoad 26/60 Superdex75 26/60 prep column in 20 mM sodium phosphate buffer pH 7.4, 150 mM NaCl, 5 mM imidazole (FIG. 35C and FIG. 36). Recombinant FKBP-L samples were compared by SDS PAGE (FIGS. 35 A and 35B) and native PAGE (FIG. 35C, inset).

Analytical HPLC and Mass Spectrometry

50 µg samples of recombinant FKBP-L with and without 100 mM DTT were run on an analytical Jupiter 5u c5 column with a 0-73% gradient of acetonitrile over 30 minutes. Peaks were collected and analysed by electrospray mass spectrometry.

Gel Permeation Analyses

The following molecular weight standards were run on a Superosel12 10/300 GL column in buffer (20 mM $NaH_2PO_4$ pH 7.4, 150 mM NaCl, 5 mM imidazole): blue dextran, alcohol dehydrogenase, bovine serum albumin, ovalbumin, carbonic anhydrase and cytochrome c. The elution volumes of the peaks were used to calculate Kav for full length recombinant FKBP-L, from which the molecular mass could be calculated from the calibration curve. The Kav was calculated as $$Kav=(Ve-Vo)/(Vt-Vo)$$

where Ve is the elution volume, Vo is the void volume (elution volume for blue dextran) and Vt is the total column volume. Kav was plotted against log molecular weight to give a straight line from which the equation was extracted and used to estimate the molecular weight for a given Ve.

For analysis, 140 µg samples of recombinant FKBP-L with and without 100 mM DTT were run under the same conditions and the estimated molecular masses estimated from the Ve as described above. In addition the column was equilibrated in buffer +1 mM DTT and a further sample of FKBP-L pretreated with DTT was run under these conditions (FIG. 36).

Protein Cross-Linking using Glutaraldehyde

Figure 37:
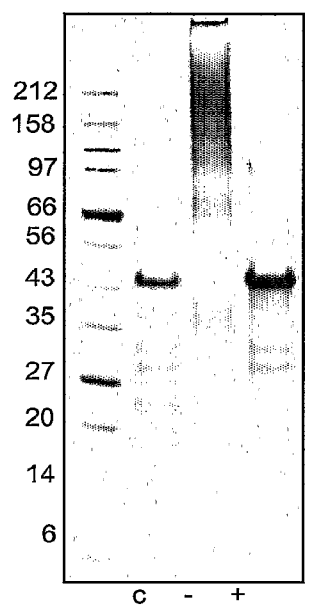
FIG. 37 shows glutaraldehyde cross-linking of recombinant FKBP-L in the presence (+) and absence (−) of 100 mM DTT in accordance with alternate embodiments of the present invention. Lane c is the control (no DTT).

A 1% final concentration of glutaraldehyde was added to 25 µg recombinant FKBP-L (dialysed) in 500 µl buffer (20 mM $NaH_2PO_4$ pH 7.4, 150 mM NaCl, ~5 mM imidazole) for 30 seconds. The reaction was quenched by adding $NaBH_4$, the protein precipitated with Na deoxycholate and TCA and analysed by SDS PAGE under reducing conditions (FIG. 37).

These experiments show that the recombinant FKBP-L protein expressed and purified and dialysed here showed single band purity upon SDS PAGE analysis under reducing conditions (FIG. 35A). SDS PAGE analysis and native PAGE analysis of FKBP-L (FIG. 35B and FIG. 35C respectively) under non-reducing conditions (FIG. 35B lane 3 and FIG. 35C) and reducing conditions (FIG. 35B lane 4 and FIG. 35C) shows that FKBP-L forms higher molecular weight multimeric species through the formation of intermolecular disulphide bond formation between cysteine residues within the protein.

Analytical HPLC analysis of recombinant FKBP-L followed by electrospray mass spectrometry gave a mass of 42,257 (expected 42,220) for the reduced FKBP-L, confirming the identity of the protein.

Gel permeation analysis was used to try to gain information about the quaternary structure of recombinant FKBP-L (FIG. 36). Under the conditions described, the reduced FKBP-L elutes with an average elution volume 12 ml. From calibration of the column with a series of molecular weight standards, an elution volume of 12 ml corresponds to a mass of 99 KDa. Similarly glutaraldehyde cross-linking of recombinant FKBP-L in the presence of DTT consistently showed a band on SDS PAGE analysis running at 97 kDa (FIG. 37). These results indicate that FKBP-L may form homodimeric and/or homotrimeric species through noncovalent association. This is consistent with the predicted presence of tetratricopeptide repeats within the FKBP-L amino acid sequence, which are known to induce trimerisation in other proteins.

Example 31

Generation of FKBP-L Antibodies

FKBP-L (variant Thr181, Gly186), cloned into the BamHI and PstI sites of the pRSET-A vector, was expressed in BL21 (DE3) to give the corresponding N-terminal poly-histidine tagged protein (SEQ ID NO: 1). A sequence verified clone was transformed into BL21(DE3) *E. coli* cells and cultured to log phase, and target protein expression induced by addition of isopropyl-b-D-thiogalactoside (IPTG, 1 mM) and incubated for a further 4 hours at 37° C. Cell pellets were resuspended and lysed in 50 mM $NaH_2PO_4$, pH 8.0, containing 8 M urea, 300 mM NaCl and 10 mM imidazole. The crude denatured lysate was clarified by centrifugation (10,000 g, 60 minutes at 4° C.), prior to application to a IMAC column charged with $Ni^{2+}$ ions HiTrap 1 ml column (GE Healthcare). Non-specifically bound material was washed from the column using 50 mM $NaH_2PO_4$, pH 8.0, containing 8 M urea, 300 mM NaCl and 20 mM imidazole, followed by on-column refolding by reduction of the urea from 8 to 0 M over 200 column volumes. Refolded column bound material was washed with a further 20 column volumes of 50 mM $NaH_2PO_4$, pH 8.0, 300 mM NaCl and 20 mM imidazole, then eluted with 50 mM $NaH_2PO_4$, pH 8.0, 300 mM NaCl, and 250 mM imidazole. Protein fractions were collected and desalted into PBS.

Rabbits were immunized (following standard UK Home Office guidelines) with the recombinant protein and boosts were given every 3 weeks until four boosts were completed. Serum was collected and evaluated against recombinant FKPP-L (generated as the antigen) by western blot analysis. An FKBPL band of approximately 39 kDa was detected.

Embodiments of the present invention therefore provide methods and compositions comprising FKBP-L. In certain embodiments, FKBP-L and its peptide fragments are polypeptides with clinical utility as anti-angiogenic and/or anti-metastatic agents for use in treatment of cancer and/or other conditions where such therapy would be expected to have a positive prognostic outcome. The polypeptide has demonstrable growth-inhibiting effects on selected cancer cells indicative of a potential secondary or primary therapeutic effect on specified tumors.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method of inhibiting angiogenesis in a subject in need thereof, comprising administering to the subject a therapeutically effective amount of a composition comprising an isolated polypeptide and a pharmaceutical carrier;
   wherein the subject in need thereof has a disorder mediated by angiogenesis;
   wherein the isolated polypeptide comprises a biologically active fragment of FKBP-L comprising no more than 200 amino acids of full length FKBP-L;
   wherein the biologically active fragment comprises SEQ ID NO: 11;
   wherein the biologically active fragment is not SEQ ID NO: 10, or SEQ ID NO: 14; and
   wherein the full length FKBP-L consists of SEQ ID NO: 1, SEQ ID NO: 2 or SEQ ID NO: 29.

2. The method of claim 1, wherein the disorder mediated by angiogenesis is an inflammatory disorder.

3. The method of claim 1, wherein the disorder mediated by angiogenesis is an ocular disorder.

4. The method of claim 1, wherein the disorder mediated by angiogenesis is cancer.

5. The method of claim 4, wherein the cancer is chosen from colorectal carcinoma, gastric carcinoma, signet ring type, esophageal carcinoma, intestinal type, mucinous type, pancreatic carcinoma, lung carcinoma, breast carcinoma, renal carcinoma, bladder carcinoma, prostate carcinoma, testicular carcinoma, ovarian carcinoma, endometrial carcinoma, thyroid carcinoma, liver carcinoma, larynx carcinoma, mesothelioma, neuroendocrine carcinomas, neuroectodermal tumors, melanoma, gliomas, neuroblastomas, sarcomas, leiomyosarcoma, fibrosarcoma, liposarcoma, chondrosarcoma, leukemia, and lymphoma metastasis.

6. The method of claim 4, wherein administration of the composition further results in at least one anti-tumor effect chosen from reduction of tumor cell migration and reduction of metastasis in the subject.

7. The method of claim 4, wherein administration of the composition further results in at least one anti-tumor effect chosen from reduction of tumor cell growth and reduction of tumor cell proliferation in the subject.

8. The method of claim 1, wherein the composition is administered in combination with at least one further treatment chosen from a chemotherapeutic agent, a chemopreventative agent, radiotherapy, and a combination of the same.

9. The method of claim 8, wherein the at least one chemotherapeutic agent or chemopreventative agent comprises at least one agent chosen from endostatin, angiostatin, VEGF inhibitors, cytotoxic agents, alkaloids, antimetabolites, cancer growth inhibitors, gene therapy therapeutics, cancer vaccines, interferons, Aldesleukin, monoclonal antibodies, radiotherapy, and hormonal therapy.

10. The method of claim 9, wherein the cytotoxic agents are chosen from adriamycin, daunomycin, cis-platinum, etoposide, taxol, and taxotere.

11. The method of claim 9, wherein the alkaloids are chosen from vincristine and farnesyl transferase inhibitors.

12. The method of claim 9, wherein the cancer growth inhibitors are chosen from bortezomib, erlotinib, gefitinib, imatinib, and sorafenib.

13. The method of claim 9, wherein the hormonal therapy is chosen from anastrozole, bicalutamide, buserelin, cyproterone, diethylstilbestrol, exemestane, flutamide, fulvestrant, goserelin, letrozole, leuprorelin, medroxyprogesterone, megestrol acetate, tamoxifen, toremifene, and triptorelin.

14. The method of claim 9, wherein the monocolonal antibodies are chosen from 90Y-ibritumomab tiuxetan, alemtuzumab, bevacizumab, cetuximab, gemtuzumab, iodine 131 (131 I) tositumomab, panitumumab, rituximab, and trastuzumab.

15. The method of claim 1, wherein the composition is administered in combination with supportive therapy and wherein the supportive therapy is chosen from bisphosphonates, blood transfusions, erythropoietin, haematopoietic growth factors, plasma exchange, platelet transfusions, steroids, hyperbaric oxygen therapy, hyperthermia treatment, and photodynamic therapy.

16. The method of claim 8, wherein the at least one chemotherapeutic agent or chemopreventative agent comprises at least one agent chosen from chemotherapy drugs and antiangiogenics.

17. The method of claim 8, wherein the at least one chemotherapeutic agent or chemopreventative agent is chosen from amsacrine, bleomycin, busulfan, capecitabine, carboplatin, carmustine, chlorambucil, cisplatin, cladribine, crisantaspase, cycolophosphamide, cytarabine, dacarbazine, dactinomycine, daunorubicin, docetaxel, doxorubicin, epirubicin, etoposide, fludarabine, fluorouracil, gemcitabine, gliadel implants, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, streptozocin, tegafur-uracil, temozolomide, teniposide, thiotepa, tioguanine, topotecan, treosulfan, vinblastine, vincristine, vindesine, and vinorelbine.

18. The method of claim 1, wherein the isolated polypeptide is linked to a polymer and wherein the polymer is chosen from dextrans, polyvinyl pyrrolidones, and polyethylene glycol.

19. The method of claim 18, wherein the polymer polyethylene glycol.

20. The method of claim 1, wherein the isolated polypeptide is linked to a molecule chosen from carbohydrates, monosaccharides, oligosaccharides, polysaccharides, glycolipids, heterocyclic compounds, nucleosides, and nucleotides.

21. The method of claim 1, wherein the isolated polypeptide is a modified polypeptide, and wherein the modified polypeptide is chosen from phosphopeptides, cyclic peptides, peptides containing D-amino acids, and peptides containing radiolabels.

22. The method of claim 21, wherein the modified polypeptide is chosen from peptides containing D-amino acids and peptides containing radiolabels.

23. The method of claim 1, wherein the isolated polypeptide is modified by the addition of biotin.

24. The method of claim 1, wherein the isolated polypeptide is modified by the addition of a moiety to facilitate crosslinking, wherein the moiety is chosen from benzophenone, maleimide, and activated esters.

25. The method of claim 1, wherein the isolated polypeptide is modified by the addition of a moiety to facilitate crosslinking and wherein the moiety is chosen from heterobifunctional cross-linking agents containing maleimide and an activated ester.

26. The method of claim 1, wherein the composition is a sustained release formulation or is in a sustained release carrier.

27. The method of claim 1, wherein the composition is administered in microspheres or liposomes.

28. The method of claim 26, wherein the sustained release carrier comprises one or more of polylactides copolymers of L-glutamic acid and gamma ethyl-L-glutamate, poly (2-hydroxyethyl-methacrylate), or ethylene vinyl acetate.

29. The method of claim 1, wherein the isolated polypeptide is administered at a dosage ranging from 0.00003 mg/kg/day to 30 mg/kg/day.

30. The method of claim 1, wherein the isolated peptide is administered at a dosage ranging from 0.003 mg/kg/day to 3 mg/kg/day.

31. The method of claim 1, wherein the isolated peptide is administered at a dosage ranging from 0.03 mg/kg/day to 0.3 mg/kg/day.

32. The method of claim 1, wherein the composition is administered orally, parenterally, topically, by inhalation, intranasally, or rectally.

33. The method of claim 1, wherein the composition is administered intravenously, intramuscularly, intracisternally, intradermally, intrathecally, epidurally, or by infusion.

34. The method of claim 1, wherein the composition comprises at least one additive chosen from pharmaceutically acceptable excipients, carriers, preservatives, buffers, stabilizers, antioxidants, and other additives.

35. The method of claim 1, wherein the composition is in a form chosen from a tablet, capsule, powder, and liquid.

36. The method of claim 35, wherein the liquid comprises at least one additive chosen from liquid carriers, petroleum, animal oils, vegetable oils, mineral oils, synthetic oils, physiological saline solutions, saccharide solutions, and glycols.

37. The method of claim 1, wherein the composition is administered in combination with bevacizumab.

38. The method of claim 1, wherein the composition is administered in combination with sorafinib.

39. The method of claim 5, wherein the cancer is ovarian cancer.

40. The method of claim 5, wherein the cancer is renal cancer.

41. The method of claim 5, wherein the cancer is lung cancer.

42. The method of claim 5, wherein the cancer is a glioma.

43. The method of claim 39, wherein the composition is administered in combination with at least one further treatment chosen from a chemotherapeutic agent, a chemopreventative agent, radiotherapy, and a combination of the same.

44. The method of claim 43, wherein the at least one further treatment is bevacizumab.

45. The method of claim 40, wherein the composition is administered in combination with sorafinib.

46. The method of claim 1, wherein the isolated polypeptide consists of SEQ ID NO: 3, SEQ ID NO: 4, SEQ ID NO: 5, SEQ ID NO:6, SEQ ID NO: 11, SEQ ID NO: 12, SEQ ID NO: 13, SEQ ID NO: 15, SEQ ID NO: 19, SEQ ID NO:23, or SEQ ID NO: 28.

* * * * *

SEQUENCE LISTING

```
<160> NUMBER OF SEQ ID NOS: 58

<210> SEQ ID NO 1
<211> LENGTH: 385
<212> TYPE: PRT
<213> ORGANISM: Homo sapiens

<400> SEQUENCE: 1

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Met Glu Thr Pro Pro Val Asn Thr Ile Gly Glu Lys
        35                  40                  45

Asp Thr Ser Gln Pro Gln Gln Glu Trp Glu Lys Asn Leu Arg Glu Asn
    50                  55                  60

Leu Asp Ser Val Ile Gln Ile Arg Gln Gln Pro Arg Asp Pro Pro Thr
65                  70                  75                  80

Glu Thr Leu Glu Leu Glu Val Ser Pro Asp Pro Ala Ser Gln Ile Leu
                85                  90                  95

Glu His Thr Gln Gly Ala Glu Lys Leu Val Ala Glu Leu Glu Gly Asp
                100                 105                 110

Ser His Lys Ser His Gly Ser Thr Ser Gln Met Pro Glu Ala Leu Gln
            115                 120                 125

Ala Ser Asp Leu Trp Tyr Cys Pro Asp Gly Ser Phe Val Lys Lys Ile
        130                 135                 140

Val Ile Arg Gly His Gly Leu Asp Lys Pro Lys Leu Gly Ser Cys Cys
145                 150                 155                 160
```

```
Arg Val Leu Ala Leu Gly Phe Pro Phe Gly Ser Gly Pro Pro Glu Gly
                165                 170                 175
Trp Thr Glu Leu Thr Met Gly Val Gly Pro Trp Arg Glu Glu Thr Trp
            180                 185                 190
Gly Glu Leu Ile Glu Lys Cys Leu Glu Ser Met Cys Gln Gly Glu Glu
            195                 200                 205
Ala Glu Leu Gln Leu Pro Gly His Thr Gly Pro Val Gly Leu Thr
210                 215                 220
Leu Ala Ser Phe Thr Gln Gly Arg Asp Ser Trp Glu Leu Glu Thr Ser
225                 230                 235                 240
Glu Lys Glu Ala Leu Ala Arg Glu Glu Arg Ala Arg Gly Thr Glu Leu
                245                 250                 255
Phe Arg Ala Gly Asn Pro Glu Gly Ala Ala Arg Cys Tyr Gly Arg Ala
                260                 265                 270
Leu Arg Leu Leu Leu Thr Leu Pro Pro Gly Pro Pro Glu Arg Thr
        275                 280                 285
Val Leu His Ala Asn Leu Ala Ala Cys Gln Leu Leu Gly Gln Pro
        290                 295                 300
Gln Leu Ala Ala Gln Ser Cys Asp Arg Val Leu Glu Arg Glu Pro Gly
305                 310                 315                 320
His Leu Lys Ala Leu Tyr Arg Arg Gly Val Ala Gln Ala Ala Leu Gly
                325                 330                 335
Asn Leu Glu Lys Ala Thr Ala Asp Leu Lys Lys Val Leu Ala Ile Asp
                340                 345                 350
Pro Lys Asn Arg Ala Ala Gln Glu Glu Leu Gly Lys Val Val Ile Gln
                355                 360                 365
Gly Lys Asn Gln Asp Ala Gly Leu Ala Gln Gly Leu Arg Lys Met Phe
            370                 375                 380
Gly
385

<210> SEQ ID NO 2
<211> LENGTH: 349
<212> TYPE: PRT
<213> ORGANISM: Homo sapiens

<400> SEQUENCE: 2

Met Glu Thr Pro Pro Val Asn Thr Ile Gly Glu Lys Asp Thr Ser Gln
1               5                   10                  15
Pro Gln Gln Glu Trp Glu Lys Asn Leu Arg Glu Asn Leu Asp Ser Val
            20                  25                  30
Ile Gln Ile Arg Gln Gln Pro Arg Asp Pro Thr Glu Thr Leu Glu
        35                  40                  45
Leu Glu Val Ser Pro Asp Pro Ala Ser Gln Ile Leu Glu His Thr Gln
    50                  55                  60
Gly Ala Glu Lys Leu Val Ala Glu Leu Glu Gly Asp Ser His Lys Ser
65                  70                  75                  80
His Gly Ser Thr Ser Gln Met Pro Glu Ala Leu Gln Ala Ser Asp Leu
                85                  90                  95
Trp Tyr Cys Pro Asp Gly Ser Phe Val Lys Lys Ile Val Ile Arg Gly
            100                 105                 110
His Gly Leu Asp Lys Pro Lys Leu Gly Ser Cys Cys Arg Val Leu Ala
        115                 120                 125
Leu Gly Phe Pro Phe Gly Ser Gly Pro Pro Glu Gly Trp Thr Glu Leu
    130                 135                 140
```

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Ala Glu Leu Gln
                165                 170                 175

Leu Pro Gly His Thr Gly Pro Val Gly Leu Thr Leu Ala Ser Phe
                180                 185                 190

Thr Gln Gly Arg Asp Ser Trp Glu Leu Glu Thr Ser Glu Lys Glu Ala
                195                 200                 205

Leu Ala Arg Glu Glu Arg Ala Arg Gly Thr Glu Leu Phe Arg Ala Gly
                210                 215                 220

Asn Pro Glu Gly Ala Ala Arg Cys Tyr Gly Arg Ala Leu Arg Leu Leu
225                 230                 235                 240

Leu Thr Leu Pro Pro Pro Gly Pro Pro Glu Arg Thr Val Leu His Ala
                245                 250                 255

Asn Leu Ala Ala Cys Gln Leu Leu Leu Gly Gln Pro Gln Leu Ala Ala
                260                 265                 270

Gln Ser Cys Asp Arg Val Leu Glu Arg Glu Pro Gly His Leu Lys Ala
                275                 280                 285

Leu Tyr Arg Arg Gly Val Ala Gln Ala Ala Leu Gly Asn Leu Glu Lys
                290                 295                 300

Ala Thr Ala Asp Leu Lys Lys Val Leu Ala Ile Asp Pro Lys Asn Arg
305                 310                 315                 320

Ala Ala Gln Glu Glu Leu Gly Lys Val Val Ile Gln Gly Lys Asn Gln
                325                 330                 335

Asp Ala Gly Leu Ala Gln Gly Leu Arg Lys Met Phe Gly
                340                 345

<210> SEQ ID NO 3
<211> LENGTH: 199
<212> TYPE: PRT
<213> ORGANISM: Homo sapiens

<400> SEQUENCE: 3

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
                20                  25                  30

Ile Gln Ile Arg Gln Gln Pro Arg Asp Pro Thr Glu Thr Leu Glu
                35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
                100                 105                 110

His Gly Leu Asp Lys Pro Lys Leu Gly Ser Cys Cys Arg Val Leu Ala
                115                 120                 125

Leu Gly Phe Pro Phe Gly Ser Gly Pro Pro Glu Gly Trp Thr Glu Leu
                130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln

```
                    165                 170                 175
Leu Pro Gly His Thr Gly Pro Val Gly Leu Thr Leu Ala Ser Phe
                180                 185                 190

Thr Gln Gly Arg Asp Ser Trp
            195

<210> SEQ ID NO 4
<211> LENGTH: 150
<212> TYPE: PRT
<213> ORGANISM: Homo sapiens

<400> SEQUENCE: 4

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro
145                 150

<210> SEQ ID NO 5
<211> LENGTH: 85
<212> TYPE: PRT
<213> ORGANISM: Homo sapiens

<400> SEQUENCE: 5

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser
                85

<210> SEQ ID NO 6
<211> LENGTH: 57
<212> TYPE: PRT
<213> ORGANISM: Homo sapiens

<400> SEQUENCE: 6
```

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
                20                  25                  30

Ile Gln Ile Arg Gln Gln Pro Arg Asp Pro Thr Glu Thr Leu Glu
        35                  40                  45

Leu Glu Val Ser Pro Asp Pro Ala Ser
    50                  55

<210> SEQ ID NO 7
<211> LENGTH: 47
<212> TYPE: PRT
<213> ORGANISM: Homo sapiens

<400> SEQUENCE: 7

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
                20                  25                  30

Ile Gln Ile Arg Gln Gln Pro Arg Asp Pro Thr Glu Thr Leu
        35                  40                  45

<210> SEQ ID NO 8
<211> LENGTH: 39
<212> TYPE: PRT
<213> ORGANISM: Homo sapiens

<400> SEQUENCE: 8

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
                20                  25                  30

Ile Gln Ile Arg Gln Gln Pro
        35

<210> SEQ ID NO 9
<211> LENGTH: 33
<212> TYPE: PRT
<213> ORGANISM: Homo sapiens

<400> SEQUENCE: 9

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
                20                  25                  30

Ile

<210> SEQ ID NO 10
<211> LENGTH: 24
<212> TYPE: PRT
<213> ORGANISM: Homo sapiens

<400> SEQUENCE: 10

Gln Ile Arg Gln Gln Pro Arg Asp Pro Thr Glu Thr Leu Glu Leu
1               5                   10                  15

Glu Val Ser Pro Asp Pro Ala Ser
                20

<210> SEQ ID NO 11

```
<211> LENGTH: 18
<212> TYPE: PRT
<213> ORGANISM: Homo sapiens

<400> SEQUENCE: 11

Gln Gln Pro Arg Asp Pro Pro Thr Glu Thr Leu Glu Leu Glu Val Ser
1               5                   10                  15

Pro Asp

<210> SEQ ID NO 12
<211> LENGTH: 25
<212> TYPE: PRT
<213> ORGANISM: Homo sapiens
<220> FEATURE:
<221> NAME/KEY: BINDING
<222> LOCATION: (24)..(25)
<223> OTHER INFORMATION: There is a PEG (polyethylene glycol) connection
      between residue 24 (Serine) and 25 (cystine).
<220> FEATURE:
<221> NAME/KEY: MOD_RES
<222> LOCATION: (25)..(25)
<223> OTHER INFORMATION: There is a flourophore (Alexa488) attached to
      the final residue (cystine)

<400> SEQUENCE: 12

Gln Ile Arg Gln Gln Pro Arg Asp Pro Pro Thr Glu Thr Leu Glu Leu
1               5                   10                  15

Glu Val Ser Pro Asp Pro Ala Ser Cys
            20                  25

<210> SEQ ID NO 13
<211> LENGTH: 24
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glutamic acid is modified to be Pyroglutamic
      Acid (PyroGlu)

<400> SEQUENCE: 13

Glu Ile Arg Gln Gln Pro Arg Asp Pro Pro Thr Glu Thr Leu Glu Leu
1               5                   10                  15

Glu Val Ser Pro Asp Pro Ala Ser
            20

<210> SEQ ID NO 14
<211> LENGTH: 23
<212> TYPE: PRT
<213> ORGANISM: Homo sapiens

<400> SEQUENCE: 14

Ile Arg Gln Gln Pro Arg Asp Pro Pro Thr Glu Thr Leu Glu Leu Glu
1               5                   10                  15

Val Ser Pro Asp Pro Ala Ser
            20

<210> SEQ ID NO 15
<211> LENGTH: 21
<212> TYPE: PRT
<213> ORGANISM: Homo sapiens

<400> SEQUENCE: 15

Gln Ile Arg Gln Gln Pro Arg Asp Pro Pro Thr Glu Thr Leu Glu Leu
1               5                   10                  15
```

Glu Val Ser Pro Asp
            20

<210> SEQ ID NO 16
<211> LENGTH: 18
<212> TYPE: PRT
<213> ORGANISM: Homo sapiens

<400> SEQUENCE: 16

Gln Ile Arg Gln Gln Pro Arg Asp Pro Pro Thr Glu Thr Leu Glu Leu
1               5                   10                  15

Glu Val

<210> SEQ ID NO 17
<211> LENGTH: 15
<212> TYPE: PRT
<213> ORGANISM: Homo sapiens

<400> SEQUENCE: 17

Gln Ile Arg Gln Gln Pro Arg Asp Pro Pro Thr Glu Thr Leu Glu
1               5                   10                  15

<210> SEQ ID NO 18
<211> LENGTH: 12
<212> TYPE: PRT
<213> ORGANISM: Homo sapiens

<400> SEQUENCE: 18

Gln Ile Arg Gln Gln Pro Arg Asp Pro Pro Thr Glu
1               5                   10

<210> SEQ ID NO 19
<211> LENGTH: 21
<212> TYPE: PRT
<213> ORGANISM: Homo sapiens

<400> SEQUENCE: 19

Gln Gln Pro Arg Asp Pro Pro Thr Glu Thr Leu Glu Leu Glu Val Ser
1               5                   10                  15

Pro Asp Pro Ala Ser
            20

<210> SEQ ID NO 20
<211> LENGTH: 18
<212> TYPE: PRT
<213> ORGANISM: Homo sapiens

<400> SEQUENCE: 20

Arg Asp Pro Pro Thr Glu Thr Leu Glu Leu Glu Val Ser Pro Asp Pro
1               5                   10                  15

Ala Ser

<210> SEQ ID NO 21
<211> LENGTH: 15
<212> TYPE: PRT
<213> ORGANISM: Homo sapiens

<400> SEQUENCE: 21

Pro Thr Glu Thr Leu Glu Leu Glu Val Ser Pro Asp Pro Ala Ser
1               5                   10                  15

<210> SEQ ID NO 22
<211> LENGTH: 12

<212> TYPE: PRT
<213> ORGANISM: Homo sapiens

<400> SEQUENCE: 22

Thr Leu Glu Leu Glu Val Ser Pro Asp Pro Ala Ser
1               5                   10

<210> SEQ ID NO 23
<211> LENGTH: 19
<212> TYPE: PRT
<213> ORGANISM: Homo sapiens

<400> SEQUENCE: 23

Arg Gln Gln Pro Arg Asp Pro Pro Thr Glu Thr Leu Glu Leu Glu Val
1               5                   10                  15

Ser Pro Asp

<210> SEQ ID NO 24
<211> LENGTH: 18
<212> TYPE: PRT
<213> ORGANISM: Homo sapiens

<400> SEQUENCE: 24

Arg Gln Gln Pro Arg Asp Pro Pro Thr Glu Thr Leu Glu Leu Glu Val
1               5                   10                  15

Ser Pro

<210> SEQ ID NO 25
<211> LENGTH: 17
<212> TYPE: PRT
<213> ORGANISM: Homo sapiens

<400> SEQUENCE: 25

Arg Gln Gln Pro Arg Asp Pro Pro Thr Glu Thr Leu Glu Leu Glu Val
1               5                   10                  15

Ser

<210> SEQ ID NO 26
<211> LENGTH: 16
<212> TYPE: PRT
<213> ORGANISM: Homo sapiens

<400> SEQUENCE: 26

Pro Arg Asp Pro Pro Thr Glu Thr Leu Glu Leu Glu Val Ser Pro Asp
1               5                   10                  15

<210> SEQ ID NO 27
<211> LENGTH: 15
<212> TYPE: PRT
<213> ORGANISM: Homo sapiens

<400> SEQUENCE: 27

Arg Asp Pro Pro Thr Glu Thr Leu Glu Leu Glu Val Ser Pro Asp
1               5                   10                  15

<210> SEQ ID NO 28
<211> LENGTH: 24
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (24)..(24)
<223> OTHER INFORMATION: Final residue (Serine) ends in an amide group
      as opposed to an acid.

<400> SEQUENCE: 28

Gln Ile Arg Gln Gln Pro Arg Asp Pro Pro Thr Glu Thr Leu Glu Leu
1               5                   10                  15

Glu Val Ser Pro Asp Pro Ala Ser
            20

<210> SEQ ID NO 29
<211> LENGTH: 349
<212> TYPE: PRT
<213> ORGANISM: Homo sapiens

<400> SEQUENCE: 29

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Ser Gly Pro Pro Val Arg Leu Thr Leu Ala Ser Phe
            180                 185                 190

Thr Gln Gly Arg Asp Ser Trp Glu Leu Glu Thr Ser Glu Lys Glu Ala
        195                 200                 205

Leu Ala Arg Glu Glu Arg Ala Arg Gly Thr Glu Leu Phe Arg Ala Gly
    210                 215                 220

Asn Pro Glu Gly Ala Ala Arg Cys Tyr Gly Arg Ala Leu Arg Leu Leu
225                 230                 235                 240

Leu Thr Leu Pro Pro Gly Pro Pro Glu Arg Thr Val Leu His Ala
                245                 250                 255

Asn Leu Ala Ala Cys Gln Leu Leu Gly Gln Pro Gln Leu Ala Ala
            260                 265                 270

Gln Ser Cys Asp Arg Val Leu Glu Arg Glu Pro Gly His Leu Lys Ala
        275                 280                 285

Leu Tyr Arg Arg Gly Val Ala Gln Ala Ala Leu Gly Asn Leu Glu Lys
    290                 295                 300

Ala Thr Ala Asp Leu Lys Lys Val Leu Ala Ile Asp Pro Lys Asn Arg
```

```
                    305                 310                 315                 320
Ala Ala Gln Glu Glu Leu Gly Lys Val Val Ile Gln Gly Lys Asn Gln
                325                 330                 335
Asp Ala Gly Leu Ala Gln Gly Leu Arg Lys Met Phe Gly
                340                 345
```

<210> SEQ ID NO 30
<211> LENGTH: 1050
<212> TYPE: DNA
<213> ORGANISM: Homo sapiens

<400> SEQUENCE: 30

| | | | | |
|---|---|---|---|---|
| atggagacgc | caccagtcaa | tacaattgga | gaaaaggaca | cctctcagcc gcaacaagag | 60 |
| tgggaaaaga | accttcggga | gaaccttgat | tcagttattc | agattaggca gcagccccga | 120 |
| gaccctccta | ccgaaacgct | tgagctggaa | gtaagcccag | atccagccag ccaaattcta | 180 |
| gagcatactc | aaggagctga | aaaactggtt | gctgaacttg | aaggagactc tcataagtct | 240 |
| catggatcaa | ccagtcagat | gccagaggcc | cttcaagctt | ctgatctctg gtactgcccc | 300 |
| gatgggagct | tgtcaagaa | gatcgtaatc | cgtggccatg | gcttggacaa acccaaaacta | 360 |
| ggctcctgct | gccgggtact | ggctttgggg | tttccttccg | gatcagggcc gccagagggc | 420 |
| tggacagagc | taactatggg | cgtagggcca | tggagggagg | aaacttgggg ggagctcata | 480 |
| gagaaatgct | tggagtccat | gtgtcaaggt | gaggaagcag | agcttcagct gcctgggcac | 540 |
| tctggacctc | ctgtcaggct | cacactggca | tccttcactc | aaggccgaga ctcctgggag | 600 |
| ctggagacta | gcgagaagga | agccctggcc | agggaagaac | gtgcaagggg cacagaacta | 660 |
| tttcgagctg | ggaaccctga | aggagctgcc | cgatgctatg | gacgggctct tcggctgctc | 720 |
| ctgactttac | ccccacctgg | ccctccagaa | cgaactgtcc | ttcatgccaa tctggctgcc | 780 |
| tgtcagttgt | tgctagggca | gcctcagttg | gcagcccaga | gctgtgaccg ggtgttggag | 840 |
| cgggagcctg | gccatttaaa | ggccttatac | gaagggggg | ttgcccaggc tgcccttggg | 900 |
| aacctggaaa | aagcaactgc | tgacctcaag | aaggtgctgg | cgatagatcc caaaaaccgg | 960 |
| gcagcccagg | aggaactggg | gaaggtggtc | attcagggga | gaaccagga tgcagggctg | 1020 |
| gctcagggtc | tgcgcaagat | gtttggctga | | | 1050 |

<210> SEQ ID NO 31
<211> LENGTH: 1050
<212> TYPE: DNA
<213> ORGANISM: Homo sapiens

<400> SEQUENCE: 31

| | | | | |
|---|---|---|---|---|
| atggagacgc | caccagtcaa | tacaattgga | gaaaaggaca | cctctcagcc gcaacaagag | 60 |
| tgggaaaaga | accttcggga | gaaccttgat | tcagttattc | agattaggca gcagccccga | 120 |
| gaccctccta | ccgaaacgct | tgagctggaa | gtaagcccag | atccagccag ccaaattcta | 180 |
| gagcatactc | aaggagctga | aaaactggtt | gctgaacttg | aaggagactc tcataagtct | 240 |
| catggatcaa | ccagtcagat | gccagaggcc | cttcaagctt | ctgatctctg gtactgcccc | 300 |
| gatgggagct | tgtcaagaa | gatcgtaatc | cgtggccatg | gcttggacaa acccaaaacta | 360 |
| ggctcctgct | gccgggtact | ggctttgggg | tttccttccg | gatcagggcc gccagagggc | 420 |
| tggacagagc | taactatggg | cgtagggcca | tggagggagg | aaacttgggg ggagctcata | 480 |
| gagaaatgct | tggagtccat | gtgtcaaggt | gaggaagcag | agcttcagct gcctgggcac | 540 |
| actggacctc | ctgtcgggct | cacactggca | tccttcactc | aaggccgaga ctcctgggag | 600 |

```
ctggagacta gcgagaagga agccctggcc agggaagaac gtgcaagggg cacagaacta      660
tttcgagctg ggaaccctga aggagctgcc cgatgctatg gacgggctct tcggctgctc      720
ctgactttac ccccacctgg ccctccagaa cgaactgtcc ttcatgccaa tctggctgcc      780
tgtcagttgt tgctagggca gcctcagttg gcagcccaga gctgtgaccg ggtgttggag      840
cgggagcctg gccatttaaa ggccttatac cgaaggdggg ttgcccaggc tgcccttggg      900
aacctggaaa aagcaactgc tgacctcaag aaggtgctgg cgatagatcc caaaaaccgg      960
gcagcccagg aggaactggg gaaggtggtc attcaggga agaaccagga tgcagggctg     1020
gctcagggtc tgcgcaagat gtttggctga                                     1050

<210> SEQ ID NO 32
<211> LENGTH: 102
<212> TYPE: DNA
<213> ORGANISM: Artificial
<220> FEATURE:
<223> OTHER INFORMATION: Homo Sapiens

<400> SEQUENCE: 32
atggagacgc caccagtcaa tacaattgga gaaaaggaca cctctcagcc gcaacaagag       60
tgggaaaaga accttcggga gaaccttgat tcagttattt ag                        102

<210> SEQ ID NO 33
<211> LENGTH: 119
<212> TYPE: DNA
<213> ORGANISM: Artificial
<220> FEATURE:
<223> OTHER INFORMATION: Homo Sapiens

<400> SEQUENCE: 33
atggagacgc caccagtcaa tacaattgga gaaaaggaca cctctcagcc gcaacaagag       60
tgggaaaaga accttcggga gaaccttgat tcagttattc agattaggca gcagccccg      119

<210> SEQ ID NO 34
<211> LENGTH: 143
<212> TYPE: DNA
<213> ORGANISM: Artificial
<220> FEATURE:
<223> OTHER INFORMATION: Homo Sapiens

<400> SEQUENCE: 34
atggagacgc caccagtcaa tacaattgga gaaaaggaca cctctcagcc gcaacaagag       60
tgggaaaaga accttcggga gaaccttgat tcagttattc agattaggca gcagccccga     120
gaccctccta ccgaaacgct tga                                             143

<210> SEQ ID NO 35
<211> LENGTH: 174
<212> TYPE: DNA
<213> ORGANISM: Artificial
<220> FEATURE:
<223> OTHER INFORMATION: Homo sapiens

<400> SEQUENCE: 35
atggagacgc caccagtcaa tacaattgga gaaaaggaca cctctcagcc gcaacaagag       60
tgggaaaaga accttcggga gaaccttgat tcagttattc agattaggca gcagccccga     120
gaccctccta ccgaaacgct tgagctggaa gtaagcccag atccagccag ctaa           174

<210> SEQ ID NO 36
```

<211> LENGTH: 258
<212> TYPE: DNA
<213> ORGANISM: Artificial
<220> FEATURE:
<223> OTHER INFORMATION: Homo sapiens

<400> SEQUENCE: 36

```
atggagacgc caccagtcaa tacaattgga gaaaaggaca cctctcagcc gcaacaagag      60
tgggaaaaga accttcggga gaaccttgat tcagttattc agattaggca gcagccccga     120
gaccctccta ccgaaacgct tgagctggaa gtaagcccag atccagccag ccaaattcta     180
gagcatactc aaggagctga aaaactggtt gctgaacttg aaggagactc tcataagtct     240
catggatcaa ccagttag                                                    258
```

<210> SEQ ID NO 37
<211> LENGTH: 453
<212> TYPE: DNA
<213> ORGANISM: Artificial
<220> FEATURE:
<223> OTHER INFORMATION: Homo sapiens

<400> SEQUENCE: 37

```
atggagacgc caccagtcaa tacaattgga gaaaaggaca cctctcagcc gcaacaagag      60
tgggaaaaga accttcggga gaaccttgat tcagttattc agattaggca gcagccccga     120
gaccctccta ccgaaacgct tgagctggaa gtaagcccag atccagccag ccaaattcta     180
gagcatactc aaggagctga aaaactggtt gctgaacttg aaggagactc tcataagtct     240
catggatcaa ccagtcagat gccagaggcc cttcaagctt ctgatctctg gtactgcccc     300
gatgggagct ttgtcaagaa gatcgtaatc cgtggccatg gcttggacaa acccaaacta     360
ggctcctgct gccgggtact ggctttgggg tttccttttcg gatcagggcc gccagagggc     420
tggacagagc taactatggg cgtagggcca tga                                  453
```

<210> SEQ ID NO 38
<211> LENGTH: 600
<212> TYPE: DNA
<213> ORGANISM: Artificial
<220> FEATURE:
<223> OTHER INFORMATION: Homo sapiens

<400> SEQUENCE: 38

```
atggagacgc caccagtcaa tacaattgga gaaaaggaca cctctcagcc gcaacaagag      60
tgggaaaaga accttcggga gaaccttgat tcagttattc agattaggca gcagccccga     120
gaccctccta ccgaaacgct tgagctggaa gtaagcccag atccagccag ccaaattcta     180
gagcatactc aaggagctga aaaactggtt gctgaacttg aaggagactc tcataagtct     240
catggatcaa ccagtcagat gccagaggcc cttcaagctt ctgatctctg gtactgcccc     300
gatgggagct ttgtcaagaa gatcgtaatc cgtggccatg gcttggacaa acccaaacta     360
ggctcctgct gccgggtact ggctttgggg tttccttttcg gatcagggcc gccagagggc     420
tggacagagc taactatggg cgtagggcca tggagggagg aaacttgggg ggagctcata     480
gagaaatgct tggagtccat gtgtcaaggt gaggaagcag agcttcagct gcctgggcac     540
tctggacctc ctgtcaggct cacactggca tccttcactc aaggccgaga ctcctggtag     600
```

<210> SEQ ID NO 39
<211> LENGTH: 600
<212> TYPE: DNA
<213> ORGANISM: Artificial

<220> FEATURE:
<223> OTHER INFORMATION: Homo sapiens

<400> SEQUENCE: 39

| | | | | | |
|---|---|---|---|---|---|
| atggagacgc | caccagtcaa | tacaattgga | gaaaaggaca | cctctcagcc | gcaacaagag | 60 |
| tgggaaaaga | accttcggga | gaaccttgat | tcagttattc | agattaggca | gcagcccga | 120 |
| gaccctccta | ccgaaacgct | tgagctggaa | gtaagcccag | atccagccag | ccaaattcta | 180 |
| gagcatactc | aaggagctga | aaaactggtt | gctgaacttg | aaggagactc | tcataagtct | 240 |
| catggatcaa | ccagtcagat | gccagaggcc | cttcaagctt | ctgatctctg | gtactgcccc | 300 |
| gatgggagct | ttgtcaagaa | gatcgtaatc | cgtggccatg | gcttggacaa | acccaaacta | 360 |
| ggctcctgct | gccgggtact | ggctttgggg | tttcctttcg | gatcagggcc | gccagagggc | 420 |
| tggacagagc | taactatggg | cgtagggcca | tggagggagg | aaacttgggg | ggagctcata | 480 |
| gagaaatgct | tggagtccat | gtgtcaaggt | gaggaagcag | agcttcagct | gcctgggcac | 540 |
| actggacctc | ctgtcgggct | cacactggca | tccttcactc | aaggccgaga | ctcctggtag | 600 |

<210> SEQ ID NO 40
<211> LENGTH: 18
<212> TYPE: DNA
<213> ORGANISM: Artificial
<220> FEATURE:
<223> OTHER INFORMATION: Homo sapiens

<400> SEQUENCE: 40
atggccaggc tcccgctc                                                   18

<210> SEQ ID NO 41
<211> LENGTH: 18
<212> TYPE: DNA
<213> ORGANISM: Artificial
<220> FEATURE:
<223> OTHER INFORMATION: Homo sapiens

<400> SEQUENCE: 41
cttcccaagc ctcccaag                                                   18

<210> SEQ ID NO 42
<211> LENGTH: 20
<212> TYPE: DNA
<213> ORGANISM: Artificial
<220> FEATURE:
<223> OTHER INFORMATION: Homo sapiens

<400> SEQUENCE: 42
agaagacggg tcctccagtt                                                 20

<210> SEQ ID NO 43
<211> LENGTH: 20
<212> TYPE: DNA
<213> ORGANISM: Artificial
<220> FEATURE:
<223> OTHER INFORMATION: Homo sapiens

<400> SEQUENCE: 43
gagtcaacgg atttggtcgt                                                 20

<210> SEQ ID NO 44
<211> LENGTH: 20
<212> TYPE: DNA
<213> ORGANISM: Artificial
<220> FEATURE:

<223> OTHER INFORMATION: Homo sapiens

<400> SEQUENCE: 44
ttgattttgg agggatctcg                                                    20

<210> SEQ ID NO 45
<211> LENGTH: 39
<212> TYPE: DNA
<213> ORGANISM: Artificial
<220> FEATURE:
<223> OTHER INFORMATION: Homo sapiens

<400> SEQUENCE: 45
gaaccttgat tcagttattt agattaggca gcagccccg                               39

<210> SEQ ID NO 46
<211> LENGTH: 39
<212> TYPE: DNA
<213> ORGANISM: Artificial
<220> FEATURE:
<223> OTHER INFORMATION: Homo sapiens

<400> SEQUENCE: 46
cggggctgct gcctaatcta ataactgaa tcaaggttc                                39

<210> SEQ ID NO 47
<211> LENGTH: 38
<212> TYPE: DNA
<213> ORGANISM: Artificial
<220> FEATURE:
<223> OTHER INFORMATION: Homo sapiens

<400> SEQUENCE: 47
cagattaggc agcagccctg agaccctcct accgaaac                                38

<210> SEQ ID NO 48
<211> LENGTH: 38
<212> TYPE: DNA
<213> ORGANISM: Artificial
<220> FEATURE:
<223> OTHER INFORMATION: Homo sapiens

<400> SEQUENCE: 48
gtttcggtag gagggtctca gggctgctgc ctaatctg                                38

<210> SEQ ID NO 49
<211> LENGTH: 31
<212> TYPE: DNA
<213> ORGANISM: Artificial
<220> FEATURE:
<223> OTHER INFORMATION: Homo sapiens

<400> SEQUENCE: 49
cctaccgaaa cgctttagct ggaagtaagc c                                       31

<210> SEQ ID NO 50
<211> LENGTH: 31
<212> TYPE: DNA
<213> ORGANISM: Artificial
<220> FEATURE:
<223> OTHER INFORMATION: Homo sapiens

<400> SEQUENCE: 50
ggcttacttc cagctaaagc gtttcggtag g                                       31

```
<210> SEQ ID NO 51
<211> LENGTH: 33
<212> TYPE: DNA
<213> ORGANISM: Artificial
<220> FEATURE:
<223> OTHER INFORMATION: Homo sapiens

<400> SEQUENCE: 51
cccagatcca gccagctaaa ttctagagca tac                                33

<210> SEQ ID NO 52
<211> LENGTH: 33
<212> TYPE: DNA
<213> ORGANISM: Artificial
<220> FEATURE:
<223> OTHER INFORMATION: Homo sapiens

<400> SEQUENCE: 52
gtatgctcta gaatttagct ggctggatct ggg                                33

<210> SEQ ID NO 53
<211> LENGTH: 31
<212> TYPE: DNA
<213> ORGANISM: Artificial
<220> FEATURE:
<223> OTHER INFORMATION: Homo sapiens

<400> SEQUENCE: 53
catggatcaa ccagttagat gccagaggcc c                                  31

<210> SEQ ID NO 54
<211> LENGTH: 31
<212> TYPE: DNA
<213> ORGANISM: Artificial
<220> FEATURE:
<223> OTHER INFORMATION: Homo sapiens

<400> SEQUENCE: 54
gggcctctgg catctaactg gttgatccat g                                  31

<210> SEQ ID NO 55
<211> LENGTH: 29
<212> TYPE: DNA
<213> ORGANISM: Artificial
<220> FEATURE:
<223> OTHER INFORMATION: Homo sapiens

<400> SEQUENCE: 55
ggcgtagggc catgaaggga ggaaacttg                                     29

<210> SEQ ID NO 56
<211> LENGTH: 29
<212> TYPE: DNA
<213> ORGANISM: Artificial
<220> FEATURE:
<223> OTHER INFORMATION: Homo sapiens

<400> SEQUENCE: 56
caagtttcct cccttcatgg ccctacgcc                                     29

<210> SEQ ID NO 57
<211> LENGTH: 28
<212> TYPE: DNA
<213> ORGANISM: Artificial
<220> FEATURE:
<223> OTHER INFORMATION: Homo sapiens
```

```
<400> SEQUENCE: 57
ccgagactcc tggtagctgg agactagc                                              28

<210> SEQ ID NO 58
<211> LENGTH: 28
<212> TYPE: DNA
<213> ORGANISM: Artificial
<220> FEATURE:
<223> OTHER INFORMATION: Homo sapiens

<400> SEQUENCE: 58
gctagtctcc agctaccagg agtctcgg                                              28
```